US010398936B2

(12) United States Patent
Quatrochi et al.

(10) Patent No.: US 10,398,936 B2
(45) Date of Patent: Sep. 3, 2019

(54) INTERACTIVE ATHLETIC TRAINING LOG

(71) Applicant: NIKE, Inc., Beaverton, OR (US)

(72) Inventors: Danielle M. Quatrochi, Portland, OR (US); Jason Nims, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 433 days.

(21) Appl. No.: 14/726,164

(22) Filed: May 29, 2015

(65) Prior Publication Data
US 2015/0258383 A1 Sep. 17, 2015

Related U.S. Application Data

(63) Continuation of application No. 13/569,997, filed on Aug. 8, 2012, which is a continuation of application
(Continued)

(51) Int. Cl.
A63B 69/00 (2006.01)
A63B 24/00 (2006.01)
(Continued)

(52) U.S. Cl.
CPC ........ A63B 24/0075 (2013.01); A61B 5/0022 (2013.01); A61B 5/1118 (2013.01); A61B 5/6807 (2013.01); A61B 5/7465 (2013.01); A63B 69/0028 (2013.01); A63B 71/0622 (2013.01); A63B 71/0697 (2013.01); G06F 19/3481 (2013.01); A61B 2503/10 (2013.01);
(Continued)

(58) Field of Classification Search
None
See application file for complete search history.

(56) References Cited

U.S. PATENT DOCUMENTS 5,931,763 A 8/1999 Alessandri
2003/0182052 A1* 9/2003 DeLorme ............... G01C 21/26
701/533
(Continued)

FOREIGN PATENT DOCUMENTS

JP H11137719 A 5/1999
JP 2002269286 A 9/2002
(Continued)

OTHER PUBLICATIONS

Anonymous: "Event chain diagram", Wikipedia, Dec. 10, 2007 (Dec. 10, 2007), XP055384055, Retrieved from the Internet: URL:https://en.wikipedia.org/w/ndex.php?title=Event_chain_diagram&oldid=177007542 (retrieved on Jun. 22, 2017).
(Continued)

Primary Examiner — Bruk A Gebremichael
(74) Attorney, Agent, or Firm — Banner & Witcoff, Ltd.

(57) ABSTRACT

Systems and techniques for the collection and display of athletic information. Athletic data relating to a single person or group of people is collected at a central location, and subsequently displayed at a desired remote location so that the person or people can review and critique their performance. In addition, athletic data for multiple persons can be collected at a central location, and subsequently displayed to a user at a desired remote location, so that the user can compare his or her athletic activities to others.

15 Claims, 107 Drawing Sheets

Related U.S. Application Data

No. 12/395,047, filed on Feb. 27, 2009, now Pat. No. 8,257,228.

(60) Provisional application No. 61/032,018, filed on Feb. 27, 2008.

(51) Int. Cl.
  *A63B 71/06* (2006.01)
  *G06F 19/00* (2018.01)
  *A61B 5/11* (2006.01)
  *A61B 5/00* (2006.01)
  *A63B 22/00* (2006.01)
  *A63B 22/02* (2006.01)
  *A63B 22/06* (2006.01)

(52) U.S. Cl.
  CPC ... *A61B 2562/0219* (2013.01); *A63B 22/0056* (2013.01); *A63B 22/0076* (2013.01); *A63B 22/02* (2013.01); *A63B 22/0605* (2013.01); *A63B 22/0664* (2013.01); *A63B 24/0084* (2013.01); *A63B 2024/0025* (2013.01); *A63B 2024/0068* (2013.01); *A63B 2071/0625* (2013.01); *A63B 2220/12* (2013.01); *A63B 2220/30* (2013.01); *A63B 2220/34* (2013.01); *A63B 2220/40* (2013.01); *A63B 2220/803* (2013.01); *A63B 2220/836* (2013.01); *A63B 2225/15* (2013.01); *A63B 2225/20* (2013.01); *A63B 2225/50* (2013.01); *A63B 2230/00* (2013.01); *A63B 2230/04* (2013.01); *A63B 2230/207* (2013.01); *A63B 2230/75* (2013.01)

(56) References Cited

U.S. PATENT DOCUMENTS

2005/0107723 A1    5/2005  Wehman et al.
2006/0136173 A1*  6/2006  Case, Jr. ............... A63B 24/00
                                                   702/182

FOREIGN PATENT DOCUMENTS

| | | |
|---|---|---|
| JP | 2004310273 A | 11/2004 |
| JP | 2006136717 A | 6/2006 |
| JP | 2011514192 A | 5/2011 |
| WO | 2004110568 A1 | 12/2004 |

OTHER PUBLICATIONS

Anonymous: "Program evaluation and review technique",Wikipedia, Feb. 19, 2009 (Feb. 19, 2009), XP055384060, Retrieved from the Internet: URL:https://en.wikipedia.org/w/index.php?title=Program_evaluation_and_review_techniques&oldid=192636578 (retrieved on Jun. 22, 2017).

Anonymous: Bullet graph?, Wikipedia, Aug. 12, 2007 (Aug. 12, 2007), XP055384086, Retrieved from the Internet:URL:https://en.wikipedia.org/w/index.php?title=Bullet_graph&oldid=150749131 (retrieved on Jun. 22, 2017).

* cited by examiner

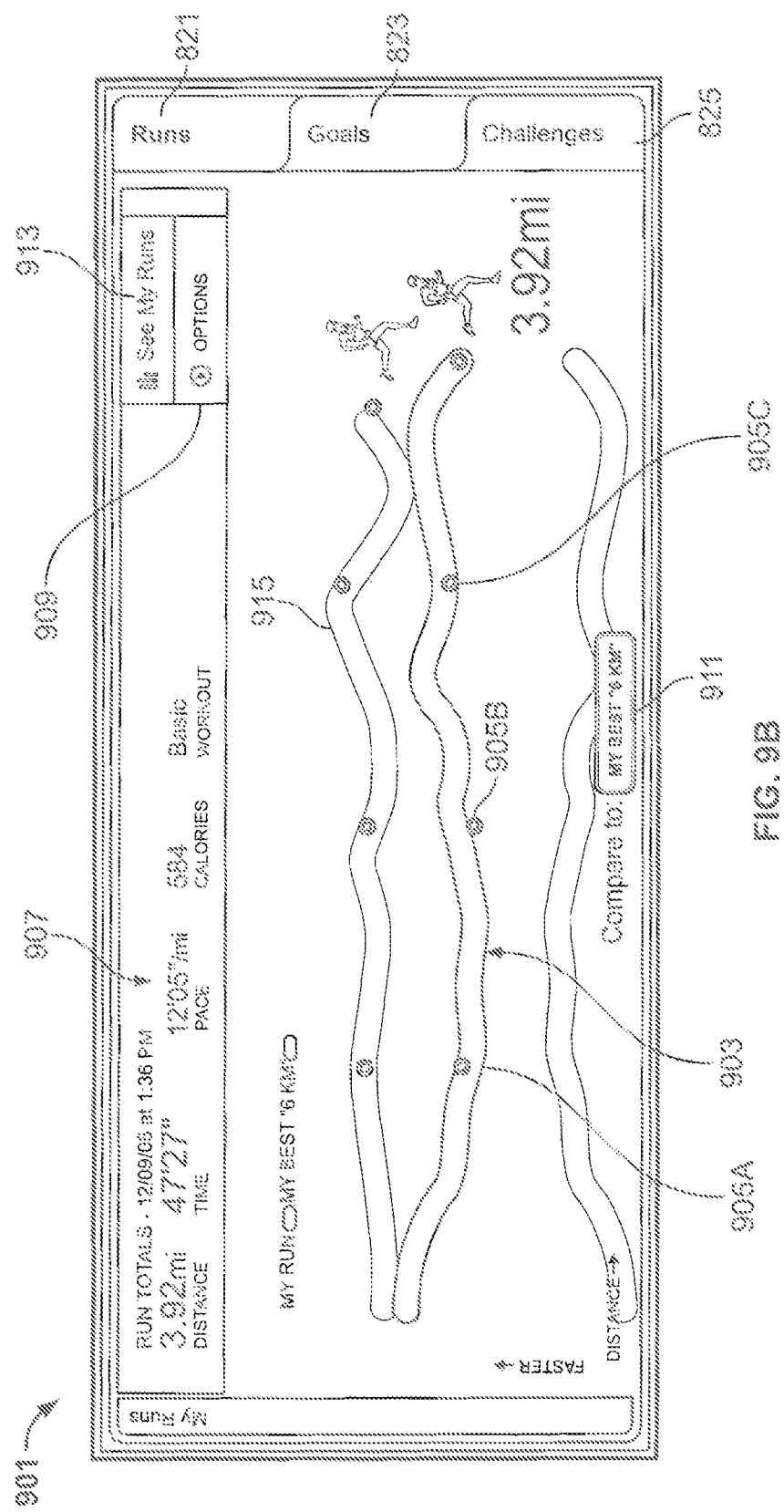

JennyBaxter
> EDIT

I have completed 2 runs for a total of 1.12mi. My average pace is 12'57" per mi.

MY RECORDS

BLOG
FORUMS

HOME

Training

Check out a featured training program

| Coach Jay Walk to Run Training | 10k Training | ½ Marathon Training | Marathon Training |

See all programs >

Create your own training program >

Train with a team
Joining a team and sharing training advice is a great way to get fit and stay motivated. Check out Teams >

LOGO

MY RUNS | CHALLENGES | COMMUNITY | GEAR & MUSIC | SUPPORT

INTERACTIVE ATHLETIC TRAINING LOG

RELATED APPLICATION

The present application is a continuation of and claims benefit of and priority to U.S. patent application Ser. No. 13/569,997, filed on Aug. 8, 2012, which is a continuation of U.S. patent application Ser. No. 12/395,047 filed on Feb. 27, 2009, claims the benefit of and priority to U.S. patent application Ser. No. 61/032,018 filed on Feb. 27, 2008, which application is incorporated by reference and made a part hereof.

FIELD OF THE INVENTION

The present invention relates to the collection and display of athletic information. Some aspects of the invention have particular applicability to the collection of athletic information from a plurality of different people over a network, and displaying the collected information for comparison and training purposes.

BACKGROUND OF THE INVENTION

While most people appreciate the importance of physical fitness, many have difficulty finding the motivation required to maintain a regular exercise program. Some people find it particularly difficult to maintain an exercise regimen that involves continuously repetitive motions, such as running, walking and bicycling.

Experienced athletes and trainers have found that feedback provides many people with motivation to maintain a regular exercise program. When a person can directly experience the results provided by an exercise program, that person typically will be encouraged to continue exercising. Unfortunately, the physical improvements obtained from exercise often come too slowly to provide sufficient motivation for many people to maintain a regular exercise program. It would therefore be useful for many athletes to have a more immediate, visual type of feedback to provide motivation for regular exercise.

Many experienced athletes and trainers also have found that competition may provide an even stronger motivation to maintain a regular exercise program. Some athletes, for example, will be more motivated to exercise when competing against a partner than by exercising alone. These athletes may, for example, exercise with a partner, enter into athletic contests such as races, or even just compare their current performance ability with a friend's.

BRIEF SUMMARY OF THE INVENTION

Various aspects of the invention relate to the collection and display of athletic information. With some implementations of the invention, athletic data relating to a single person is collected and displayed so that the person can fully critique his or her performance. For example, a set of athletic data corresponding to athletic activity performed by a person over a first time period may be displayed as a graph. If the set of athletic data is generated from, e.g., a person running or walking, then the person's speed may be plotted against his or her distance over the time period for the activity. With some implementations, the set of athletic data can be analyzed, and the analysis results can be displayed simultaneously with the graph. For example, with a set of athletic data obtained from a person running, the data can be analyzed to determine the change in speed (i.e., acceleration or deceleration) between fixed distances (first mile, second mile, etc.). This information can then be displayed with the graph, so that the person can review when and how much he or she changed speed during the run.

With still other implementations of the invention, a person can compare a set of athletic data with another set of athletic data having a desired characteristic. For example, if a selected set of athletic data is generated from, e.g., a person running over a particular time period, then the person may wish to compare his or her performance for that "run" with his or her best speed for a similar previous run. Thus, if the run covered a distance of, e.g., 4 miles, earlier sets of athletic data will be analyzed to determine which data sets correspond to runs of approximately 4 miles. The data set having, e.g., the highest mean speed can then be identified, and data from that previously data set displayed simultaneously with data from the selected data set. For example, data from each athletic data set may be plotted as graph and rendered on a display. The person can then compare the selected set of athletic data with the set of athletic data representing his or her "best" speed in detail.

Still further, some implementations may collect sets of athletic data obtained over different time periods, and concurrently display data from these sets. Thus, if a person has multiple runs over a period of days, data from each run may be simultaneously displayed. For example, an icon, such as a bar or line, can be displayed for each data set. A dimension of the icon, such as, e.g., its height, can then correspond to some data in that data set, such as the median speed of the run or the total distance traveled over the run. With some implementations, data from multiple sets may be aggregated and displayed. For examples, runs falling within a specified category (e.g., occurring during the same week or month) can be grouped together, and the total distance data (or, alternatively, the total time data) for each data set in a group can be added together. An icon, such as a bar or line, then can be displayed to represent the sum of the data from each group. A dimension of the icon, such as, e.g., its height, may correspond to the data added together from its corresponding group of data sets.

In addition, some examples of the invention may allow a person to specify a goal related to an athletic activity. A person may, e.g., set a goal of running a specified total distance within a specified period of time. With these implementations of the invention, data from multiple sets of a person's athletic data may be aggregated and displayed in contrast with the person's specified goal. The goal may be displayed, for example, as an empty shape, like an oval. The aggregated data may then be displayed as fill within the empty shape. Thus, if the aggregated data shows that the person is within 80% of his or her goal, then the shape representing the goal will be displayed as 80% filled.

With some implementations, sets of athletic data may be obtained from a plurality of different persons and displayed. For example, one or more sets of data from each of a plurality of different persons may be collected. Data from each person's data sets can then be aggregated and displayed to each person. For example, a set of athletic data can be generated for each run a person makes. For each person, data from his or her data sets, such as distance data, can be added up. An icon, such as a bar or line, can then be displayed for each person to represent the sum of the data from his or her data sets. A dimension of the icon, such as, e.g., its height, may correspond to the sum of the data added from each of a person's data sets.

Still further, some examples of the invention may allow a person to "invite" one or more other persons to share athletic data corresponding to their athletic activities. With some implementations of the invention, for example, a user may send an invitation via electronic mail or a similar electronic medium to one or more other persons. Athletic data from only those invited persons may then be displayed simultaneously as noted above. This arrangement allows each invited person (including the inviting host, who inherently invites himself or herself and thus is considered an invitee as well) to compare his or her current athletic data with the other invitees.

With still other implementations of the invention, a person may alternately or additional specify a common goal for the invitees. For example, the inviting host may specify a total combined distance that the invitees (including the host) are to run within a specified amount of time. Data from multiple sets of athletic data for each invitee may be aggregated and displayed in contrast with the person's specified goal. Again, the goal may be represented by the display of, for example, an empty shape, like an oval. The data aggregated from each invitee may then be displayed as fill within the empty shape. Thus, if the aggregated data shows that the collective athletic activity of the invitees is within 60% of the specified goal, then the shape representing the goal will be displayed as 60% filled.

For yet other implementations of the invention, the data collected from one or more users or athletes may form the basis for a training tool to aid the users or athletes attain personal goals. The goals may be established by a individual trainer, coach, team leader, or other expert.

These and other features of the invention will become apparent from the following detailed description.

BRIEF DESCRIPTION OF THE DRAWINGS

FIGS. 8A-8F, 9A and 9B illustrate examples of user interfaces that may be provided to display athletic data for a user according to various implementations of the invention.

FIGS. 17-40 illustrate another example of a user interface that may be provided as a training tool for a user.

FIGS. 63-88 illustrate an example if a user interface that may be provided as a training tool for a team.

DETAILED DESCRIPTION OF THE INVENTION

Figure 1:
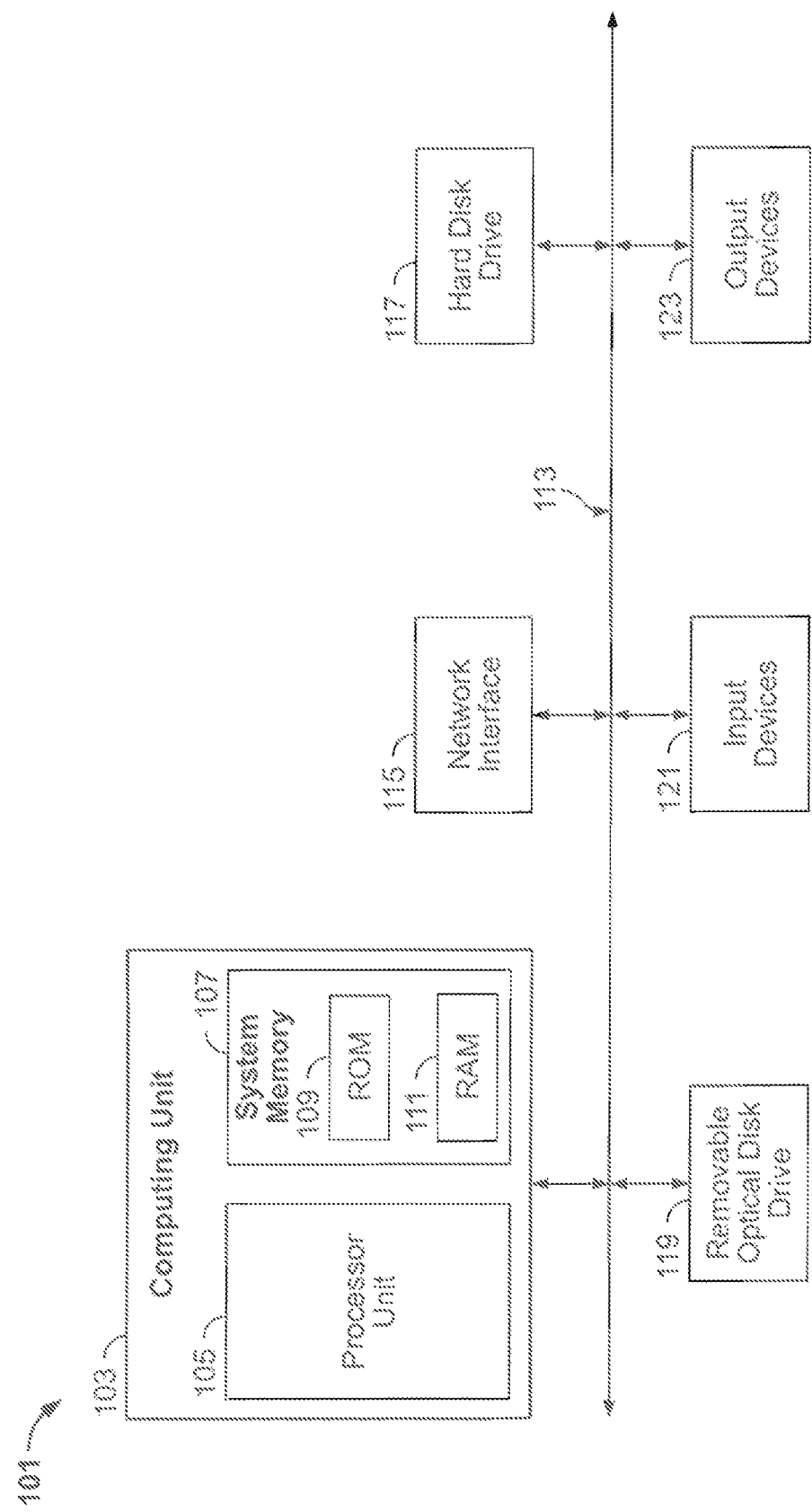
FIG. 1 illustrates a computing device that may be used to implement various examples of the invention.

Operating Environment
Overview

Aspects of the invention relate to the measurement, collection and display of athletic information. As will be appreciated by those of ordinary skill in the art, athletic information must first be obtained from an individual person. With various implementations of the invention, one or more different athletic information monitoring devices may be used to measure and record athletic data corresponding to athletic activity performed by a person. Typically, an athletic information monitoring device will incorporate a sensor for measuring parameters relating to the person being monitored, and a computing device for processing the parameters measured by the sensor.

Once an athletic information monitoring device has recorded athletic information for a person's athletic activity, the person may then transfer the recorded athletic information to one or more separate devices, in order to view the recorded athletic data. A user may, for example, download the recorded athletic information from an athletic information monitoring device to a separate collection device. The collection device may, in turn, transfer the athletic information collected from the athletic information monitoring device to a separate display configuration device, where the athletic information can be organized and configured for subsequent viewing with, e.g., still another device. As will be discussed in more detail below, various implementations of the invention will allow a person to record, collect and display athletic information using a group of computing devices communicating over a network, such as the Internet.

For example, some implementations of the invention may allow a person to measure and record athletic information using a special-purpose computing device. The user can then transfer the recorded athletic information to a local computing device, such as a personal desktop or laptop computer. More particularly, a user can download recorded athletic information from the athletic information monitoring device to a collection software tool on a local computer that acts as a "client" in a computer network. The collection software tool will then transfer the downloaded athletic information through the network to a remote "server" computer. A display configuration software tool on the remote server computer will then save the transferred athletic information. Later, a person can use the client computer or another local computer to retrieve the stored athletic information from the server computer. In response to a display request from a local computer, the display configuration software tool will configure the requested athletic information for display on the local computer, and then transmit the configured athletic information to the local computer for display.

Computing Device

Various examples of the invention may be implemented using electronic circuitry configured to perform one or more functions. For example, with some embodiments of the invention, the athletic information monitoring device, the collection device, the display device or any combination thereof may be implemented using one or more application-specific integrated circuits (ASICs). More typically, however, components of various examples of the invention will be implemented using a programmable computing device executing firmware or software instructions, or by some combination of purpose-specific electronic circuitry and firmware or software instructions executing on a programmable computing device.

Accordingly, FIG. 1 shows one illustrative example of a computer 101 that can be used to implement various embodiments of the invention. As seen in this figure, the computer 101 has a computing unit 103. The computing unit 103 typically includes a processing unit 105 and a system memory 107. The processing unit 105 may be any type of processing device for executing software instructions, but will conventionally be a microprocessor device. The system memory 107 may include both a read-only memory (ROM) 109 and a random access memory (RAM) 111. As will be appreciated by those of ordinary skill in the art, both the read-only memory (ROM) 109 and the random access memory (RAM) 111 may store software instructions for execution by the processing unit 105.

The processing unit 105 and the system memory 107 are connected, either directly or indirectly, through a bus 113 or alternate communication structure to one or more peripheral devices. For example, the processing unit 105 or the system memory 107 may be directly or indirectly connected to additional memory storage, such as the hard disk drive 115, the removable magnetic disk drive 117, the optical disk drive 119, and the flash memory card 121. The processing unit 105 and the system memory 107 also may be directly or indirectly connected to one or more input devices 123 and one or more output devices 125. The input devices 123 may include, for example, a keyboard, touch screen, a remote control pad, a pointing device (such as a mouse, touchpad, stylus, trackball, or joystick), a scanner, a camera or a microphone. The output devices 125 may include, for example, a monitor display, television, printer, stereo, or speakers.

Still further, the computing unit 103 will be directly or indirectly connected to one or more network interfaces 127 for communicating with a network. This type of network interface 127, also sometimes referred to as a network adapter or network interface card (NIC), translates data and control signals from the computing unit 103 into network messages according to one or more communication protocols, such as the Transmission Control Protocol (TCP), the Internet Protocol (IP), and the User Datagram Protocol (UDP). These protocols are well known in the art, and thus will not be discussed here in more detail. An interface 127 may employ any suitable connection agent for connecting to a network, including, for example, a wireless transceiver, a power line adapter, a modem, or an Ethernet connection.

It should be appreciated that, in addition to the input, output and storage peripheral devices specifically listed above, the computing device may be connected to a variety of other peripheral devices, including some that may perform input, output and storage functions, or some combination thereof. For example, the computer 101 may be connected to a digital music player, such as an IPOD® brand digital music player available from Apple, Inc. of Cupertino, Calif. As known in the art, this type of digital music player can server as both an output device for a computer (e.g., outputting music from a sound file or pictures from an image file) and a storage device. In addition, this type of digital music play also can serve as an input device for inputting recorded athletic information, as will be discussed in more detail below.

In addition to a digital music player, the computer 101 may be connected to or otherwise include one or more other peripheral devices, such as a telephone. The telephone may be, for example, a wireless "smart phone." As known in the art, this type of telephone communicates through a wireless network using radio frequency transmissions. In addition to simple communication functionality, a "smart phone" may also provide a user with one or more data management functions, such as sending, receiving and viewing electronic messages (e.g., electronic mail messages, SMS text messages, etc.), recording or playing back sound files, recording or playing back image files (e.g., still picture or moving video image files), viewing and editing files with text (e.g., Microsoft Word or Excel files, or Adobe Acrobat files), etc. Because of the data management capability of this type of telephone, a user may connect the telephone with the computer 101 so that their data maintained may be synchronized.

Of course, still other peripheral devices may be included with our otherwise connected to a computer 101 of the type illustrated in FIG. 1, as is well known in the art. In some cases, a peripheral device may be permanently or semi-permanently connected to the computing unit 103. For example, with many computers, the computing unit 103, the hard disk drive 117, the removable optical disk drive 119 and a display are semi-permanently encased in a single housing. Still other peripheral devices may be removably connected to the computer 101, however. The computer 101 may include, for example, one or more communication ports through which a peripheral device can be connected to the computing unit 103 (either directly or indirectly through the bus 113). These communication ports may thus include a parallel bus port or a serial bus port, such as a serial bus port using the Universal Serial Bus (USB) standard or the IEEE 1394 High Speed Serial Bus standard (e.g., a Firewire port). Alternately or additionally, the computer 101 may include a wireless data "port," such as a Bluetooth interface, a Wi-Fi interface, an infrared data port, or the like.

It should be appreciated that a computing device employed according various examples of the invention may include more components than the computer 101 illustrated in FIG. 1, fewer components than the computer 101, or a different combination of components than the computer 101. Some implementations of the invention, for example, may employ one or more computing devices that are intended to have a very specific functionality, such as a digital music player or server computer. These computing devices may thus omit unnecessary peripherals, such as the network interface 115, removable optical disk drive 119, printers, scanners, external hard drives, etc. Some implementations of the invention may alternately or additionally employ computing devices that are intended to be capable of a wide variety of functions, such as a desktop or laptop personal computer. These computing devices may have any combination of peripheral devices or additional components as desired.

Athletic Information Monitoring Device

Figure 2:
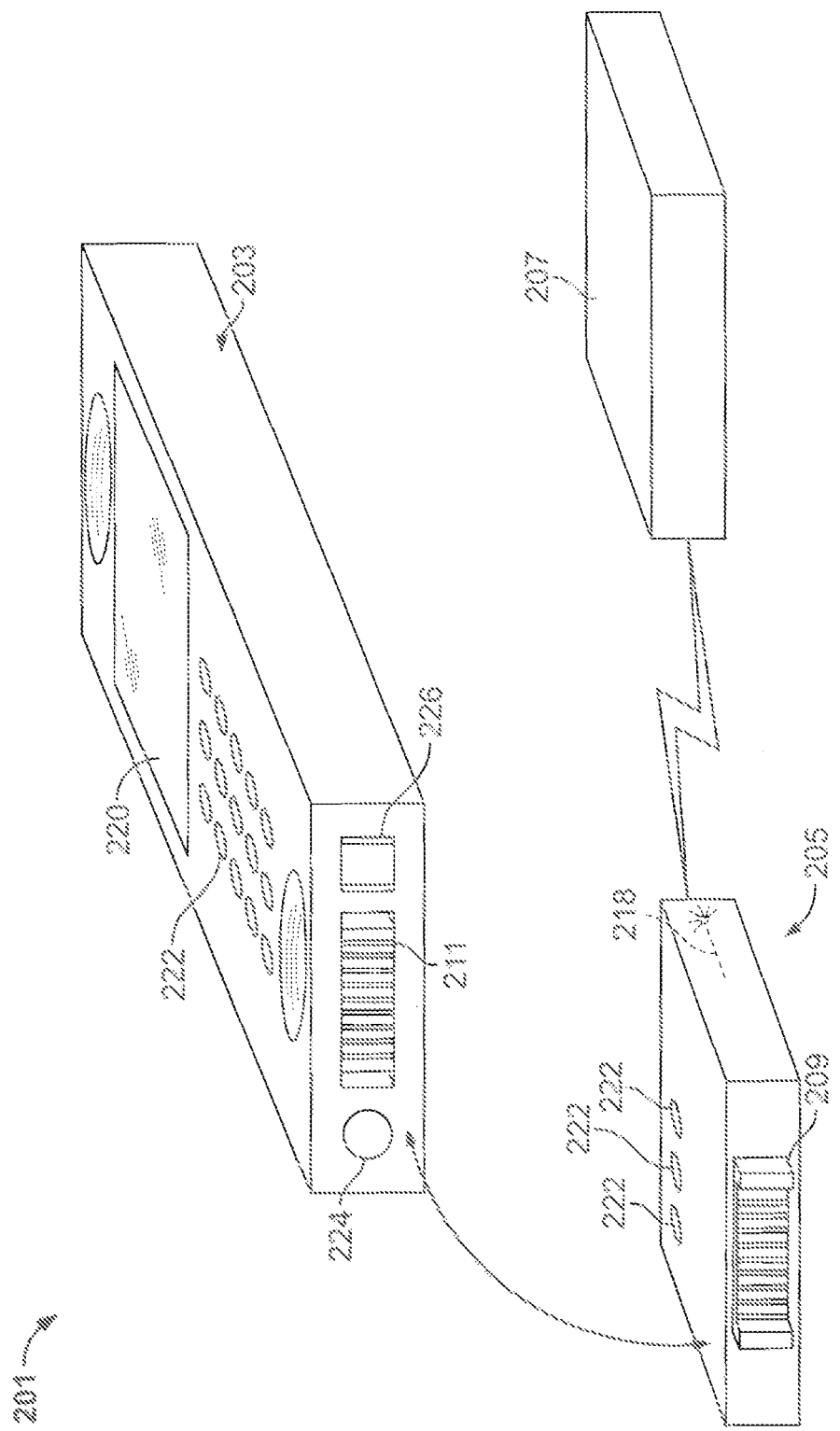
FIGS. 2 and 3 illustrate an example of an athletic information monitoring device that may be employed according to various examples of the invention.

FIG. 2 illustrates one example of an athletic information monitoring device 201 that may be employed according to various examples of the invention to measure athletic information corresponding a user's athletic activity. As shown in this figure, the athletic information monitoring device 201 includes a digital music player 203, an electronic interface device 205, and an athletic parameter measurement device 207. As will be described in more detail, the digital music player 203 is (releasably) connected to the electronic interface device 205, and the combination is worn or otherwise carried by the user while he or she is performing an athletic activity, such as running or walking The athletic parameter measurement device 207 also is worn or carried by the user while he or she is performing an athletic activity, and measures one or more athletic parameters relating to the athletic performance being performed by the user. The athletic parameter measurement device 207 transmits signals to the electronic interface device 205 that correspond to the measured athletic parameter. The electronic interface device 205 receives the signals from the athletic parameter measurement device 207, and provides the received information to the digital music player 203.

Figure 3:
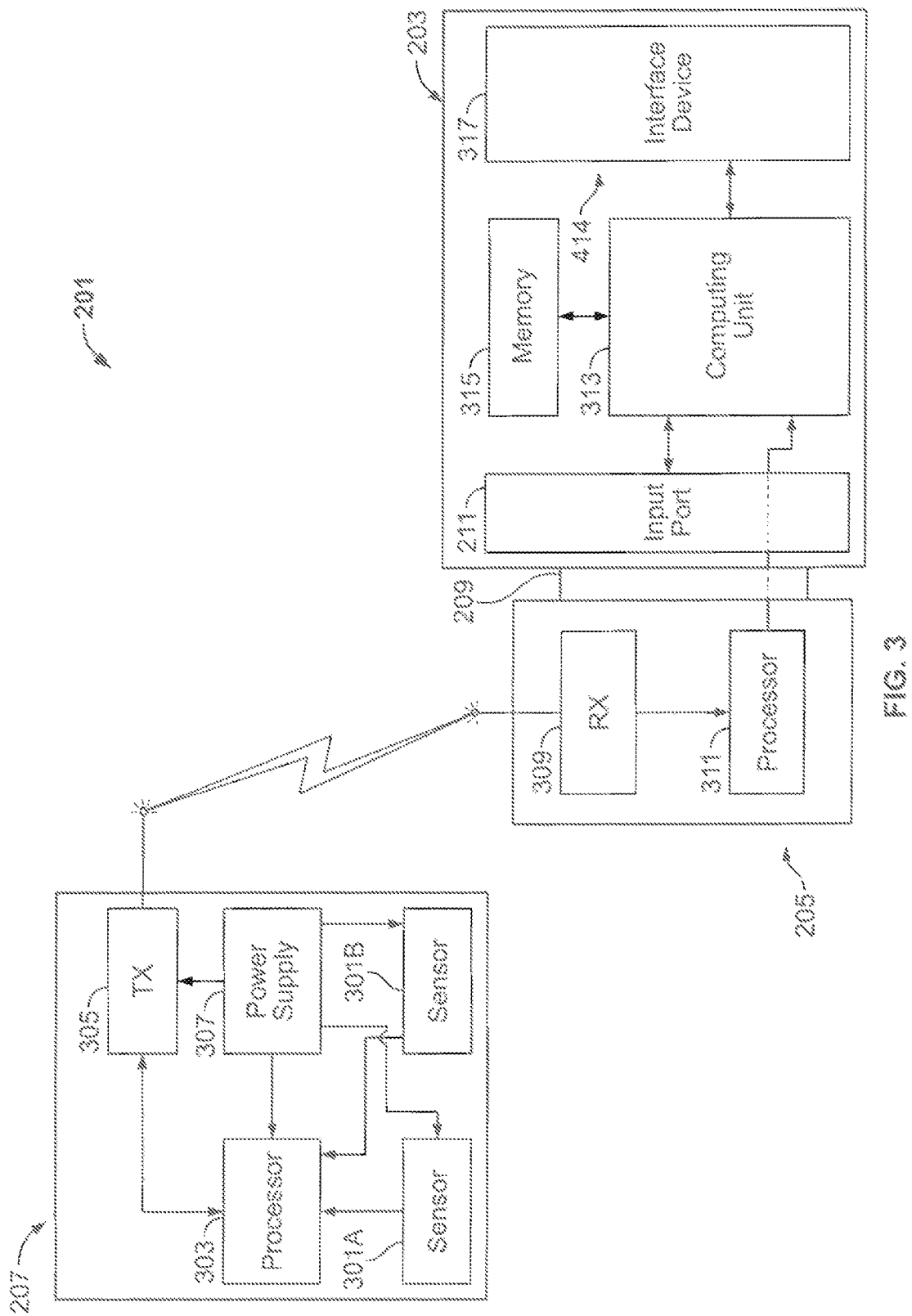
Figure 4:
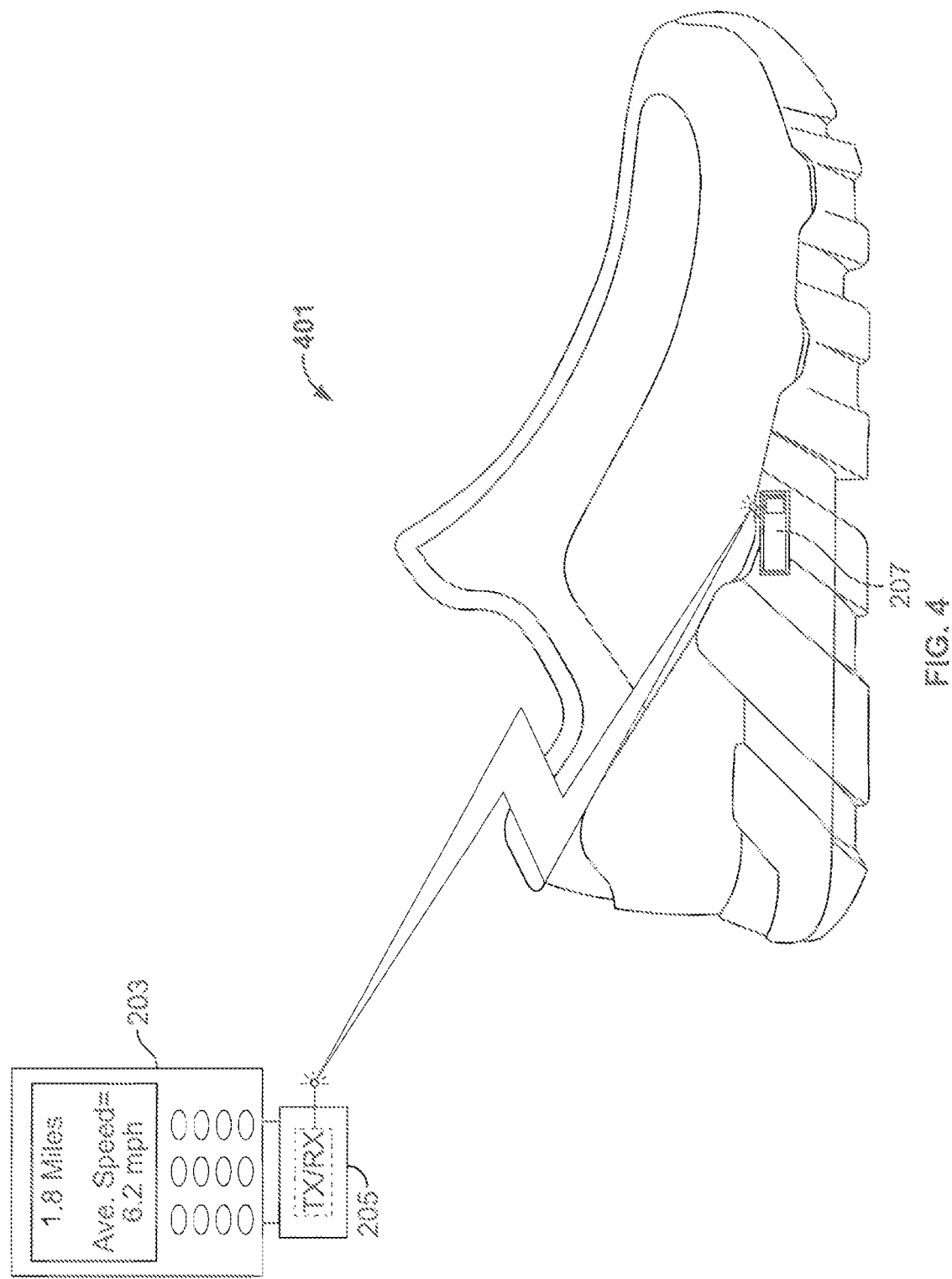
FIG. 4 illustrates one environment in which an athletic parameter measurement device according to various examples of the invention may be employed.

As shown in more detail in FIG. 3, the athletic parameter measurement device 207 includes one or more sensors 301 for measuring an athletic parameter associated with a person wearing or otherwise using the athletic parameter measurement device 207. With the illustrated implementations, for example, the sensors 301A and 301B may be accelerometers (such as piezoelectric accelerometers) for measuring the acceleration of the athletic parameter measurement device 207 in two orthogonal directions. The athletic parameter measurement device 207 is carried or otherwise worn by a user to measure the desired athletic parameter while the user exercises. For example, as shown in FIG. 4, the athletic parameter measurement device 207 may be located the sole of a user's shoe 401 while the user walks or runs. With this arrangement, the sensors 301 will produce electrical signals corresponding to the movement of the user's foot. As known in the art, these signals can then be used to generate athletic data representative of the athletic activity performed by the user.

The athletic parameter measurement device 207 also includes a processor 303 for processing the electrical signals output by the sensors 301. With some implementations of the invention, the processor 303 may be a programmable microprocessor. For still other implementations of the invention, however, the processor 303 may be a purpose-specific circuit device, such as an ASIC. The processor 303 may perform any desired operation on the signals output from the sensors 301, such as curve smoothing, noise filtering, outlier removal, amplification, summation, integration, or the like. The processor 303 provides the processed signals to a transmitter 307. The athletic parameter measurement device 207 also includes a power supply 307, for providing power to the sensors 301, the processor 303, and the transmitter 305 as needed. The power supply 307 may be, for example, a battery.

The athletic parameter measurement device 207 transmits the processed signals to the electronic interface device 205, as seen in FIG. 4. Returning now to FIG. 3, the electronic interface device 205 includes a receiver 309 which receives the processed signals transmitted by the transmitter 305 in the athletic parameter measurement device 207. The receiver 309 relays the processed signals to a second processor 311, which processes the signals further. Like the processor 303, the processor 311 may perform any desired operation on the processed signals, such as curve smoothing, noise filtering, outlier removal, amplification, summation, integration, or the like.

The processor 303 provides the processed signals to the digital music player 203. Referring back now to FIG. 2, the electronic interface device 205 includes a connector system 209 that physically plugs into and connects with a conventional input port 211 provided on digital music player 203. The input port 211 into which the connector system 209 of the electronic interface device 205 connects may be any desired type of input port for transferring data, such as a parallel data port, a serial data port, an earphone or microphone jack, etc.) The connector system 209 may include any suitable connecting devices, such as wires, pins, electrical connectors, and the like, so as to make an electrical connection or other suitable connection with corresponding elements provided in the input port 211 of the digital music player 203 (e.g., to allow electronic and/or data communications between the interface device 205 and the electronic interface device 205). If necessary or desired, additional securing elements may be provided to securely connect the interface device 205 to the digital music player 203, such as straps, hooks, buckles, clips, clamps, clasps, retaining elements, mechanical connectors, and the like.

Returning now to FIG. 3, the processor 311 provides the processed signals to the computing unit 313. The computing unit 313 may initially store the processed signals in the memory 315. Further, with some implementations of the invention, the computing unit 313 may operate on the processed signals provided by the athletic information monitoring device 201 to generate a set of athletic data corresponding to the athletic activity performed by the user. For example, if the athletic information monitoring device 201 includes accelerometers for measuring the movement of the user's foot, the computing unit 313 may analyze the processed signals from the athletic information monitoring device 201 to generate a set of athletic data describing the user's speed at specific instances during the user's athletic activity and the total distance traveled by the user at each of those specific instances. Various techniques for determining a user's speed from accelerometer signals are described in, for example, U.S. Pat. No. 6,898,550 to Blackadar et al., entitled "Monitoring Activity Of A User In Locomotion On Foot," and issued on May 24, 2005, U.S. Pat. No. 6,882,955 to Ohlenbusch et al., entitled "Monitoring Activity Of A User In Locomotion On Foot," and issued on Apr. 19, 2005, U.S. Pat. No. 6,876,947 to Darley et al., entitled "Monitoring Activity Of A User In Locomotion On Foot," and issued on Apr. 5, 2005, U.S. Pat. No. 6,493,652 to Ohlenbusch et al., entitled "Monitoring Activity Of A User In Locomotion On Foot," and issued on Dec. 10, 2002, U.S. Pat. No. 6,298,314 to Blackadar et al., entitled "Detecting The Starting And Stopping Of Movement Of A Person On Foot," and issued on Oct. 2, 2001, U.S. Pat. No. 6,052,654 to Gaudet et al., entitled "Measuring Foot Contact Time And Foot Loft Time Of A Person In Locomotion," and issued on Apr. 18, 2000, U.S. Pat. No. 6,018,705 to Gaudet et al., entitled "Measuring Foot Contact Time And Foot Loft Time Of A Person In Locomotion," and issued on Jan. 25, 2000, each of which are incorporated entirely herein by reference.

The athletic data set may also include a time value associated with each speed value and/or each distance value. If the athletic information monitoring device 201 can be employed to collect athletic information from different users, then the athletic data computing unit 313 may additionally prompt the user to identify himself or herself in some way. This identification information may then be included with the athletic data set generated from the information provided by the athletic information monitoring device 201. Once the computing unit 313 has generated a set of athletic data from the information provided by the athletic information monitoring device 201, the computing unit 313 may store the athletic data set in the memory 315. As will be discussed in more detail below, when the digital music player 203 subsequently is connected to a computing device implementing an athletic information collection tool, the computing unit 313 will download the athletic data to a display configuration tool hosted on a remote computing device.

While wireless communication between the between the athletic parameter measurement device 207 and the interface device 205 is described for the embodiments illustrated in FIGS. 2-4, any desired manner of communicating between the athletic parameter measurement device 207 and the interface device 205 may be used without departing from the invention, including wired connections. Also, any desired way of placing data derived from the physical or physiological data from the athletic parameter measurement device 207 in the proper form or format for display on or output from electronic device 210 may be provided without departing from the invention. For example, if desired, the athletic parameter measurement device 207 may be specially designed and/or programmed for use with one or more specific electronic devices, e.g., pre-programmed and/or wired to operate with a specific device or devices and to provide output data in a form and format suitable for those devices. In this situation, the interface devices 205 may be marketed and sold to specifically target certain electronic devices, such as specific models of digital music players and even other electronic devices, such as telephones, watches, personal digital assistants, etc. As another alternative, if desired, the interface devices 205 may be programmed at a later time to operate with a wide variety of different electronic devices, e.g., by downloading display or device driver and/or format data for specific electronic devices from the Internet, from disk, or from another source, etc.

If desired, in accordance with at least some examples of this invention, the electronic interface device 205 may further include a display 220 and/or a user input system 222, such as one or more rotary input devices, switches, buttons (as shown in the illustrated example in FIG. 2), mouse or trackball elements, touch screens, or the like, or some combination thereof. The display 220 may be employed to show, for example, information relating to music being played by the digital music player 203, information relating to the athletic information signals being received by the digital music player 203, athletic data being generated by the digital music player 203 from the received athletic information signals, etc. The user input system 222 may be employed, for example: to control one or more aspects of the processing of the input data received via interface device 205, to control input data receipt (e.g., timing, types of information received, on-demand data requests, etc.), to control data output to or by the electronic device 203, to control the athletic parameter measurement device 207, etc. Alternatively or additionally, if desired, the input system on the digital music player 203 (e.g., buttons 222, a touch screen, a digitizer/stylus based input, a rotary input device, a trackball or roller ball, a mouse, etc.), may be used to provide user input data to the interface device 205 and/or to the athletic parameter measurement device 207. As still another example, if desired, a voice input system may be provided with the interface device 205 and/or the digital music player 203, e.g., to enable user input via voice commands. Any other desired type of user input system, for control of any system elements and/or for any purpose, may be provided without departing from the invention.

The digital music player 203 may include additional input and/or output elements, e.g., such as ports 224 and 226 shown in FIG. 2, e.g., for headphones (or other audio output), power supplies, wireless communications, infrared input, microphone input, or other devices. If desired, and if these ports 224 and/or 226 would be covered when the interface device 205 is attached to the electronic device 203, the interface device 205 may be equipped with similar external ports to ports 224 and/or 226, and internal circuitry may be provided in the interface device 205 to enable the user to plug the same additional devices into the interface device 205 as they might plug into the digital music player 203 and still take advantage of the same functions (e.g., to thereby allow the necessary data, signals, power, and/or information to pass through the interface device 205 to the user, to another output, and/or to the digital music player 203).

It should be appreciated that, while some specific embodiments of the invention described above relate to a digital music player 203, alternate examples of the invention may be implemented using any portable electronic device. For example, with some implementations of the invention, the athletic parameter measurement device 207 may be used in conjunction with a mobile telephone, a watch, a personal digital assistant, anther type of music player (such as a compact disc or satellite radio music player), a portable computer, or any other desired electronic device. Still further, some implementations of the invention may alternately or additionally omit the use of the interface device 205. For example, the athletic parameter measurement device 207 may be configured to communicate using the Bluetooth wireless communication protocol, so that it can be employed with Bluetooth-capable mobile telephones, personal digital assistants, watches or personal computers. Of course, still other wireless or wired communication techniques could be employed while omitting the interface device 205.

It also should be appreciated that, while a specific example of an athletic parameter measurement device 207 has been described above for ease of understanding, any type of desired athletic parameter measurement device 207 can be employed with various embodiments of the invention. For example, with some implementations of the invention, the athletic parameter measurement device 207 may be a heart rate monitor, a blood oxygen monitor, a satellite positioning device (e.g., a Global Positioning Satellite (GPS) navigation device), a device for measuring the electrical activity of the user (e.g., an EKG monitor), or any other device that measures one or more physical parameters of the user. Still further, the athletic parameter measurement device 207 may measure one or more operational parameters of some device being manipulated by the user, such as the speed and/or distance of a bicycle, the speed and/or work performed by a treadmill, rowing machine, elliptical machine, stationary bicycle, the speed and/or distance traveled by skis (water or snow), skates (roller or ice), or snowshoes or the like worn by the user, etc.

Also, while the athletic parameter measurement device 207 has been described as being separate for the digital music player 203 or other portable electronic device that receives the signals from the athletic parameter measurement device 207, with some implementations of the invention the athletic parameter measurement device 207 may be incorporated into the digital music player 203 or other portable electronic device. For example, some implementations of the invention may employ a music player, mobile telephone, watch or personal digital assistant that incorporates accelerometers, a satellite positioning device, or any other desired device for measuring athletic activity. Still further, it should be appreciated that various implementations of the invention may employ a plurality of athletic parameter measurement devices 207, incorporated into the digital music player 203 or other portable electronic device, separate from the digital music player 203 or other portable electronic device, or some combination thereof.

Athletic Collection And Display Tools

Figure 5:
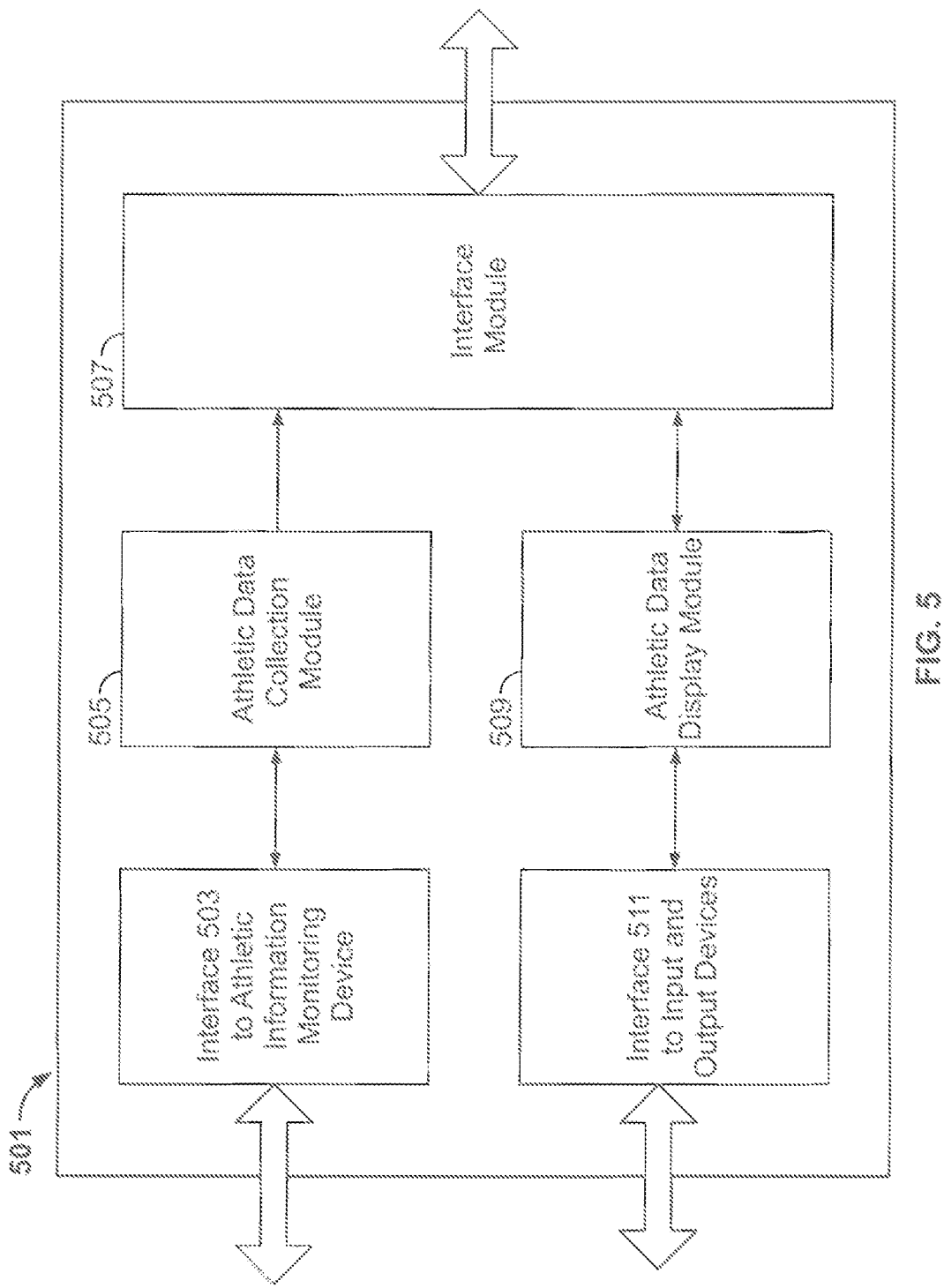
FIG. 5 illustrates an example of an athletic information collection and display device that may be employed to collect and/or display athletic data according to various implementations of the invention.

FIG. 5 illustrates an example of an athletic information collection and display device 501 that may be employed to collect and/or display athletic data according to various implementations of the invention. As will be discussed in more detail below, the athletic information collection and display device 501 may both collect and display athletic data. The athletic information collection and display device 501 may be implemented using any suitable variation of the computing device 101 previously described. In some situations, however, the information collection and display device 501 may be commercially implemented using a desktop or laptop personal computer using, e.g., a version of the Microsoft Windows operating system available from Microsoft Corporation of Redmond, Wash., a version of the Apple Macintosh operating system available for Apple Corporation of Cupertino, Calif., or a version of the Unix or Linux operating systems available from a plurality of vendors.

As shown FIG. 5, the athletic information collection and display device 501 includes an interface 503 for receiving data from the athletic information monitoring device 201. The interface 503 may be implemented using, e.g., electrical components, software components (such as application program interfaces (APIs)), or some combination thereof. The athletic information collection and display device 501 also has an athletic data collection module 505. With various examples of the invention, the athletic data collection module 505 may detect when the digital music player 203 or other portable electronic device storing one or more athletic data sets is connected to the athletic information collection and display device 501 through the interface 503, establish a communication session with the digital music player 203 or other portable electronic device to retrieve the athletic data set or sets. In some implementations of the invention, the athletic data collection module 505 may delete athletic data sets from the digital music player 203 or other portable electronic device after the athletic data sets have been retrieved.

With some examples of the invention, the athletic data collection module 505 may perform some further operations on the athletic data sets retrieved from the digital music player 203 or other portable electronic device. For example, if the athletic information monitoring device 201 can be employed to collect athletic information from different users, then the athletic data collection module 505 may additionally prompt the user to identify himself or herself (if this information was not previously obtained by the athletic information collection and display device 501). This identification information may then be included with the retrieved athletic data sets.

As previously noted, the athletic information collection and display device 501 typically will generate sets of athletic data from information measured by one or more athletic parameter measurement devices 207. With some embodiments of the invention, however, the athletic information collection and display device 501 may instead store the raw information provided by the athletic parameter measurement devices 207. With these embodiments, the athletic data collection module 505 may retrieve the raw information from the digital music player 203 or other portable electronic device, and then generate athletic data sets from the raw information itself. Of course, still other examples of the invention may divide functions relating to the generation of athletic data from the raw information measured by athletic parameter measurement devices 207 between the athletic data collection module 505 and the digital music player 203 or other portable electronic device as desired.

The athletic data collection module 505 may be implemented by, for example, software instructions executed by a computing unit 113 of a computing device 101. With some examples of the invention the athletic data collection module 505 may be implemented by a conventional software tool, such as a browser. Alternately, athletic data collection module 505 may be implemented by a purpose-specific software tool or by a conventional software tool enhanced to perform athletic data collection functions. For example, the athletic data collection module 505 may be implemented by a software tool that incorporates a conventional browser to perform a variety of functions. These functions may include, e.g., selecting, purchasing, and downloading music and video content in addition to collecting athletic data from a digital music player 203 or other portable electronic device.

Once the athletic data collection module 505 has collected the processed signals provided by the athletic information monitoring device 201, the athletic data collection module 505 transmits the athletic data set to an athletic data display configuration device 601 through an interface module 507. The athletic information collection and display device 501 may communicate with the athletic data display configuration device 601 through a conventional network, such as the Internet. With these configurations, the interface module 507 may be implemented using any conventional type of network interface, such as a network interface card. Of course, any type of desired hardware or software combination alternately may be used to allow the athletic data collection module 505 to send the collected athletic data to the athletic data display configuration device 601. With some implementations of the invention, the athletic data collection module 505 may automatically forward collected athletic data to the athletic data display configuration device 601. For example, the athletic data collection module 505 may attempt to forward collected athletic data to the athletic data display configuration device 601 immediately after collection, at a prescheduled interval, upon the detection of a network connection to the athletic data display configuration device 601, or some combination thereof. Alternately or additionally, the athletic data collection module 505 may prompt a user to specify when collected athletic data is sent to the athletic data display configuration device 601.

Figure 6:
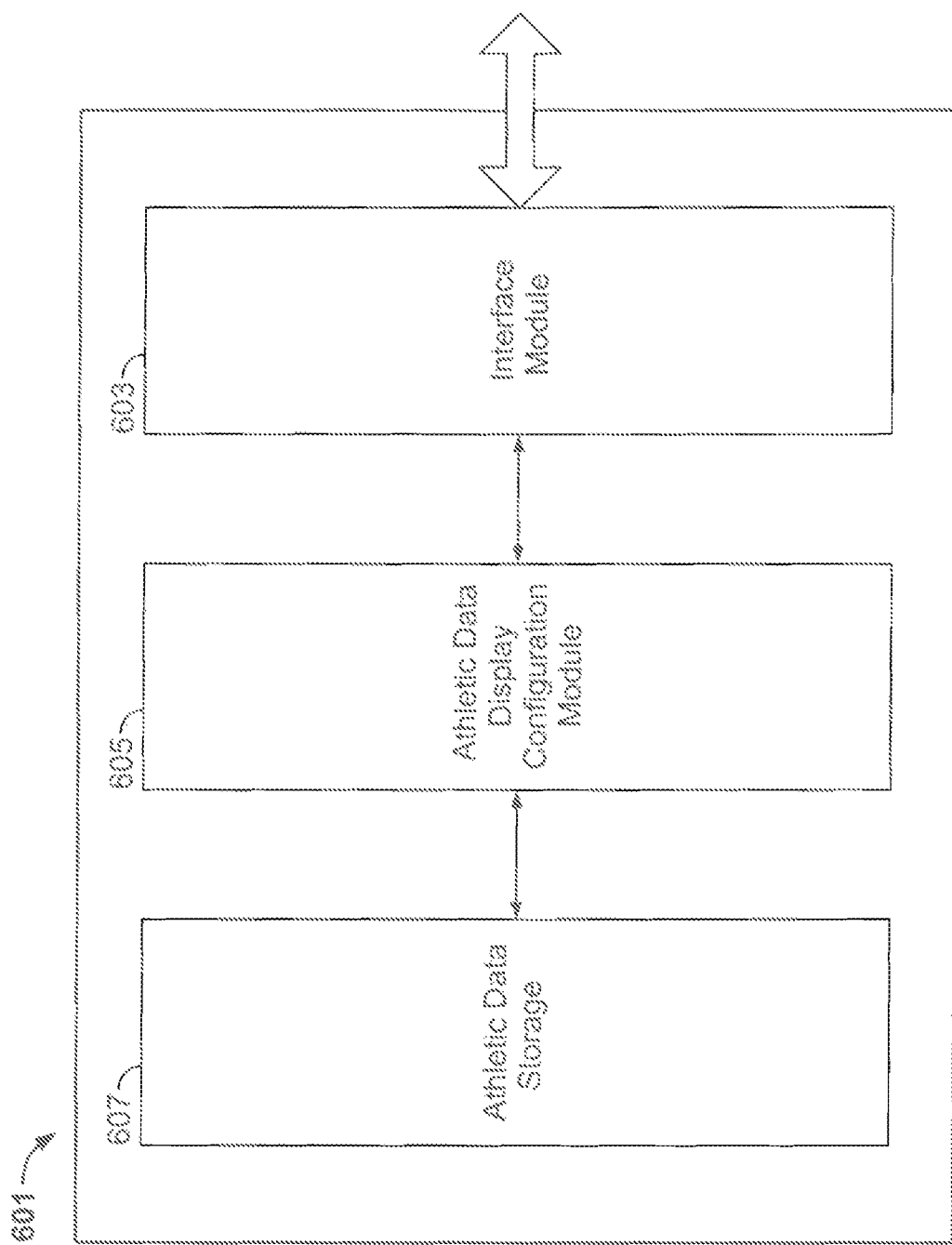
FIG. 6 illustrates an example of an athletic data display configuration device that may be employed according to various examples of the invention.

FIG. 6 illustrates an example of an athletic data display configuration device 601 that may be employed according to various examples of the invention. As seen in this figure, the athletic data display configuration device 601 includes an interface module 603 for communicating with the athletic information collection and display device 501. As previously noted, the athletic information collection and display device 501 may communicate with the athletic data display configuration device 601 through a conventional network, such as the Internet. With these configurations, the interface module 603 may be implemented using any conventional type of network interface, such as a network interface card. Of course, any type of desired hardware or software combination alternately may be used to allow the athletic data display configuration device 601 to communicate with the athletic information collection and display device 501.

The athletic data display configuration device 601 also includes an athletic data display configuration module 605, and an athletic data storage 607. When the interface 603 of the athletic data display configuration device 601 receives athletic data from the athletic information collection and display device 501, it provides the received athletic data to the athletic data display configuration module 605. The athletic data display configuration module 603 may then store the athletic data in the athletic data storage 607 for future use. As will be discussed in more detail below, the athletic data display configuration module 605 also will retrieve athletic data from the athletic data storage 607, and configure the retrieved athletic data for display through one or more user interfaces in a manner that is meaningful to a user.

Returning now to FIG. 5, when a user wishes to view information relating to his or her athletic activities (or the athletic activities of another, as will be discussed in more detail below), the user submits this request to the athletic information collection and display device 501. More particularly, the user can employ conventional input and output devices, such as a keyboard, mouse, display and the like. The display request is then provided to an athletic data display module 509 through a conventional interface input/output interface 511. As well known in the art, the interface input/output interface 511 may be implemented using any desired combination of hardware and software components, such as conventional application programming interfaces (APIs) used to detect and process input from input devices, and to send data to and otherwise control output devices.

With some examples of the invention, the athletic data display module 509 may be implemented using any conventional tool for receiving input to request and control the display of data, and then subsequently displaying the data in the manner requested. For example, the athletic data display module 509 may be implemented using a conventional browser program, such as Microsoft Internet Explorer, Mozilla Firefox, or Opera executing on a computing unit 113. With still other embodiments of the invention, the athletic data display module 509 may be implemented using a conventional browser program that has been enhanced by one or more display tools, such as an ActiveX plug-in, a Java script or a version of the Macromedia Flash Player or Adobe Flash Player, available from Adobe Systems Incorporated of San Jose, Calif. In still other embodiments of the invention, the athletic data display module 509 may be implemented by, for example, a purpose-specific software tool for displaying athletic data.

As will be discussed in more detail below, when a user activates the athletic data display module 509, he or she is provided with a user interface prompting the use to select what collected athletic data he or she wishes to view, the format in which the user wishes to view the collected athletic data, etc. This user interface may be generated by the athletic data display module 509, the athletic data display configuration module 605, or some combination thereof. When a user employs the provided user interface to submit a request to view athletic data, the athletic data display module 509 relays the request to the athletic data display configuration module 605. In response, the athletic data display configuration module 605 configures the requested athletic data for display by the athletic data display module 509. For example, as will be discussed in more detail below, a user may request to view the total distance run by a user for each day in a one week period. In response, the athletic data display configuration module 605 will retrieve the relevant distance data from the athletic data storage 607. It will then configure the retrieved distance data to be displayed through a desired image (e.g., a bar graph), and provide the configured athletic data to the athletic data display module 509 for display to the user.

It should be noted that, with some embodiments of the invention, the data display configuration functions may be divided between the athletic data display module 509 and the athletic data display configuration module 605. For example, if the athletic data display module 509 is implemented by a simple browser, then the athletic data display module 509 may serve as a "thin client" for the athletic data display configuration module 605. That is, all of the data display configuration functions may be performed by the athletic data display configuration module 605. The athletic data display module 509 will then only display the information provided to it. Alternately, if the athletic data display module 509 is implemented by a purpose-specific software tool, then most or all of the data display configuration functions may be performed by the athletic data display module 509. With these examples, the athletic data display configuration module 605 may be used only to store and retrieve athletic data from the athletic data storage 607.

Figure 7:
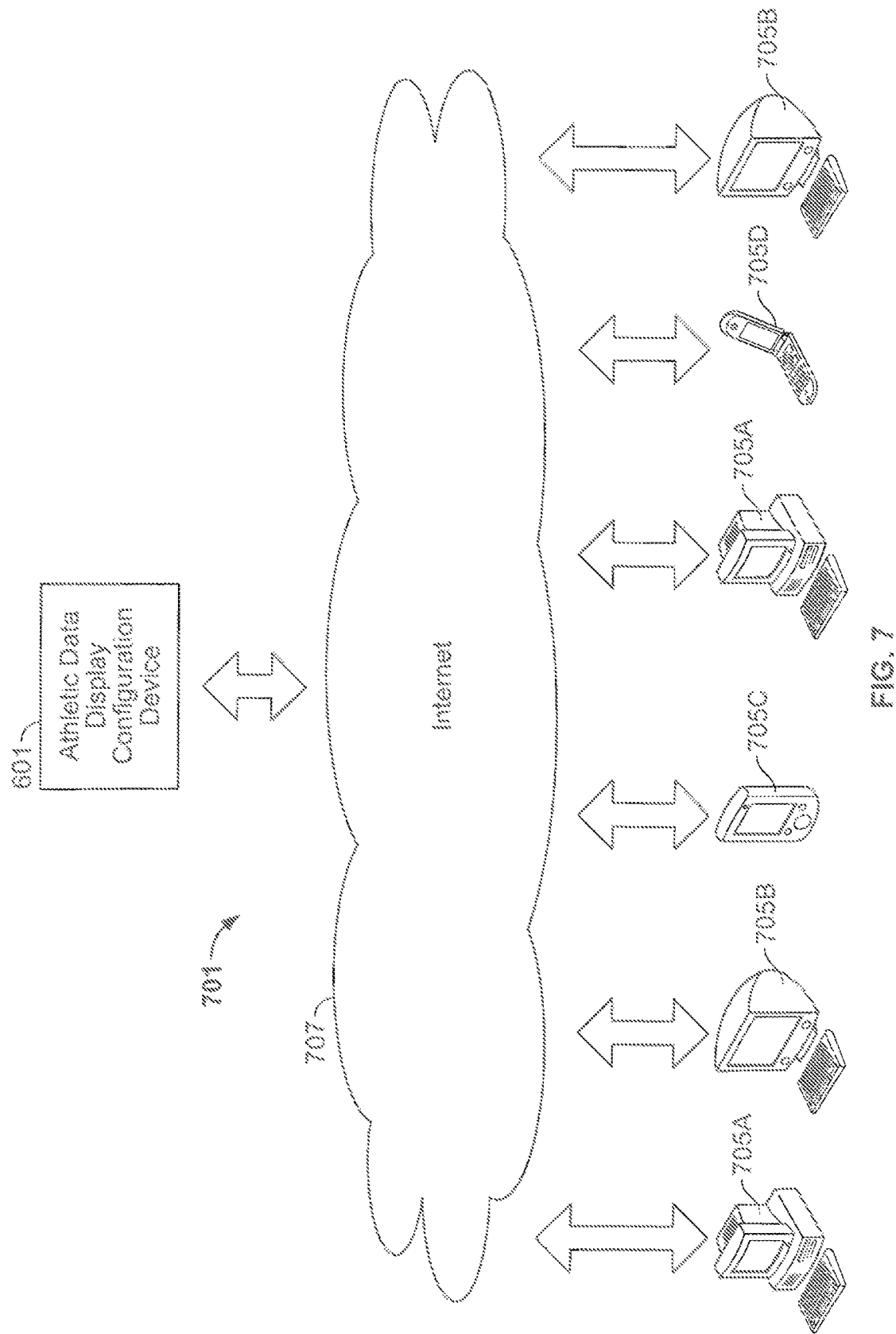
FIG. 7 illustrates a network including an athletic data display configuration device and a plurality of client devices of the type that may be employed according to various examples of the invention.

Typically, the athletic data display configuration device 601 will be implemented at a remote location from the athletic information collection and display device 501. The athletic information collection and display device 501 then may be connected to the athletic data display configuration device 601 through an electronic communication network, as previously noted. The electronic communication network may be a public network, such as the Internet, a private network, or include some combination of both. For example, FIG. 7 illustrates a network 701 including an athletic data display configuration device 601 and a plurality of client devices 705 for collecting and/or displaying athletic data. These client devices 705 may include personal computers 705A using some version of the Microsoft Windows operating systems available from Microsoft Corporation of Redmond, Wash., personal computers 705B using some version of the Apple operating system, personal digital assistants 705C and telephones 705D. Of course, various examples of the invention may alternately or additionally include any other desired electronic device that can be configured to collect and/or display athletic data as discussed above.

It should be appreciated that a client device 705 may perform an athletic data collection function, an athletic data display function, or both. That is, while the example of the athletic information collection and display device 501 described above is capable of both collecting and displaying athletic data, some client devices 705 may only collect athletic data. Further, some client devices may only display athletic data. For example, a user may employ a GPS-equipped smart telephone to collect athletic data and transmit the collected athletic data to the athletic data display configuration device 601. The user may then employ a personal computer equipped with only a conventional browser to subsequently download and display the collected athletic data.

Display of a User's Athletic Information

Display of Athletic Activity Values

In response to receiving a request to review athletic information from a user via the athletic data display module 509, the athletic data display configuration module 605 will determine the user's identity. The athletic data display configuration module 605 will then retrieve the athletic data associated with the user from the athletic data storage 607.

Next, the athletic data display configuration module 605 will prepare a user interface for displaying the requested athletic data, and transmit the user interface with the athletic data to the athletic data display module 509 for display to the user.

Figure 8A:
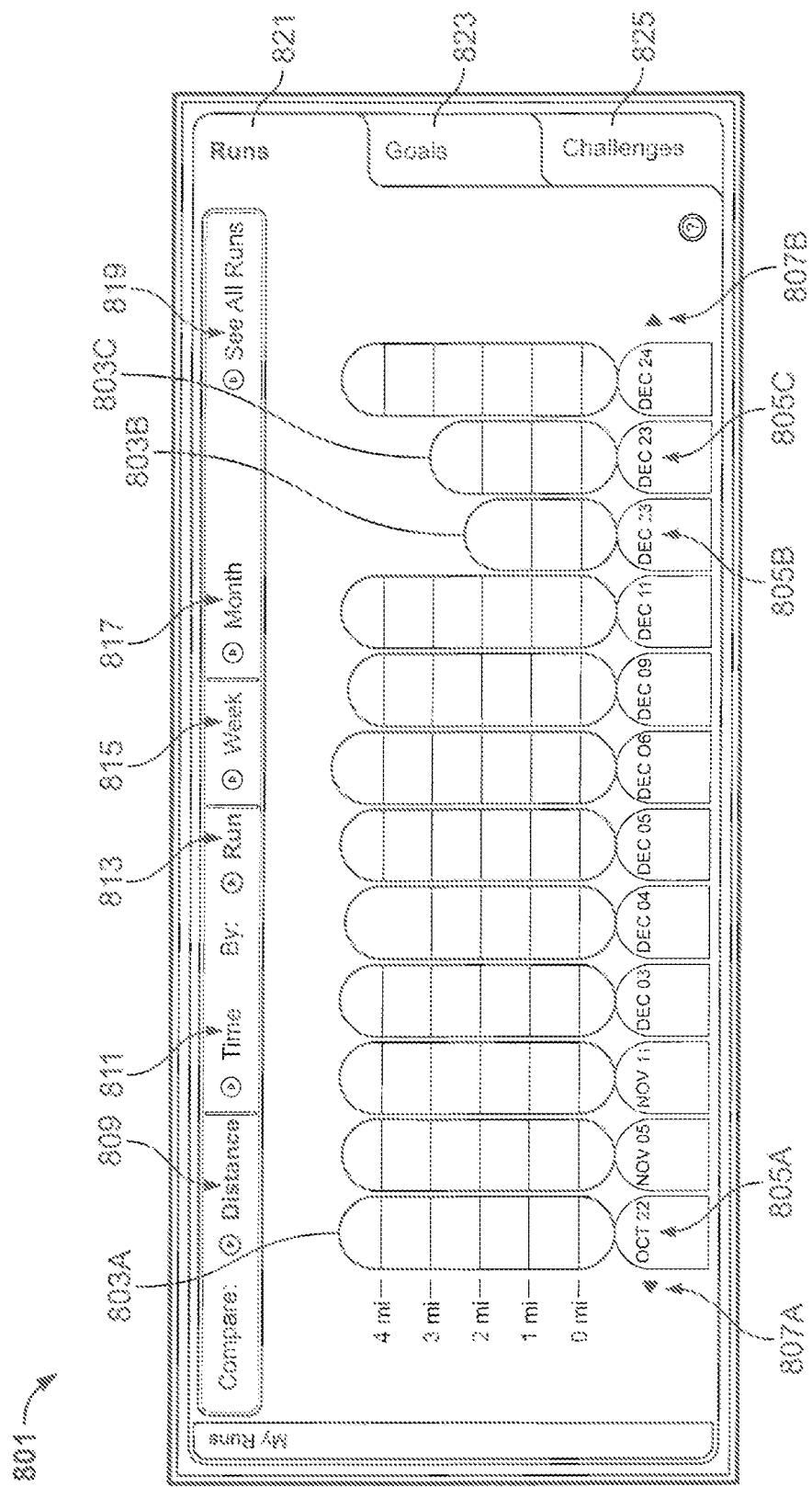

FIG. 8A illustrates an example of an initial user interface that may be provided to a user according to various implementations of the invention. As seen in this figure, the user interface 801 includes a plurality of icons 803. Each icon 803 represents an athletic data value corresponding to an athletic activity performed by the user over a specified time period. More particularly, each icon 803 represents a distance value corresponding to athletic activity performed by a user. A calendar date field 805 associated with each icon 803 is shown at the bottom of each icon 803 to indicate the date on which the corresponding athletic activity was performed, as illustrated in FIG. 8. The user interface 801 also displays a number of control buttons 807-819 that allow the user to select what athletic data values will be displayed in the user interface as well as the time periods for which the athletic data values will be displayed. In addition, the interface 801 includes tabs 821-825, which will be discussed in more detail below.

As shown in FIG. 8A, the user has activated the "Distance" button 809 and the "Run" button 813. In response, the display 801 initially shows an icon 803 for the each of the most recent, e.g., twelve sets of athletic data collected by the server that corresponds to the user. As previously noted, each data set includes athletic data values generated from athletic information measured during a single, discrete athletic activity performed by a person over a particular time period. Further, the height of each icon 803 will correspond to the total distance value included in the set of athletic data represented by the icon 803. For example, on October 22, the user traveled a total distance of 4.05 miles during a run, whereas the user traveled a total distance of only 1.59 miles during a first run on December 23. Accordingly, the icon 803A corresponding to the athletic activity on October 22 will be proportionally larger than the icon 803B representing the athletic data collected for the user's first run on December 23, as shown in this figure. If the user wishes to view icons 803 for athletic activities performed before or after the athletic activities corresponding to the displayed icons 803, the user can view those additional icons 803 by activating the desired arrow buttons 807.

Figure 8B:
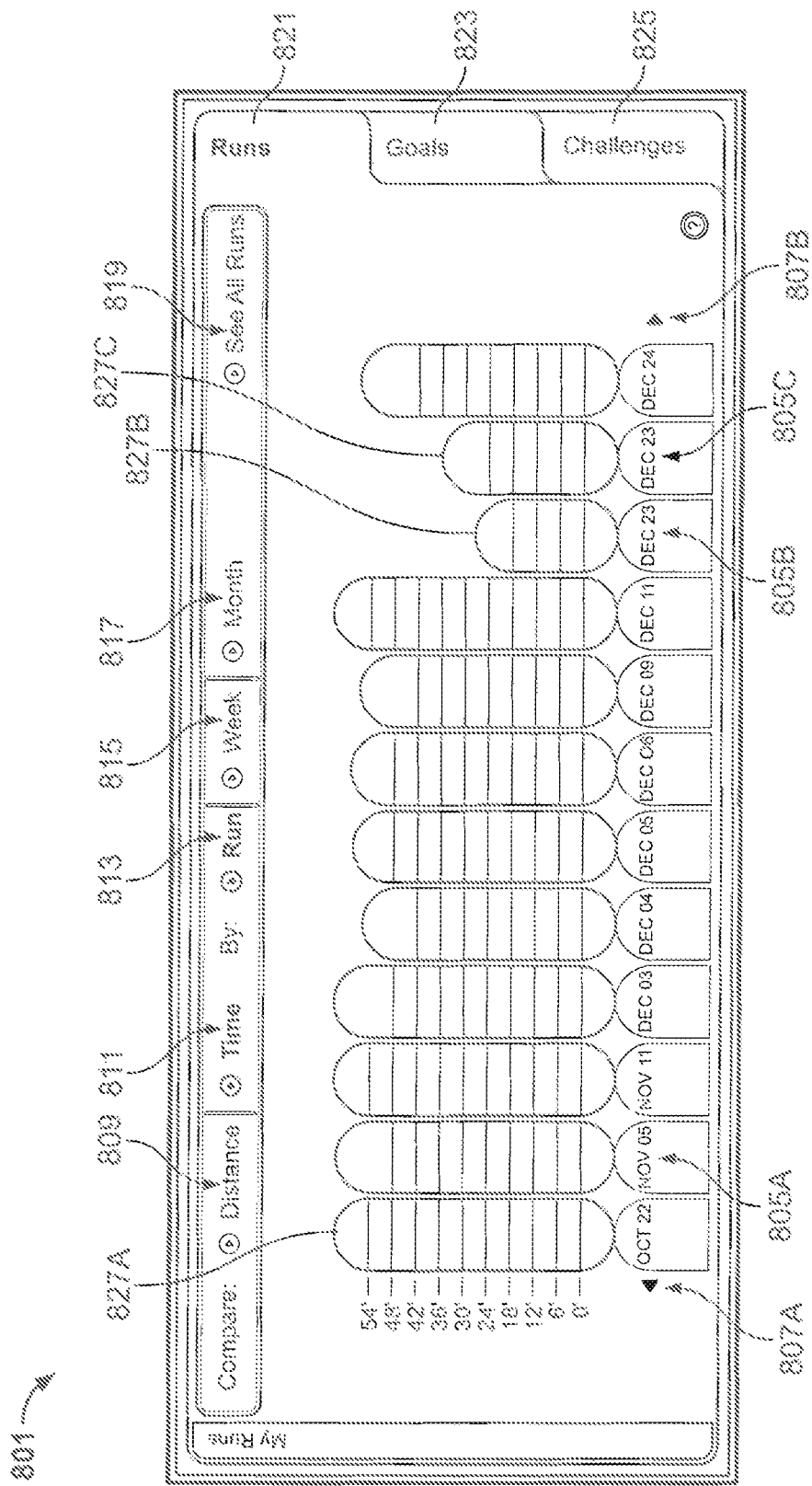

If a user subsequently selects the "Time" button 811, the athletic data display configuration module 605 will reconfigure the user interface 801 to display new icons 827 so that each icon 827 represents a total time value for each of the data sets. For example, as shown in FIG. 8B, the height of each icon 827 will correspond to the total time value in each represented data set. For example, if the length of the user's run on October 22 was 54 minutes, 2 seconds, whereas the duration of the user's first run on December 23 was only 18 minutes, 11 seconds, then the icon 827A corresponding to the athletic data set for October 22 will be proportionally taller than the icon 827B representing the athletic data set collected for the user's run on December 23.

In addition to displaying only distance and time information, the user interface 801 may optionally display additional information. For example, with some implementations of the invention, a user may employ a pointing device to select a specific icon 803 or 827. In response to the selection by, e.g. positioning a cursor over the icon, the user interface 801 may display additional information from the athletic data set represented by the selected icon. For example, the user interface 801 may use, e.g., a pop-up display (not shown) to display data values for the total distance, time, speed, and calories burned for the athletic activity represented by the selected icon 803 or 827. Still further, the user interface may use, e.g., color information to distinguish between the most-recently collected sets of athletic data and athletic data sets that were collected at an earlier time. Thus, the icons 803 or 827 representing data sets collected during the most recent download from an athletic information monitoring device 201 may be illustrated using, e.g., a light green color, while icons 803 or 827 representing previously-collected athletic data sets may be displayed with a dark green color.

Figure 9A:
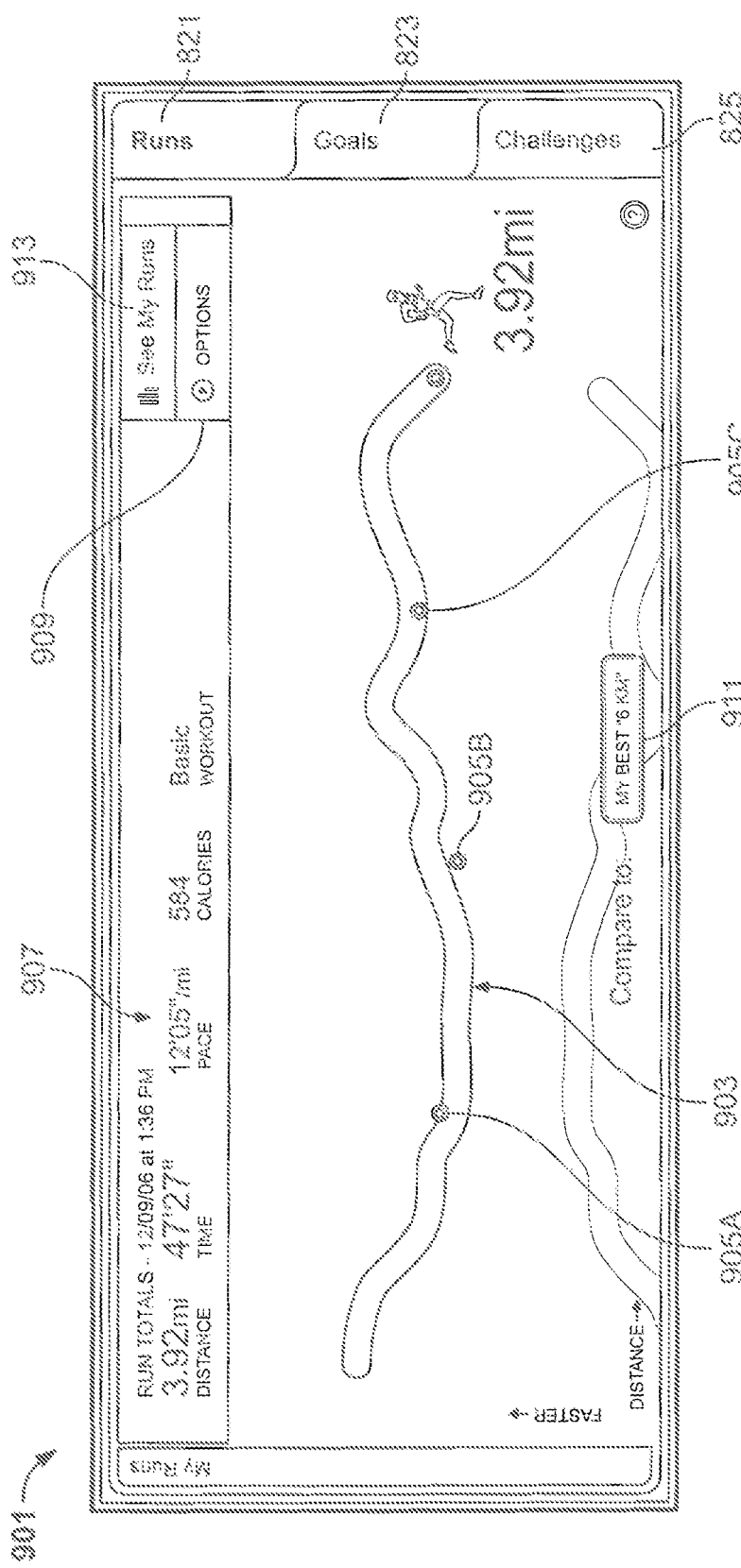

With some implementations of the invention, a user may obtain still more detailed information regarding an athletic data set by "activating" the icon 803 or 827 representing the athletic data set. For example, a user may position a cursor over a desired icon 803 or 827 using a pointing device, and then depress a selection button to activate the icon 803 or 827. In response, the athletic data display configuration module 605 will configure and provide a user interface graphically illustrating the data values in the corresponding athletic data set in more detail. For example, as illustrated in FIG. 9A, various implementations of the inventions may display a user interface 901 plotting a first type of data in the data set against a second type of data in the data set to provide a visual graph 903. More particularly, as illustrated in this figure, the athletic data display configuration module 605 will plot speed values in the athletic data set against distance values data in the athletic data set, providing the graph 903. In this manner, a user can view what his or her instantaneous speed was at various points during the run. In addition, the graph 903 may include other relevant information such as, for example, an icon showing the type of athletic activity (e.g., running) and an indication on of the total distance traveled.

With some implementations of the invention, the graph 903 also may include specific distance waypoints 905, which will show the particular speed value measured at the distance during the athletic activity represented by the position of the waypoint 905. For example, if the user employs a pointing device to move a cursor over waypoint 905A, the user interface 901 will display a pop-up window (not shown) indicating that the user had an average speed of 12 minutes, 12 seconds at the first mile. Similarly, if the user employs a pointing device to move a cursor over the waypoint 905B, the user interface 901 will display a pop-up window (not shown) indicating that the user had an average speed of 12 minutes, 17 seconds at the second mile. If the user then employs a pointing device to move a cursor over the waypoint 905C, the user interface 901 will display a pop-up window (not shown) indicating that the user had an average speed of 12 minutes, 3 seconds at the third mile.

The user interface 901 also may include a value field 907 indicating the total distance value, total time value, total average pace value, total calories burned value, and athletic activity type value corresponding to the represented athletic activity. It also may include an "Options" button 909. If the user activates the "Options" button 909, the interface 901 may display additional command buttons (not shown) that allow the user to name the selected athletic data set or delete the athletic data set. Still further, the interface may include a "Comparison" button 911.

If the user selects the "Comparison" button 911, the athletic data display configuration module 605 will determine a time or distance classification for the selected athletic activity. For example, if the total distance value collected for the selected athletic activity is approximately 6 kilometers, then the athletic data display configuration module 605 will classify the athletic data set corresponding to the selected athletic activity as a "6 kilometer" athletic data set. Similarly, if the total distance value collected for the selected athletic activity is proximal to another specified distance category (e.g., 1 mile, 10 kilometers, 15 kilometers, 10 miles, 26 miles, etc.), then the athletic data display configuration module 605 will classify the athletic data set based upon the relevant category.

After the athletic data display configuration module 605 has classified the athletic data set, it examines the other athletic data sets in that classification to determine which athletic data set has the highest total distance value (or, if the classification is based upon time or speed, the lowest total time value or the highest average speed value). Once the athletic data display configuration module 605 identifies the "best" set of athletic data for the determined classification, it will then reconfigure the user interface 901 to include a graph of this "best" athletic data set as shown in FIG. 9B. As seen in this figure, the graph 915 may have the same characteristics and features as the graph 905 representing the selected athletic activity session.

If the user selects the "See My Runs" button 913, the athletic data display configuration module 605 will configure and provide the interface 801 for display, as shown in FIGS. 8A and 8B. Returning now to those figures, if the user selects the "Week" button 815 or the "Month" button 817, the athletic data display configuration module 605 will modify the user interface 801 to display one or more icons representing an aggregation of multiple sets of athletic data. More particularly, the athletic data display configuration module 605 will aggregate data values from each athletic data set based upon the designated time period.

Figure 8C:
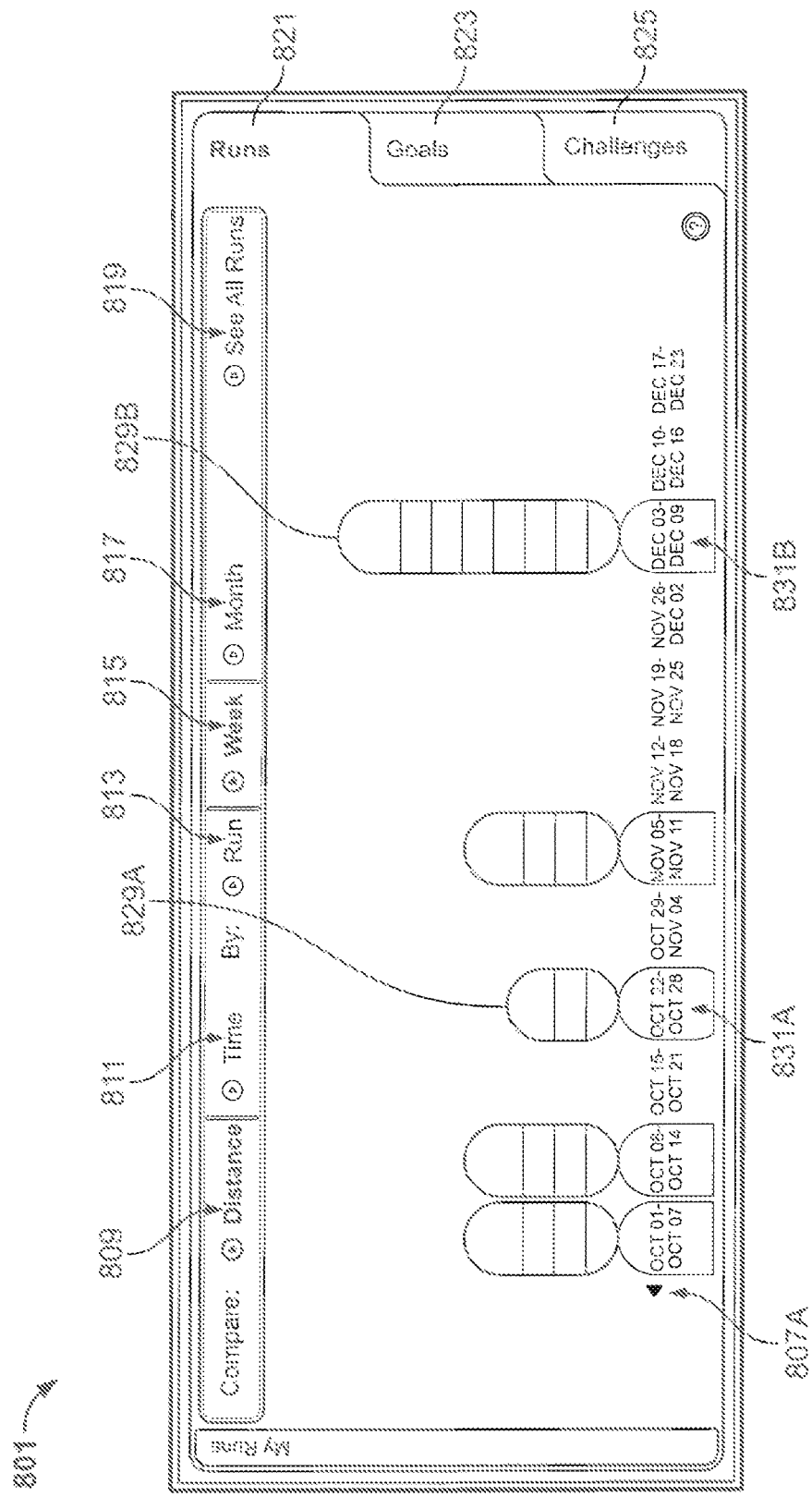

For example, if the user has selected the "Distance" button 809 in addition to the "Week" button 815, then the athletic data display configuration module 605 will add up the total distance data values for each set of athletic data corresponding to an athletic activity session occurring within a particular calendar week. The athletic data display configuration module 605 will then modify the user interface 801 to include icons 829, where each icon 829 graphically represents the sum of total distance values in the athletic data sets generated during a particular week. The athletic data display configuration module 605 may also modify the user interface 801 to include a calendar week field 831 specifying the calendar week to which each icon 829 is associated. As shown in FIG. 8C, the height of each icon represents the sum of the total distance values for each athletic data set for the specified week period. For example, the user may have run a total of 4.05 miles during the weekly period from October 22 to October 28. On the other hand, the user may have run a total distance of 20.25 miles during the week period of December 3 to December 9. Accordingly, the icon 829B representing the aggregated athletic data for the week of December 3 to December 9 will be proportionally larger than the icon 829A representing the athletic data aggregated from the athletic data sets obtained for the week of October 22 to October 28.

Figure 8D:
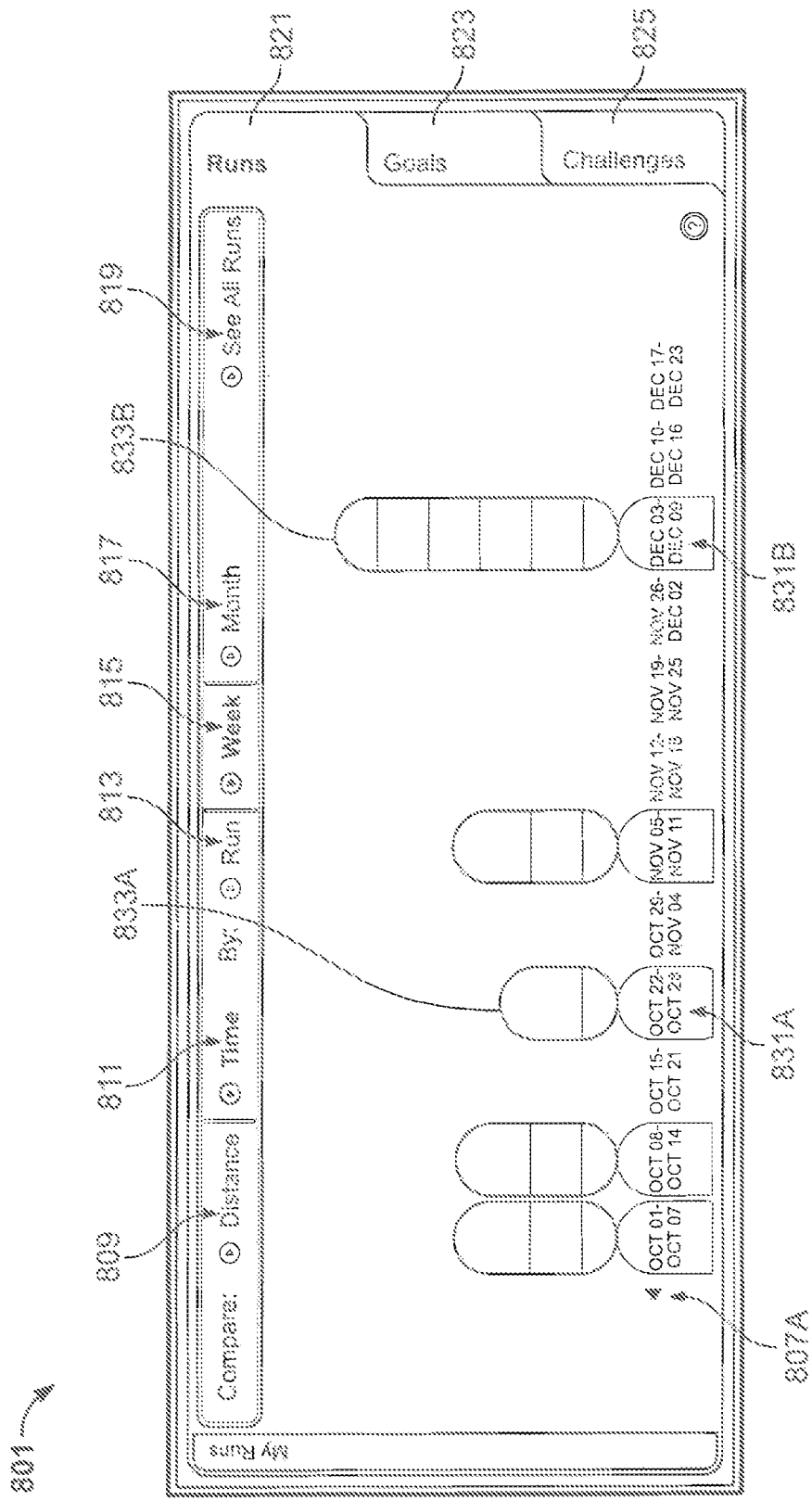

Similarly, if the user selects the "Time" button 811, the athletic data display configuration module 605 will modify the user interface 801 to display icons 833 that represent the sum of total time values for aggregated sets of athletic data. More particularly, as shown in FIG. 8D, a height of each icon 833 will represent the sum of the total time values for each athletic data set obtained during the corresponding weekly period. For example, if a user ran for a total time of 54 minutes 2 seconds during the week from October 22 to October 28, but ran for a total time of 4 hours 7 minutes and 24 seconds during the week of December 3 to December 9, then the icon 833B representing the aggregation of athletic data for the week of December 3 to December 9 will be proportionally larger than the icon 833A representing the aggregation of athletic data for the weekly period of October 22 to October 28.

Figure 8E:
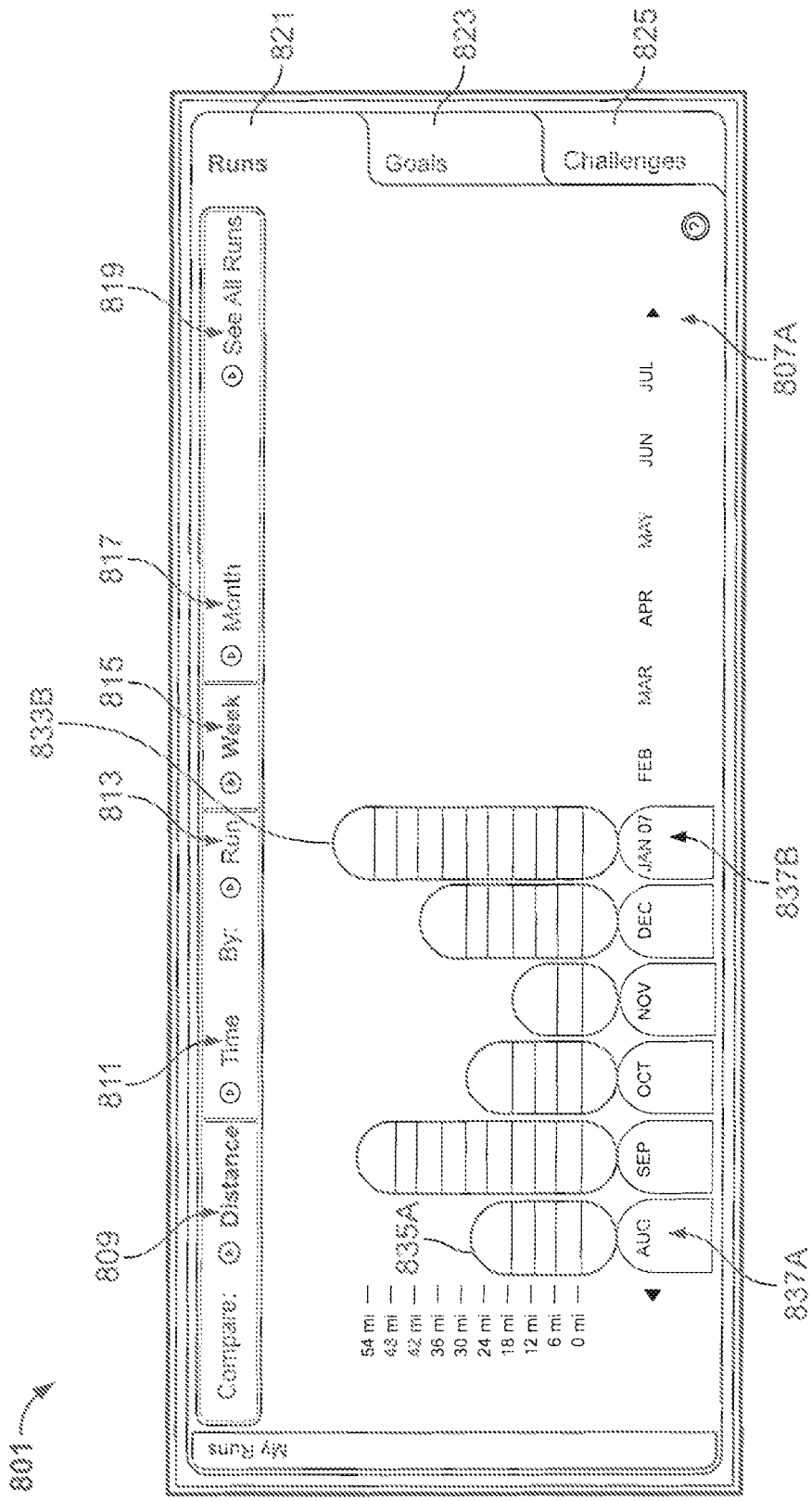

Similarly, if the user selects the "Month" button 817, the athletic data display configuration module 605 will modify the user interface 801 to display icons representing the aggregations of data values from athletic data sets obtained over each monthly time period. For example, if the user has selected the "Distance" button 809 as well, the user interface 801 may display an icon 835 representing the aggregation of total distance values from data sets obtained for athletic activity sessions performed during each calendar month, as illustrated in FIG. 8E. The user interface 801 also may include a calendar month field 837 specifying the calendar month to which each icon 835 is associated. As shown in this figure, the user interface 801 thus includes an icon 835A representing the aggregation of total distance values from data sets obtained for athletic activity sessions performed during the month of August, and another icon 835B representing the aggregation of total distance values from data sets obtained for athletic activity sessions performed during the month of January. The height of the icon 835A represents the sum of the total distance values for each athletic data set obtained for athletic activity sessions performed in August (i.e., 18.84 miles), while the height of the icon 835B correspond to the sum of each of the total distance data values for each athletic data set obtained for athletic activity sessions performed in January (i.e., 58.84 miles).

Figure 8F:
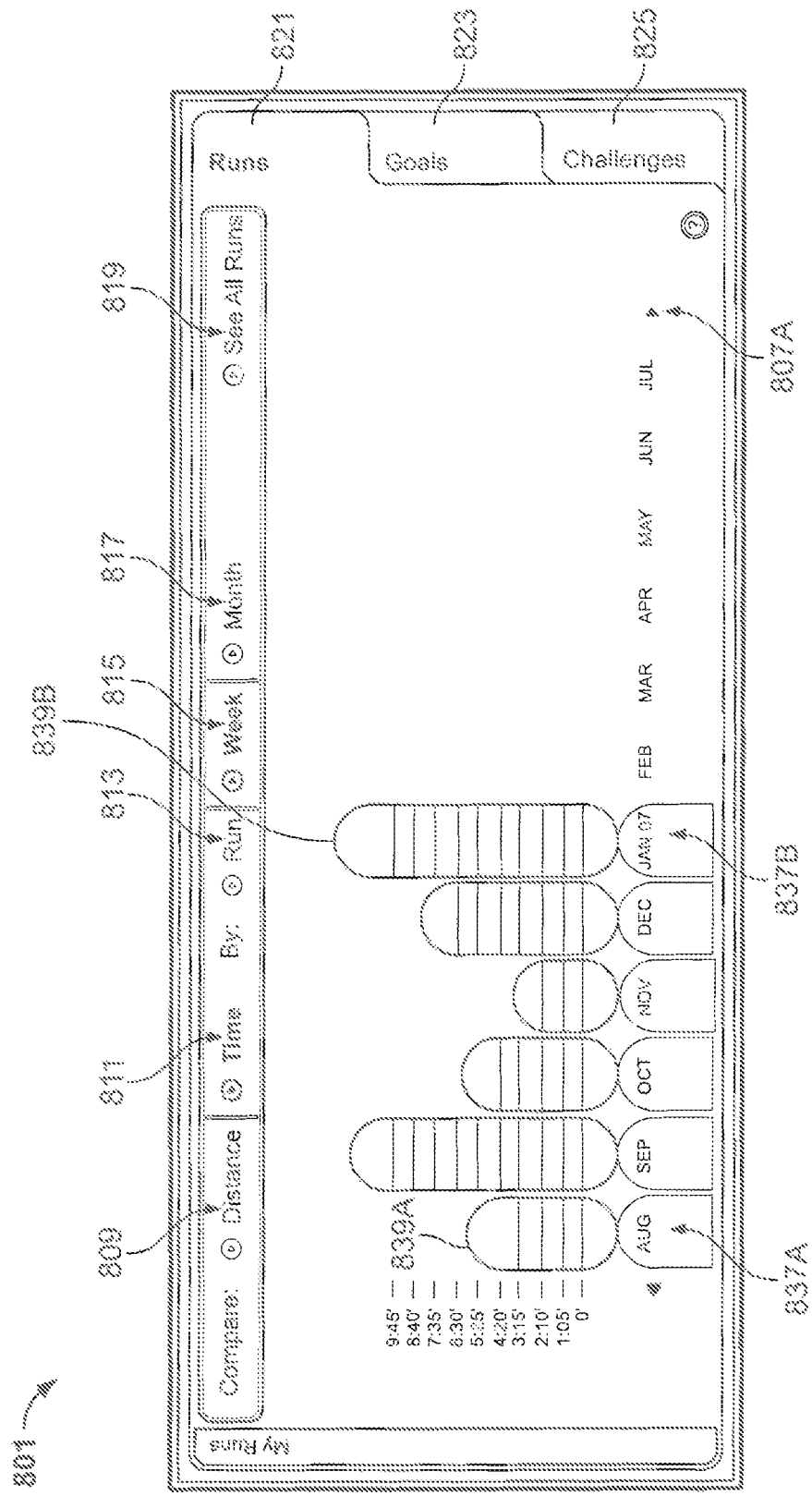

If, on the other hand, the user has selected the "Time" button 811, the user interface 801 may display an icon 839 representing the aggregation of total time values from data sets obtained for athletic activity sessions performed during each calendar month, as illustrated in FIG. 8F. As shown in this figure, the user interface 801 thus includes an icon 839A representing the aggregation of total distance values from data sets obtained for athletic activity sessions performed during the month of August, and another icon 839B representing the aggregation of total time values from data sets obtained for athletic activity sessions performed during the month of January. The height of the icon 839A represents the sum of the total time values for each athletic data set obtained for athletic activity sessions performed in August (i.e., 4 hours, 6 minutes, 1 second), while the height of the icon 839B correspond to the sum of each of the total time data values for each athletic data set obtained for athletic activity sessions performed in January (i.e., 10 hours, 47 minutes, 27 seconds).

In addition to displaying only distance and time information, the user interface 801 may optionally display additional information aggregated from multiple sets of athletic data. For example, with some implementations of the invention, a user may employ a pointing device to select a specific icon 829, 833, 835 or 839. In response to the selection by, e.g. positioning a cursor over the icon, the user interface 801 may display additional information from the aggregation of athletic data sets represented by the selected icon. For example, the user interface 801 may provide, e.g., a pop-up display (not shown) to display sum of total distance data values corresponding to the aggregation of athletic activity information represented by the selected icon, the some of the total time data values corresponding to the aggregation of athletic activity information represented by the selected icon, the average of the average speed data values corresponding to the aggregation of athletic activity information represented by the selected icon speed, and the sum of the calories burned data values data values corresponding to the aggregation of athletic activity information represented by the selected icon.

It should be noted that the athletic data display configuration module 605 (or, with some implementations of the invention, the athletic data display module 509) may aggregate data from multiple athletic data sets in advance of receiving a request to display aggregated athletic data from a user. Alternately, the athletic data display configuration module 605 (or, with some implementations of the invention, the athletic data display module 509) may aggregate data from multiple athletic data sets only in response to a specific request from a user to view the aggregated data.

Display of Goals

Figure 10:
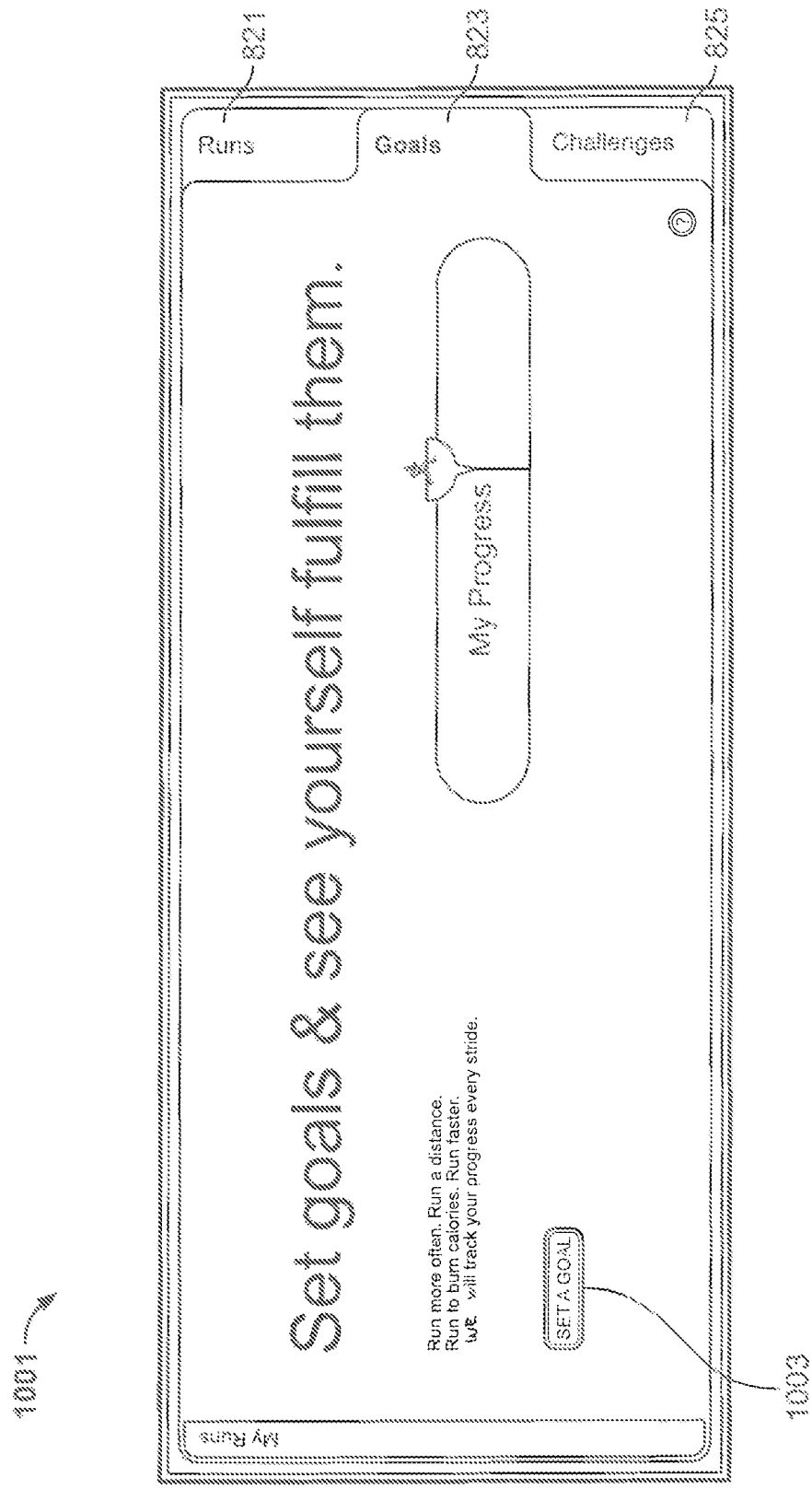
FIGS. 10 and 11A-11E illustrate examples of user interfaces that may be provided to select goals for a user according to various implementations of the invention.

In addition to displaying specific athletic data values or aggregates of athletic data values, various embodiments of the invention may alternately or additionally permit a user to set a goal relating to his or her athletic activities, and then view one or more images graphically illustrating the user's progress toward accomplishing those goals. For example, with the embodiments illustrated in FIGS. 8A-9B, a user can select the "Goals" tab 823 shown in these figures. In response, the athletic data display configuration module 605 may configure and provide the user interface 1001 illustrated in FIG. 10. As seen in this figure, the user interface 1001 includes a "Set A Goal" button 1003 prompting the user to select a desired goal relating to his or her athletic activities.

When the user activates the "Set A Goal" button 1003, the athletic data display configuration module 605 will configure and provide the user interface 1101 shown in FIG. 11. As seen in this figure, the user interface 1101 includes a "More Often" button 1103, a "Distance" button 1105, a "Burn More Calories" button 1107, a "Faster" button 1109, and a "Back" button 1111. As known in the art, activating the "Back" button 1111 will cause the athletic data display configuration module 605 (or, with some examples of the invention, the athletic data display module 509) to configure and display the previously displayed configuration of the user interface 1101, or if the currently displayed configuration of the user interface 1101 is its initial configuration, a previously shown user interface.

Figure 11A:
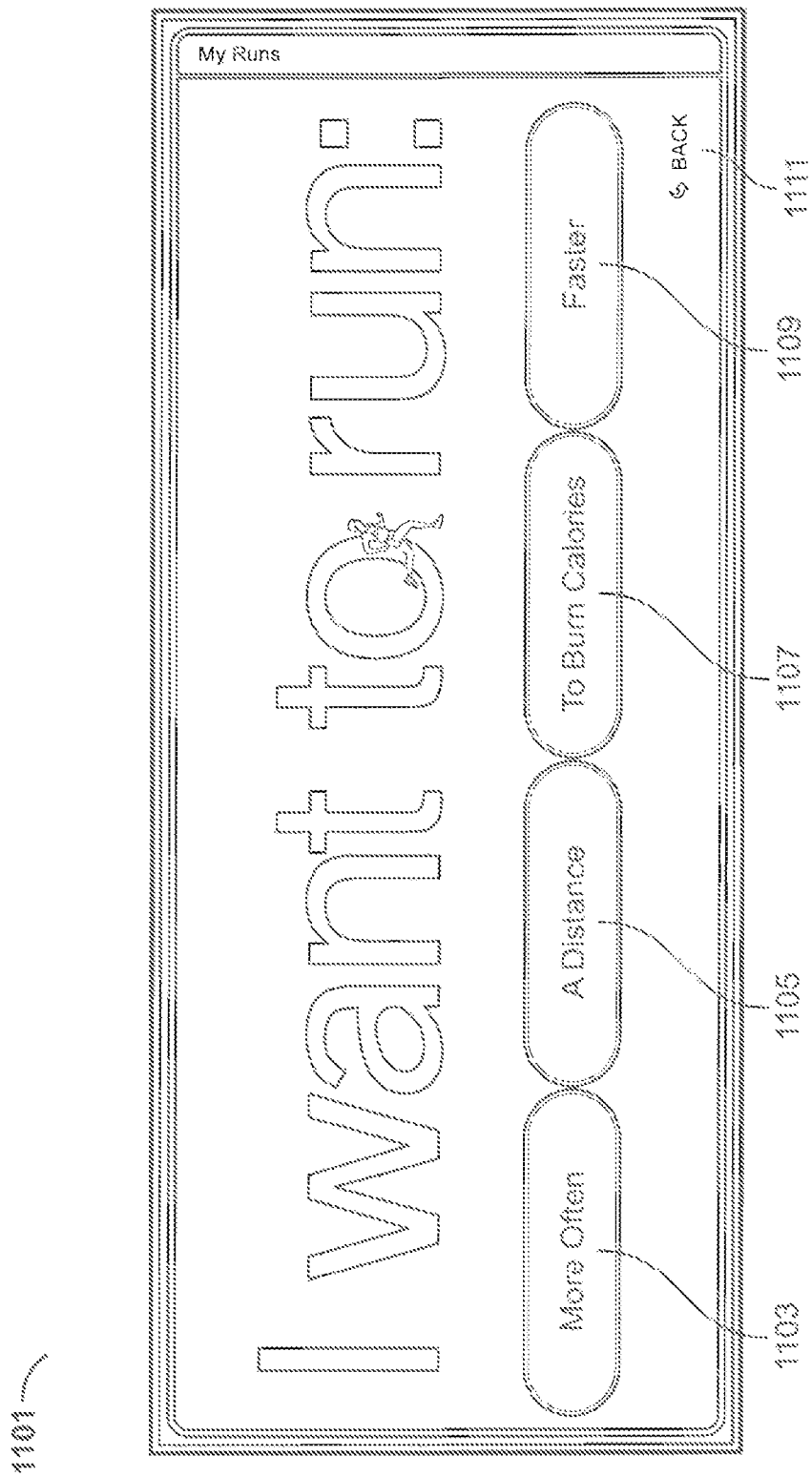
Figure 11B:
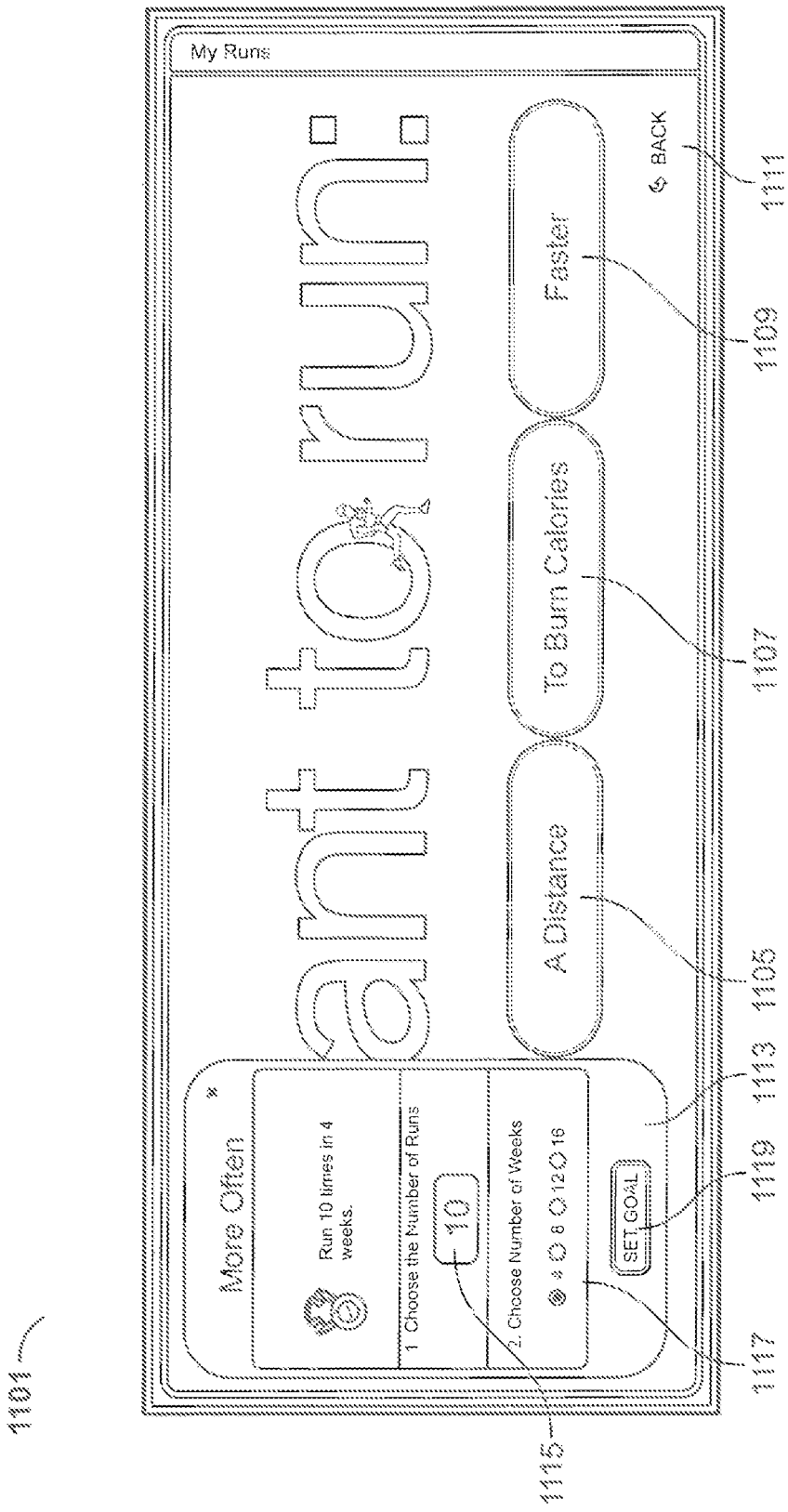

If a user wishes to perform the athletic activity more often, then the user activates the "More Often" button 1103. In response, the athletic data display configuration module 605 reconfigures the user interface 1101 to include a sub-interface 1113. As seen in FIG. 11B, the sub-interface 1113 includes a "Number Of Runs" control 1115, a "Number Of Weeks" control 1117, and a "Set Goal" button 1119. By employing the "Number Of Runs" control 1115, a user can specify the number of runs (or the number of times to perform some other athletic activity, if appropriate) he or she wishes to make within a desired time period. Similarly, by employing the "Number Of Weeks" control 1117, a user can specify the number of weeks making up the desired time period allowed to reach the desired goal. In the illustrated example, the "Number Of Runs" control 1115 is a field control (i.e., having a field in which a value can be typed in) while the "Number Of Weeks" control 1117 is a radio control, but various examples of the invention may employ alternate types of controls as desired. Once a user has specified the number of runs that must be made and specified the time period in which they must be made to meet a desired goal, the user can finalize the goal parameters by activating the "Set Goal" button 1119.

Figure 11C:
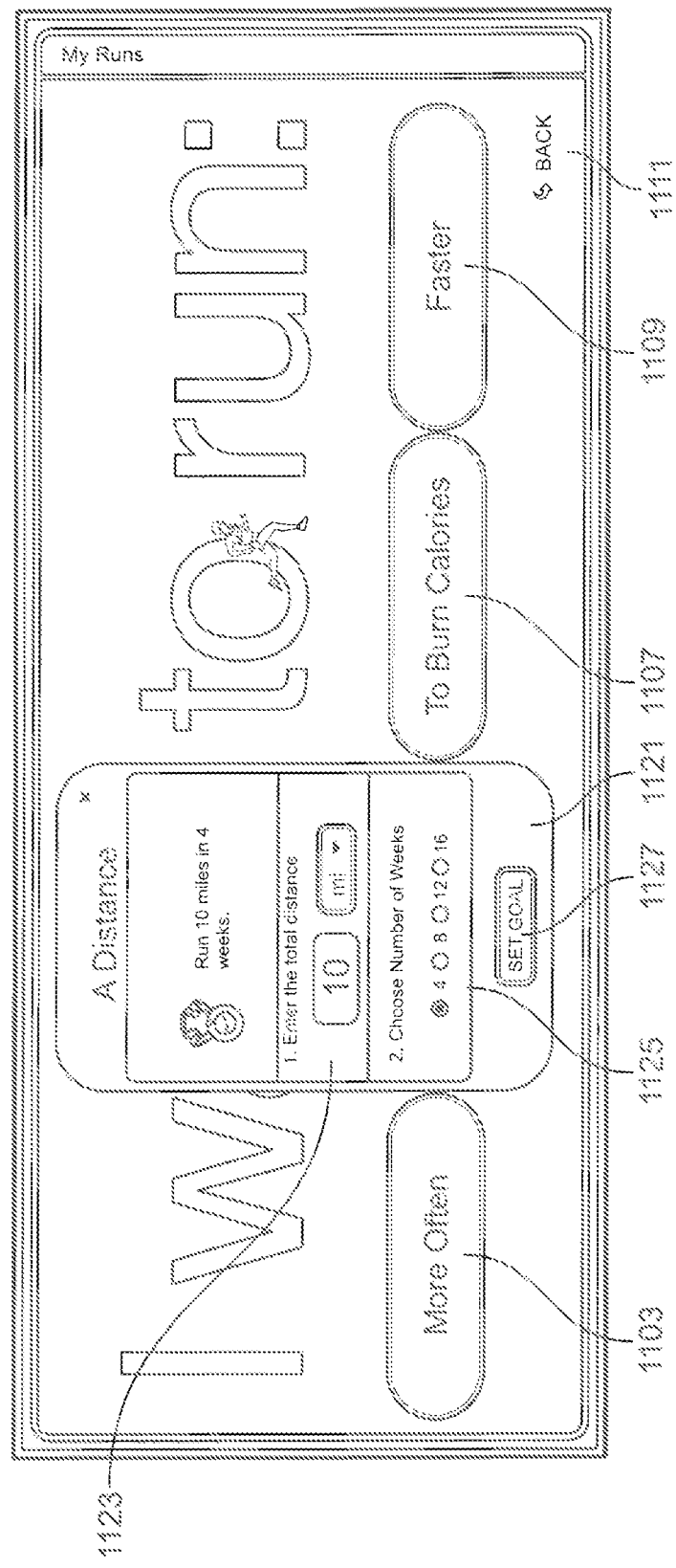

Similarly, if a user wishes to run a longer distance in a given time period, then the user activates the "Distance" button 1105. In response, the athletic data display configuration module 605 reconfigures the user interface 1101 to include a sub-interface 1121. As seen in FIG. 11C, the sub-interface 1121 includes a "Total Distance" control 1123, a "Number Of Weeks" control 1125, and a "Set Goal" button 1127. By employing the "Total Distance" control 1123, a user can specify the total distance he or she wishes to run within a desired time period. Similarly, by employing the "Number Of Weeks" control 1125, a user can specify the number of weeks making up the desired time period allowed to reach the desired goal. In the illustrated example, the "Total Distance" control 1123 is a combination control, with both a field control (i.e., a field in which a value can be typed) and a drop down menu control (i.e., to allow the user to select the units in which the distance would be measure). The "Number Of Weeks" control 1125 illustrated in FIG. 11C then is a radio control. Various examples of the invention, however, may employ alternate types of controls as desired. Once a user has specified the number of runs that must be made and specified the time period in which they must be made to meet a desired goal, the user can finalize the goal parameters by activating the "Set Goal" button 1127.

Figure 11D:
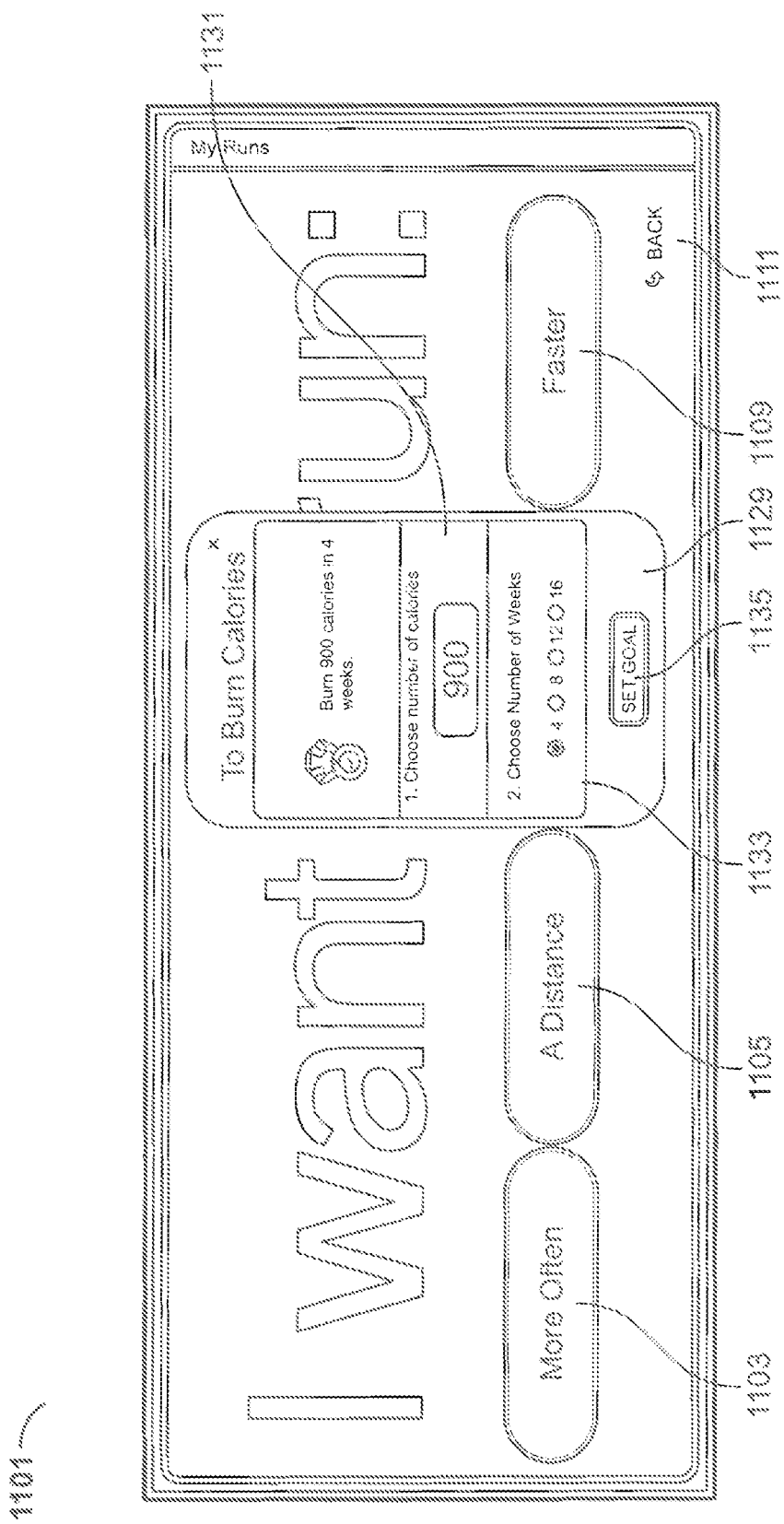

If a user wishes to burn more calories during a particular time period, then the user activates the "Burn More Calories" button 1107. In response, the athletic data display configuration module 605 reconfigures the user interface 1101 to include a sub-interface 1129. As seen in FIG. 11D, the sub-interface 1129 includes a "Number Of Calories" control 1131, a "Number Of Weeks" control 1133, and a "Set Goal" button 1135. By employing the "Number Of Calories" control 1131, a user can specify the number of calories he or she wishes to burn within a desired time period. Similarly, by employing the "Number Of Weeks" control 1133, a user can specify the number of weeks making up the desired time period allowed to burn the desired number of calories. In the illustrated example, the "Number Of Calories" control 1131 is a field control (i.e., having a field in which a value can be typed in) while the "Number Of Weeks" control 1133 is a radio control, but various examples of the invention may employ alternate types of controls as desired. Once a user has specified the number of runs that must be made and specified the time period in which they must be made to meet a desired goal, the user can finalize the goal parameters by activating the "Set Goal" button 1135.

Figure 11E:
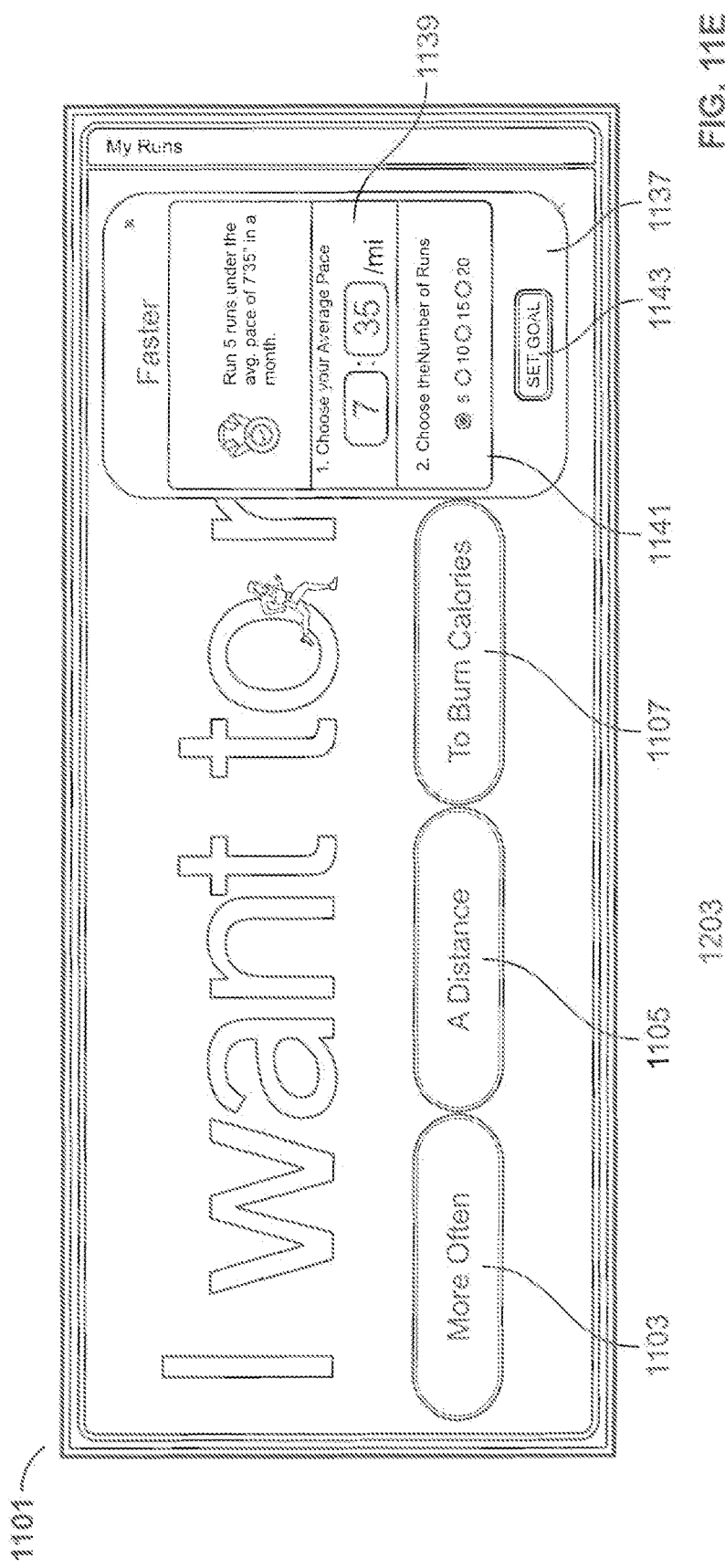

Lastly, if a user wishes to run faster for a desired number of runs, then the user activates the "Faster" button 1109. In response, the athletic data display configuration module 605 reconfigures the user interface 1101 to include a sub-interface 1137. As seen in FIG. 11E, the sub-interface 1137 includes an "Average Pace" control 1139, a "Number Of Runs" control 1141, and a "Set Goal" button 1143. By employing the "Average Pace" control 1139, a user can specify the minimum pace at which he or she wishes to travel for the desired number of runs. Similarly, by employing the "Number Of Runs" control 1141, a user can specify the number of runs for which the user wishes to run faster in order to reach the desired goal. In the illustrated example, the "Average Pace" control 1139 is a field control (i.e., having fields in which values can be typed) while the "Number Of Runs" control 1141 is a radio control, but various examples of the invention may employ alternate types of controls as desired. Once a user has specified the average pace and the number of runs for which he or she must run at or faster than the specified average pace to meet a desired goal, the user can finalize the goal parameters by activating the "Set Goal" button 1143.

Figure 12:
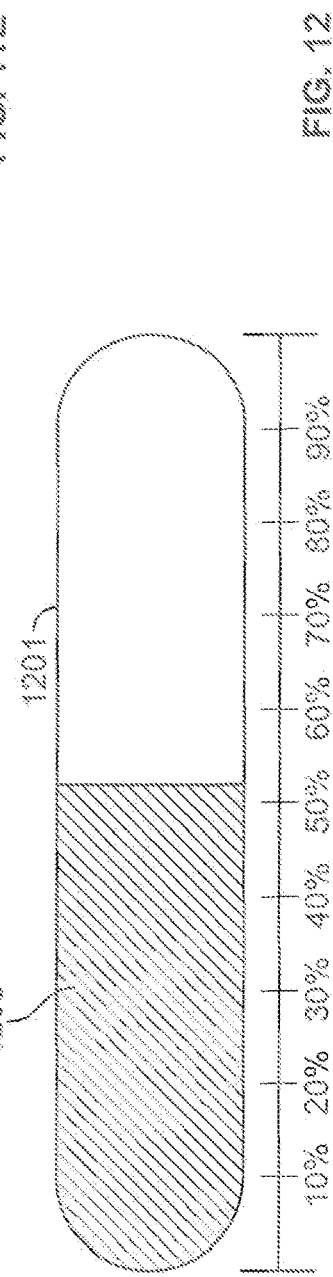
FIG. 12 illustrates an example of a user interface that may be provided to indicate a user's progress toward achieving an athletic activity goal according to various implementations of the invention.

After the user has specified a desired goal, the athletic data display configuration module 605 will monitor the athletic data collected by the athletic data collection module 505. When the user subsequently wishes to view his or her progress toward accomplishing the specified goals (by, e.g., selecting the "Goals" tab), then the athletic data display configuration module 605 will aggregate the relevant data from the collected athletic data set and configure a user interface graphically displaying the user's progress toward the specified goals. For example, with some implementations of the invention, the athletic data display configuration module 605 may configure a user interface displaying bar graph, such as the bar graph 1201 shown in FIG. 12. A portion of the bar graph corresponding to the user's progress is marked with fill 1203. Thus, in the illustrated example, the fill 1203 in the bar graph 1203 indicates that the user has accomplished more than 50% of the athletic activity required to complete his or her goal. Some implementations may simultaneously display a bar graph or other progress indicator for each goal set by the user. Still other implementations of the invention may provide controls to allow a user to select a single bar graph or other progress indicator for display in the user interface.

Display of Other User's Athletic Data

Challenges

Figure 13A:
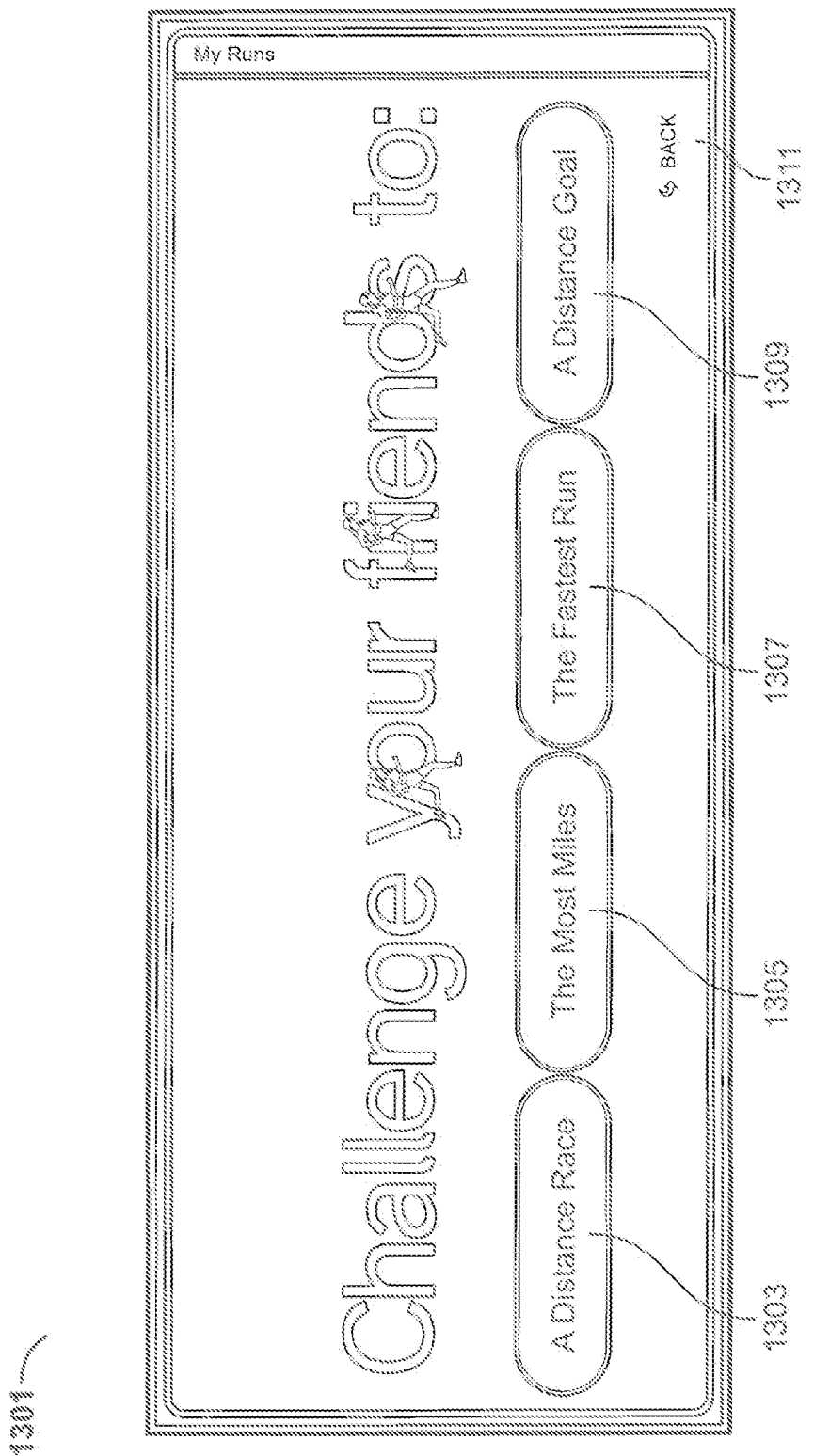
FIGS. 13A-13F illustrate examples of user interfaces that may be provided to create a challenge to other users according to various implementations of the invention.

Various examples of the invention may allow a user to "challenge" one or more other users (i.e., athletes employing embodiments of the invention) to a competition regarding athletic activities. With some implementations of the invention, for example, a user may issue a challenge to one or more other athletes by requesting the user interface 1301 shown in FIG. 13A. As seen in this figure, the interface 1301 includes a "Distance Race" button 1303, a "Most Miles" button 1305, a "Fastest Run" button 1307, a "Distance Goal" button 1309, and a "Back" button 1311. As known in the art, activating the "Back" button 1311 will cause the athletic data display configuration module 605 (or, with some examples of the invention, the athletic data display module 509) to configure and display the previously displayed configuration of the user interface 1301, or if the currently displayed configuration of the user interface 1301 is its initial configuration, a previously-shown user interface.

Figure 13B:
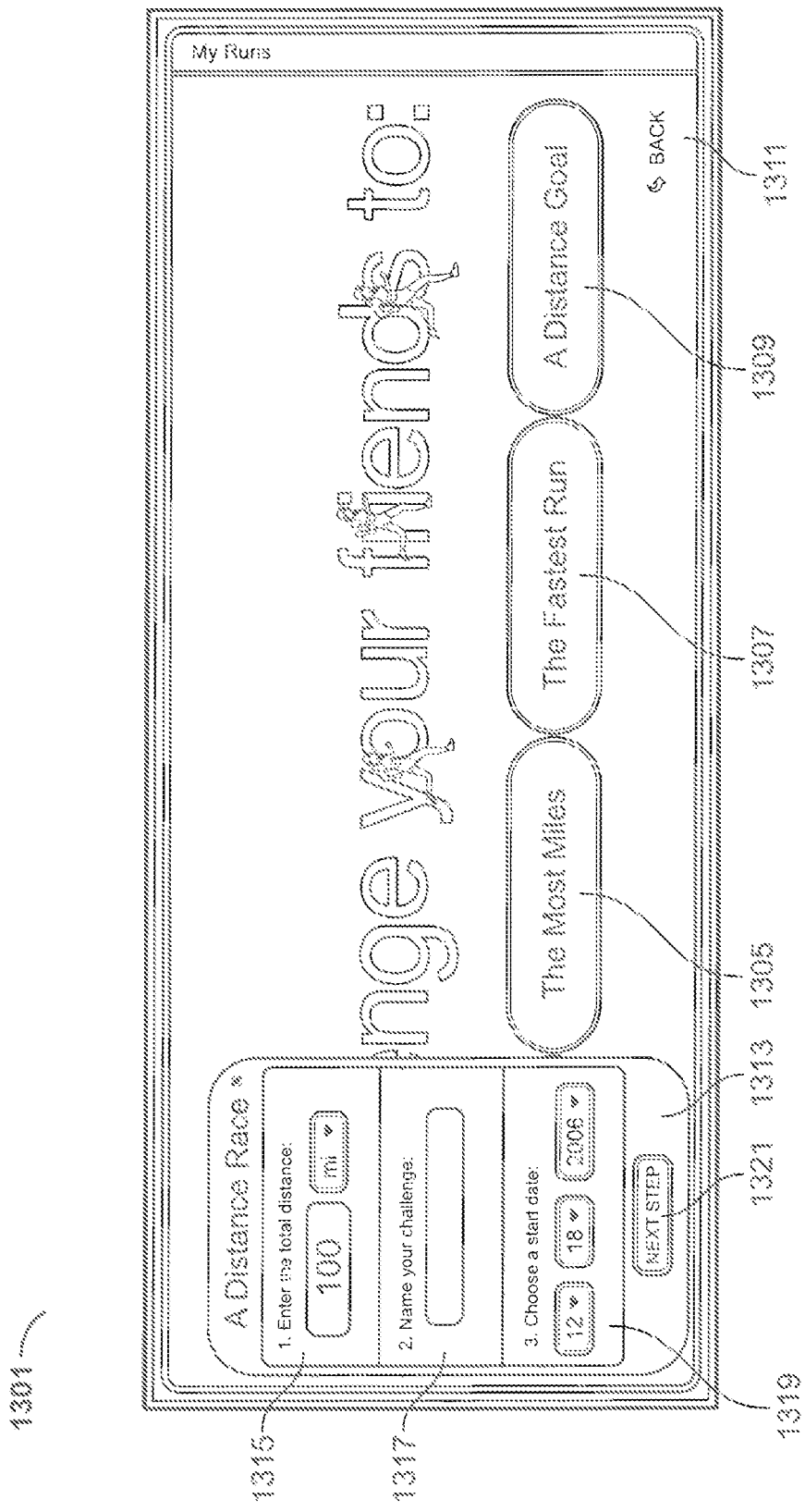

If a user wishes to establish a challenge regarding who can run a specified distance first, then the user activates the "Distance Race" button 1303. In response, the athletic data display configuration module 605 reconfigures the user interface 1301 to include a sub-interface 1313. As seen in FIG. 13B, the sub-interface 1313 includes a "Total Distance" control 1315, a "Challenge Name" control 1317, a "Start Date" control 1319, and a "Next Step" button 1321. By employing the "Total Distance" control 1315, a user can specify the total distance that a challenge participant must be the first to run in order to win the challenge. Next, the user can provide a specific name for the challenge using the "Challenge Name" control 1317. Naming each challenge allows an athlete to identify and keep track of a plurality of different challenges in which he or she may be concurrently participating. The user can then specify the starting date for the challenge using the "Start Date" control 1319. In the illustrated example, the "Total Distance" control 1315 and the "Challenge Name" control 1317 are each field controls (i.e., controls having a field in which a value can be typed), while the "Start Date" control 1319 is made up of a number of drop-down menus. It should be appreciated, however, that various examples of the invention may employ alternate types of controls as desired. Once a user has specified the parameters of the challenge, the user can begin the process of inviting specific athletes to participate in the challenge by activating the "Next Step" button 1321.

Figure 13C:
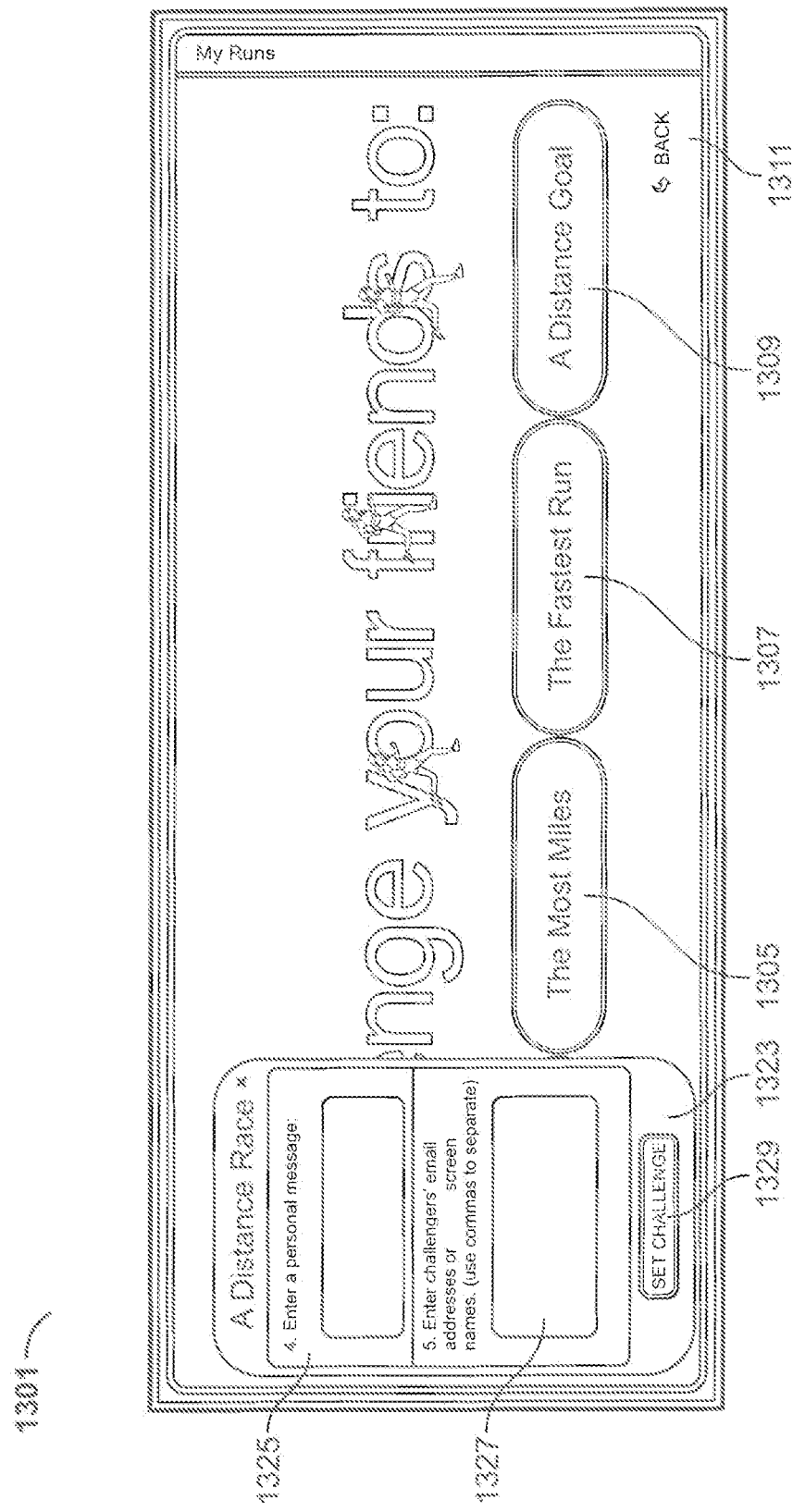

When the user activates the "Next Step" button 1321, the athletic data display configuration module 605 reconfigures the user interface 1301 to include a sub-interface 1323 in place of the "Distance Race" button 1303, as shown in FIG. 13C. As seen in this figure, the sub-interface 1323 includes a "Personal Message" control 1325, an "Email Address" control 1327, and a "Set Challenge" button 1329. The user can employ the "Personal Message" control 1325 to create a personal message to each athlete the user wishes to invite to participate in the challenge. Using the "Email Address" control 1327, the user can then specify the email address for each person he or she wishes to invite to participate in the challenge. In the illustrated example, the "Personal Message" control 1325 and the "Challenge Name" control 1317 are each field controls (i.e., controls having a field in which a value can be typed), but various examples of the invention may employ alternate types of controls as desired.

Once the user has provided the email address for each desired participant, the user can initiate the challenge by activating the "Set Challenge" button 1329. In response to the user activating the "Set Challenge" button 1329, the athletic data display configuration device 601 (or, with some implementations of the invention, the user's athletic information collection and display device 501) sends an email to each of the specified invitees. The email will contain the personal message and, e.g., an interactive prompt to join the challenge. If an invitee agrees to join the challenge by responding to the prompt, then the athletic data display configuration device 601 will be notified that the invitee has agreed to join the challenge. These types of email interactive prompts (such as the "voting" buttons provided in versions of the Outlook software tool available from Microsoft Corporation of Redmond, Wash.) are well known in the art, and will not be discussed here in detail.

After the athletic data display configuration device 601 has identified the participants in a challenge, it monitors the collected athletic data for each of the participants, and aggregates the relevant data values in the collected athletic data. For example, if the challenge is a race to determine who can be the first to run 100 miles, for each participant the athletic data display configuration device 601 will sum the total distance value in each athletic data set collected for that participant after the start date. When a participant has a sum of his or her total distance values that matches or exceeds the specified challenge distance (and is the first invitee to do so), then the athletic data display configuration device 601 will identify that participant as the winner of the challenge. In response, the athletic data display configuration device 601 will notify each participant of the winner. The athletic data display configuration device 601 may notify the participants using any desired technique, such as by sending an electronic mail message, by displaying a special-purpose interface when each participant connects to the athletic data display configuration device 601, etc. A variety of such notification techniques are well known in the art, and thus will not be discussed in detail.

With various examples of the invention, the athletic data display configuration device 601 may additionally provide updates regarding the status of a participant relative to the other participants. These updates also can be provided using any desired technique, such as by sending an electronic mail message, by displaying a special-purpose interface when each participant connects to the athletic data display configuration device 601, etc. For example, the athletic data display configuration device 601 may configure and provide a user interface showing each participant's progress toward the goal of the challenge using, e.g., bar graphs for each participant of the type previously described with regard to monitoring individual goals.

Figure 13D:
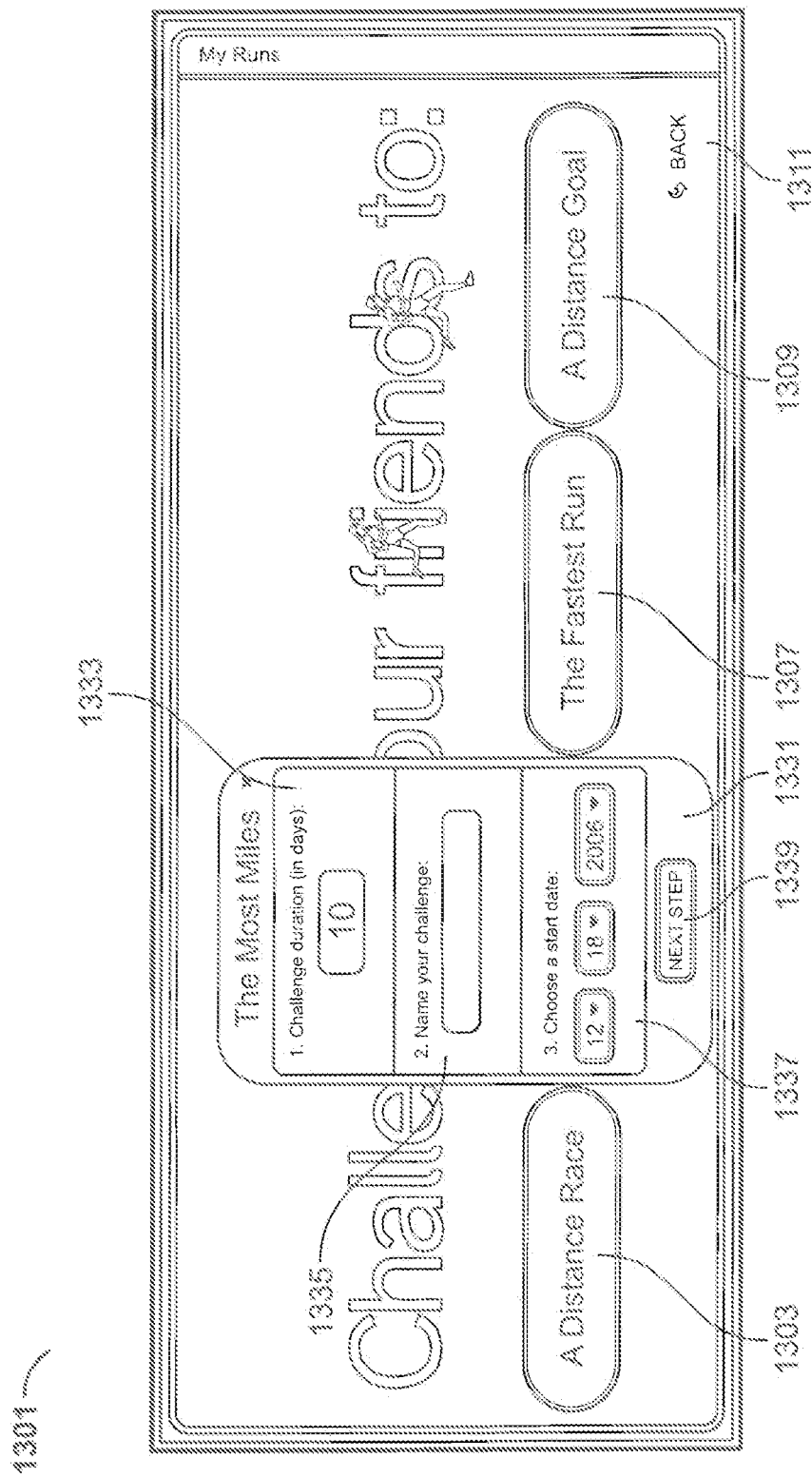

Returning now to FIG. 13A, if a user wishes to establish a challenge regarding who can run the most miles in a given period of time, then the user activates the "Most Miles" button 1305. In response, the athletic data display configuration module 605 reconfigures the user interface 1301 to include a sub-interface 1331, as seen in FIG. 13D. The sub-interface 1331 includes a "Challenge Duration" control 1333, a "Challenge Name" control 1335, a "Start Date" control 1337, and a "Next Step" button 1339. By employing the "Challenge Duration" control 1333, a user can specify the total amount of time for which a challenge participant has to run the greatest total distance in order to win the challenge. Next, the user can provide a specific name for the challenge using the "Challenge Name" control 1335. The user can then specify the starting date for the challenge using the "Start Date" control 1337. In the illustrated example, the "Challenge Duration" control 1333 and the "Challenge Name" control 1335 are each field controls (i.e., controls having a field in which a value can be typed), while the "Start Date" control 1337 is made up of a number of drop-down menus. It should be appreciated, however, that various examples of the invention may employ alternate types of controls as desired.

Once a user has specified the parameters of the challenge, the user can begin the process of inviting specific athletes to participate in the challenge by activating the "Next Step" button 1339. In response, the athletic data display configuration module 605 reconfigures the user interface 1301 to include the sub-interface 1323 in place of the "Most Miles" button 1305. (An example of sub-interface 1323 is illustrated in FIG. 13C.) As discussed in detail above, the user can employ the sub-interface 1323 to invite others to participate in the challenge, and ensure that the athletic data display configuration device 601 is informed of the participants in the challenge. As also previously discussed, the athletic data display configuration device 601 will monitor the collected athletic data for each participant, and aggregate the relevant data values from the collected athletic data to determine who wins the challenge. Still further, the athletic data display configuration device 601 can notify the participants of the winner of the challenge, and, with various examples of the invention, of the status of each participant during the challenge as described above.

Figure 13E:
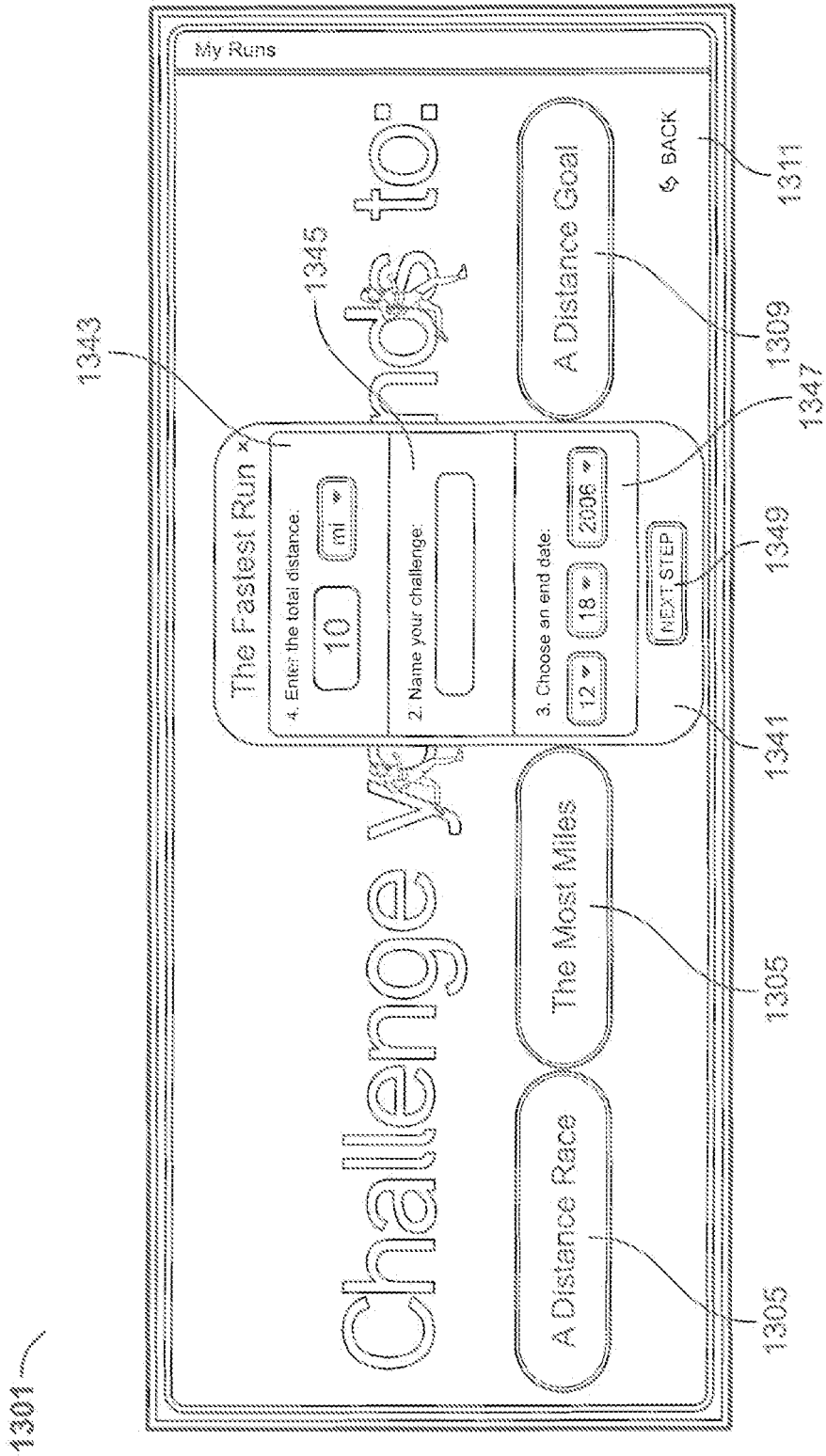

If a user wishes to establish a challenge regarding who can make the fastest run in a given period of time, then the user activates the "Fastest Run" button 1307. In response, the athletic data display configuration module 605 reconfigures the user interface 1301 to include a sub-interface 1341 as seen in FIG. 13E. The sub-interface 1341 includes a "Total Distance" control 1343, a "Challenge Name" control 1345, a "Start Date" control 1347, and a "Next Step" button 1349. By employing the "Total Distance" control 1343, a user can specify the total distance a user must run in order to have his or her run time eligible to win the challenge. Next, the user can provide a specific name for the challenge using the "Challenge Name" control 1345. The user can then specify the starting date for the challenge using the "Start Date" control 1347. In the illustrated example, the "Total Distance" control 1343 and the "Challenge Name" control 1345 are each field controls (i.e., controls having a field in which a value can be typed), while the "Start Date" control 1347 is made up of a number of drop-down menus, but various examples of the invention may employ alternate types of controls as desired.

Once a user has specified the parameters of the challenge, the user can begin the process of inviting specific athletes to participate in the challenge by activating the "Next Step" button 1349. In response, the athletic data display configuration module 605 reconfigures the user interface 1301 to include a sub-interface 1323 in place of the "Fastest Run" button 1307. (An example of sub-interface 1323 is illustrated in FIG. 13C.) As discussed in detail above, the user can employ the sub-interface 1323 to invite others to participate in the challenge, and ensure that the athletic data display configuration device 601 is informed of the participants in the challenge. As also previously discussed, the athletic data display configuration device 601 will monitor the collected athletic data for each participant, and aggregate the relevant data values from the collected athletic data to determine who wins the challenge. Still further, the athletic data display configuration device 601 can notify the participants of the winner of the challenge, and, with various examples of the invention, of the status of each participant during the challenge as described above.

Figure 13F:
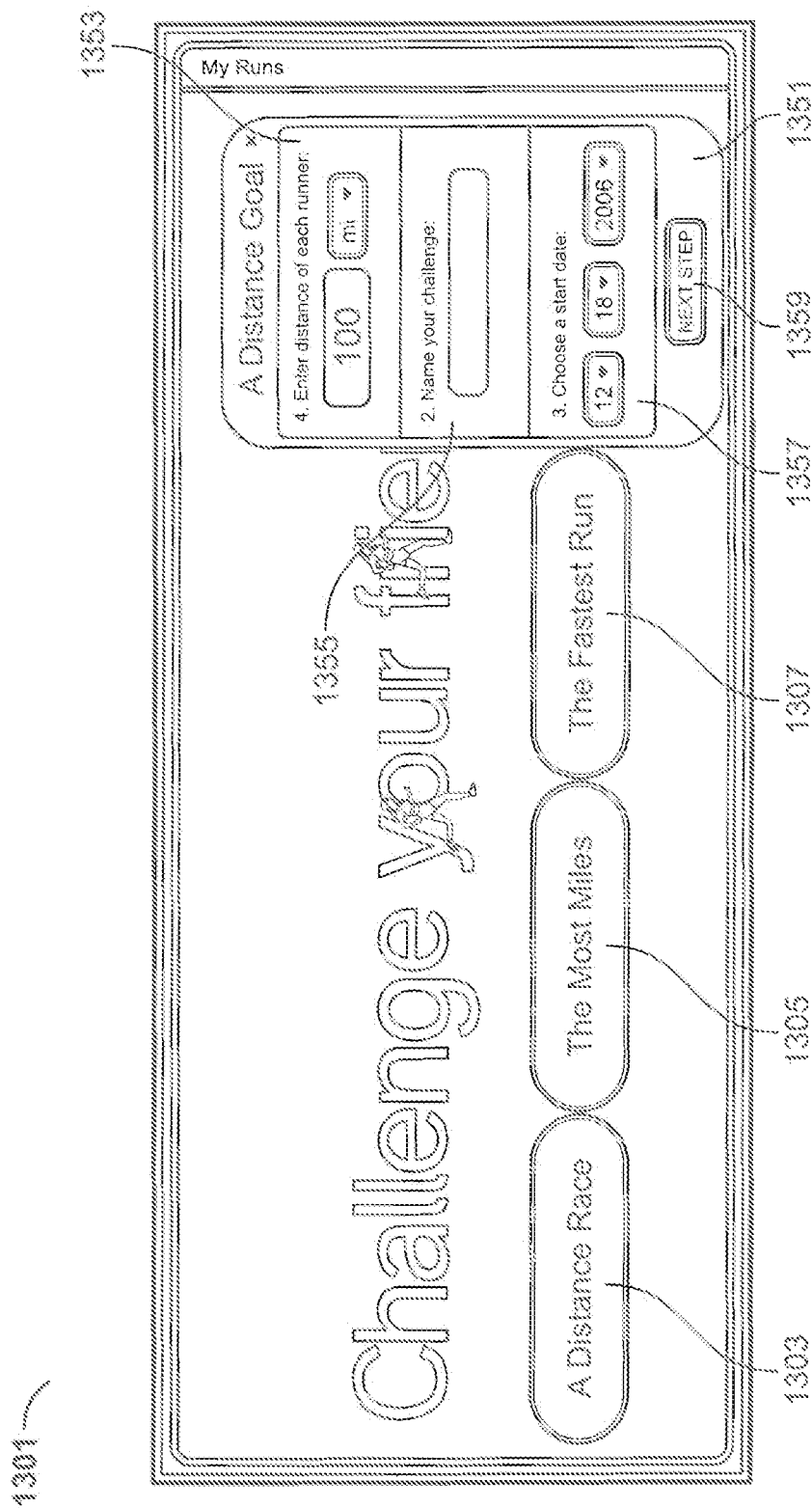

Lastly, if a user wishes to establish a challenge regarding who can run a specified distance in a given period of time, then the user activates the "Distance Goal" button 1309. In response, the athletic data display configuration module 605 reconfigures the user interface 1301 to include a sub-interface 1351. As seen in FIG. 13F, the sub-interface 1351 includes a "Total Distance" control 1353, a "Challenge Name" control 1355, a "Start Date" control 1357, and a "Next Step" button 1359. By employing the "Total Distance" control 1353, a user can specify the total distance a user must run over the specified time period in order to meet the challenge. Next, the user can provide a specific name for the challenge using the "Challenge Name" control 1355. The user can then specify the starting date for the challenge using the "Start Date" control 1357. In the illustrated example, the "Total Distance" control 1353 and the "Challenge Name" control 1355 are each field controls (i.e., controls having a field in which a value can be typed), while the "Start Date" control 1357 is made up of a number of drop-down menus, but various examples of the invention may employ alternate types of controls as desired.

Once a user has specified the parameters of the challenge, the user can begin the process of inviting specific athletes to participate in the challenge by activating the "Next Step" button 1359. In response, the athletic data display configuration module 605 reconfigures the user interface 1301 to include the sub-interface 1323 in place of the "Distance Goal" button 1309. (An example of sub-interface 1323 is illustrated in FIG. 13C.) As discussed in detail above, the user can employ the sub-interface 1323 to invite others to participate in the challenge, and ensure that the athletic data display configuration device 601 is informed of the participants in the challenge. As also previously discussed, the athletic data display configuration device 601 will monitor the collected athletic data for each participant, and aggregate the relevant data values from the collected athletic data to determine who wins the challenge. Still further, the athletic data display configuration device 601 can notify the participants of the winner of the challenge, and, with various examples of the invention, of the status of each participant during the challenge as described above.

Lists

As well as interactive comparisons of a user's athletic data with other users, such as the goals and challenges described in detail above, some implementations of the invention may alternately or additionally allow a user to passively compare his or her athletic data with other users.

For example, some implementations of the invention may provide a ranking of where a user stands with respect to other users. The ranking may be based upon a simple comparison, or it may be limited to a specific demographic group, a particular geographic region, or some combination therefore.

Figure 14A:
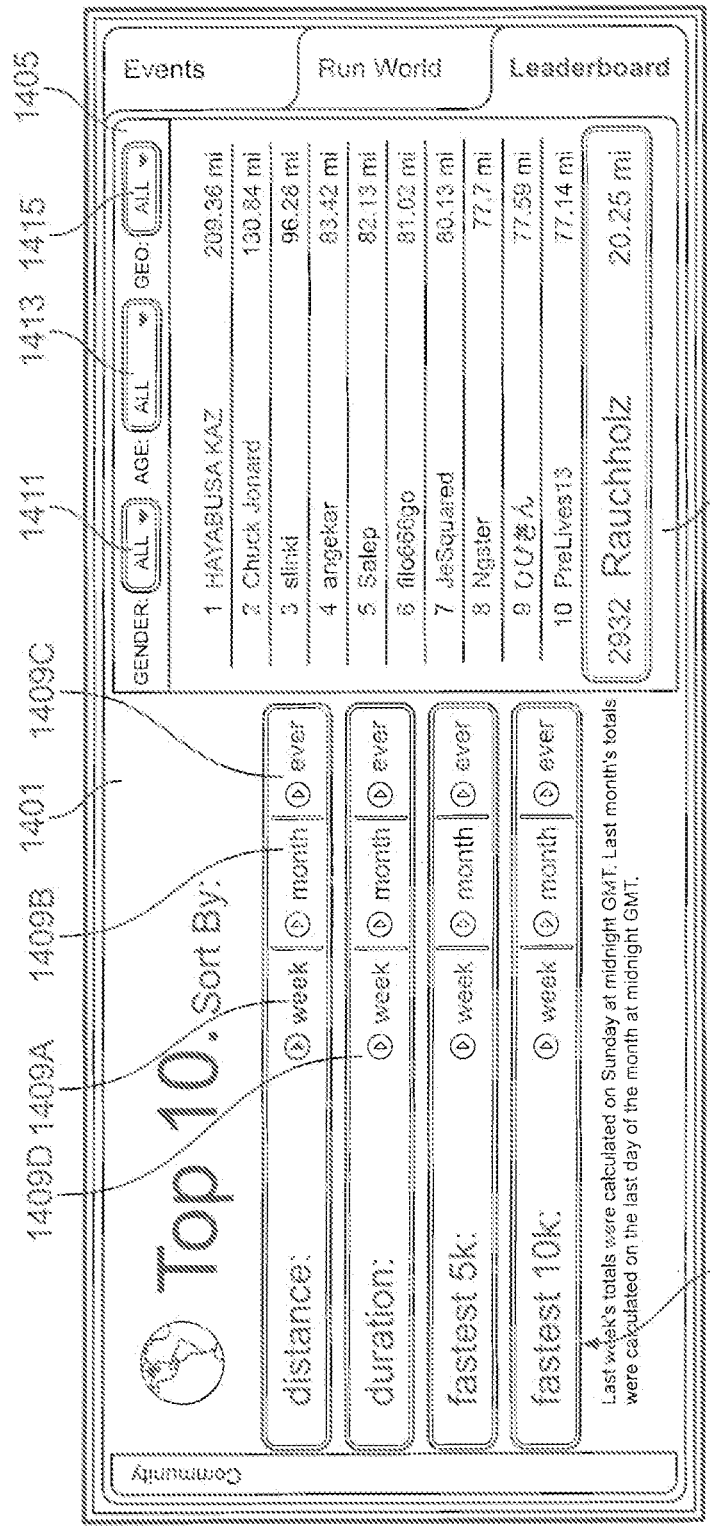
FIGS. 14A-14F illustrate examples of user interfaces that may be provided to compare a user's athletic data with the athletic data of other participating users according to various implementations of the invention.

For example, with some implementations of the invention, a user may request that the athletic data display configuration module 605 generate and display the user interface 1401 illustrated in FIG. 14A. As seen in this figure, the user interface 1401 includes a comparison criteria region 1403, a filter region 1405, and display region 1407. The comparison criteria region 1403 includes a plurality of "radio" style controls 1409, while the filter region 1405 includes a plurality of "drop-down" controls 1411-1413. The display region 1407 then displays user information based upon athletic data selected using the comparison and filter information selected using the controls 1409-1413.

More particularly, a user employs the "radio" style controls 1409 to specify the basic criteria according to which the athletic data display configuration module 605 will compare athletic data for a plurality of users. These controls 1409 are referred to herein as "radio" style controls because the selection of one of the controls (e.g., control 1409C) will automatically deselect a previously selected control, and only one control may be selected at any given time. Of course, it should be appreciated that other type of selection tools, including other types of controls, may be alternately or additionally employed with other implementations of the invention. Each control 1409 is associated with both a sorting criterion for sorting measured athletic data and a time criterion specifying a time period during which the athletic data being compared must have been measured. For example, each of controls 1409A-1409C is associated with total distance as a sorting criterion, while control 1409A is associated with a week time period, control 1409B is associated with a month time period, and control 1409C is associated with an unlimited time period. Control 1409D is then associated with a duration sorting criterion and a week time period.

With the example of the interface 1401 shown in FIG. 14A, each of the filter controls 1411-1415 are selected to "ALL," as will be discussed in more detail below. Further, the control 1409A is selected. Because the control 1409A is associated with the "distance" sorting criterion and the "week" time criterion, the athletic data display configuration module 605 will sort the aggregated distance data for participating users that was measured during the preceding week. It then lists the names of the participating users having the ten highest aggregated distance data values in the filter region 1405. In addition, the athletic data display configuration module 605 will display in the aggregated distance data values measured during the preceding week for each of the identified participating users. Still further, the athletic data display configuration module 605 will display the user's corresponding aggregated distance measured for the preceding week. With some implementations of the invention, the athletic data display configuration module 605 also may display the ranking of the user's corresponding aggregated distance information measured for the preceding week relative to those participating users having a greater aggregated distance measured for the preceding week. Thus, in the illustrated example, the user "Rauchholz" has a ranking of 2932 relative to other participating users.

With some implementations of the invention, the participating users will be any user who provides athletic data to the athletic data storage 607 (or to an affiliated athletic data storage). For still other implementations of the invention, however, the participating users may be a subset of the all of the users who provide athletic data to the athletic data storage 607 or to an affiliated athletic data storage. For example, the participating users may be only those users who agree in advance to have their data shared with other users, or those users who do not specifically indicate that they wish for their athletic data to be private. Of course, still other criteria may be used to determine which users will be treated as participating users.

Figure 14B:
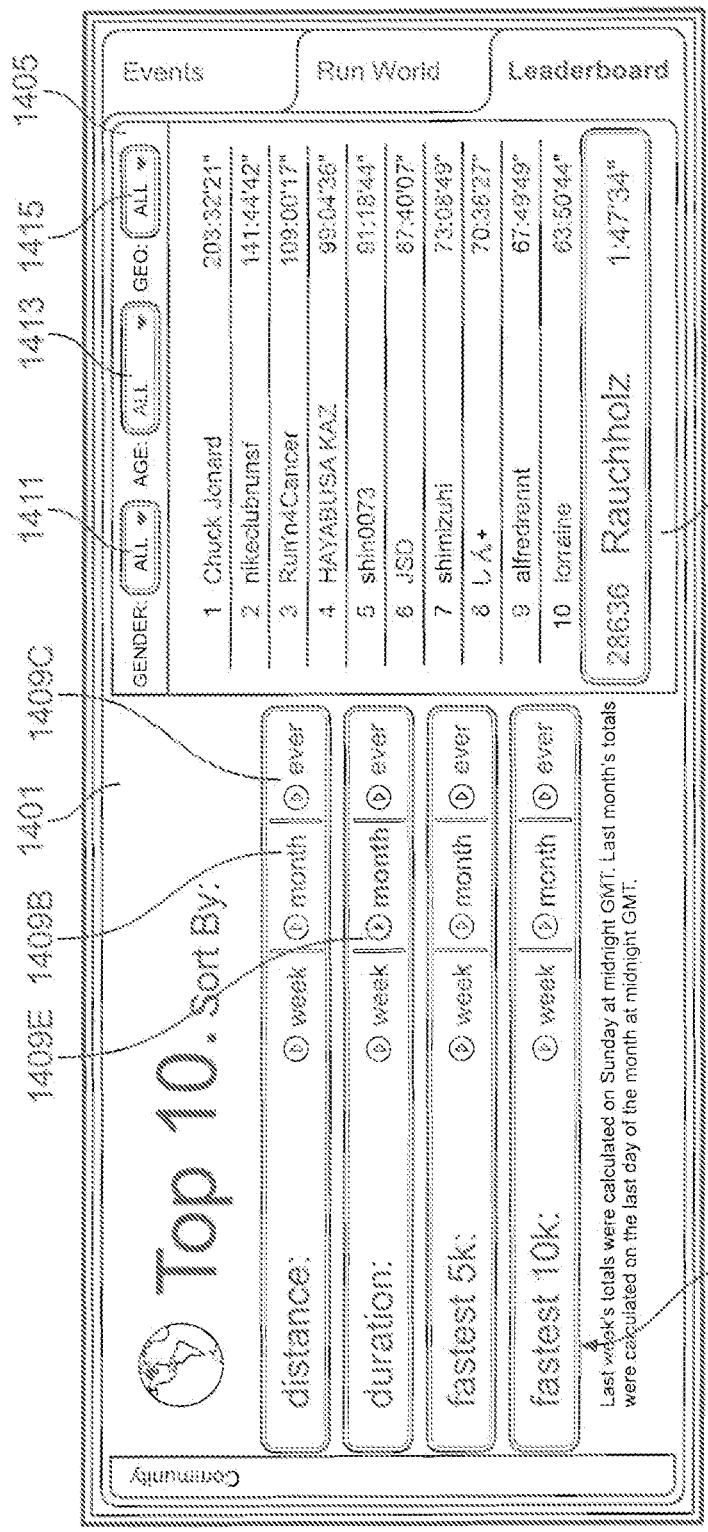

FIG. 14B illustrates another example of the interface 1401. Again, each of the filter controls 1411-1415 are selected to "ALL." Further, the control 1409E is selected, which is associated with the "duration" sorting criterion and the "month" time criterion. Accordingly, the athletic data display configuration module 605 will sort the aggregated running (or walking) duration data for participating users that was measured during the preceding month. It then lists the names of the participating users having the ten highest aggregated duration data values in the filter region 1405. In addition, the athletic data display configuration module 605 will display in the aggregated duration data values measured during the preceding month for each of the identified participating users. Still further, the athletic data display configuration module 605 will display the user's corresponding aggregated duration data measured for the preceding month. Again, the athletic data display configuration module 605 also displays the ranking of the user's corresponding aggregated duration data measured for the preceding month relative to those participating users having a greater aggregated duration value measured for the preceding month. Thus, in the illustrated example, the user "Rauchholz" has a ranking of 28636 relative to other participating users.

Figure 14C:
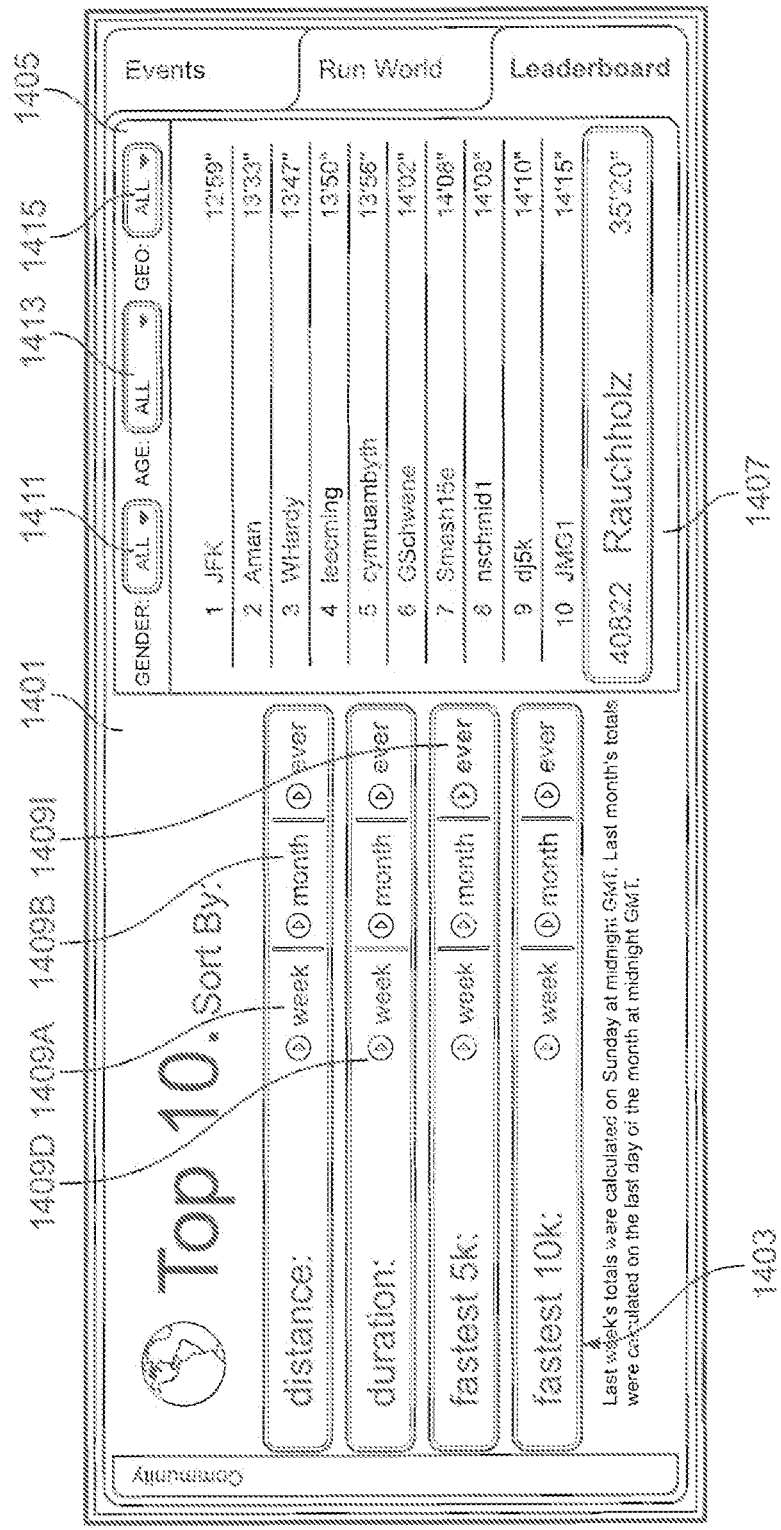

FIG. 14C illustrates yet another example of the interface 1401. Again, each of the filter controls 1411-1415 are selected to "ALL." Further, the control 14091 is selected, which is associated with the "fastest 5k" sorting criterion and the "ever" time criterion. Accordingly, the athletic data display configuration module 605 will identify and display the participating users with the ten fastest travel times for a 5k run that was measured at any time preceding the user's selection of the control 14091. In addition, the athletic data display configuration module 605 will display in the fastest 5k time value for each of the identified participating users. Still further, the athletic data display configuration module 605 will display the user's fastest measured time for a 5k run, together with a ranking of that time relative to those participating users having a faster measured time for a 5k run. Thus, in the illustrated example, the user "Rauchholz" has a ranking of 40822 relative to other participating users.

Figure 14D:
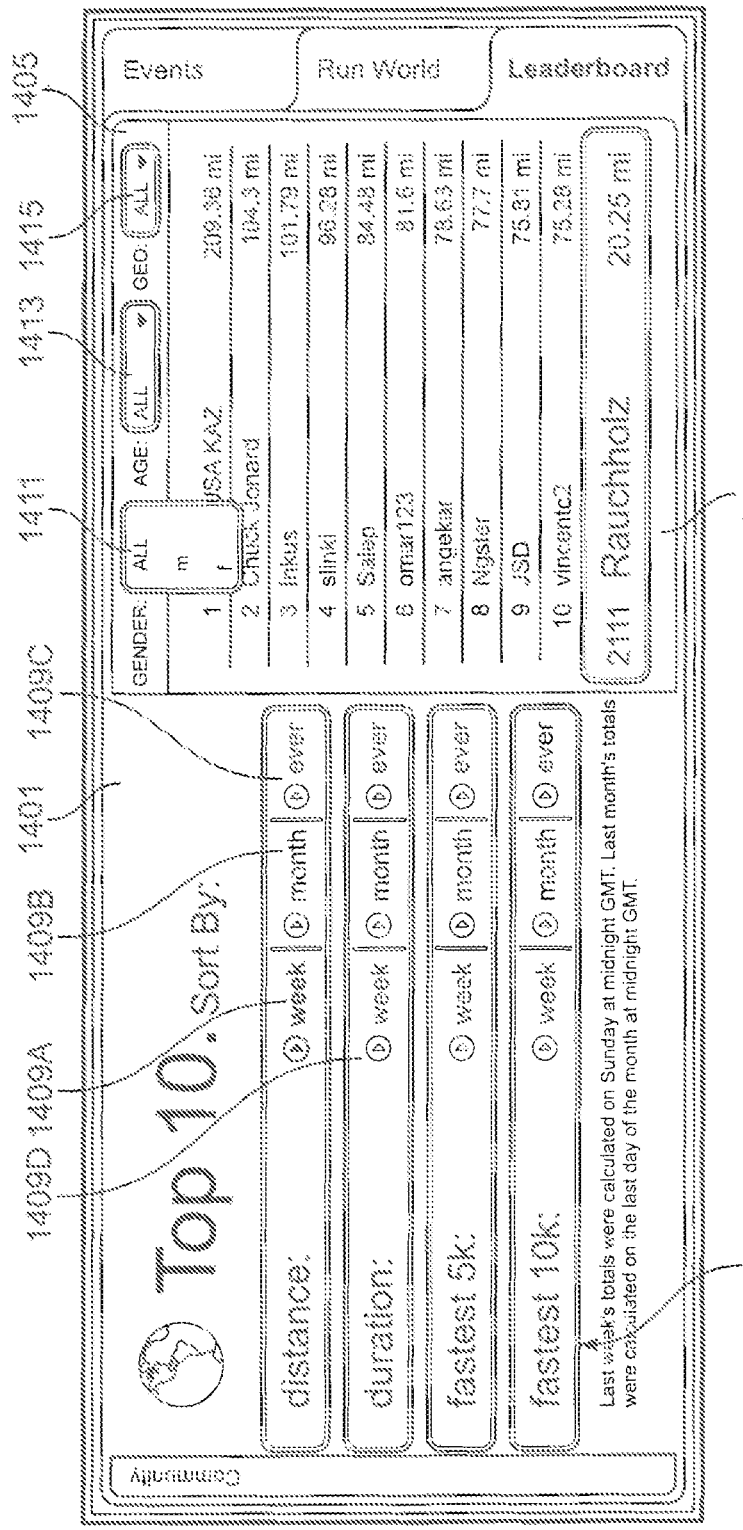
Figure 14E:
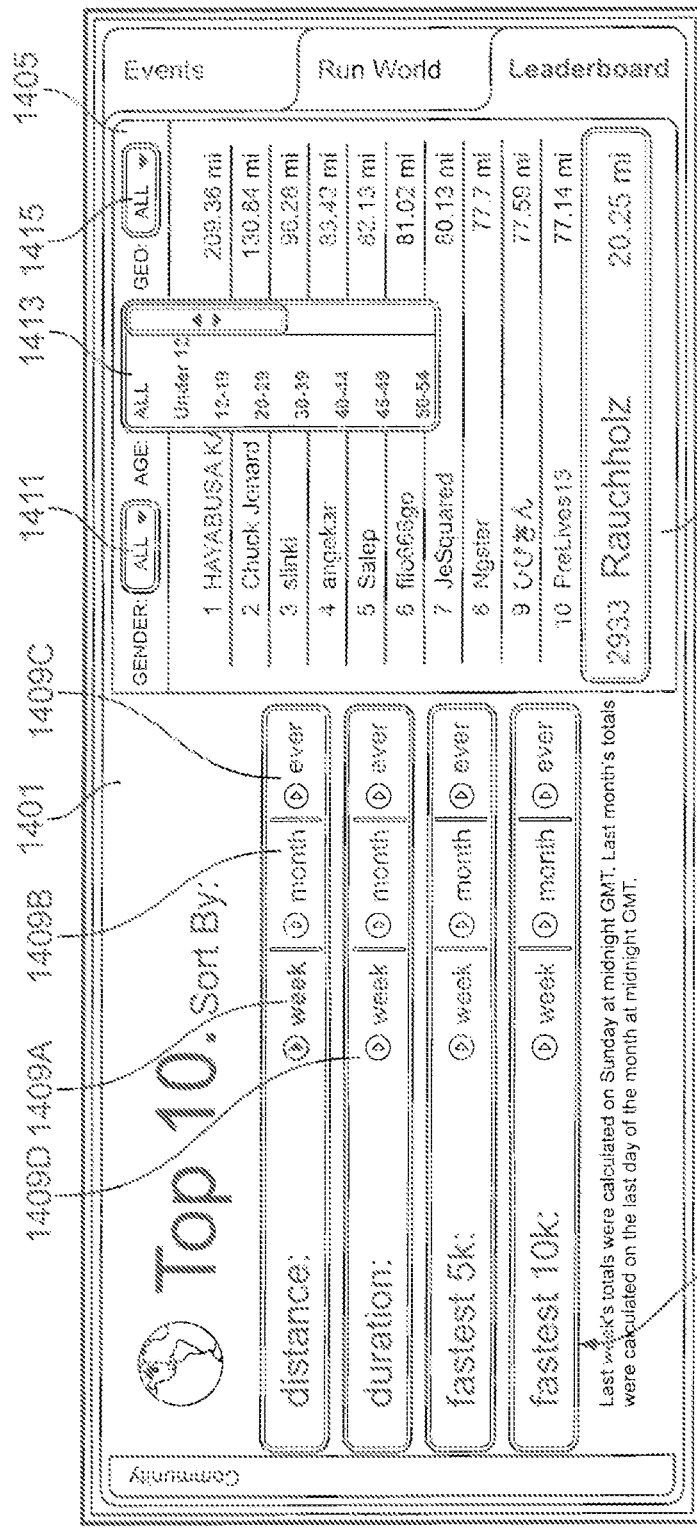
Figure 14F:
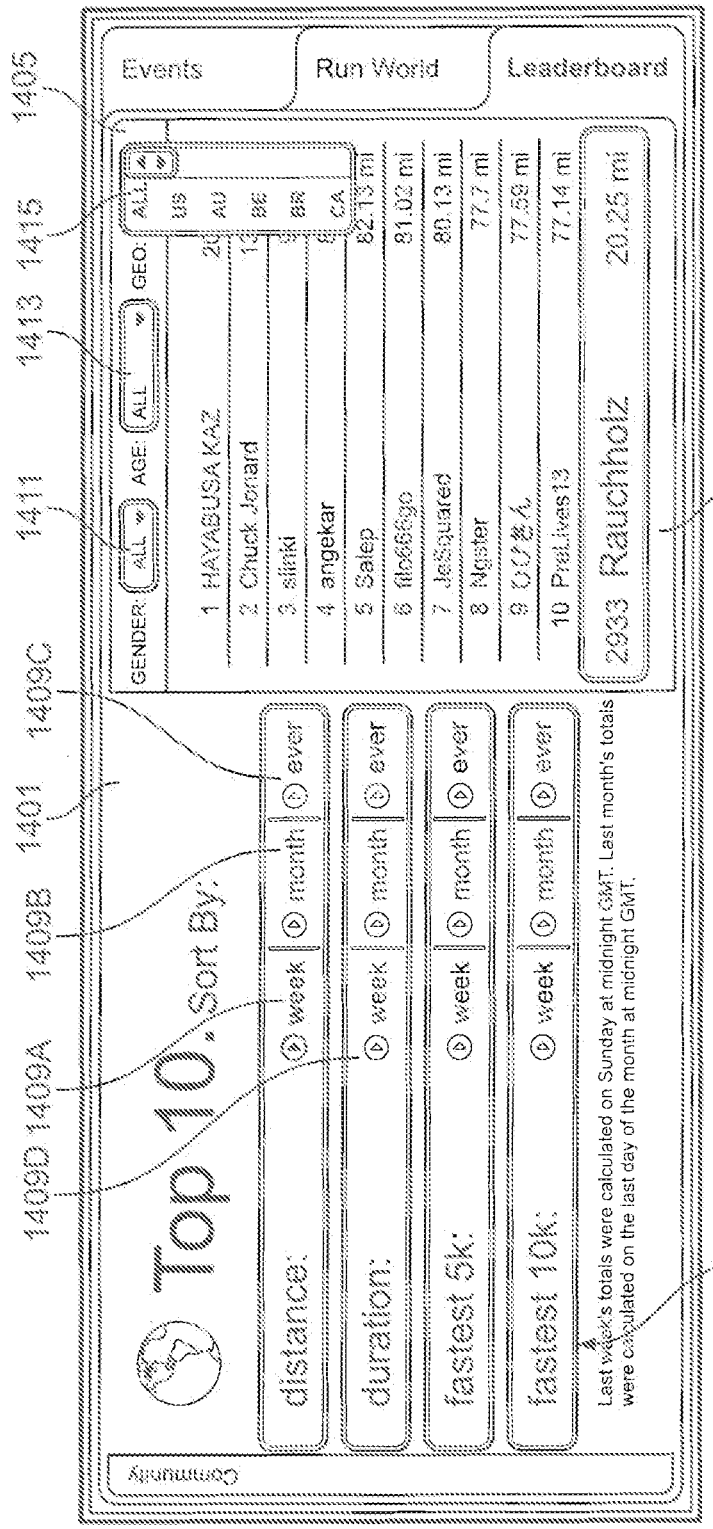

In some situations, a user may wish to limit the pool of participating users to whom the user will be compared. As previously noted, the filter region 1405 includes filter controls 1411-1415. These filter controls may be employed to limit the participating users that will be considered for a desired comparison. For example, as illustrated in FIG. 14D, a user can employ the filter control 1411 to select between including all participating users for comparison, only male participating users for comparison, or only female participating users for comparison. Similarly, as shown in FIG. 14E, a user can employ filter control 1413 to limit the comparison to only those participating users within a desired age group. Still further, as shown in FIG. 14F, a user can employ the filter control 1415 to limit the comparison to participating users within a geographic region.

It should be appreciated that, with some implementations of the invention, a user can employ each of the filters 1411-1415 simultaneously. For example, a user may employ the filter controls 1411-1415 to limit the participating users considered for comparison with the users's athletic data to only men between the ages of 40-44 residing in the United States. The information required to filter the participating users may be obtained from any available source. Conveniently, however, the information may be obtained by requesting the users to submit this information for a user profile during an initial registration process. Of course, while three specific filtering criteria have been disclosed, it should be appreciated that any desired type and/or combination of characteristics be employed as filters.

Other Features

Record Of Achievements

As discussed in detail above, various implementations of the invention may provide positive reinforcement to an athlete. For example, as discussed above, a user can employ various embodiments of the invention to set goals for himself or herself, and then track his or her progress toward attaining those goals. Similarly, a user may employ various embodiments of the invention to participate in a challenge. Once the goal is completed or the challenge is won, however, these achievements may be forgotten and thus not provide the user with any further positive reinforcement.

Figure 15:
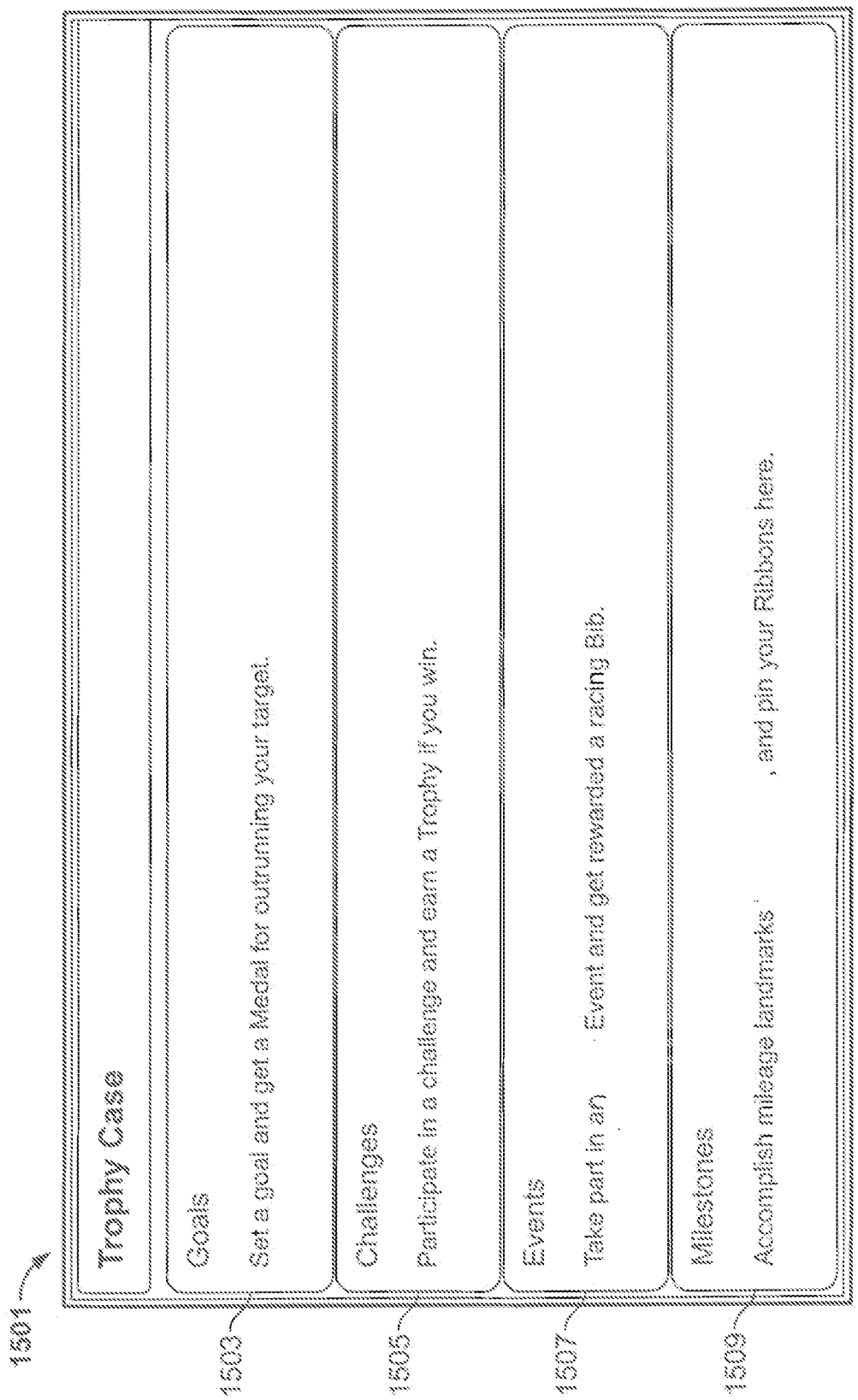
FIG. 15 illustrates an example of a user interface that may be provided to memorialize a user's athletic achievements according to various implementations of the invention.

Accordingly, some implementations of the invention may provide a feature for memorializing a user's various athletic achievements. For example, with some embodiments of the invention, the athletic data display configuration module 605 may provide a user interface, such as the user interface 1501 shown in FIG. 15, for displaying athletic achievements recorded for a user. As seen in this figure, the user interface 1501 includes a "goal" region 1503, a "challenges" region 1505, an "events" region 1507, and a "milestones" region 1509. Each of these regions can be used to display an icon representing a user's previous achievement.

For example, if a user sets and then subsequently meets a goal, the achievement of this goal will be recorded by the athletic data display configuration module 605. In response, the athletic data display configuration module 605 will display an icon, such as a representation of a medal, graphically commemorating that achievement. Similarly, if the user wins a challenge, that achievement will be recorded by the athletic data display configuration module 605. In response, the athletic data display configuration module 605 will display an icon, such as a representation of a trophy, graphically commemorating that achievement.

Still further, a user may participate in an event associated with one or more implementations of the invention. For example, a race sponsor, such as a marathon race sponsor, may affiliate itself with embodiments of the invention. If a user runs in the race, completes the race, or places in the race, then the athletic data display configuration module 605 may record that achievement. In response, the athletic data display configuration module 605 will display an icon, such as a representation of a racing bib, graphically commemorating that achievement. The athletic data display configuration module 605 may employ any desired technique to record the user's participation in the race. For example, the race sponsor may physically monitor the user's participation, and subsequently update the athletic data storage 607 directly. Alternately, the user may update the athletic data storage 607 on an honor system basis.

Of course, still more sophisticated techniques can be used to have the athletic data display configuration module 605 record the user's achievement. For example, the race sponsor or a third party may provide the user with an electronic recording device that records the user's progress through the race. The user can then download the data from the electronic recording device to the athletic data storage 607 or to the athletic data display configuration module 605. With some implementations of the invention, the electronic interface device 205 or the athletic parameter measurement device 207 may even be used to record the user's progress through the race, and to subsequently download the data from the electronic recording device to the athletic data storage 607 or to the athletic data display configuration module 605.

Still further, a user may have still other milestones associated with his or her athletic performance. For example, a user may run achieve a relatively large total distance, such as 100 kilometers, 100 miles, 250 kilometers, 250 miles, etc., run at a particularly fast speed, such as a mile in less than five minutes, or run for a relatively large total duration, such as 1000 hours. In response, the athletic data display configuration module 605 may record that milestone achievement, and then display an icon, such as a representation of an award ribbon, graphically commemorating that achievement.

In this manner, various implementations of the invention can memorialize a user's past achievements to provide the user with positive feedback to inspire future athletic performance. Of course, some implementations of the invention may memorialize alternate or additional achievements.

Resolutions

Figure 16:
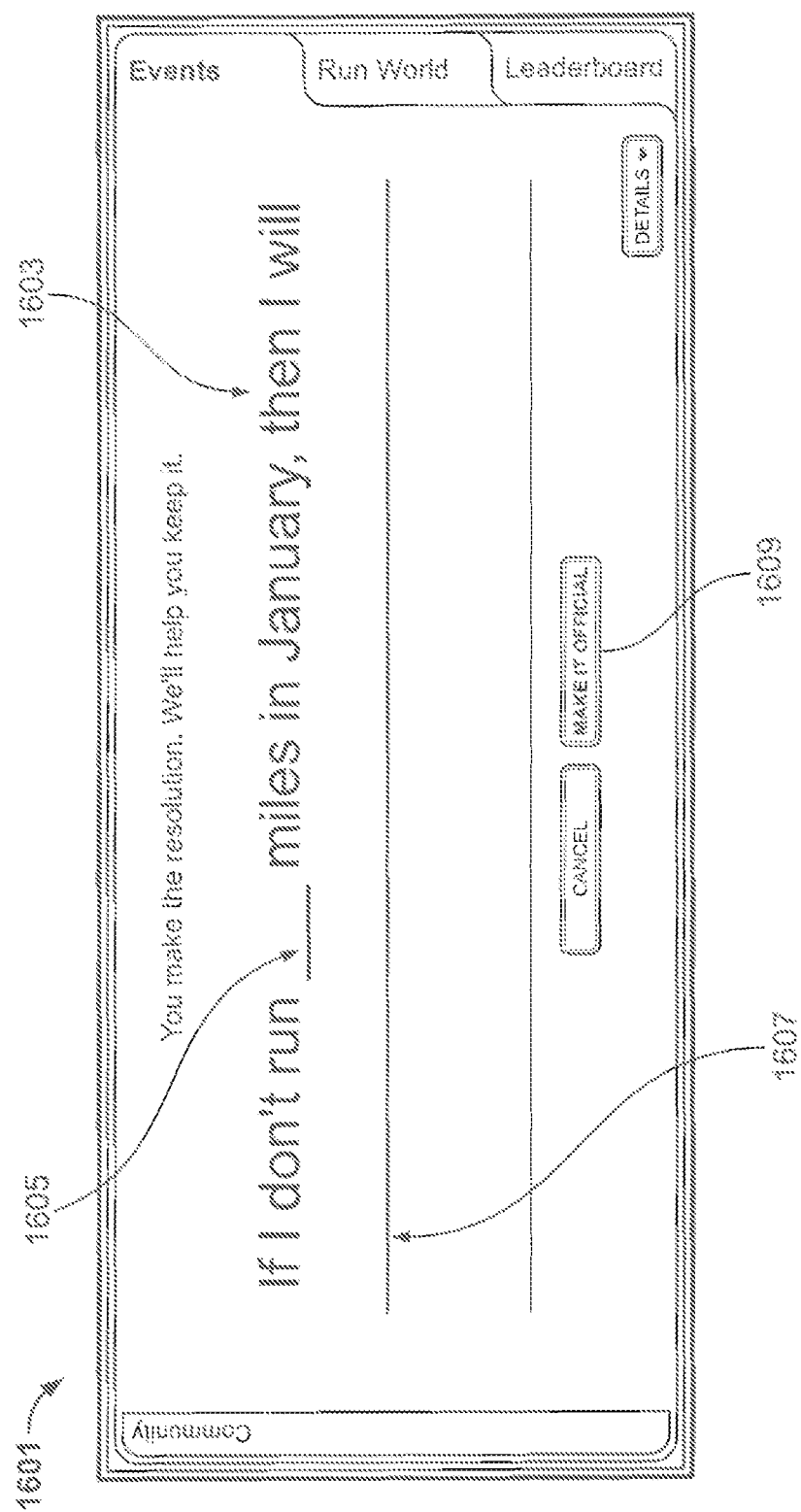
FIG. 16 illustrates an example of a user interface that may be provided to create a resolution to perform an athletic achievement according to various implementations of the invention.

Some implementations of the invention may assist a user in resolving to achieve a specific athletic achievement, and then keep that resolution. For example, various embodiments of the invention may provide a user interface like the user interface 1601 illustrated in FIG. 16. As seen in this figure, the interface 1601 provides a resolution statement 1603 with an achievement field 1605 and a consequence field 1607. The user interface also includes a submission button 1609. When a user wishes to make a resolution, he or she can insert the desired achievement goal (such as a distance) into the achievement field 1605, and some task or other action that will occur if the user does not meet the stated achievement in the consequence field 1607. Once the user has completed the information in the achievement field 1605 and the consequence field 1607, then the user actives the submission button 1609 to submit the resolution information to the athletic data display configuration module 605.

After receiving the resolution information, the athletic data display configuration module 605 will monitor the user's athletic activity to determine whether the user has complied with his or her resolution. If the athletic data display configuration module 605 determines that the user has met the stated resolution, then the athletic data display configuration module 605 may provide some type of positive feedback to the user. For example, the athletic data display configuration module 605 may send the user an electronic mail message congratulating the user on keeping his or her resolution. Alternately or additionally, the athletic data display configuration module 605 may memorialize the achievement as described above. If, however, the user does not meet the stated resolution, then the athletic data display configuration module 605 may encourage the user to perform the specified task or action. The athletic data display configuration module 605 may, for example, send an electronic mail message to the user to remind the user of his or her resolution. Of course, various implementations of the invention may perform alternate or additional actions to encourage the user to perform the specified task or action.

Individual Training

Figure 17:
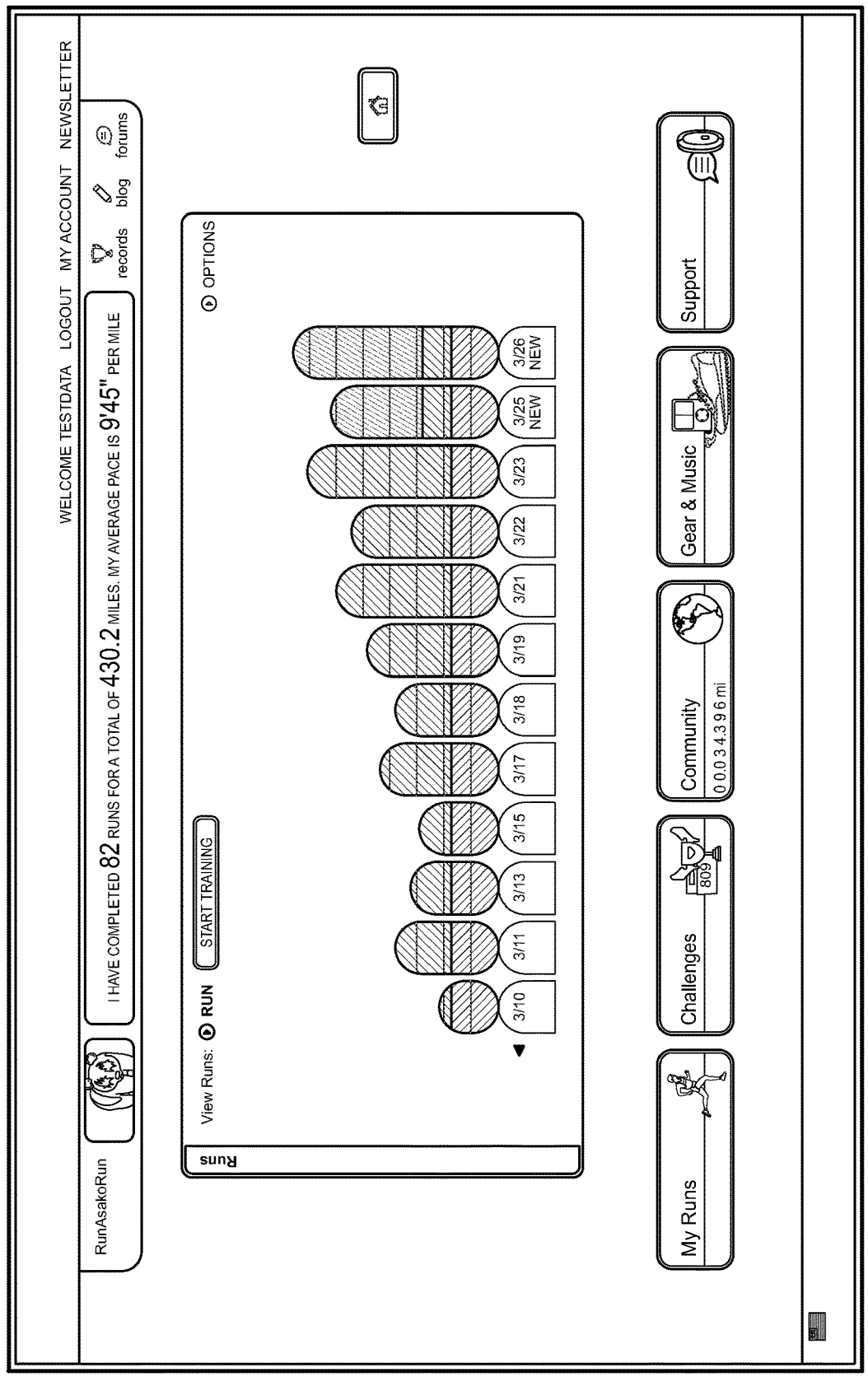

As users or athletes such a runners utilize the systems of embodiments of the present invention to collect information, a user interface of an embodiment may provide additional features and functionality for athletes to use and share information relating to their physical activity. In one exemplary form of the invention, and as illustrated by FIG. 17, athletic information is displayed on a user interface 1700 as described in greater detail below with reference to FIGS. 18-88.

Figure 18:
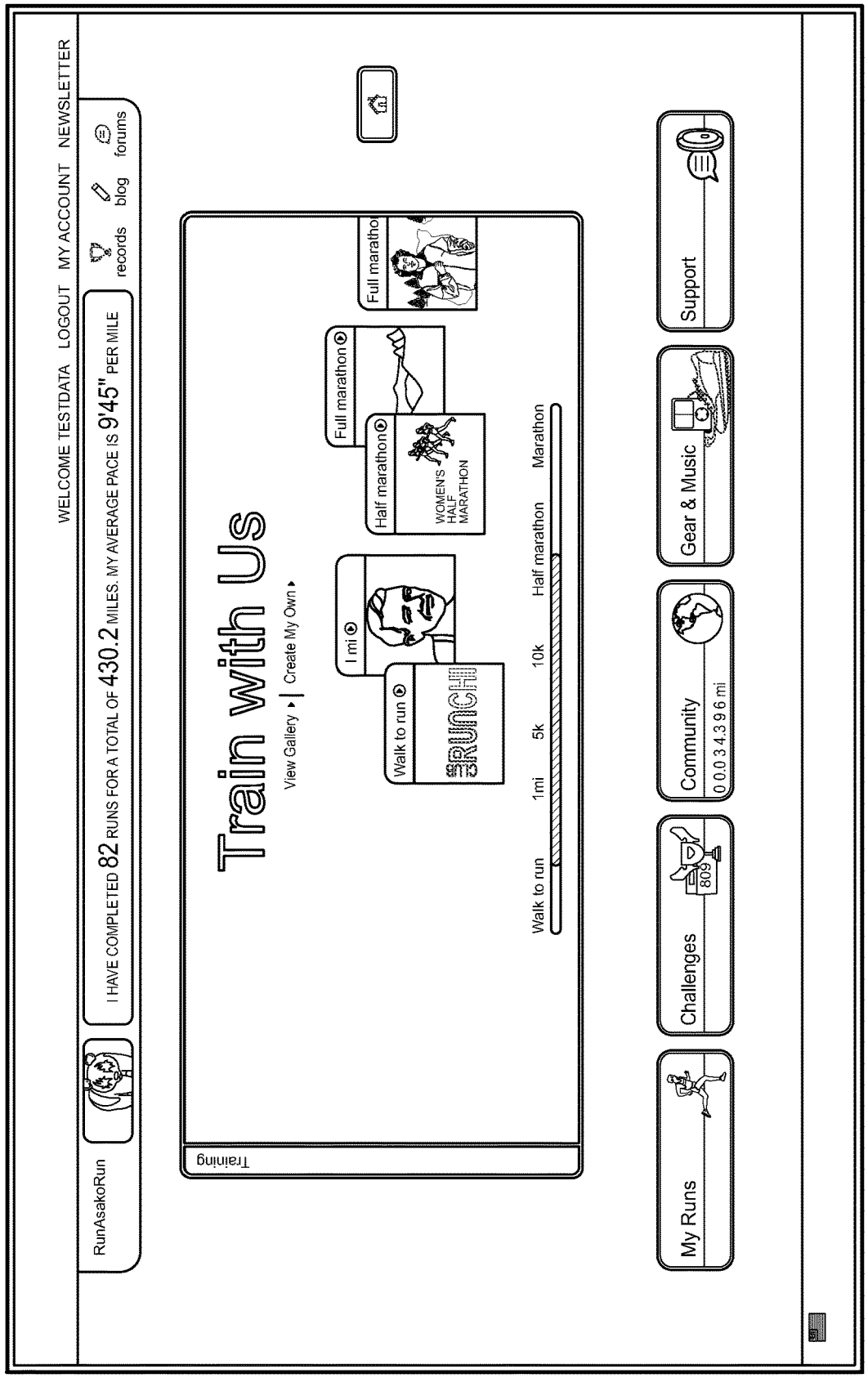

For example, FIGS. 18-62 illustrate an embodiment for which user interface 1700 may be a training aid for the user or athlete. In an embodiment, and as illustrated by FIGS. 18 and 19, a user or athlete may select from a number of pre-determined training goals. For example, a user or athlete may be new to running and may select a training program to aid their training from walking to running Current runners may select training programs designed to help endurance and/or speed in common running distances such as one mile, five kilometers, and ten kilometers. A runner may also select an event for which to train, for example a half marathon or a full marathon. Predefined training programs may originate from a variety of sources including other users, sponsors, event organizers and the like. In one example, participants of a marathon may share their training program with other users.

Figure 20:
Figure 21:
Figure 22:
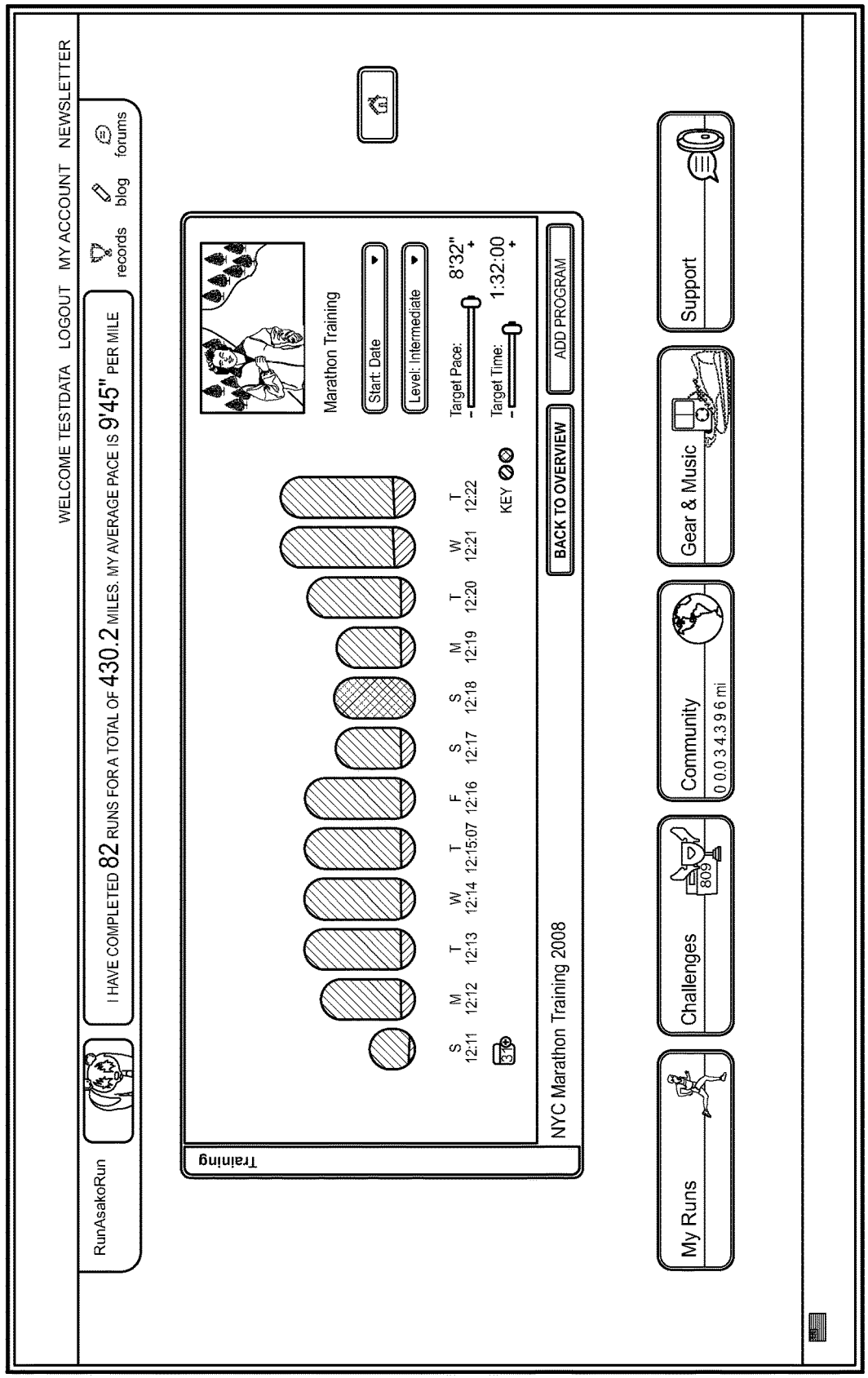
Figure 23:
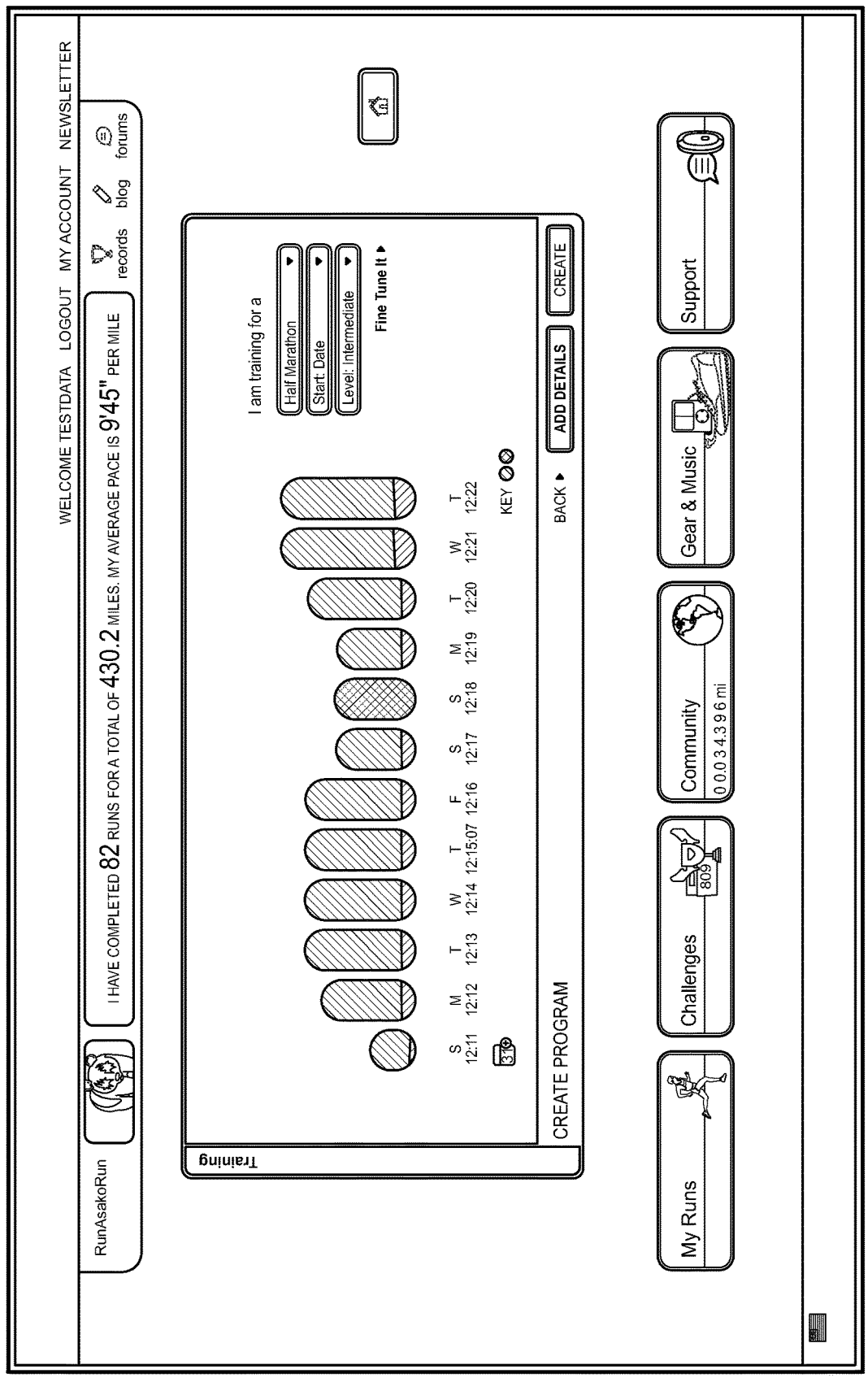
Figure 24:
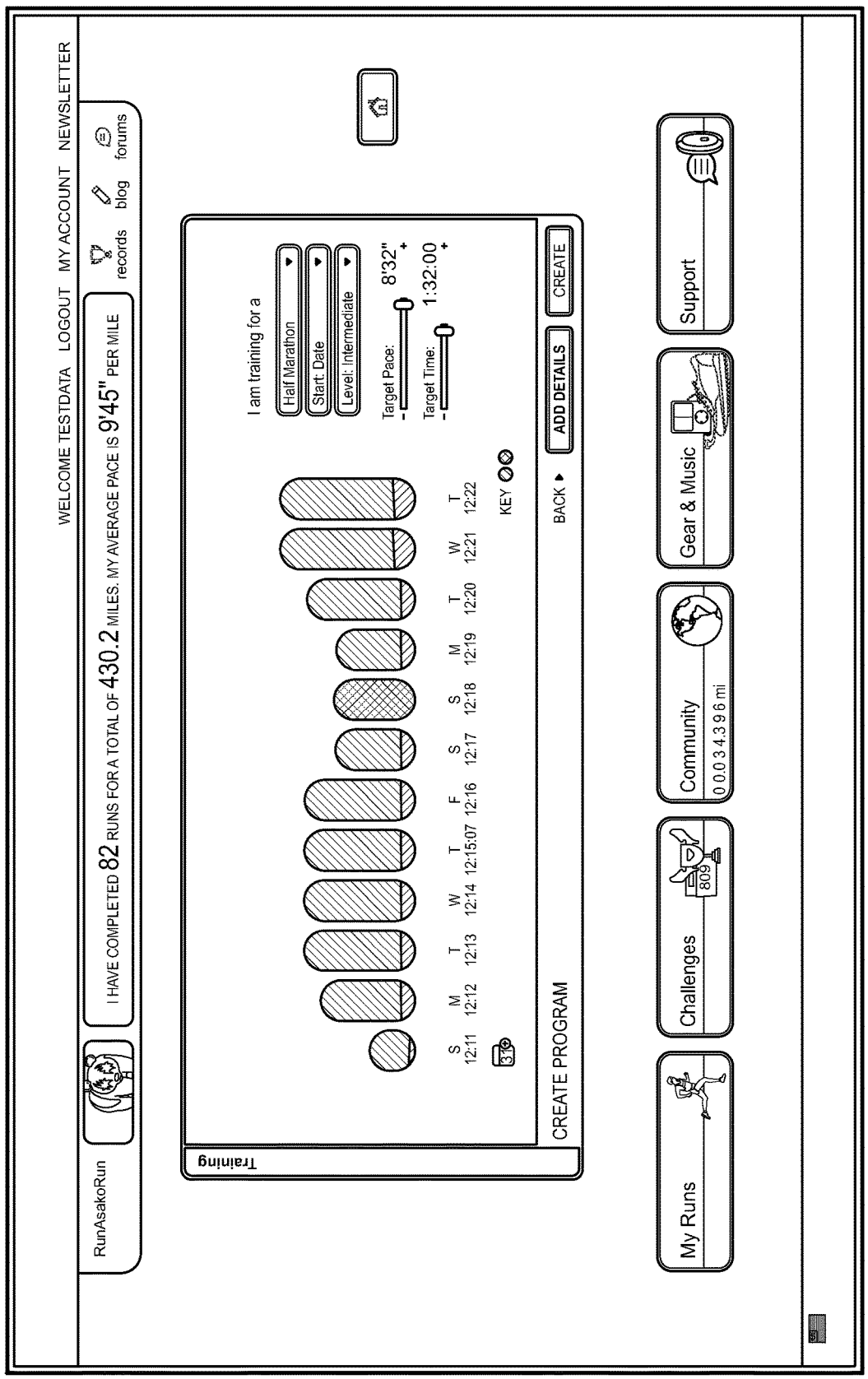

FIG. 20 illustrates that when a user or athlete selects or positions their mouse cursor atop the icon or the like indicating a training program, they may view a summary of the training program. In an embodiment, the summary may include the distance of the program (e.g., in miles or kilometers), the duration of the training program (e.g., in weeks or months), and the recommended athletic level of the user or athlete before beginning the program (e.g, novice, beginner, intermediate, advanced, and the like). FIG. 21 illustrates additional details available as an overview of the training program. The overview may explain the highlights of the training program in narrative form as well as an indication of the start date and finish date. If the user or athlete is motivated by what they read, they may add the training program via user interface 1700. They may also view a more detailed schedule including miles required on a particular day. The detailed schedule, for example as illustrated by FIGS. 22-24, will graphically illustrate the number of miles required per day and on which days, if any, the training program does not require any running Further, the user or athlete may be able to modify the start date of the program as desired or based on a goal completion date (e.g., the race or other event for which the user or athlete is training) In one or more configurations, the training program may be downloaded to a portable athletic training device (e.g., a music device configured to detect athletic performance).

A user or athlete may also be able to, depending on the program, select the skill level of the program, for example novice, beginner, intermediate, advanced, and the like. Depending on the program, the selection of a skill level may alter the number of miles required per day, alter the number of days that don't require running, and/or alter the length (e.g., in days, weeks, months, etc.) of the program to accommodate the user's or athlete's goal. For example, a beginner user or athlete participating in a marathon training program may have a longer program duration than an advanced user or athlete participating in the marathon program. Alternatively or additionally, motivational messages or comments presented to the user may be different (e.g., more motivational or encouraging) for beginners than more advanced or disciplined athletes.

Additionally, a user or athlete may globally alter the training program based on a target pace or target time. For example, a user or athlete may desire to run a mile in five minutes or may wish to run a marathon at 8 minutes per mile. The user interface 1700 may alter the training schedule in response to the user's or athlete's target pace or target time by, for example, altering the number of miles required per day, altering the number of days that don't require running, and/or altering the length (e.g., in days, weeks, months, etc.) of the program.

Figure 25:
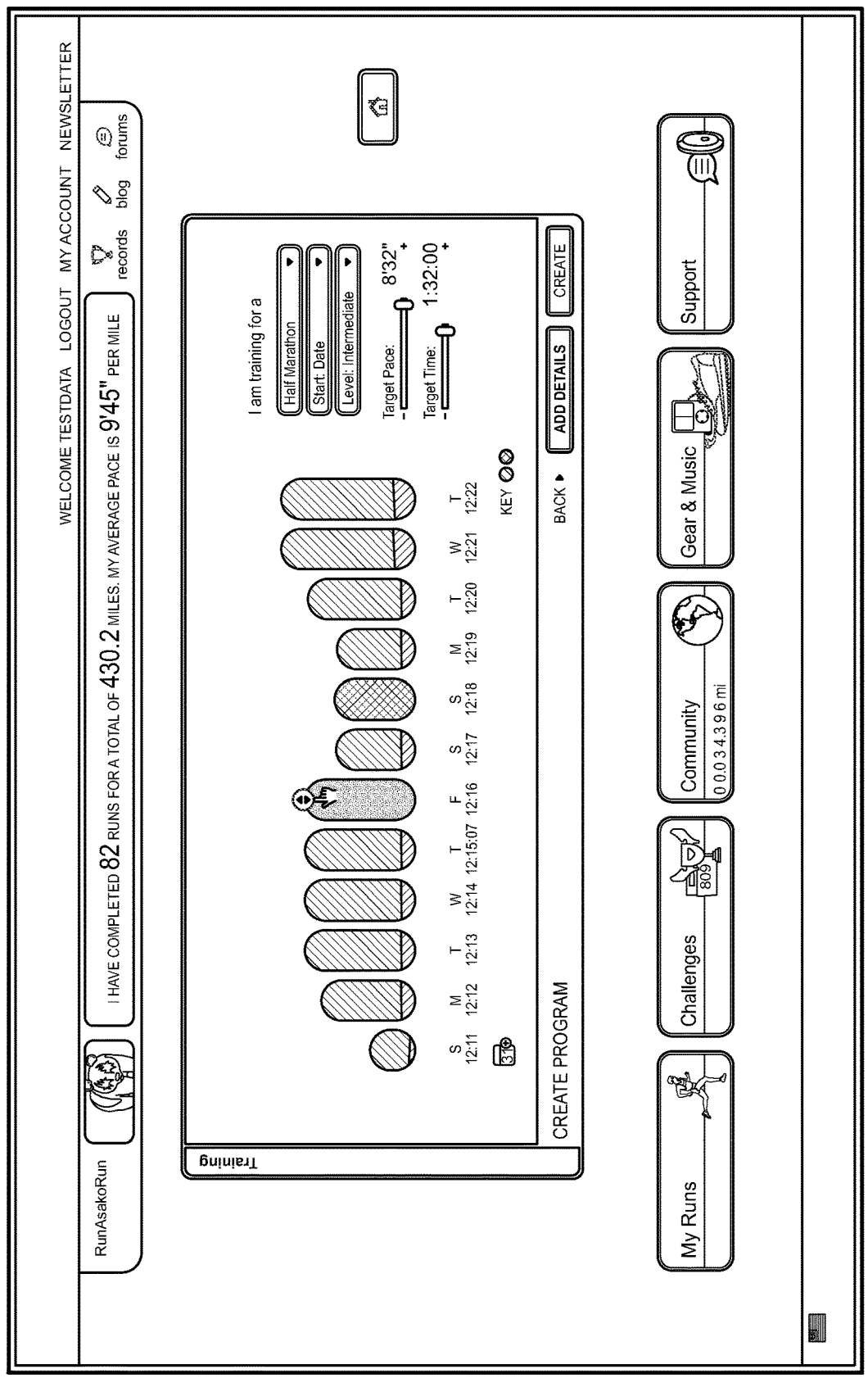
Figure 26:
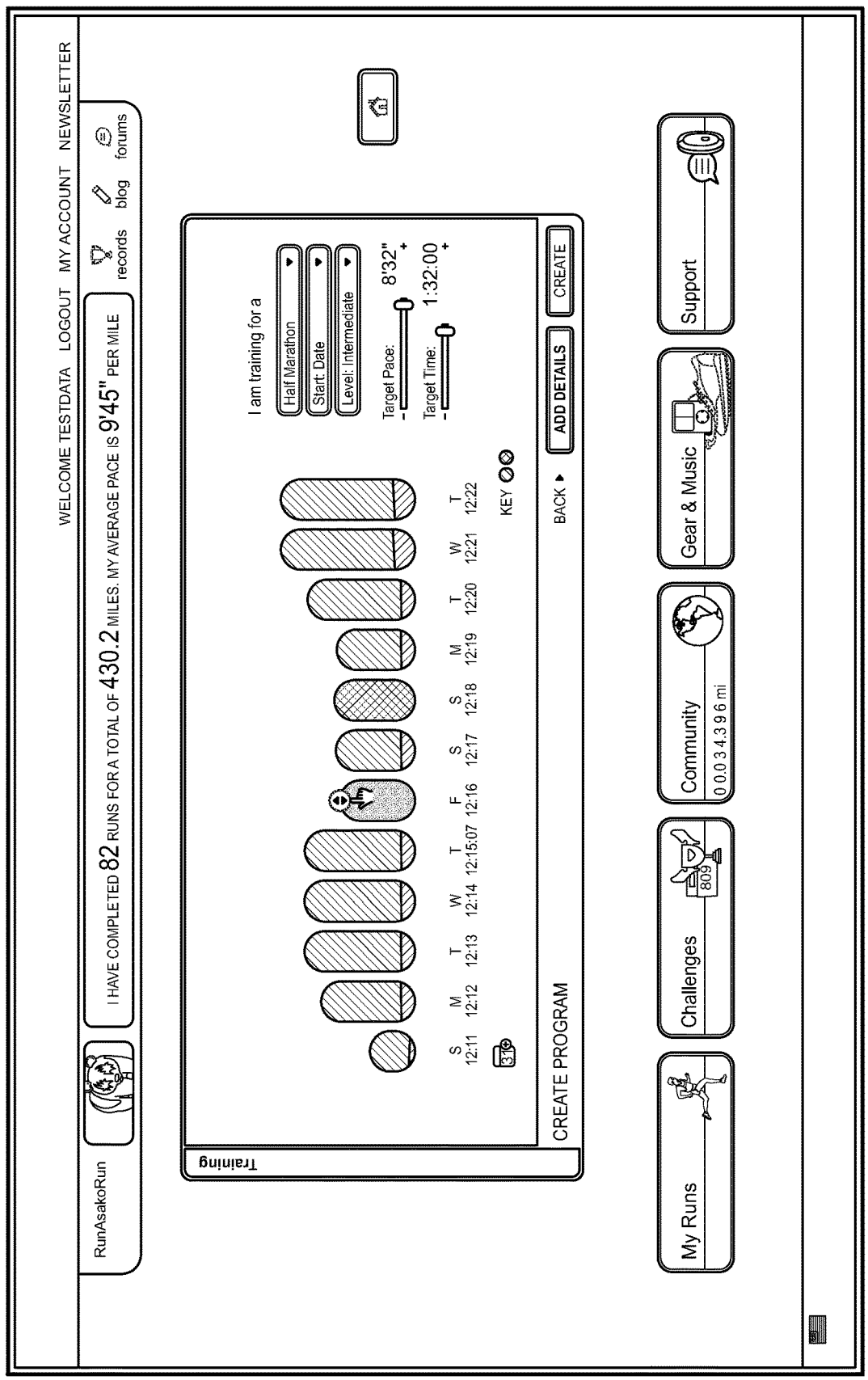
Figure 27:
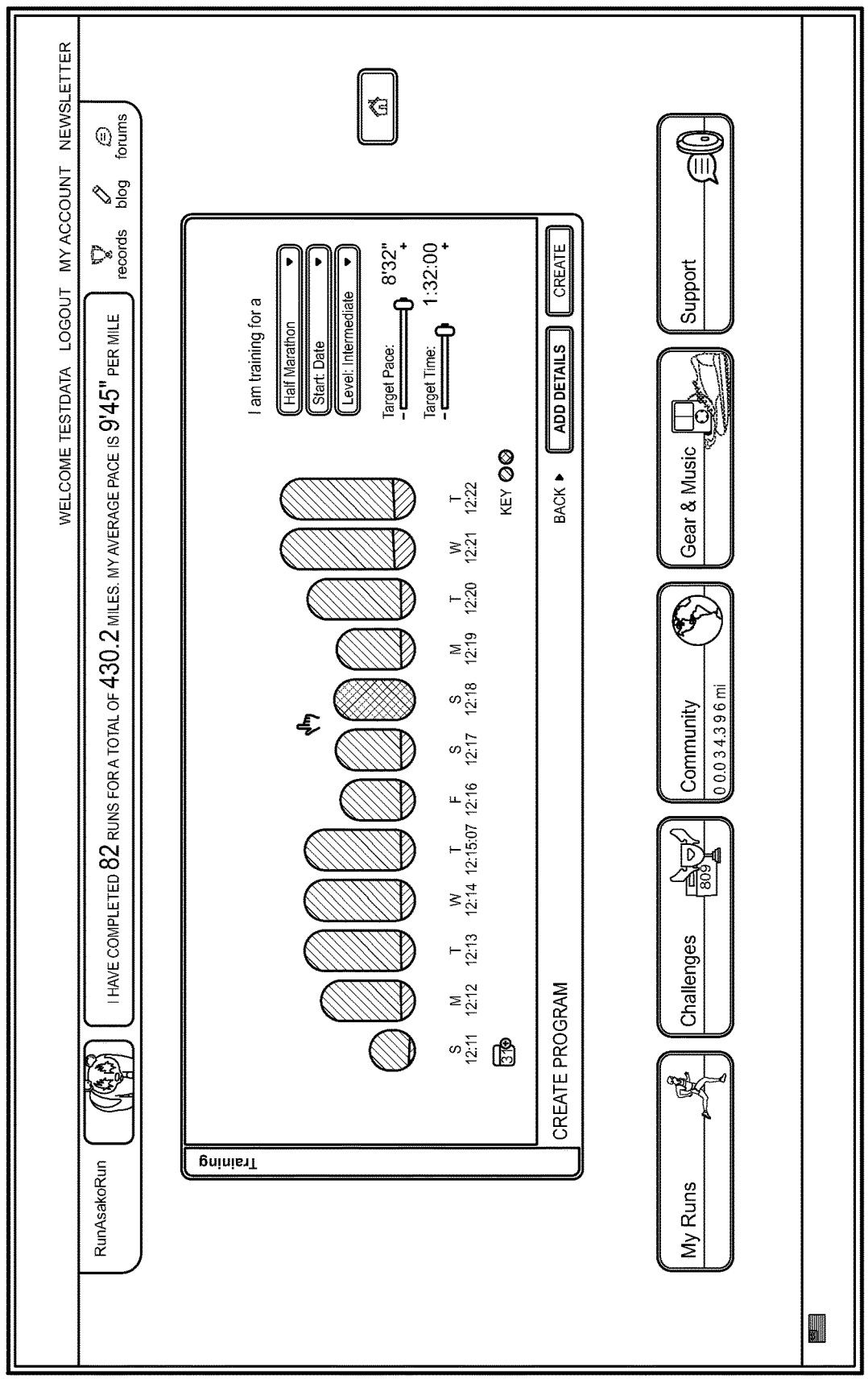
Figure 28:
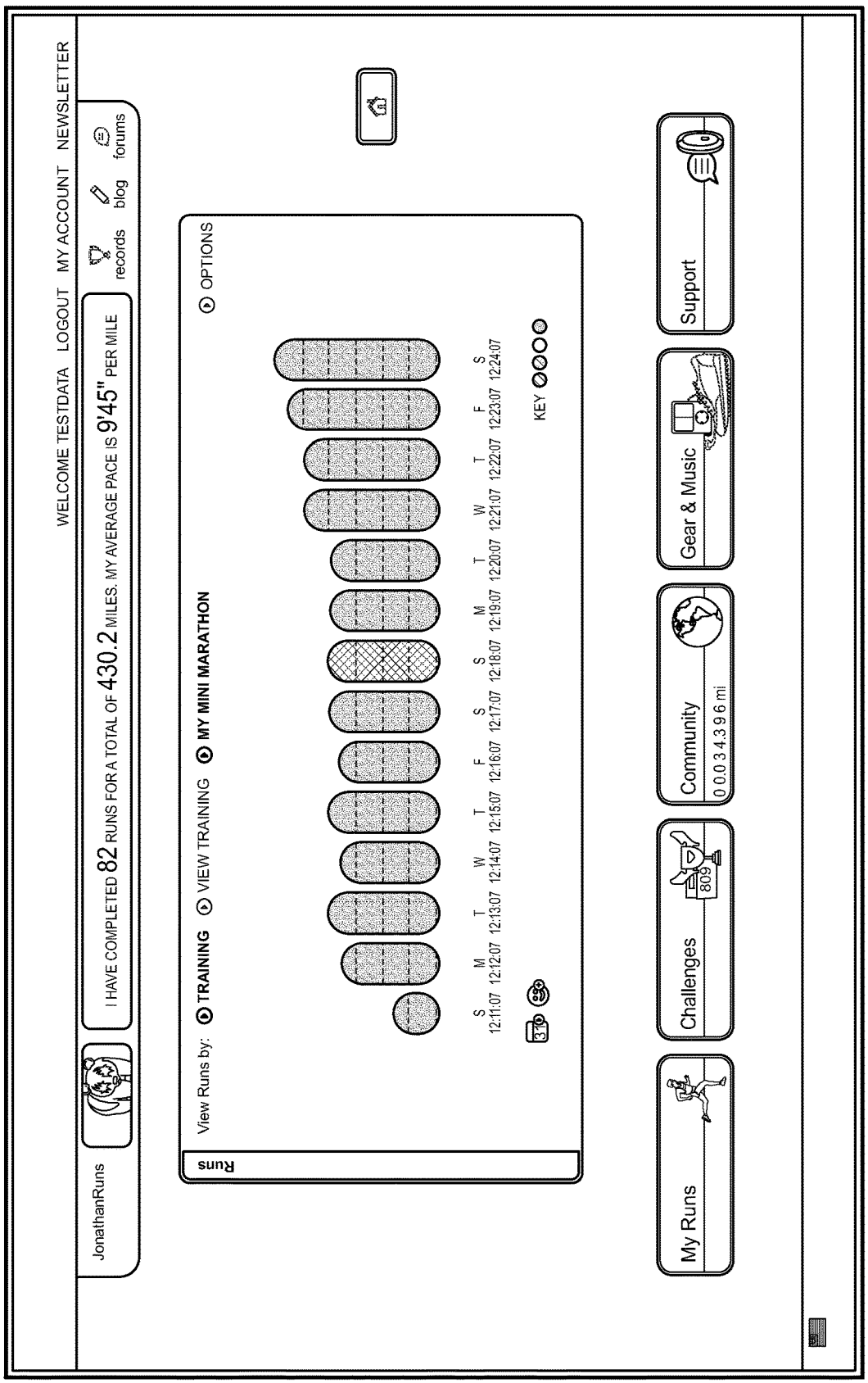

In addition to global changes, a user or athlete may make edits to particular days as illustrated by FIGS. 25-27. For example, a user or athlete may click and drag a portion of the bar representing the run distance on a particular day to increase or decrease the distance that day or to omit running altogether that day. A user or athlete may alternatively numerically input the distance for a particular day. In an embodiment, the edit may only affect those days for which the user or athlete has input an edit. In an alternate embodiment, the user interface 1700 may globally adjust the training program in response to the specific daily edits input by the user or athlete. For example, if a user adjusts the miles run on a first day, a training program system may adjust the number of miles suggested for a subsequent day to make up for the reduced miles on the first day. In another example, the training program system may extend or reduce the training program to make up for the edit. According to one or more aspects, a training program system may further provide a projected end point as compared to a specified goal. Stated differently, if a user makes a change to a training program, the training program may show that the user is projected to fall short of or exceed the goal set. Using such information, a user may adjust other days, if desired, to compensate for projected shortfall or to control an amount by which the user will exceed his or her goal. The training program system may further provide suggestions for adjusting the training program to reach the set goal in view of a user specified edit. FIG. 28 illustrates an example of a finalized training program based on the selections described above.

Figure 29:
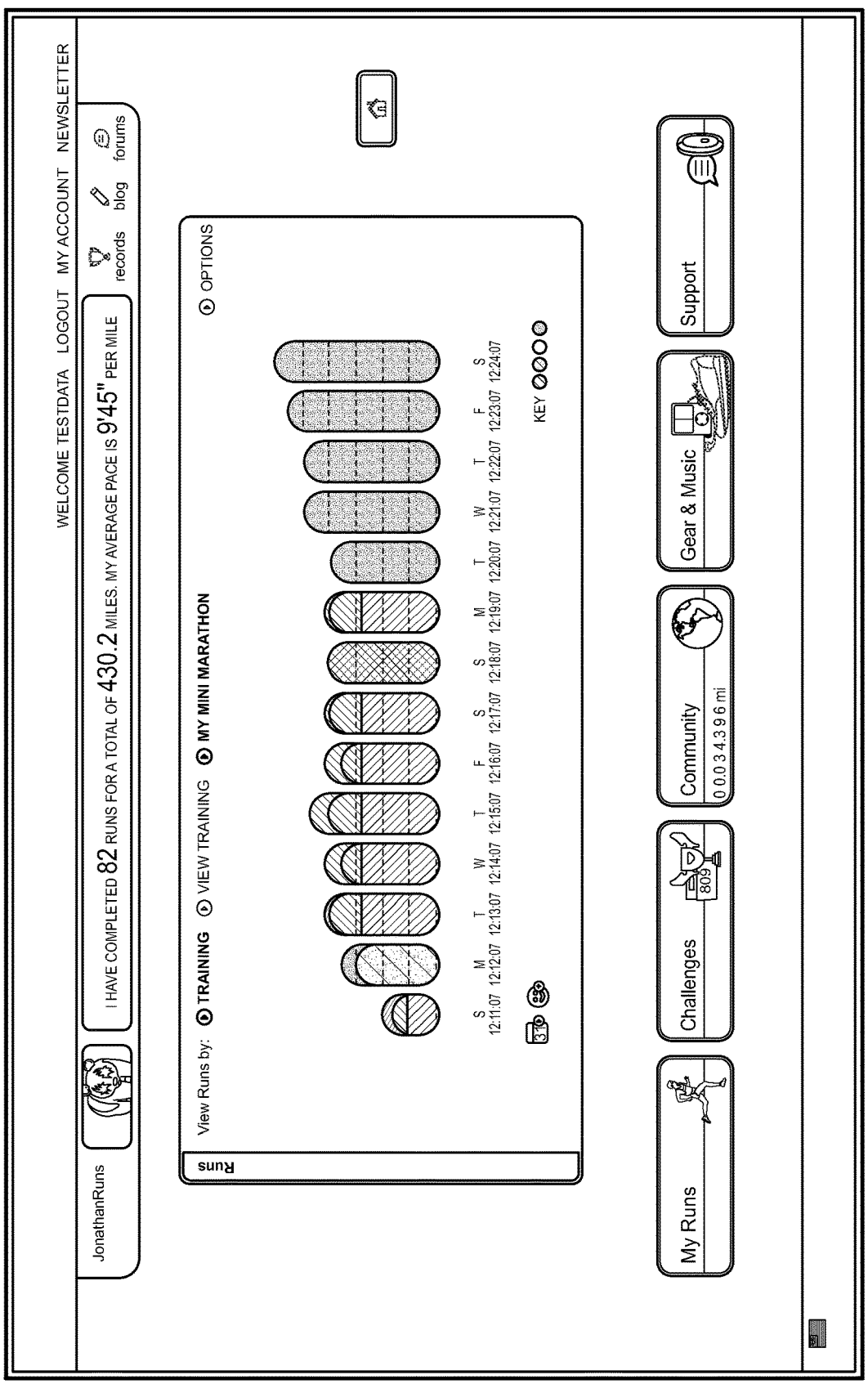

Once the user or athlete has established a goal and the user interface 1700 generates a training program to accommodate the goal (in an embodiment including the skill level selection, daily edits, etc. as introduced above), the user or athlete may begin running at the instruction of the training program. Data representing the performance of the user or athlete may be collected as described with reference to FIGS. 1-16. FIG. 29 illustrates that the actual performance of the user or athlete may be compared graphically to the training program goal on a daily basis. In an embodiment, the actual performance graphical bar may overlay the training program goal bar and/or have a transparency or color difference that allows the user or athlete to compare one to the other. In an embodiment, the actual performance graphical bar overlay may have a different appearance, color scheme, or the like depending on whether the user or athlete, met, exceeded, or fell short of the training goal on a particular day.

Figure 30:
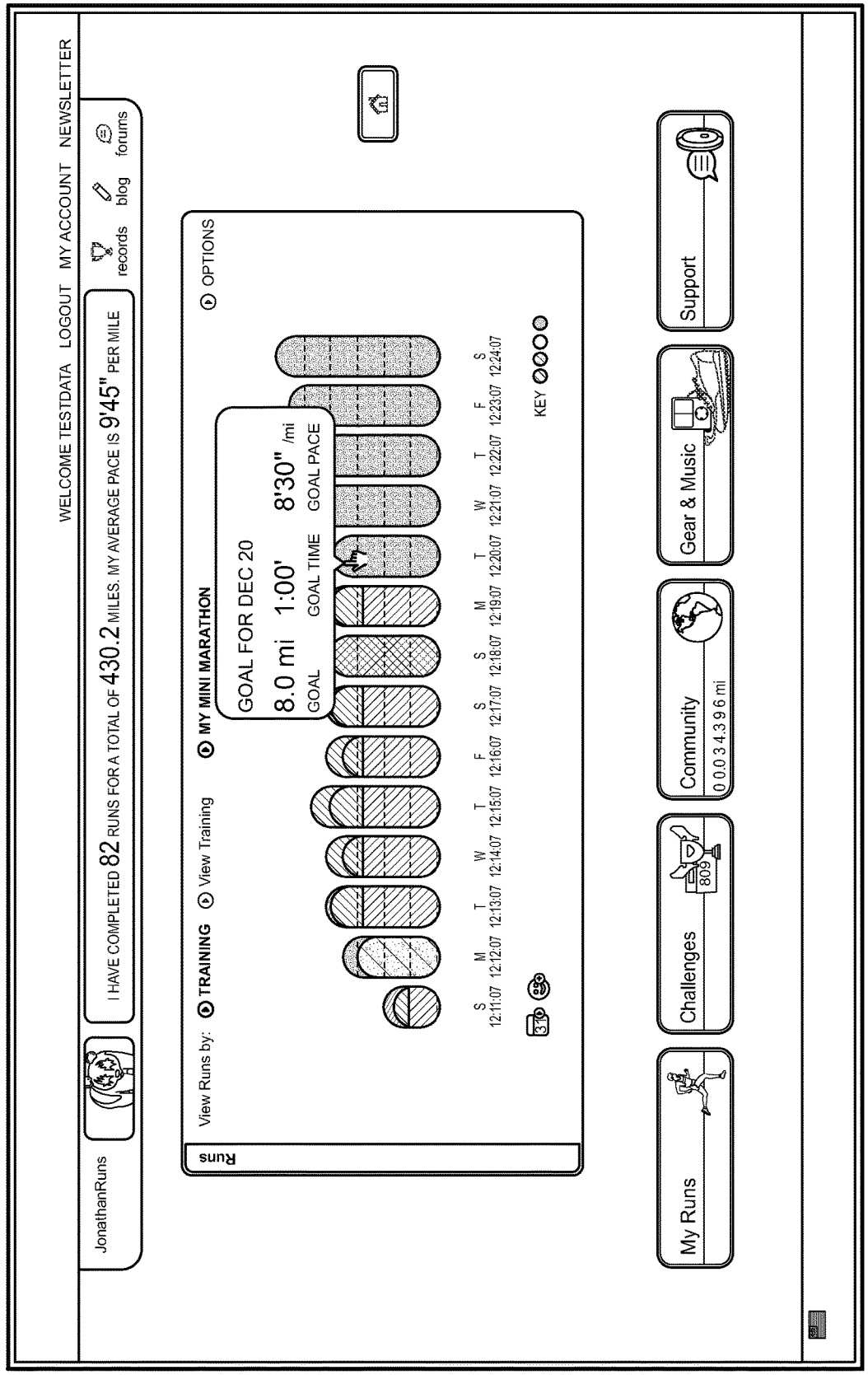
Figure 31:
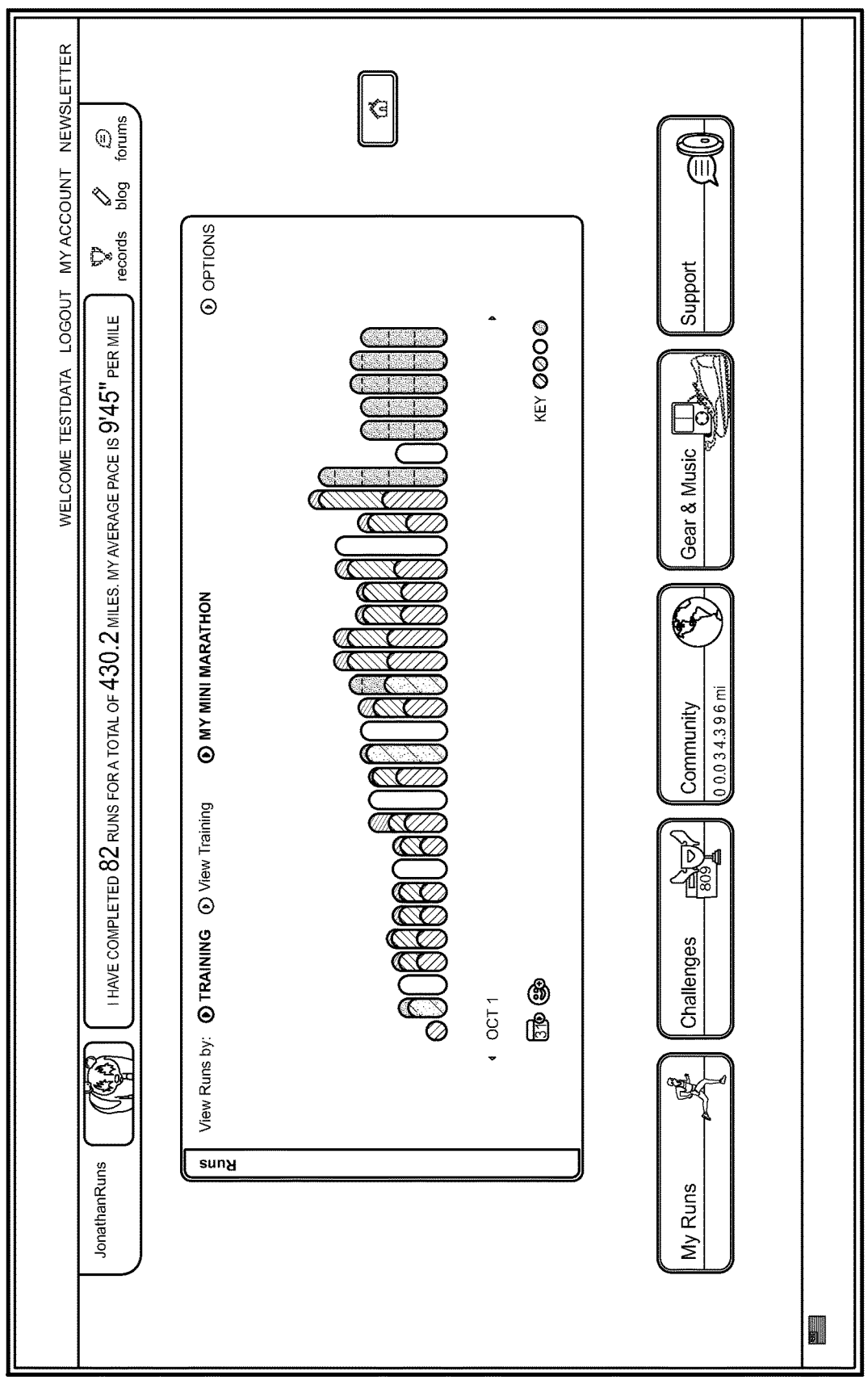
Figure 32:
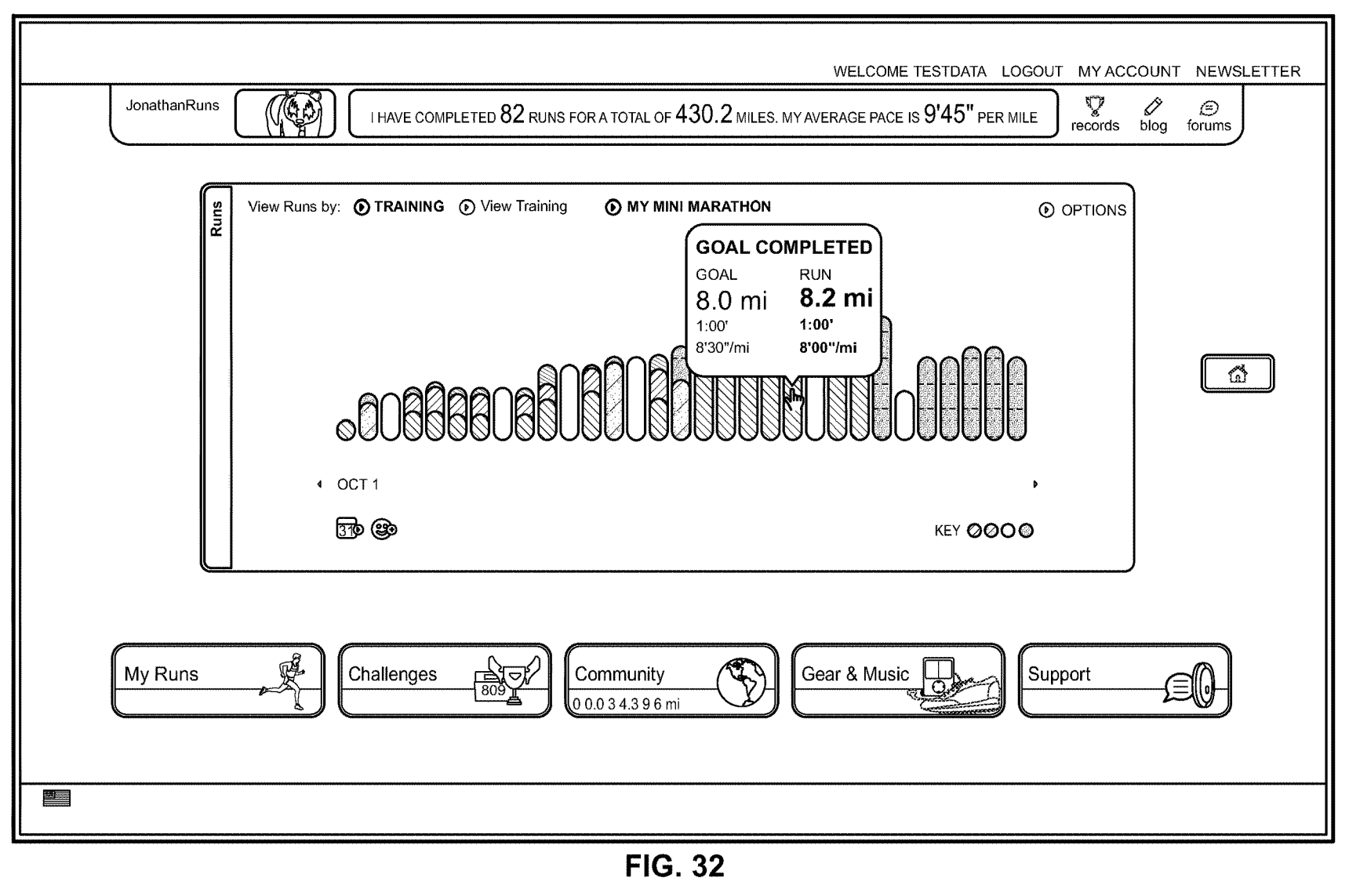
Figure 33:
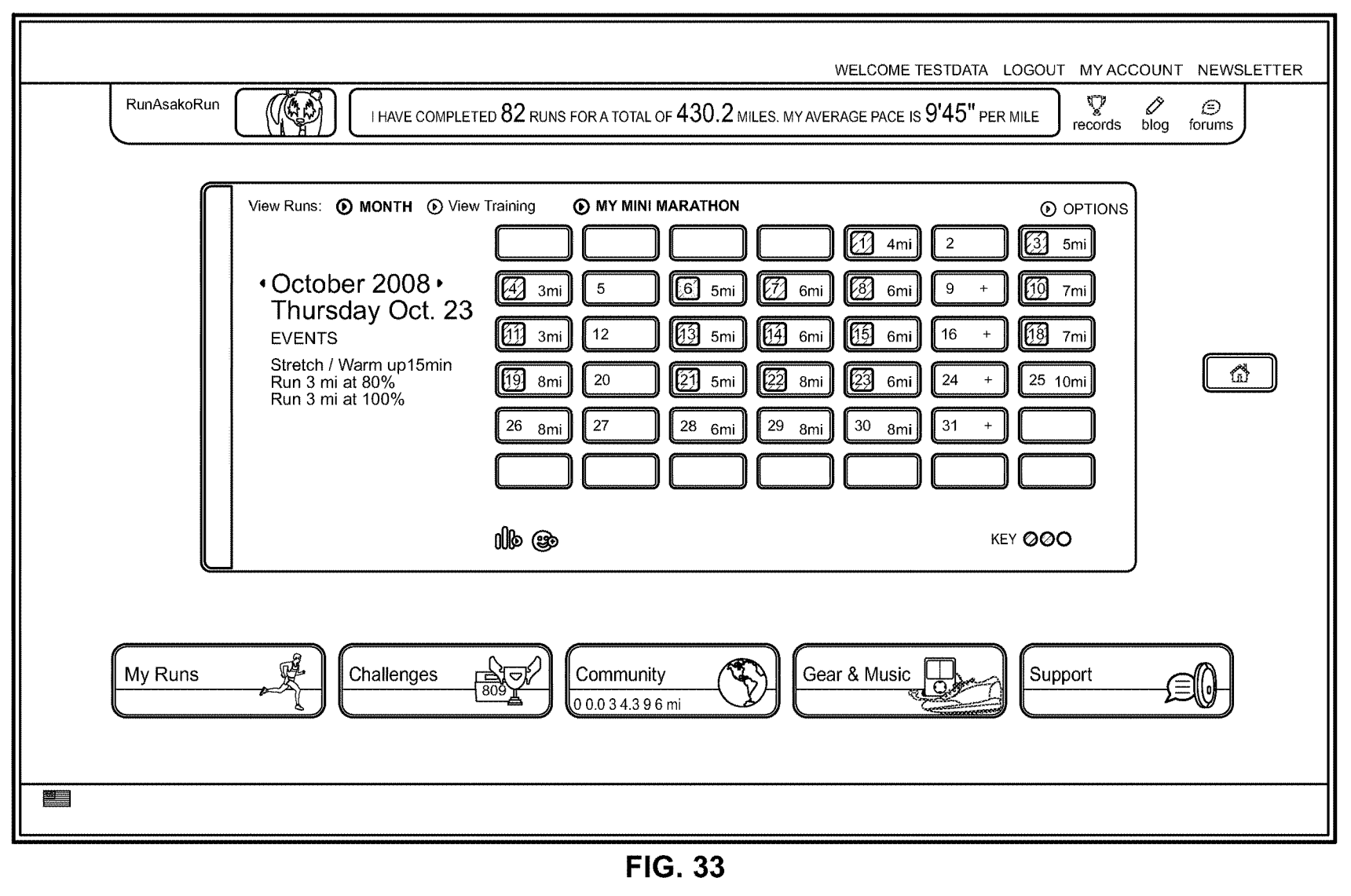
Figure 34:
Figure 35:
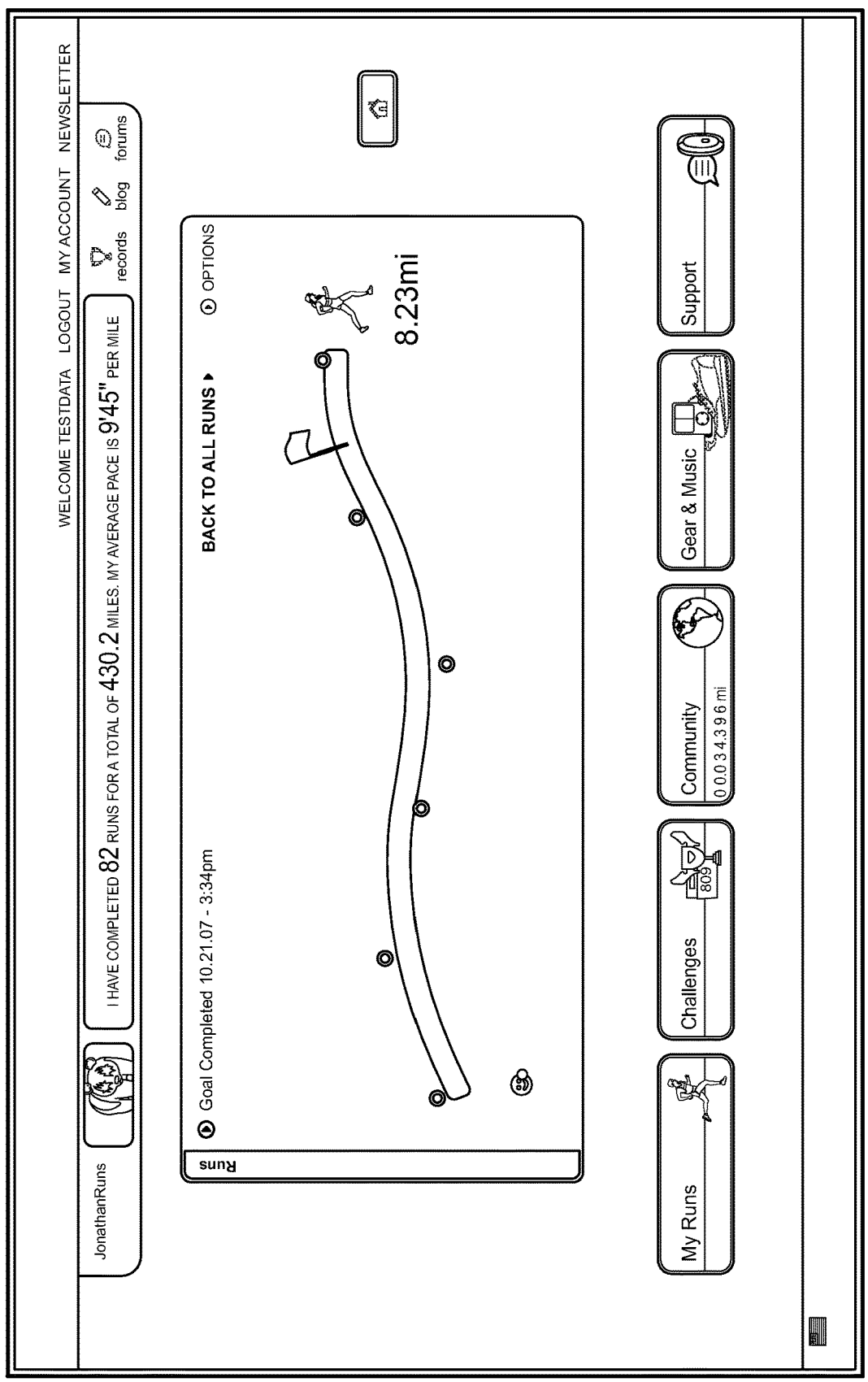
Figure 36:
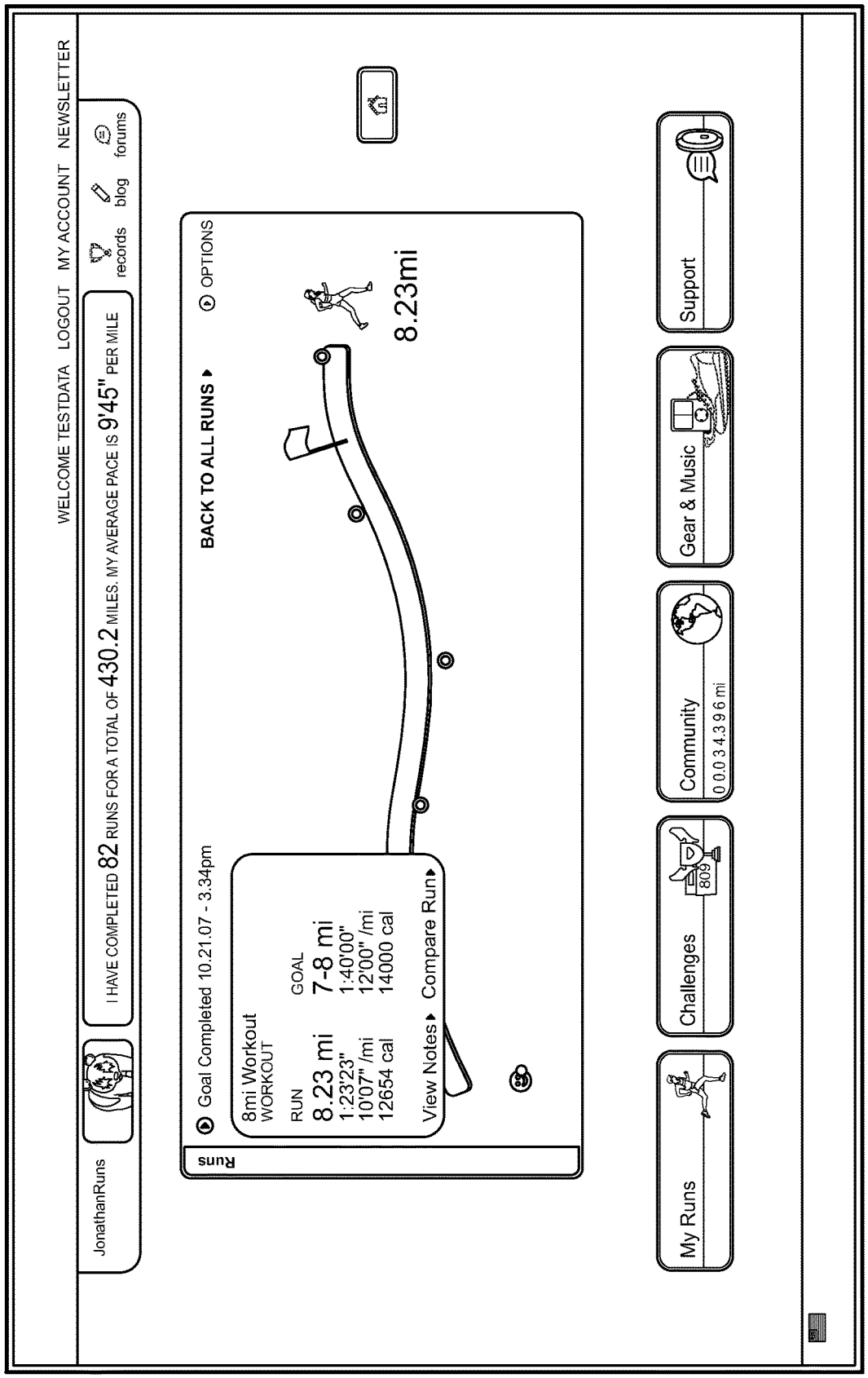
Figure 37:
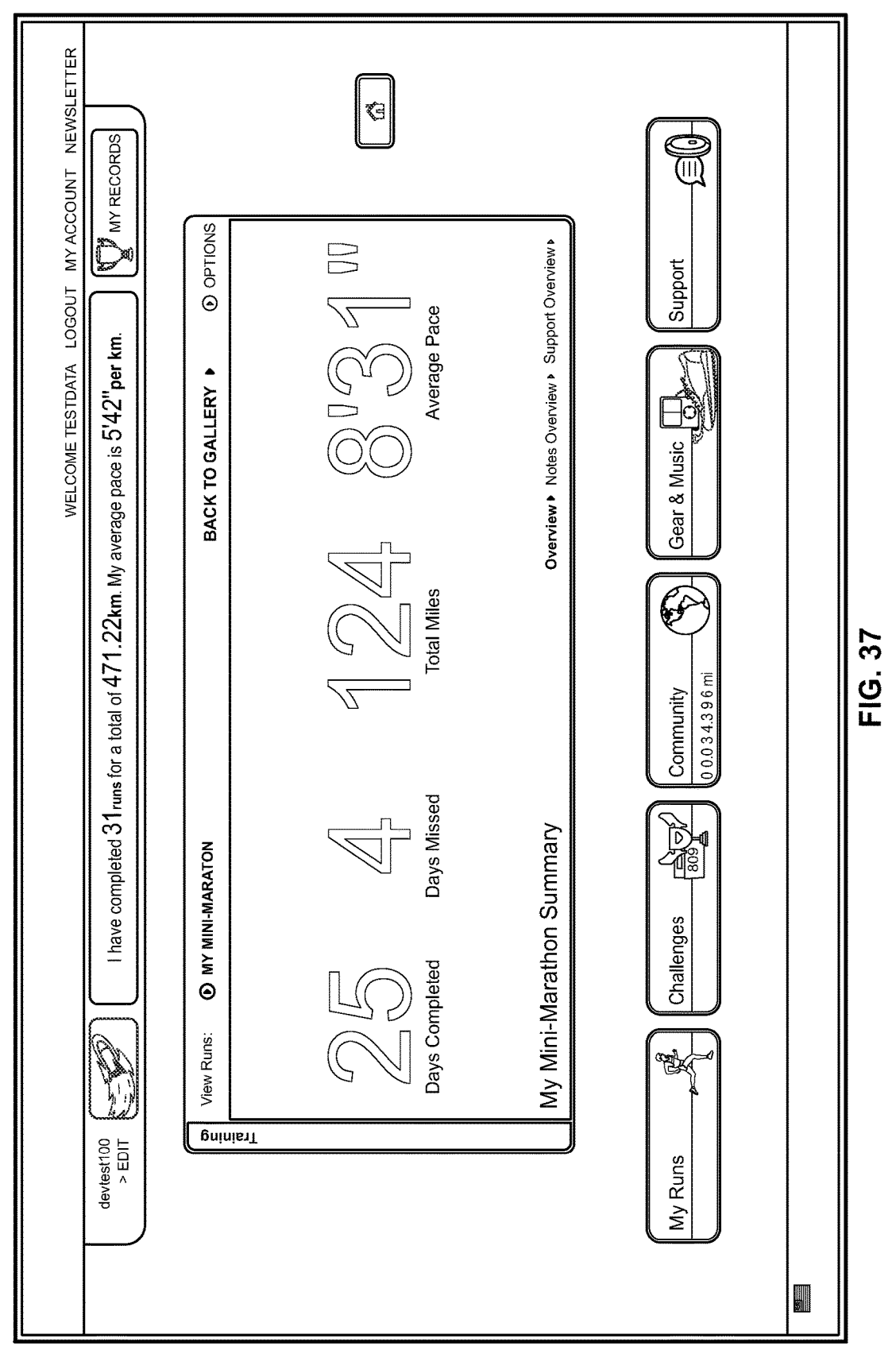
Figure 40:
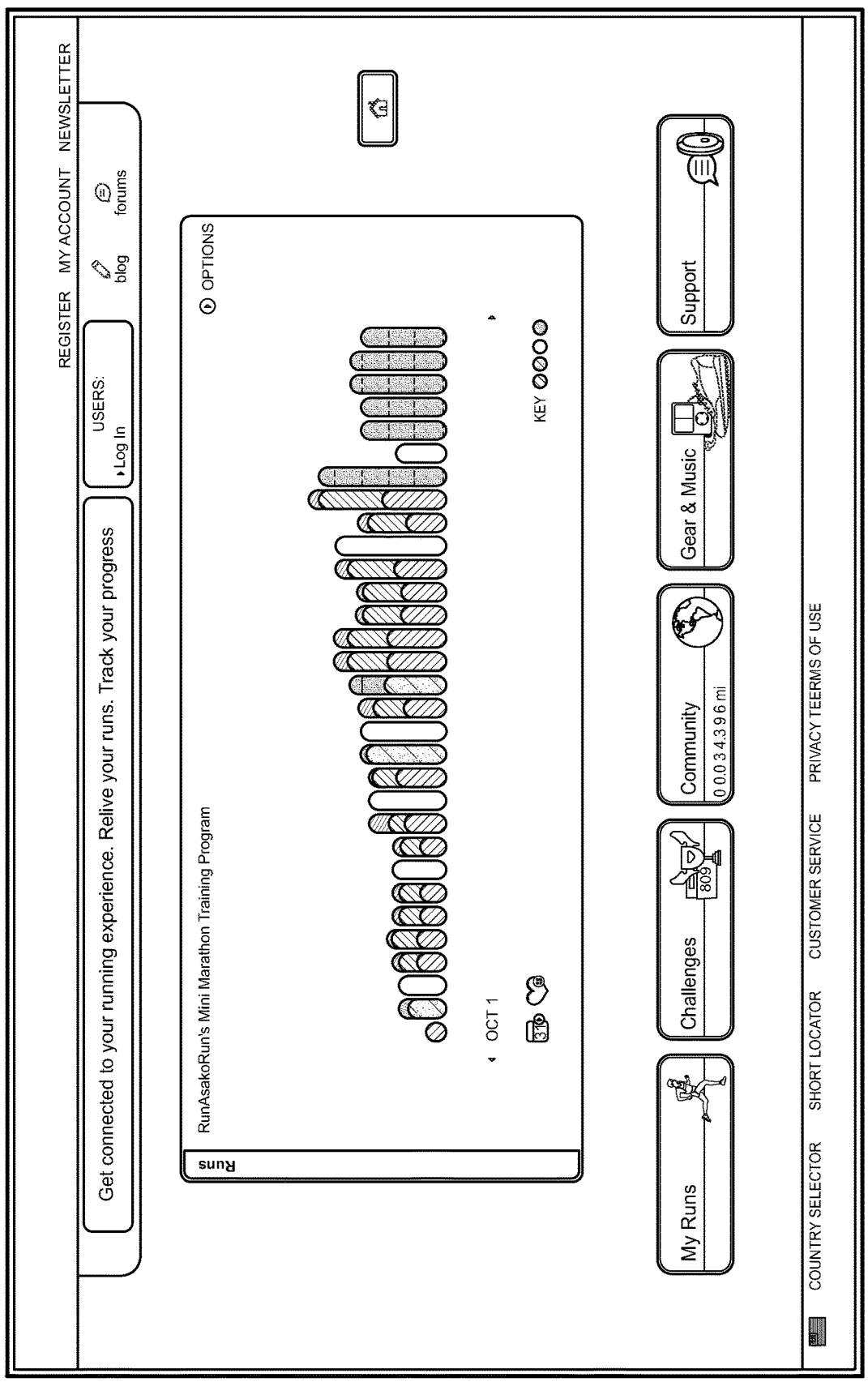

FIG. 30 illustrates that for future training program days, a user or athlete may select the day (e.g., with a mouse or keyboard) to display the numerical run goal details for that particular day. Such information may include the run distance, the goal time for the run, and/or the goal pace. A user or athlete may then be better able to identify the specific training program goals for one or more future training program dates. FIG. 31 illustrates that the user or athlete may also be able to adjust the displayed date range of the training program. Further, as illustrated by FIG. 32, if the user or athlete selects a date for which they have recorded their actual run performance, the user interface 1700 may display the numerical details for both the training program goal and actual performance for that particular date. Further, the display may indicate whether or not the goal has been completed for that date. FIGS. 33 and 34 illustrate an alternate embodiment of the user interface 1700 illustrated by FIGS. 30-32. For example, the training program and actual performance may appear on a month to month basis. Further, individual days may be color coded or otherwise identified as days on which no run is required and days on which runs are required. For days for which actual performance data has been recorded, further color coding or other identification may indicate whether or not the user or athlete achieved the training program goal. FIGS. 35 and 36 illustrate another embodiment of user interface 1700 for which the user's or athlete's progress during a particular run or within a training program is graphically displayed and for which the user or athlete may obtain numerical information representing the training program goal and/or actual performance. Further, FIG. 37 illustrates that the user interface 1700 may display an overall numerical summary of the user's or athlete's progress in a training program including days completed, days missed, total miles run and average pace (e.g., minutes per mile).

In addition to providing the user or athlete a training program, various ways to visualize the training program, and various ways to visualize their progress within the training program, the user interface 1700 of an embodiment may also allow a user or athlete to post notes regarding their training program. For example, a user or athlete may post a note regarding a new pair of shoes they purchased, a particular running route they enjoyed, or just thoughts about running in general. The notes may be private, distributed to a select group of users (e.g., family members, users or athletes participating in the same training program, users or athletes in the same geographic area, users or athletes on a team or in an organization and the like), or may be made public. In addition, those family members, users or athletes participating in the same training program, users or athletes in the same geographic area, and the like, including the public, may post notes for the user or athlete. Such notes may be used, for example, to help support, motivate, and encourage a user or athlete as they undertake a training program.

Figure 41:
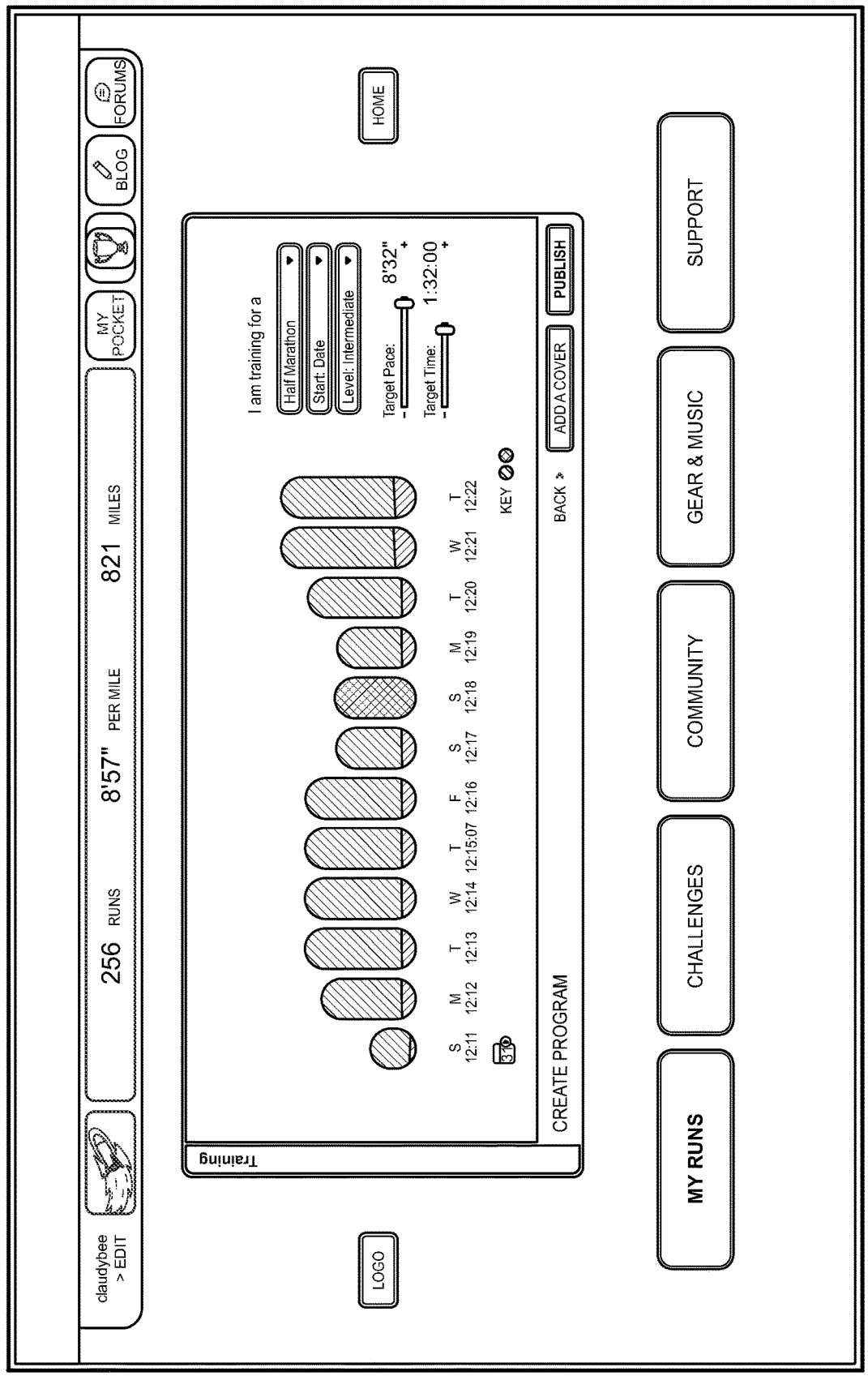
FIGS. 41-62 illustrate an alternate example of the user interface of FIGS. 17-40 that may be provided as a training tool for a user.

While the preceding figures have illustrated the selection and modification of an existing or predetermined program, for example as provided by user interface 1700, FIGS. 41-46 illustrate the creation of a new training program by the user or athlete for themselves or to share with one or more other users or athletes. For example, a coach or trainer may design a training program according to his or her experience. The coach or trainer may thereafter share the created program with their one or more students or trainees. The embodiments are not limited in this context. FIG. 41 illustrates, for example, a completed training program as has already been introduced.

Figure 42:
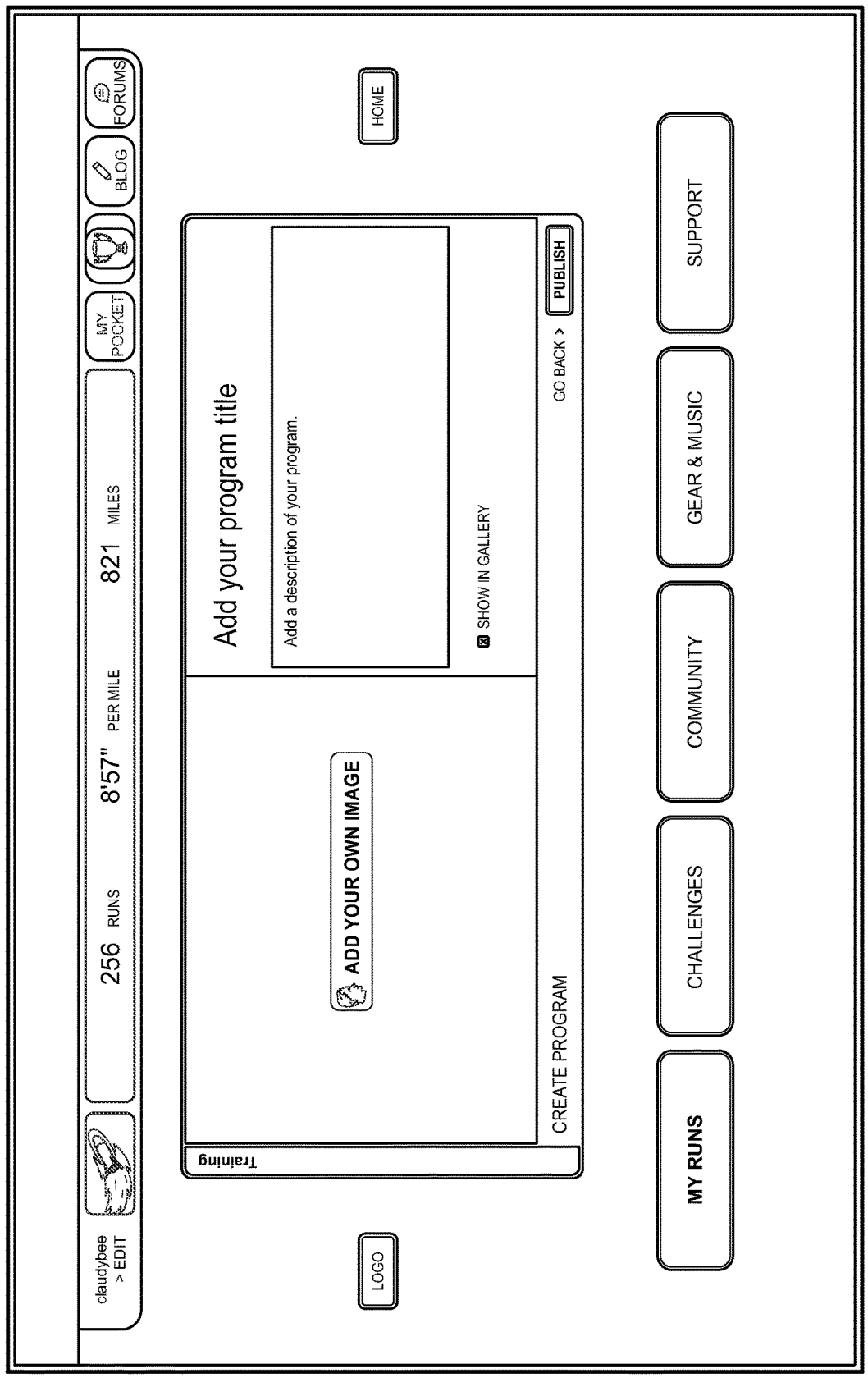
Figure 43:
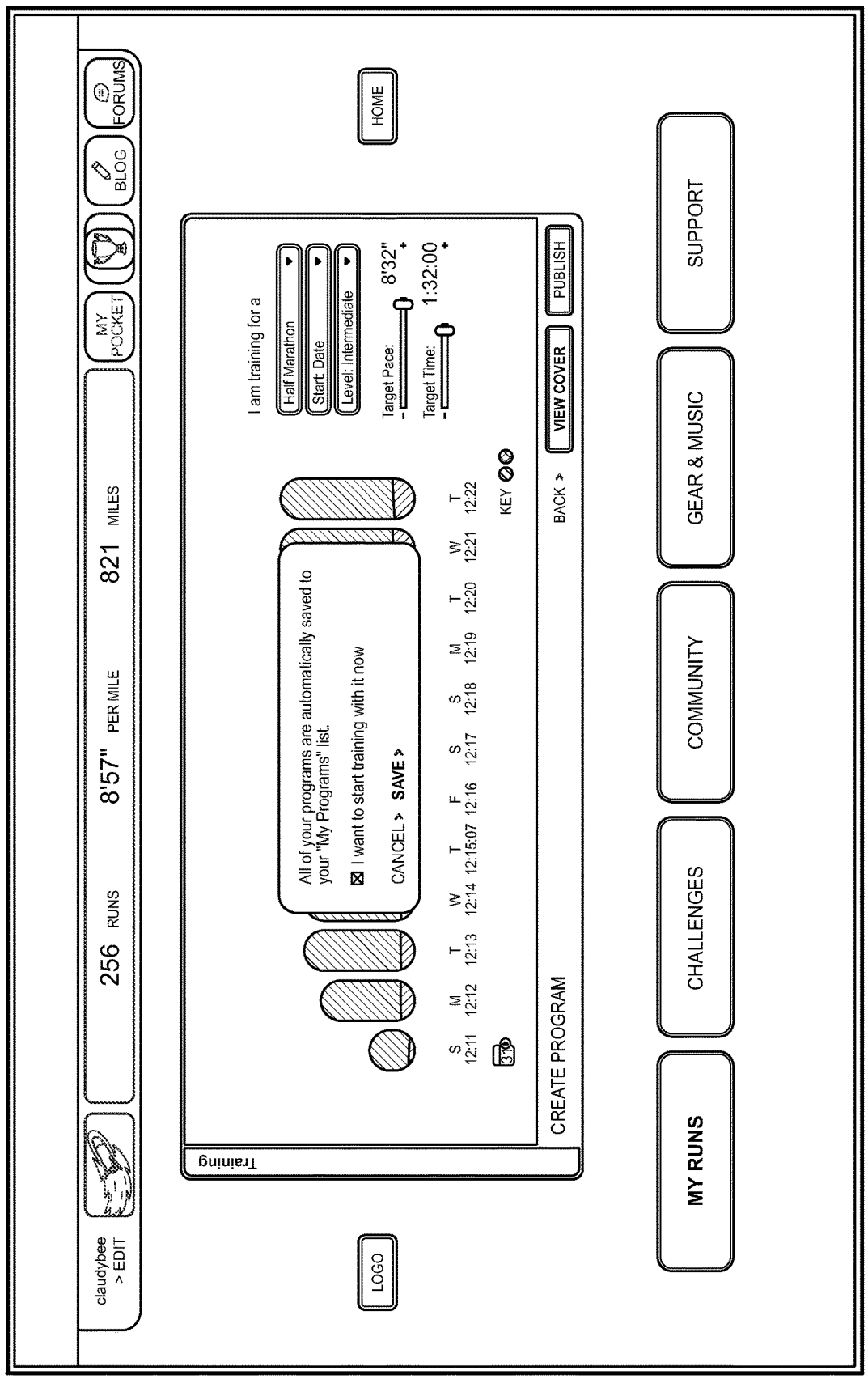

FIG. 42 illustrates the creation of a new training program. Before establishing run parameters, a user or athlete may have the opportunity to provide their training program a title, a narrative description, and an image, picture, icon, or logo representing the training program. FIG. 43 illustrates that individual days may be adjusted in terms of training program run distance. Further, the user or athlete may specify the type of event, skill level, start date, for their training program so that their training program may be classified and/or so other users or athletes can determine whether or not the training program is appropriate for their personal goals. Further, FIG. 43 illustrates that during the training program creation and/or editing, a user or athlete may save their training program, have their training program saved automatically, delete the program, or begin the training program (e.g., start training) In one arrangement, a user may save a training program that is not completed so that the user does not have to complete the training in one sitting.

Figure 44:
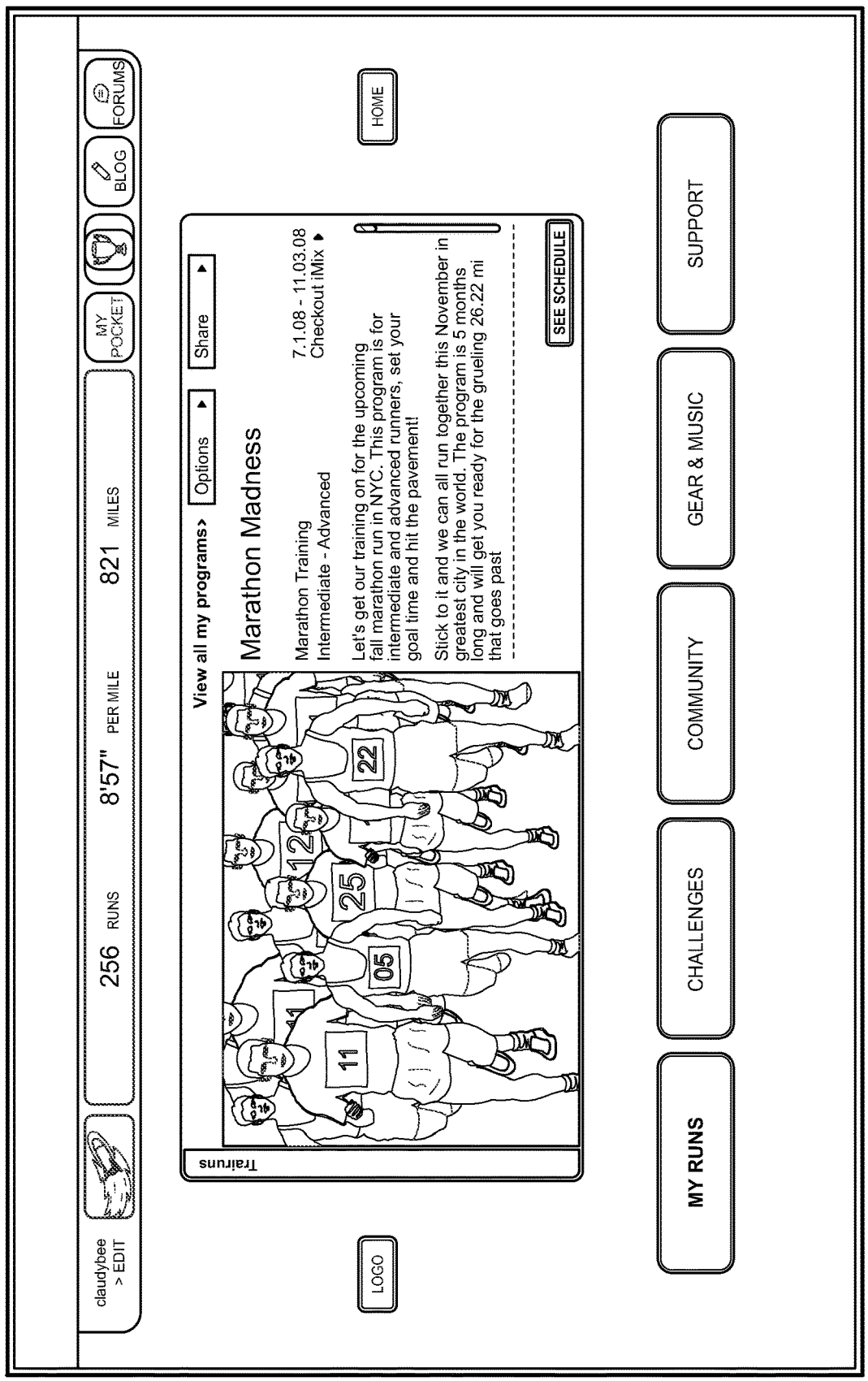
Figure 45:
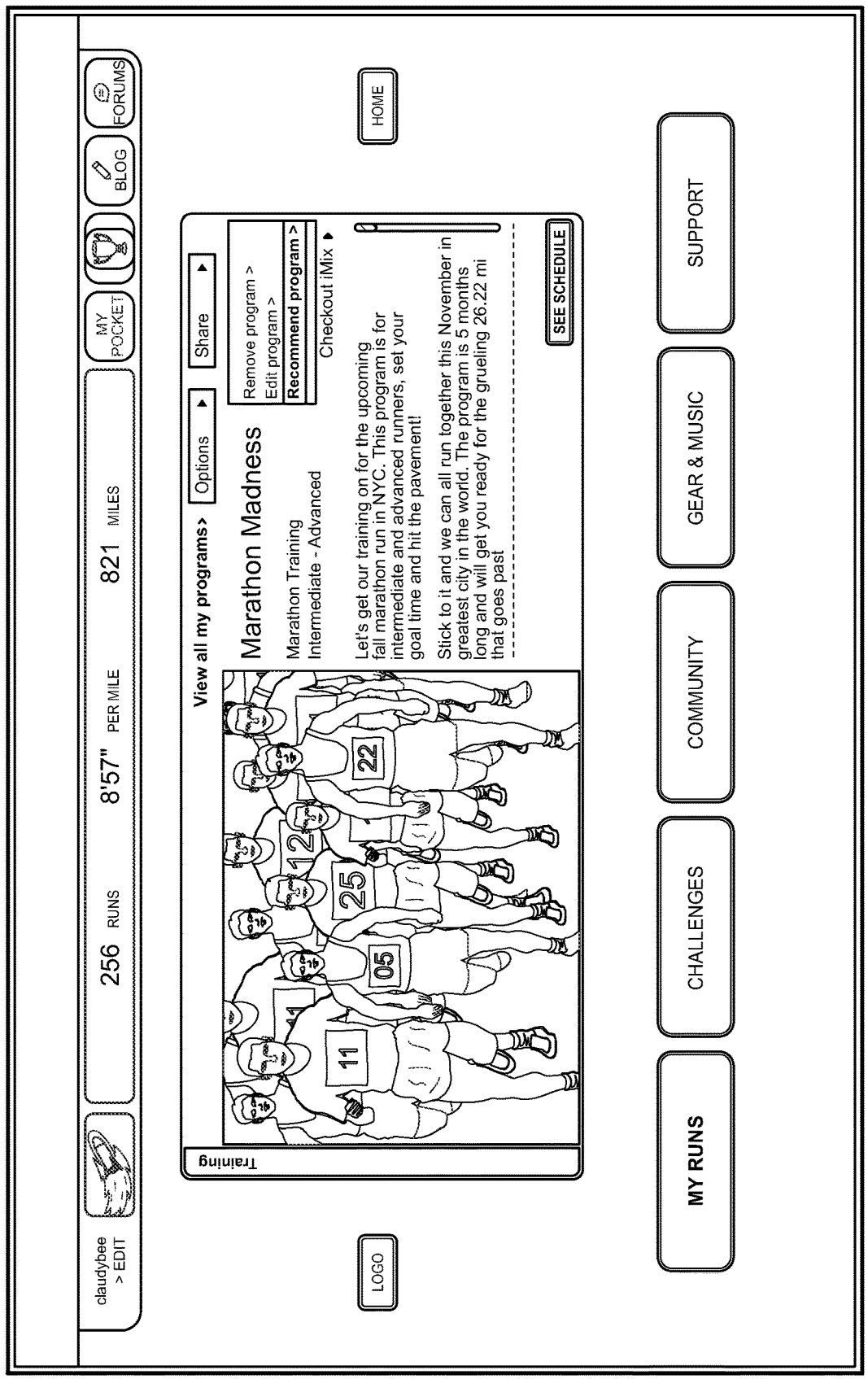
Figure 46:
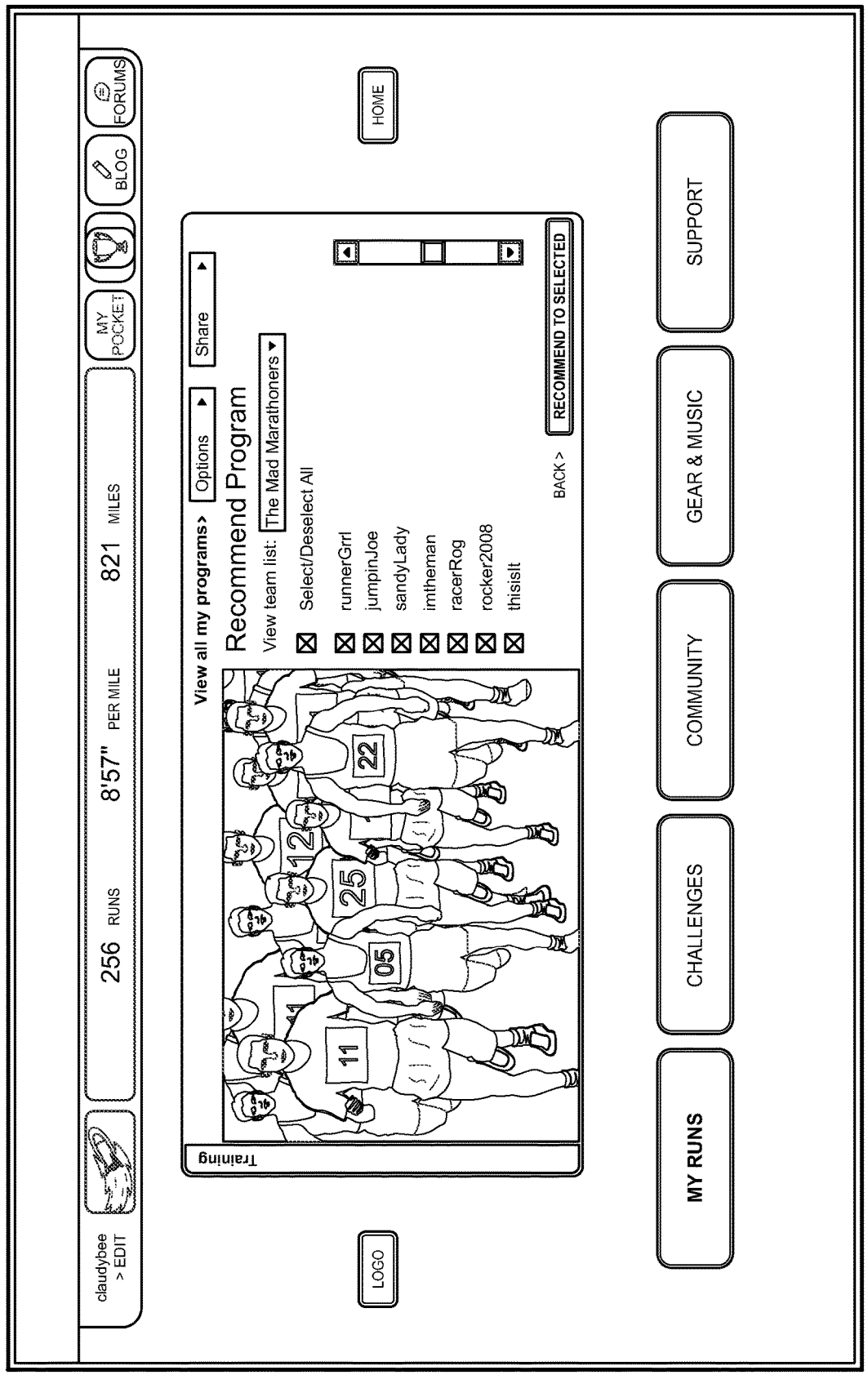

FIGS. 44-46 illustrate the management and distribution of created training programs. For example, FIG. 44 illustrates a program titled "Marathon Madness." As introduced, the title may be accompanied by an image, picture, icon, or logo (in this case, a picture of marathon runners appropriate to the purpose or goal of the training program). FIG. 44 also illustrates the recommended skill level for the training program, the start date and end date (i.e., the duration) of the training program, and a narrative description of the training program. A user or athlete, if interested, may further view the specific schedule associated with the training program. FIG. 45 illustrates that after a user or athlete has selected a training program, they may thereafter remove it from their list of programs, edit the program, or recommend the program to other users or athletes. The recommendation may be directed to individual users or athletes, members of a team, members of an organization, and the like. For example, FIG. 46 illustrates that a user or athlete may select a team or organization and then select one or more individual users or athletes associated with that team or organization to receive the training program recommendation.

FIGS. 47-62 illustrate an alternate embodiment of user interface 1700 to facilitate the training of a user or athlete. At any time during the training program, as user or athlete may review their progress summary. For example, user interface 1700 may display an overall numerical summary of the user's or athlete's progress in a training program including days completed, days missed, total miles run, and average pace (e.g., minutes per mile). Further, the user interface 1700 may display the date the training program was created or started, the recommended level for the user or athlete (e.g, novice, beginner, intermediate, advanced, and the like), and the goal time for the training program distance (e.g., one mile, five kilometers, ten kilometers, half marathon, marathon, and the like).

Figure 48:
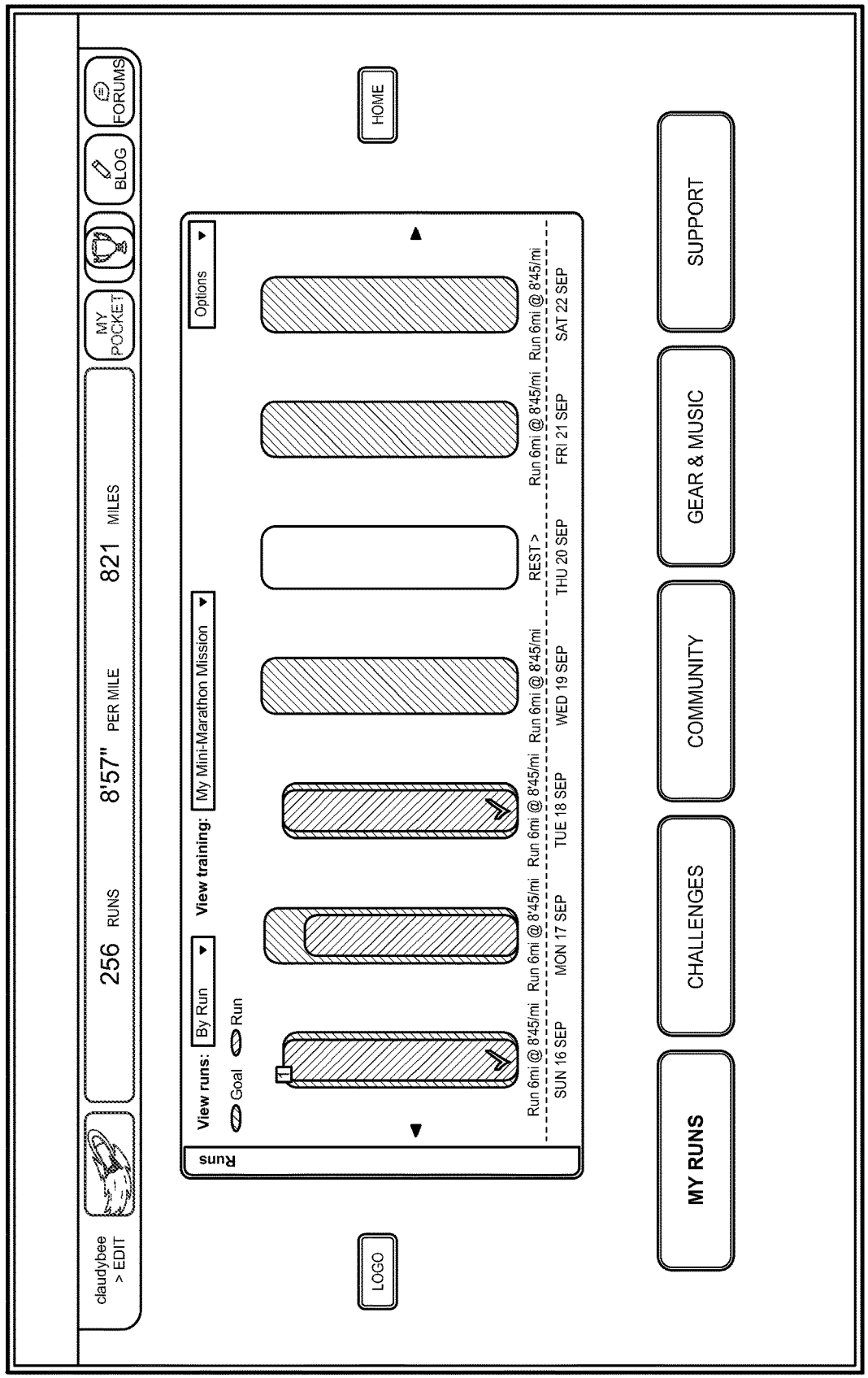

FIG. 48 illustrates the details of the training program of an embodiment including actual results. For each day, the running goal may be illustrated both graphically and numerically. More specifically, the running goal may be illustrated as a bar having a particular color, color scheme, or shape. Similarly, the actual performance may be illustrated as a bar having a particular color, color scheme, or shape. In an embodiment, the actual performance bar may further be partially transparent and overlaying the running goal. In an alternate embodiment, the actual performance bar may have, for example, a narrower width so that the running goal will still be visible as the actual performance is overlaid. Further, training program days without running goals may be labeled as rest days and may be illustrated with bars of a different color, color scheme, and/or shape than those representing days with running goals. In an embodiment, an additional indication may be illustrated, for example a check mark, for those days that the user or athlete's actual performance met or exceeded the training program goal. An alternate indication may be selected, for example an X, for those days the user or athlete's actual performance did not meet the training program goal.

Figure 49:
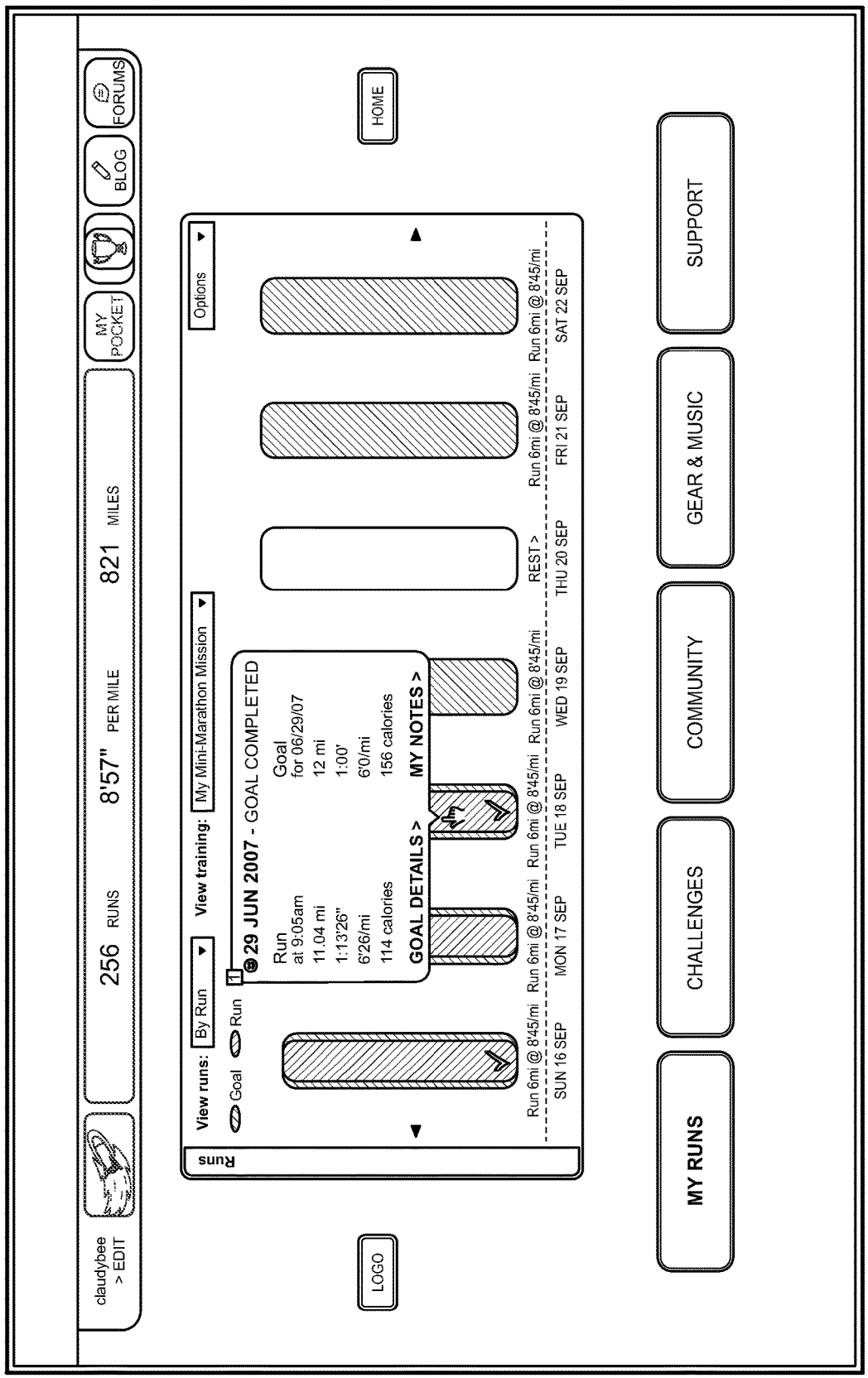

FIG. 49 illustrates that a user or athlete may select a particular day to review the numerical details of the training program goal. For example, upon selecting a particular day, the user interface 1700 may display the goal distance, the goal time, the goal pace, and the goal calorie usage. For those days on which the user or athlete has run, the user interface 1700 may also display the actual performance distance, actual performance time, actual performance pace, and actual performance calorie usage. In an embodiment, the user interface will also display a graphical indication that the actual performance did or did not meet the training goal.

Figure 50:
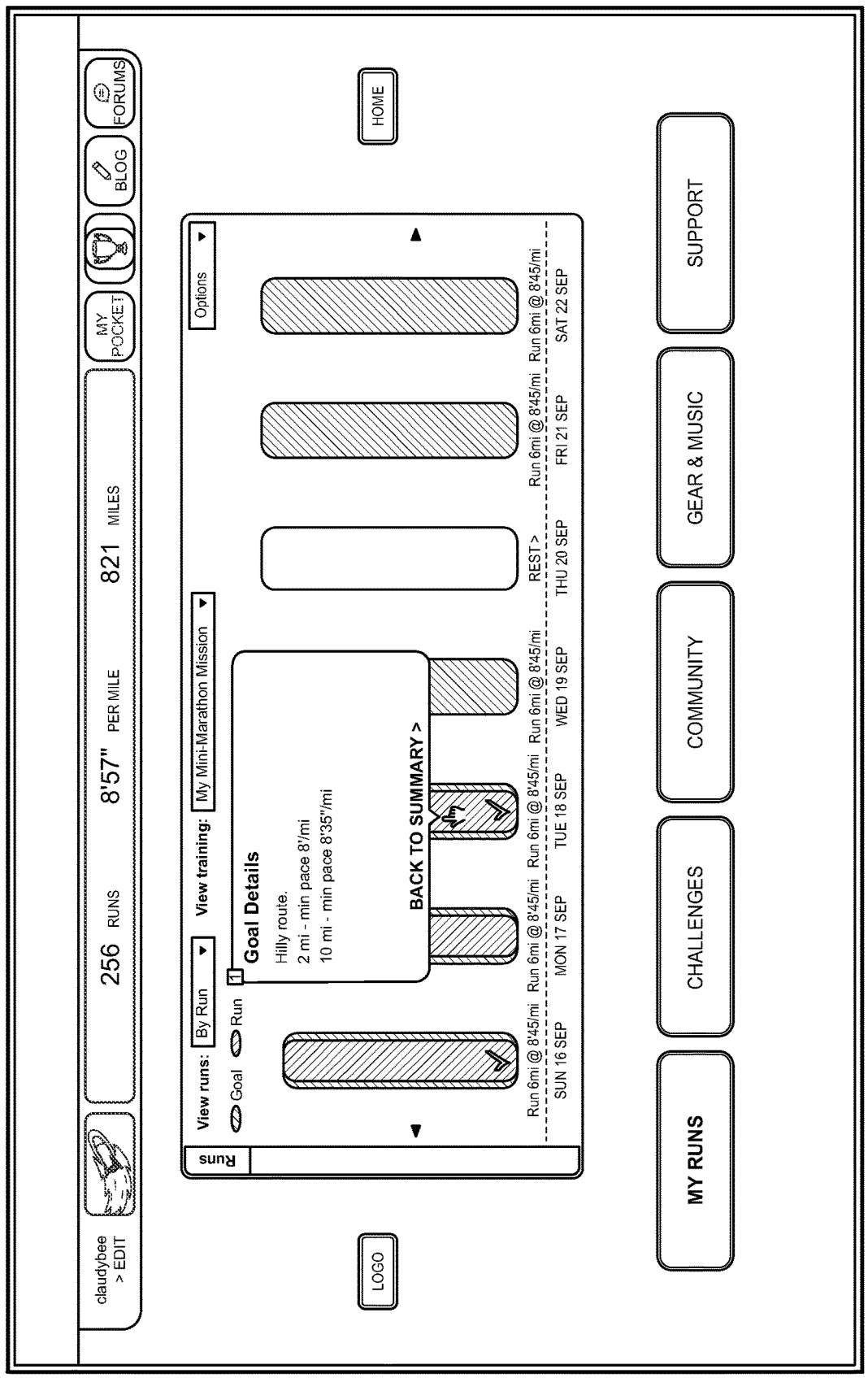
Figure 51:
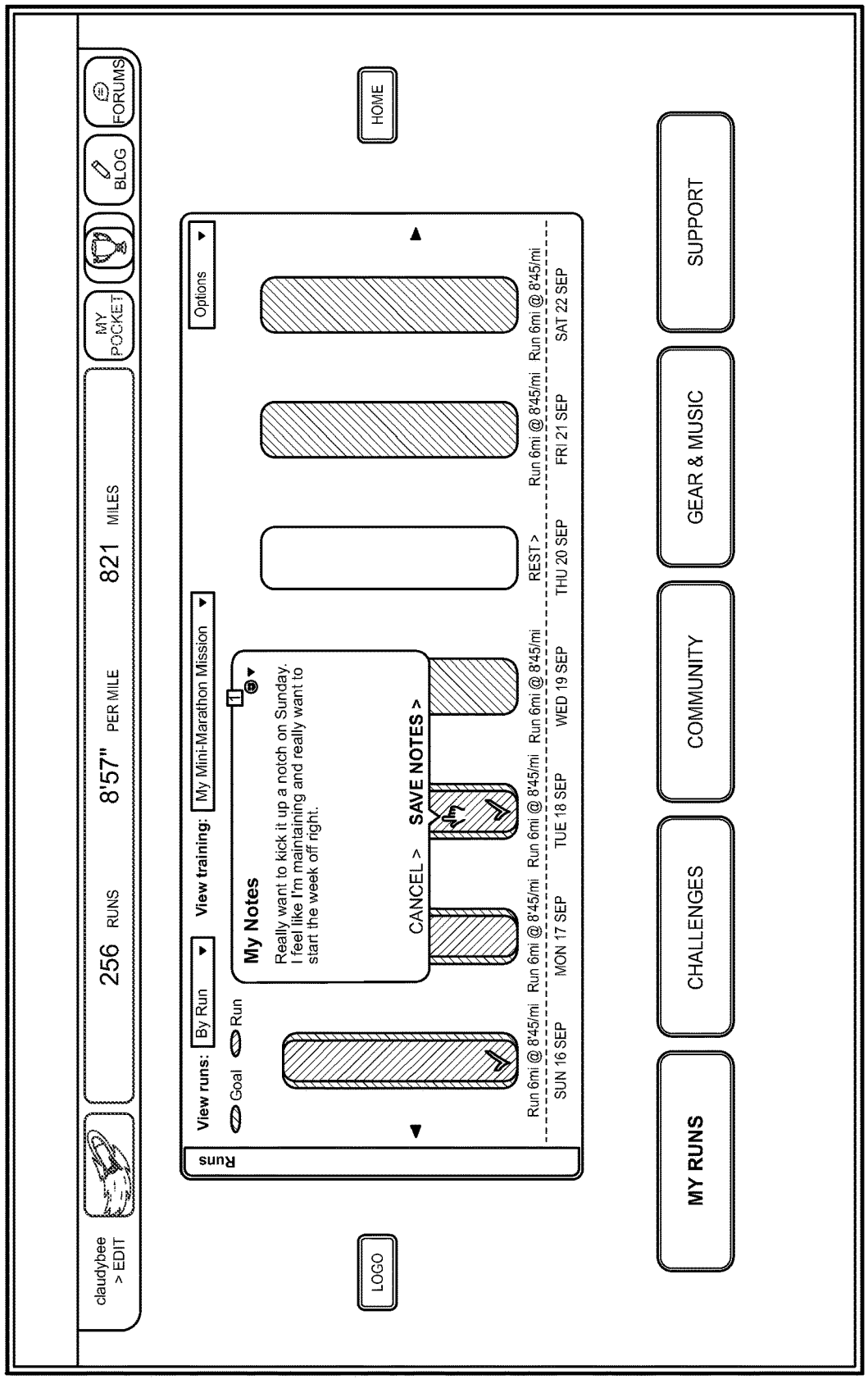
Figure 52:
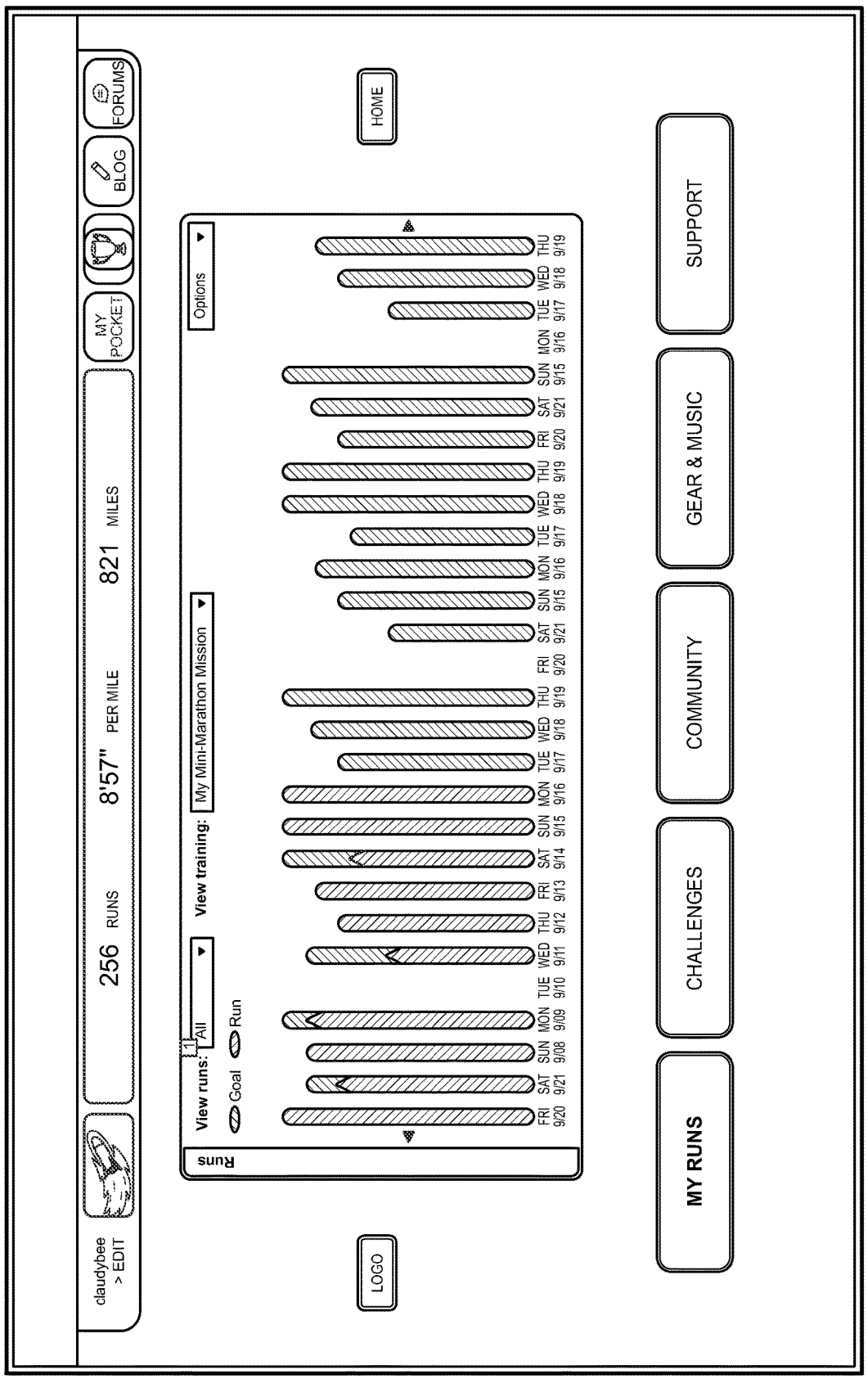
Figure 53:
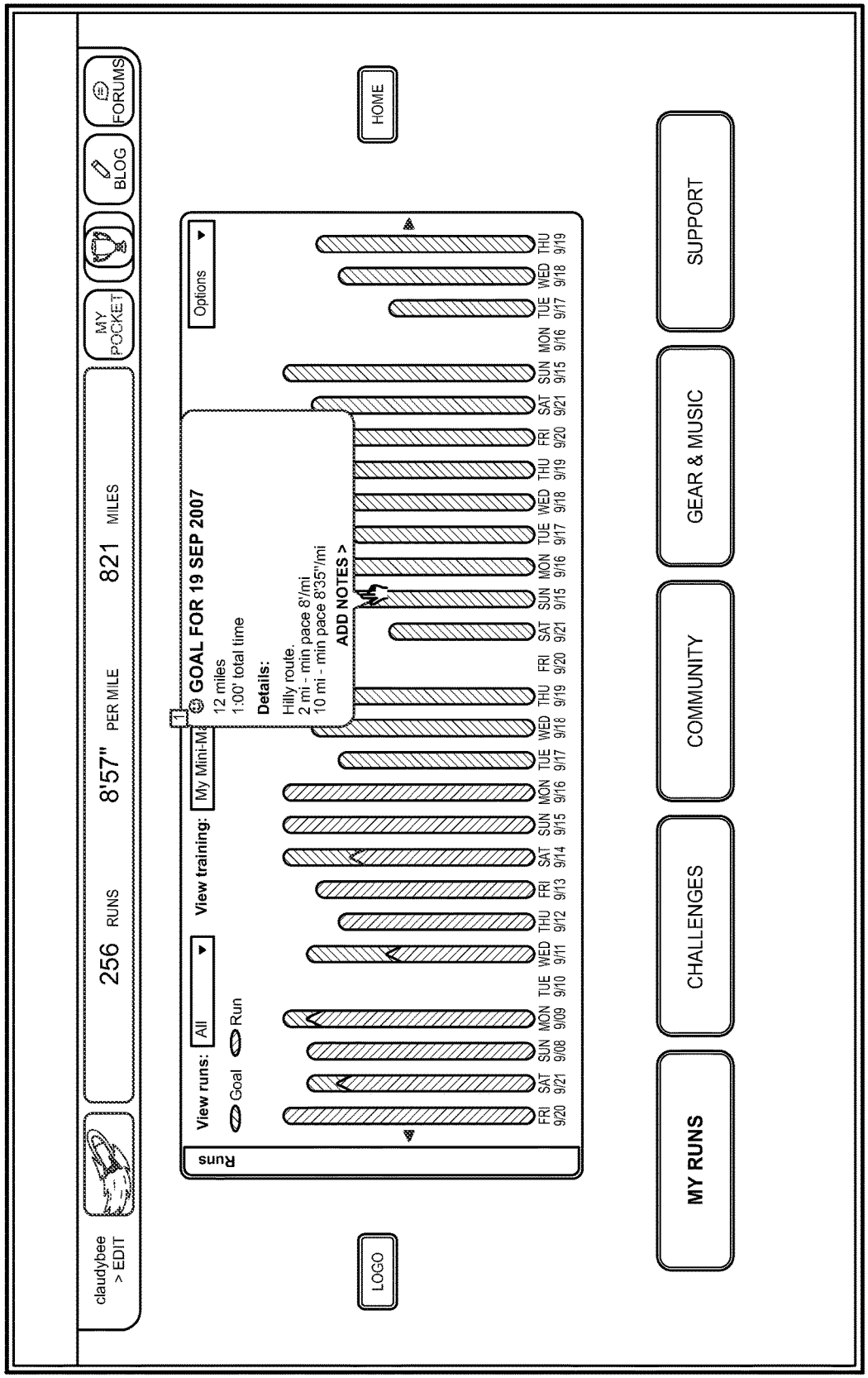
Figure 54:
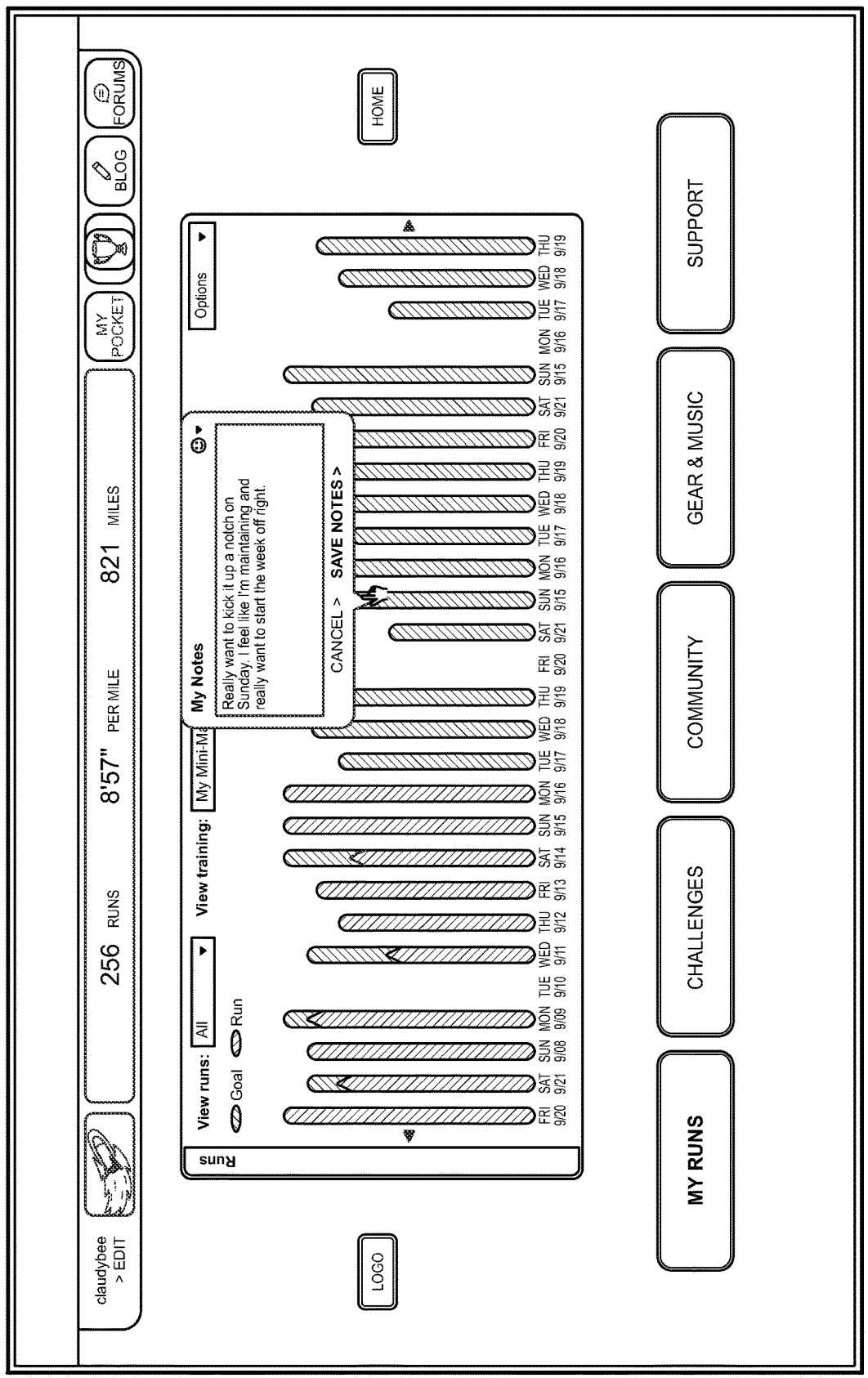

FIG. 50 illustrates that additional details may be associated with a particular training goal, actual performance, or training day. For example, the training goal details may indicate that the running route for that particular day was hilly and that the goal pace reflected that portions of the route would be more difficult (e.g., have a slower pace) than other portions. Further, FIG. 51 illustrates that the user or athlete may provide notes associated with a particular training goal, actual performance, or training day. The user or athlete may further be able to select an emotional icon (i.e., an emoticon) to reflect their mood or the like in the note(s). FIGS. 52-54 illustrate that the date range of the training program illustrated by FIGS. 48-51 may be altered to include fewer or more days. (e.g., month view versus a week view).

Figure 47:
Figure 55:
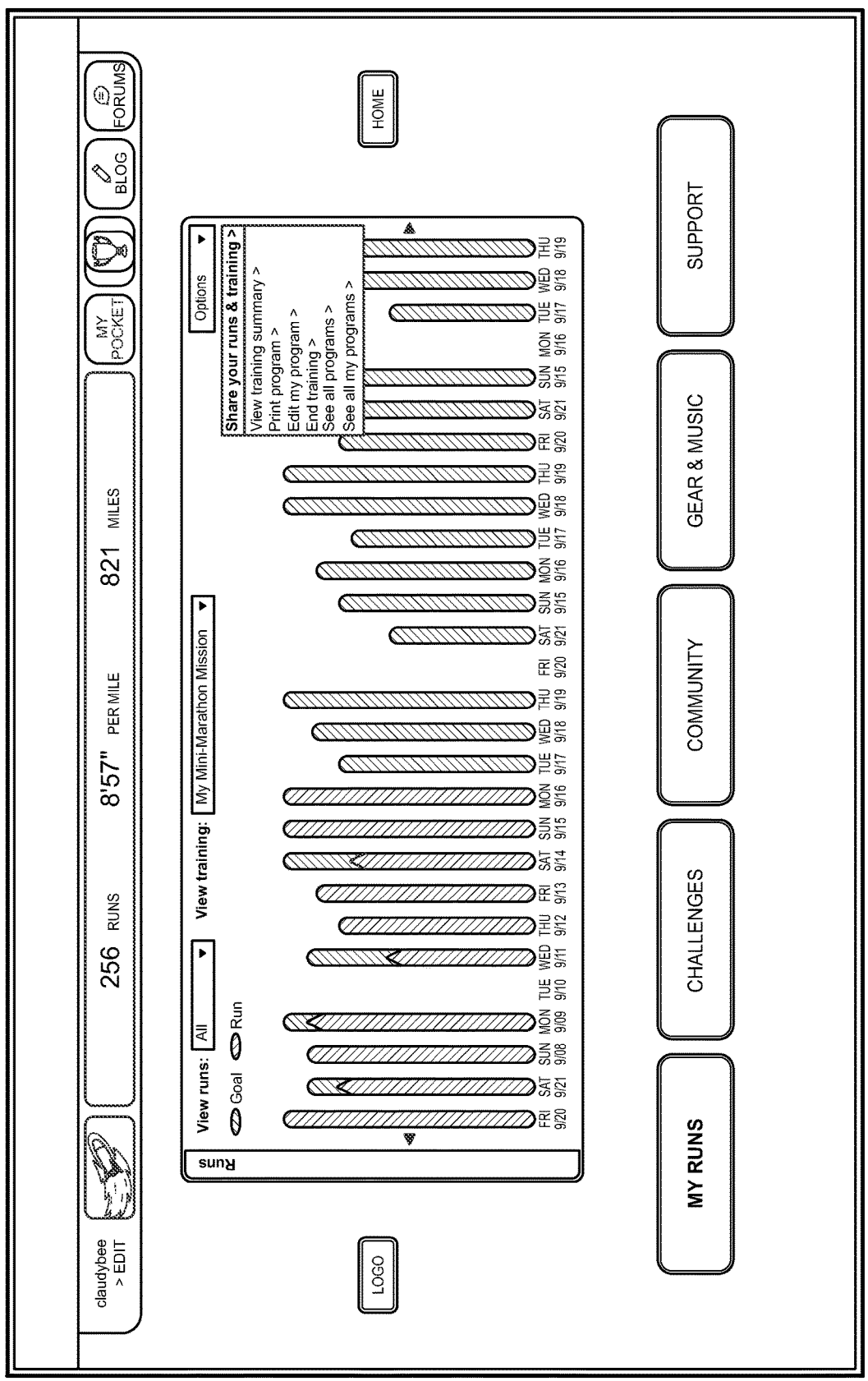

FIG. 55 illustrates that the user or athlete has a variety of options available with respect to a training program. For example, a user or athlete may share their program with one or more other users or athletes. A user or athlete may view a summary of their training program (e.g., as illustrated by FIG. 47), edit a current training program, or end training In addition, a user or athlete may search for or review additional training programs available globally or from a subset of training programs associated with the user or athlete.

Figure 56:
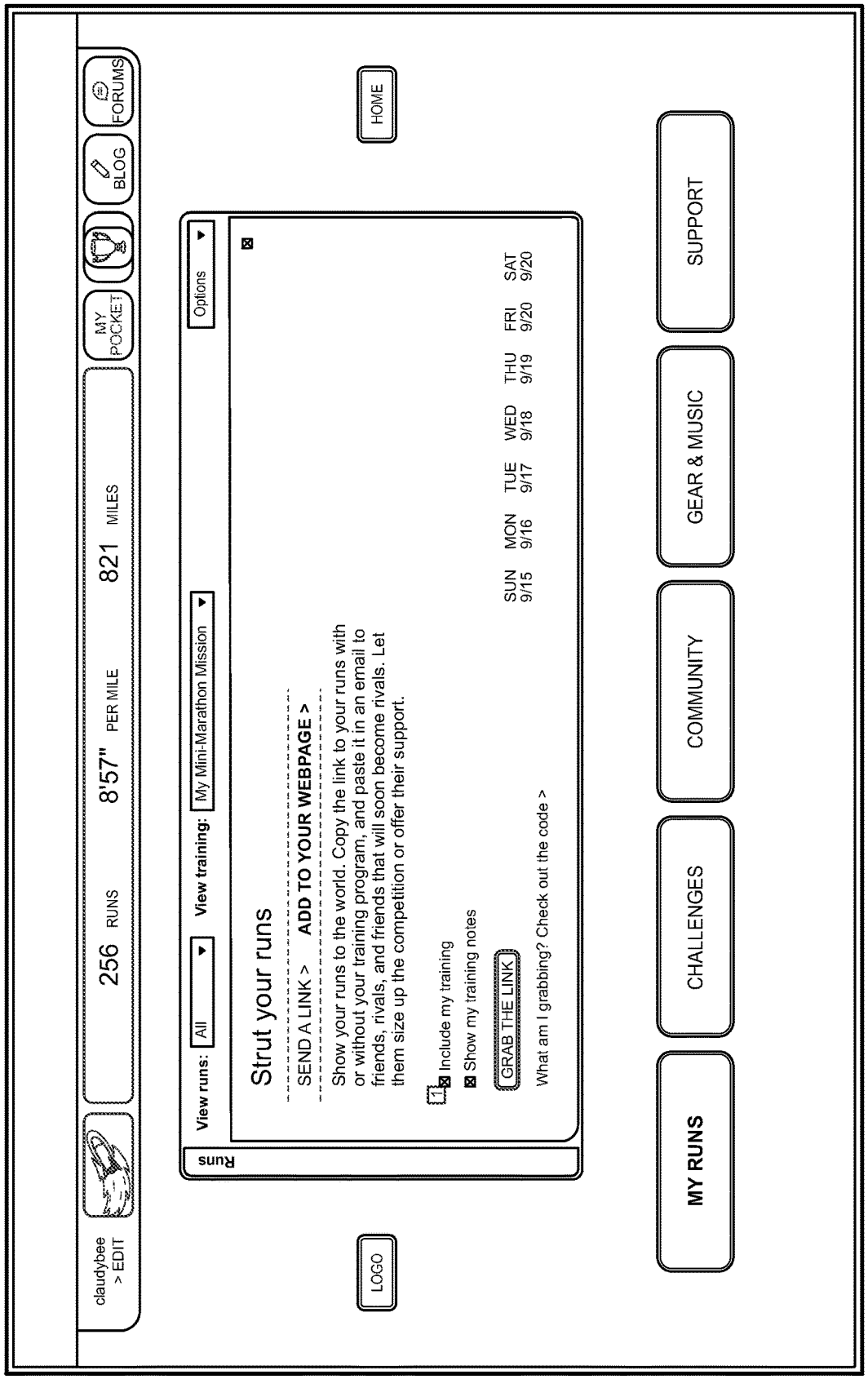

FIG. 56 illustrates that a user or athlete may distribute or post information regarding their progress in a training program. More specifically, a user or athlete may send a link (e.g., via email) to one or more recipients. Further, a user or athlete may include the information in a personal web page or social network page (e.g., as HTML code or the like). In each case, in addition to their actual performance, a user or athlete may further distribute or post their entire training program schedule and/or their notes associated with a particular training goal, actual performance, or training day.

Figure 57:
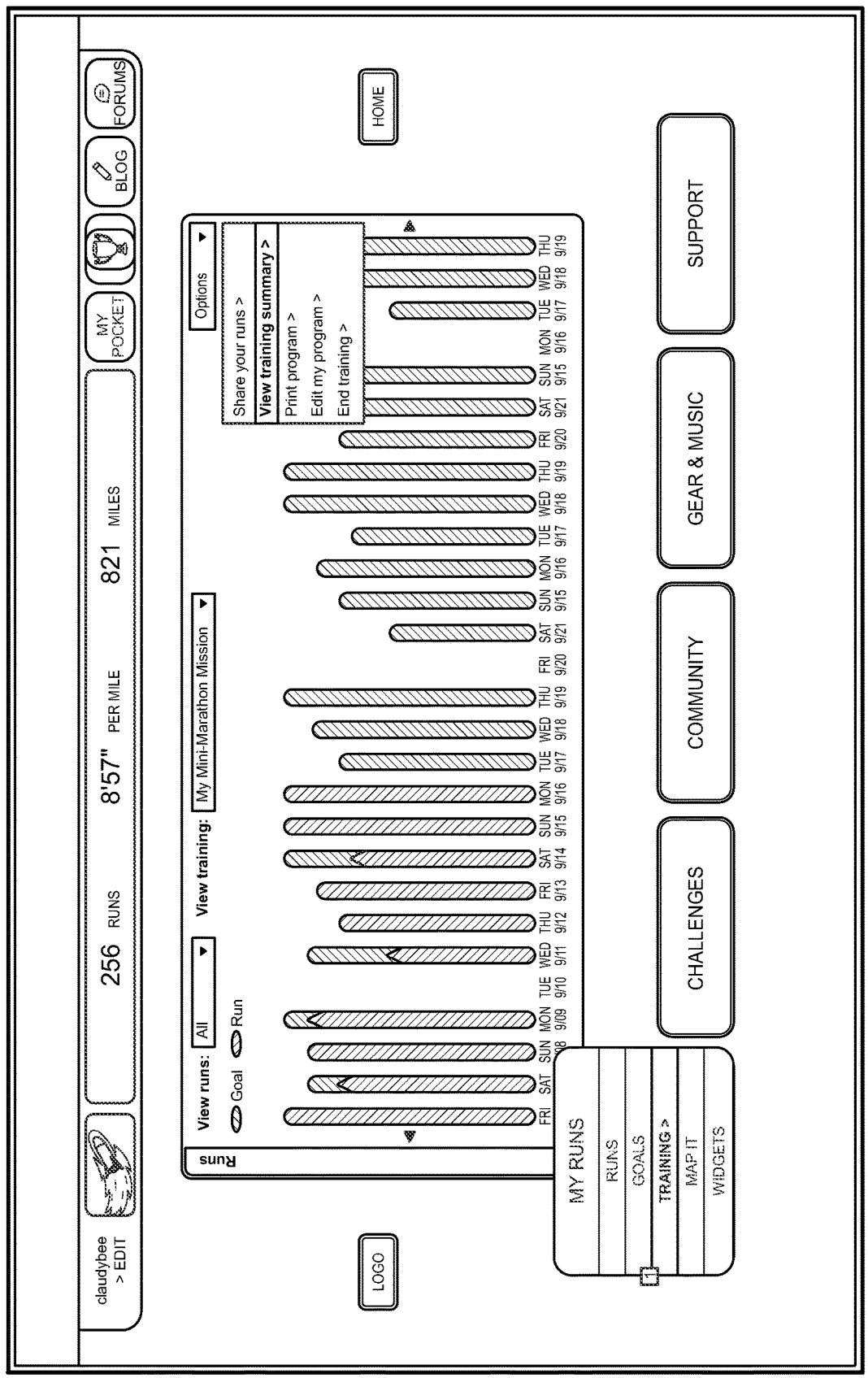
Figure 58:
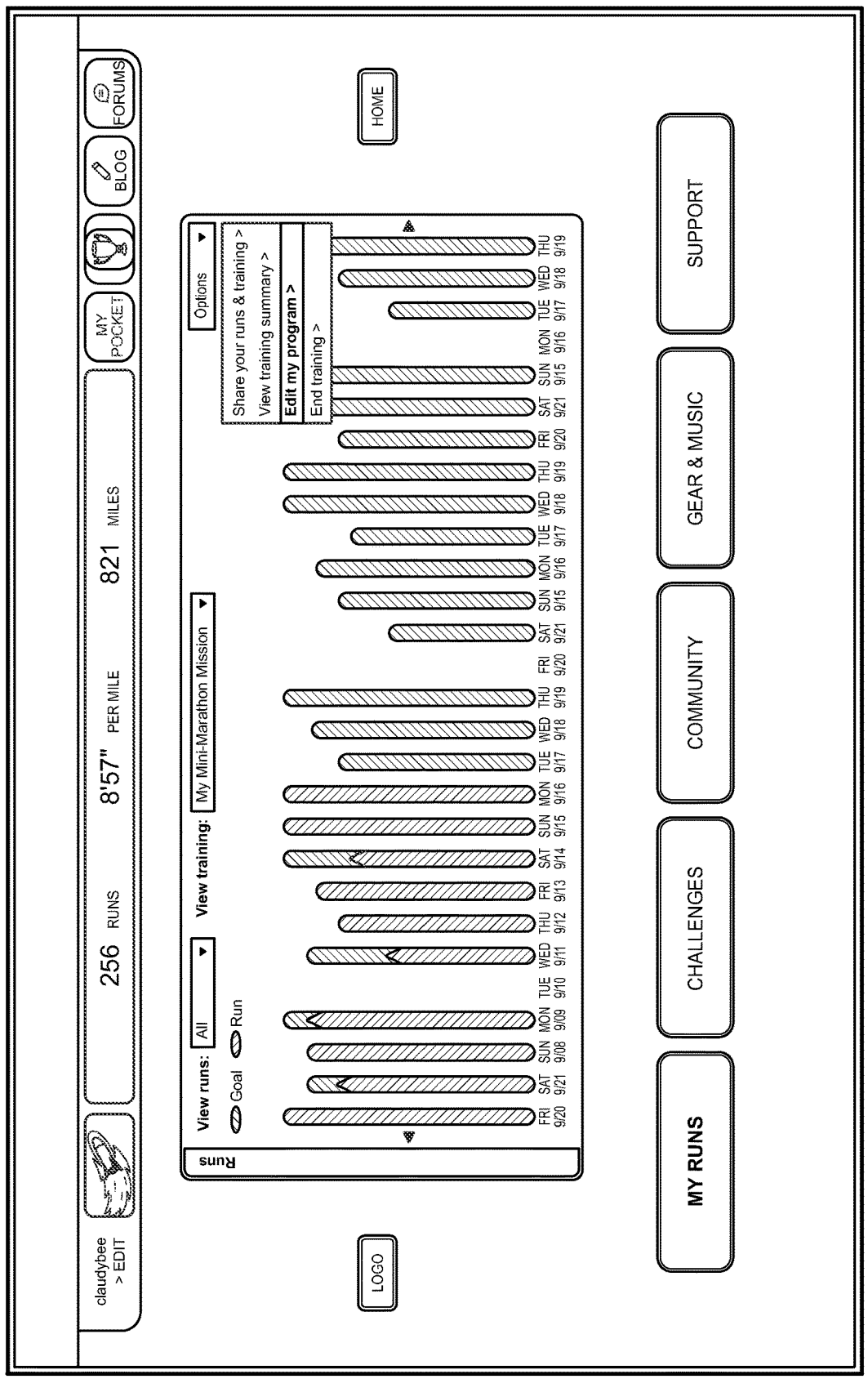
Figure 59:
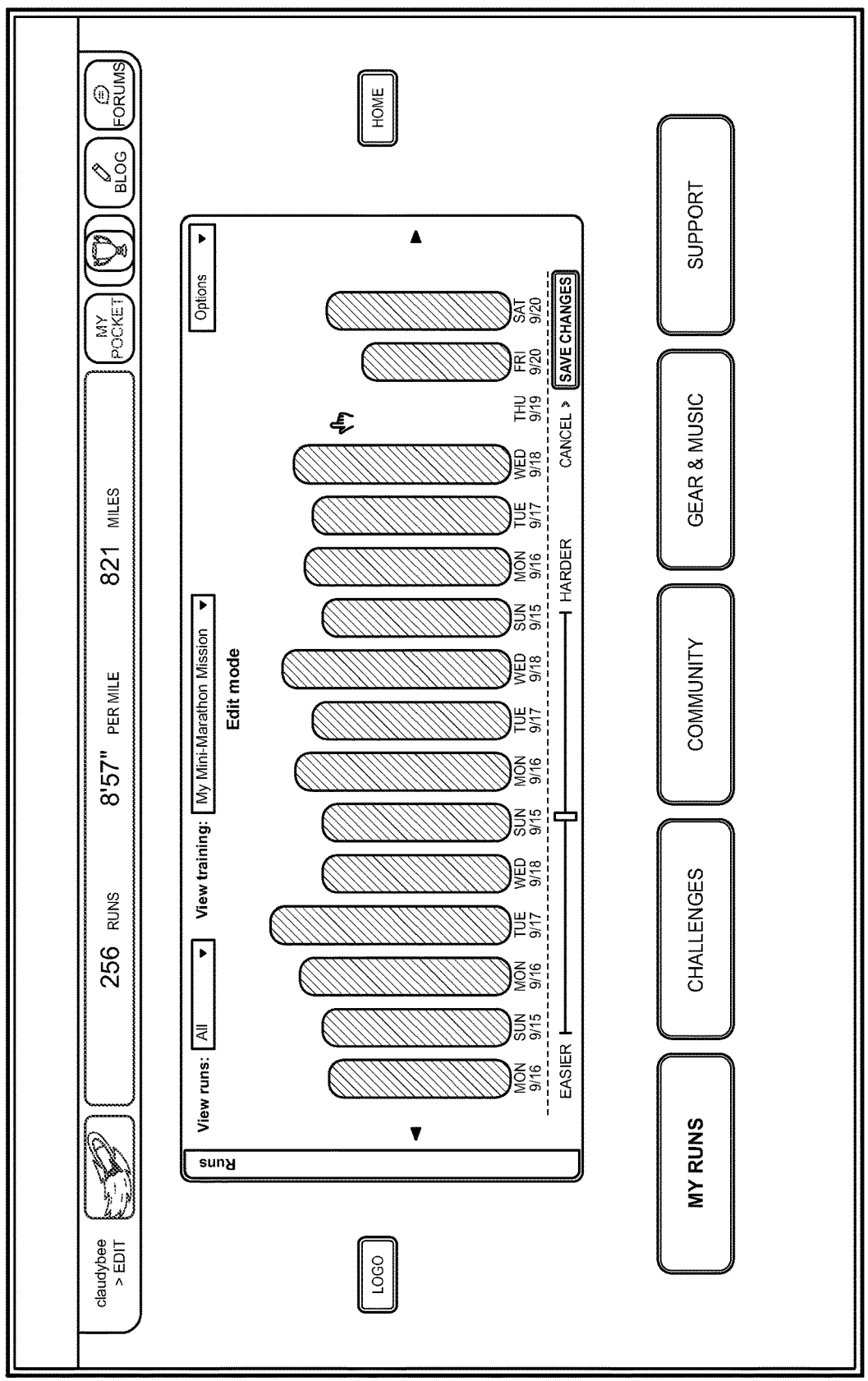
Figure 60:
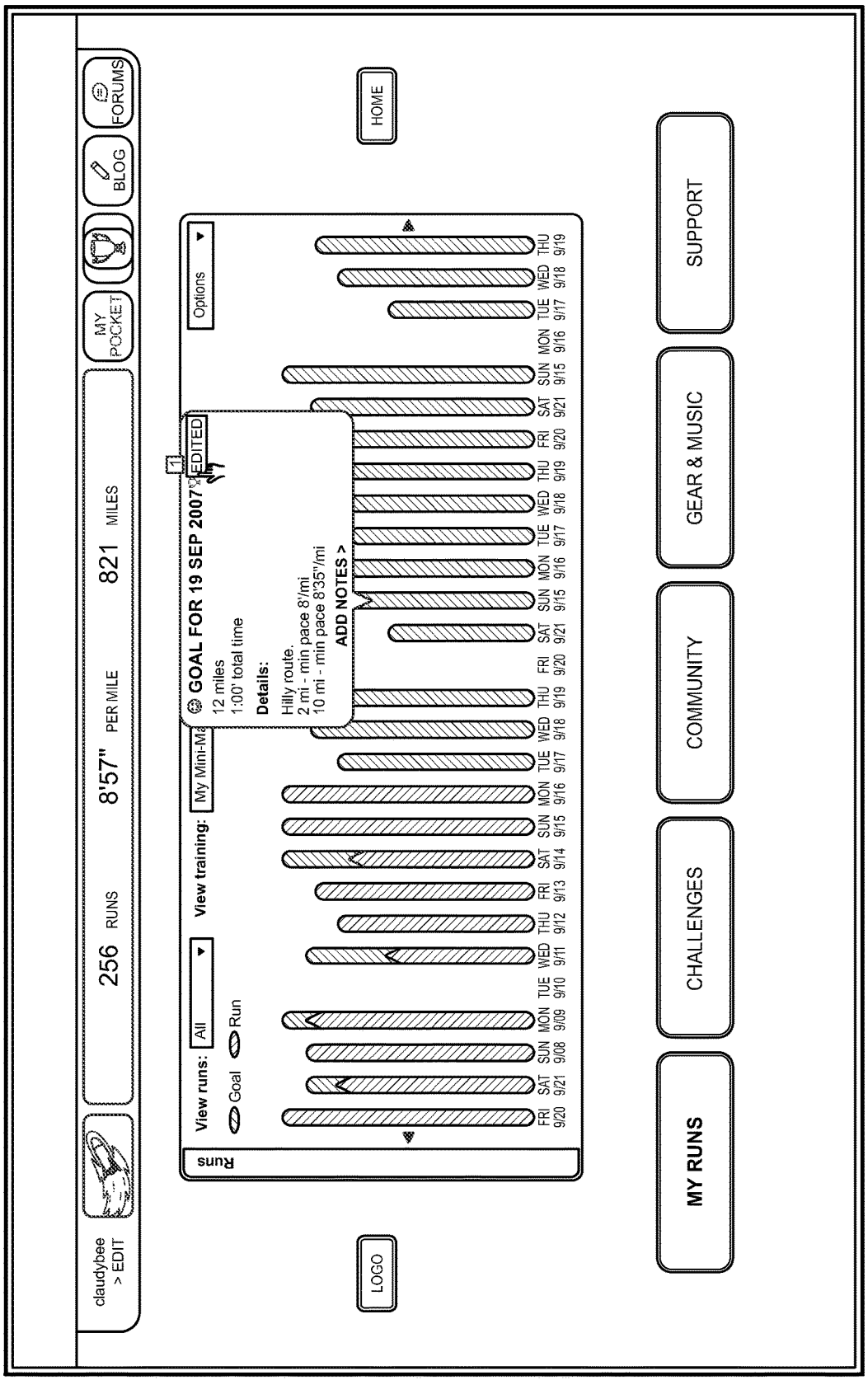

FIGS. 57-60 illustrate an alternate embodiment of user interface 1700 for editing a training program. FIG. 57 illustrates a sample training program and that the user or athlete has completed a portion of the training program. Under the options menu, and as illustrated by FIG. 58, the user or athlete may select an option to edit the program. In addition to the edit functions described above, FIG. 59 illustrates that the training program for a particular day may be dragged and dropped to another day. For example, a rest day may be dragged and dropped onto another day if, for example, the user or athlete is not available to run that other day. In an embodiment, the remainder of the training program will accommodate the switch by shifting one or more training program days to an earlier or later date. In an alternate embodiment, for example based on the insertion of an additional rest day, the end date of the training program may also be shifted. Further, in an embodiment, the end date may remain the same, but the training program may be amended (e.g., by altering run distance, run time, and/or run pace) to achieve the desired training goal by the desired ending date. The user interface of an embodiment may further provide indication whether or not such an amendment is consistent with training program constraints (e.g., based on the skill level of the user or athlete). Further, as illustrated by FIG. 60, any day that has been edited may include an indication that it has been edited. Among other reasons, a user or athlete may then edit the details or notes for a particular training day if they receive indication that the training day has been edited.

Figure 61:
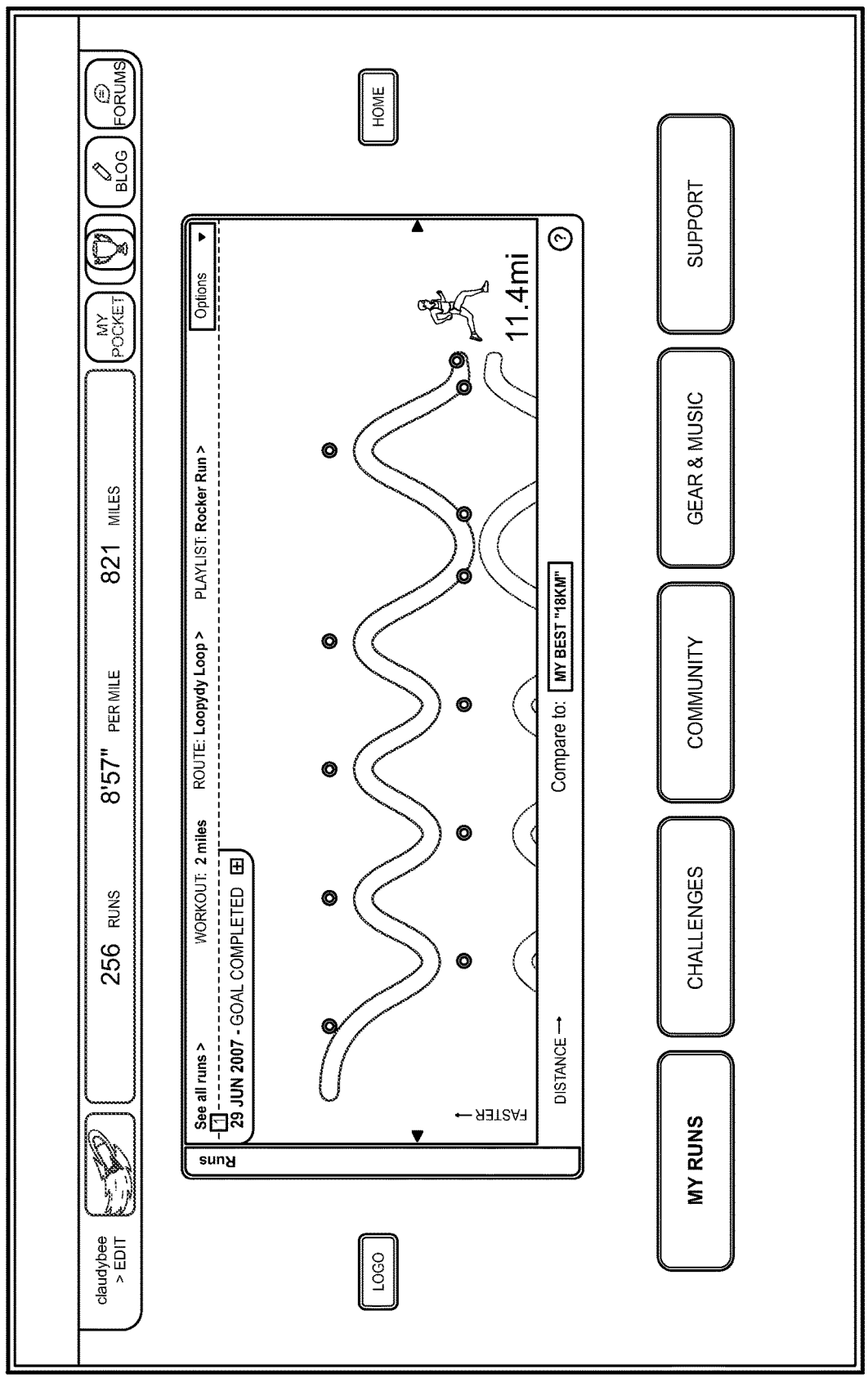
Figure 62:
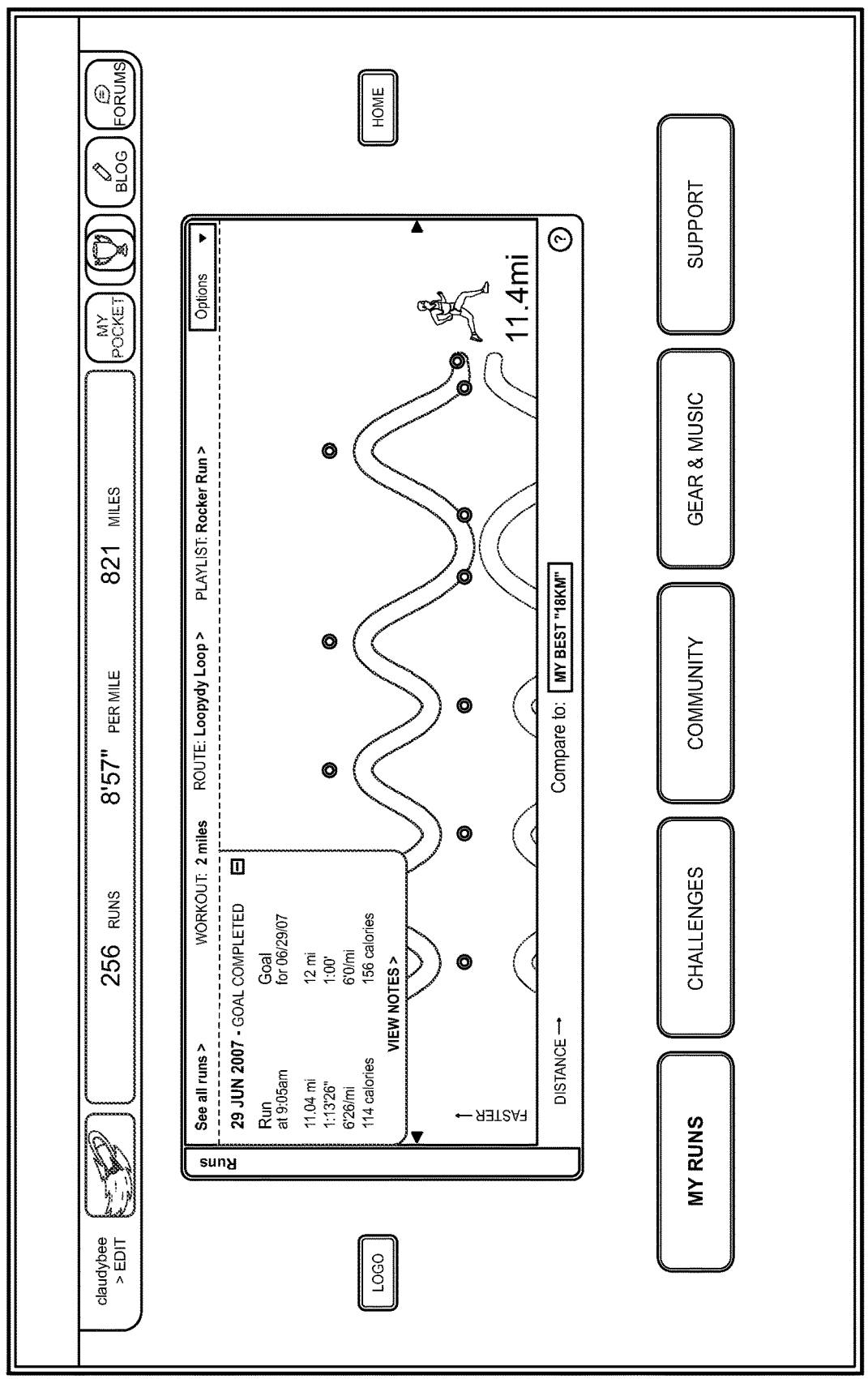

FIGS. 61 and 62 illustrate another embodiment of user interface 1700. Each illustrates a daily training program and actual performance as a function of distance run that day. In addition to a particular total distance and average pace, a daily training program may alter pace as a function of distance or time. Such interval training may improve the effectiveness of the training program in helping a user or athlete achieve their performance goal. Further, a user's or athlete's best performance for a run of a particular length may be superimposed for comparison to the actual performance on a given training day. In addition to the graphically displaying the actual performance, training program goal, and/or best performance, the user interface may further display the route name and/or music playlist (e.g., for an MP3 player or the like) name for that training day. Each can be predetermined by the user or athlete or may be supplied by the user interface 1700. For example, the route may be selected and provided by the mapping utility as described by U.S. patent application Ser. No. 12/031,380, filed Feb. 14, 2008, which is incorporated herein by reference in its entirety. FIG. 62 illustrates that the user interface 1700 may display the goal distance, the goal time, the goal pace, the goal calorie usage, actual performance distance, actual performance time, actual performance pace, and actual performance calorie usage for that training day.

Team Training

Figure 63:
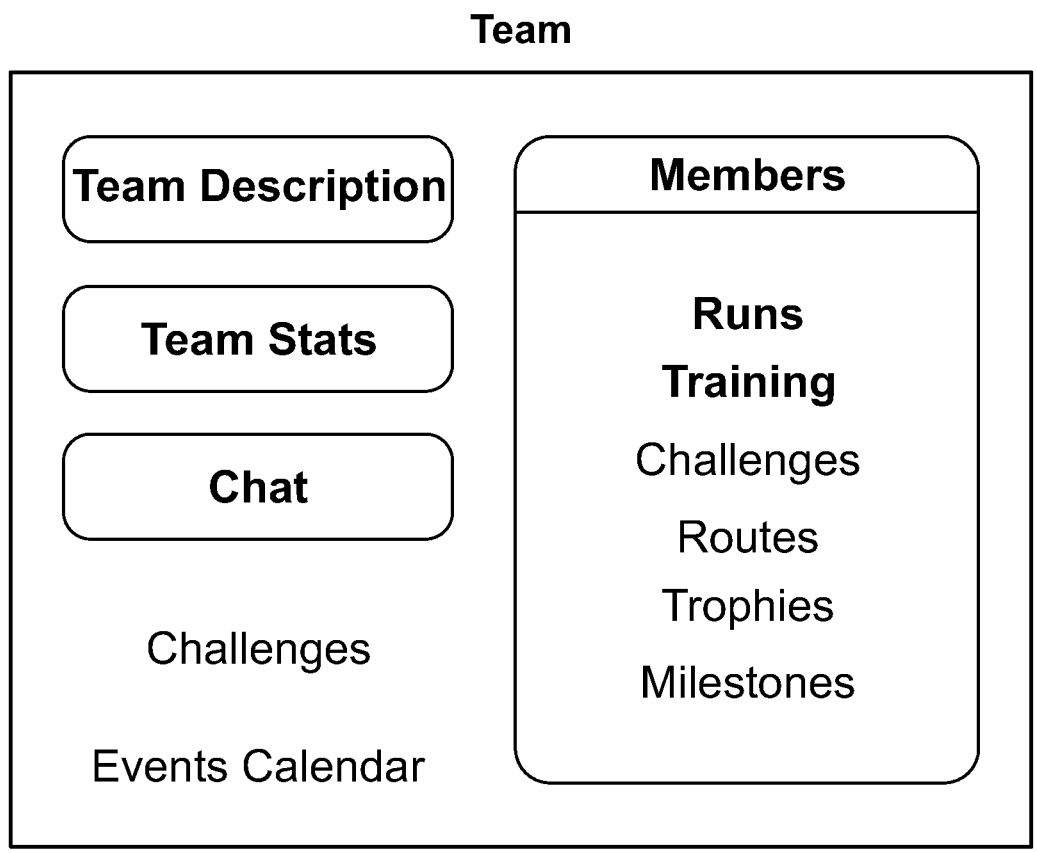

FIGS. 63-88 illustrate that the user interface 1700 may further be utilized as a team training tool. In addition to the various training program described above with reference to FIGS. 18-62, user interface 1700 may further provide tools to manage and coordinate training among teammates, organizations, clubs, and the like. FIG. 63, for example, illustrates a team portion of user interface 1700. For a selected team, organization, or club a user or athlete may view the team description, team statistics, current team challenges, and an events calendar. Further, the user or athlete may chat with other members of the team, organization, or club. Additional information may be available for individual members of the team, organization, or club. For example, for each individual, the user interface 1700 may display the member's runs, training program, challenges to which they are a party, routes they run, trophies they have earned, and/or milestones they have achieved. Challenges, routes, trophies/awards, and milestones are described in U.S. patent application Ser. No. 12/031,380, filed Feb. 14, 2008.

Figure 64:
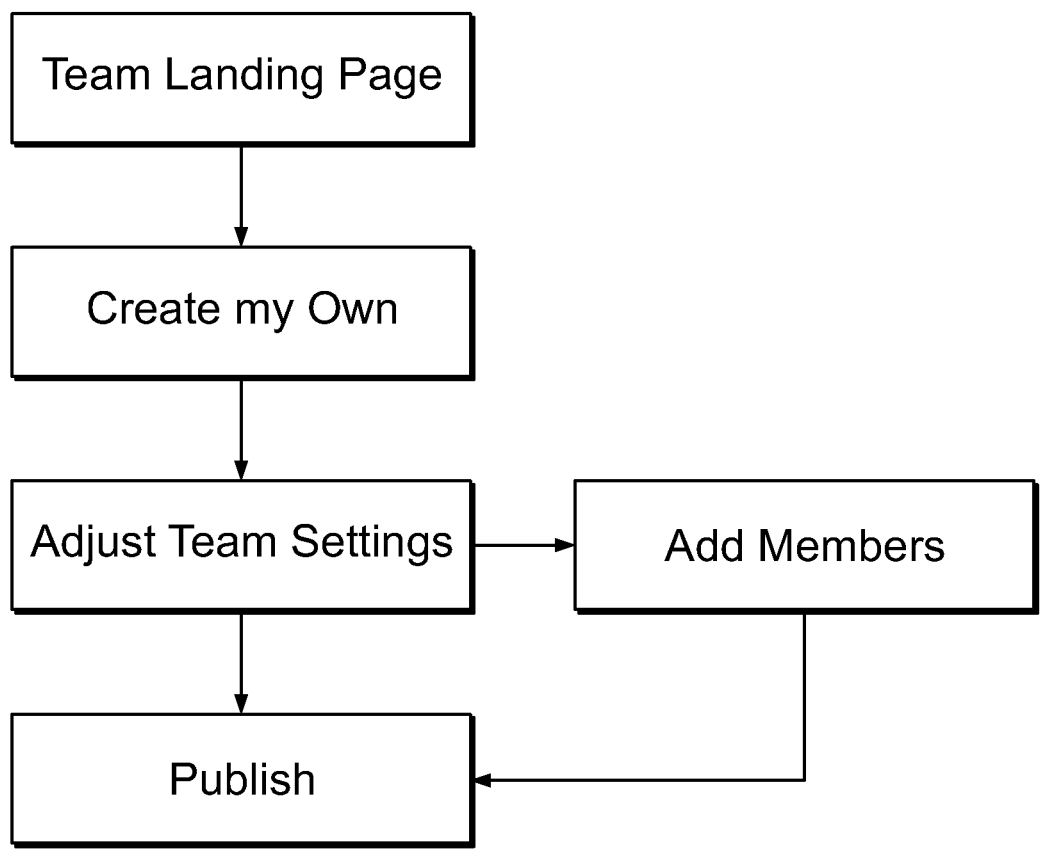
Figure 65:
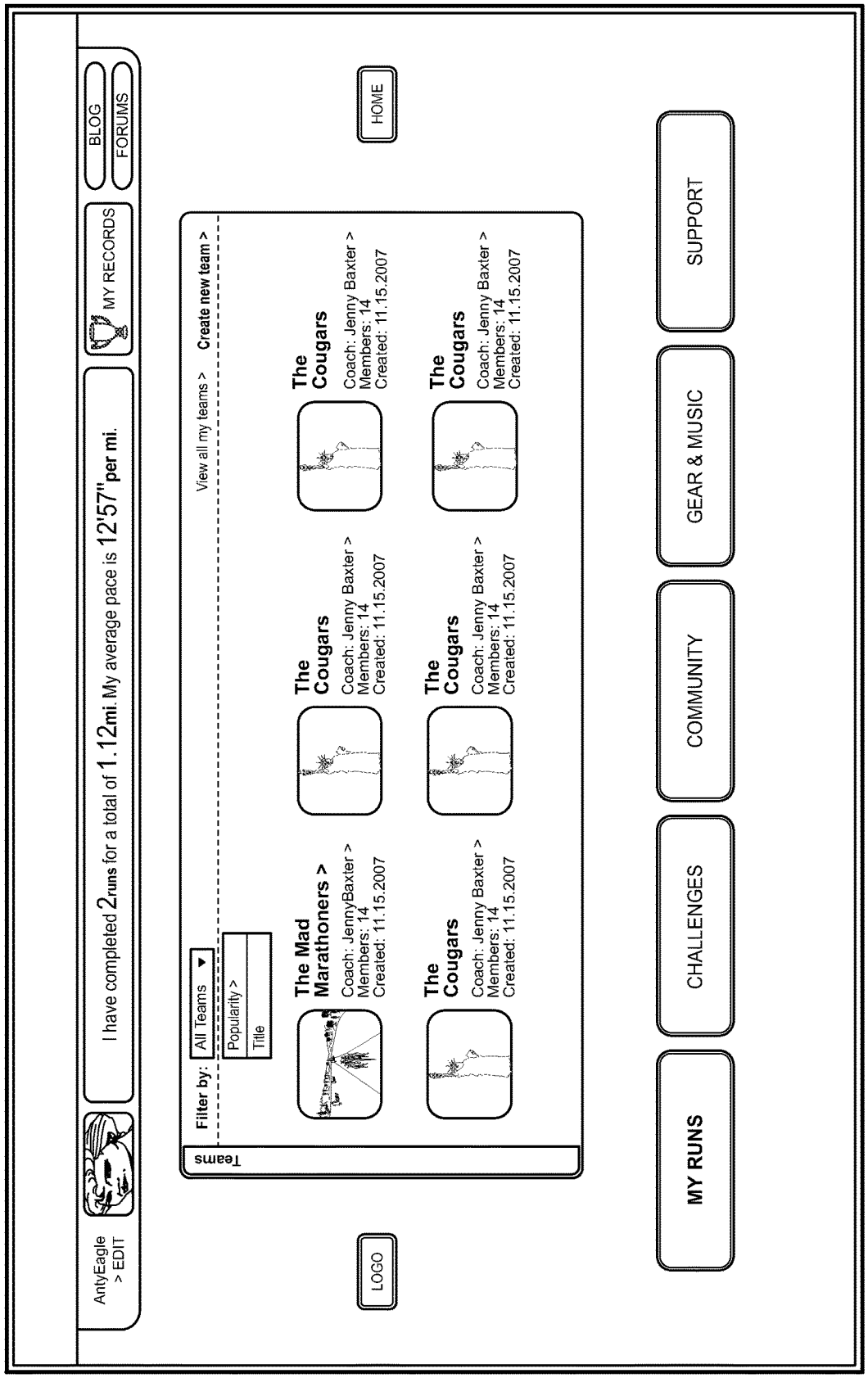

FIG. 64 illustrates a process flow to create a new team. For example, from a team landing page, a user or athlete may create their own team after which they may adjust team settings, add one or more members, and then publish the team. For example, FIG. 65 illustrates a listing of teams once created. Each team may be listed with an image (e.g., icon, picture, avatar, or the like), the name of the coach, the number of team members, and the date the team was created. The listing of teams available the user or athlete (e.g., those that are public or with which the user or athlete is associated) may further be filtered according to popularity and/or by title or team name. The listing of teams may also just represent the team(s) of which the user or athlete is a member.

Figure 66:
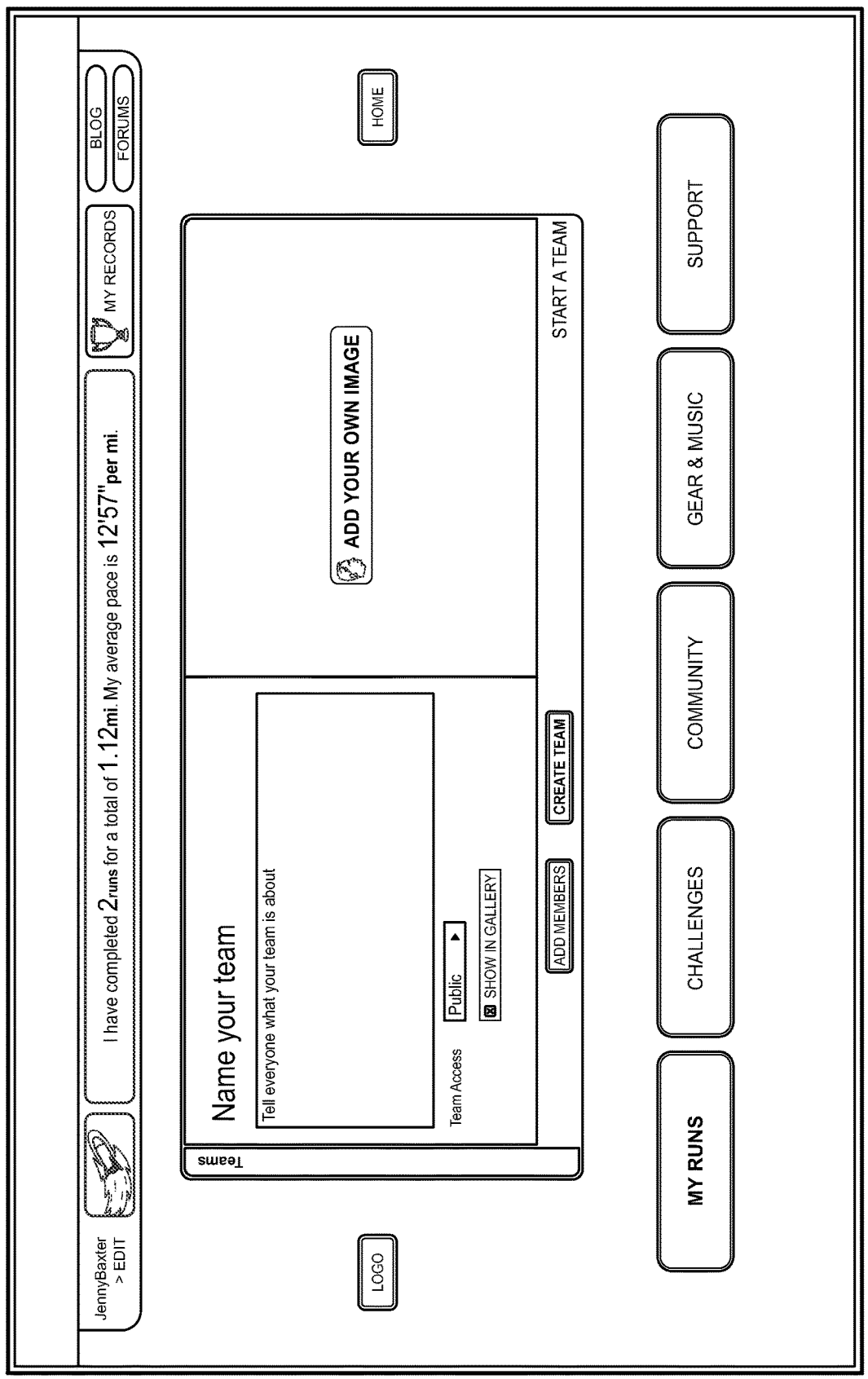
Figure 67:
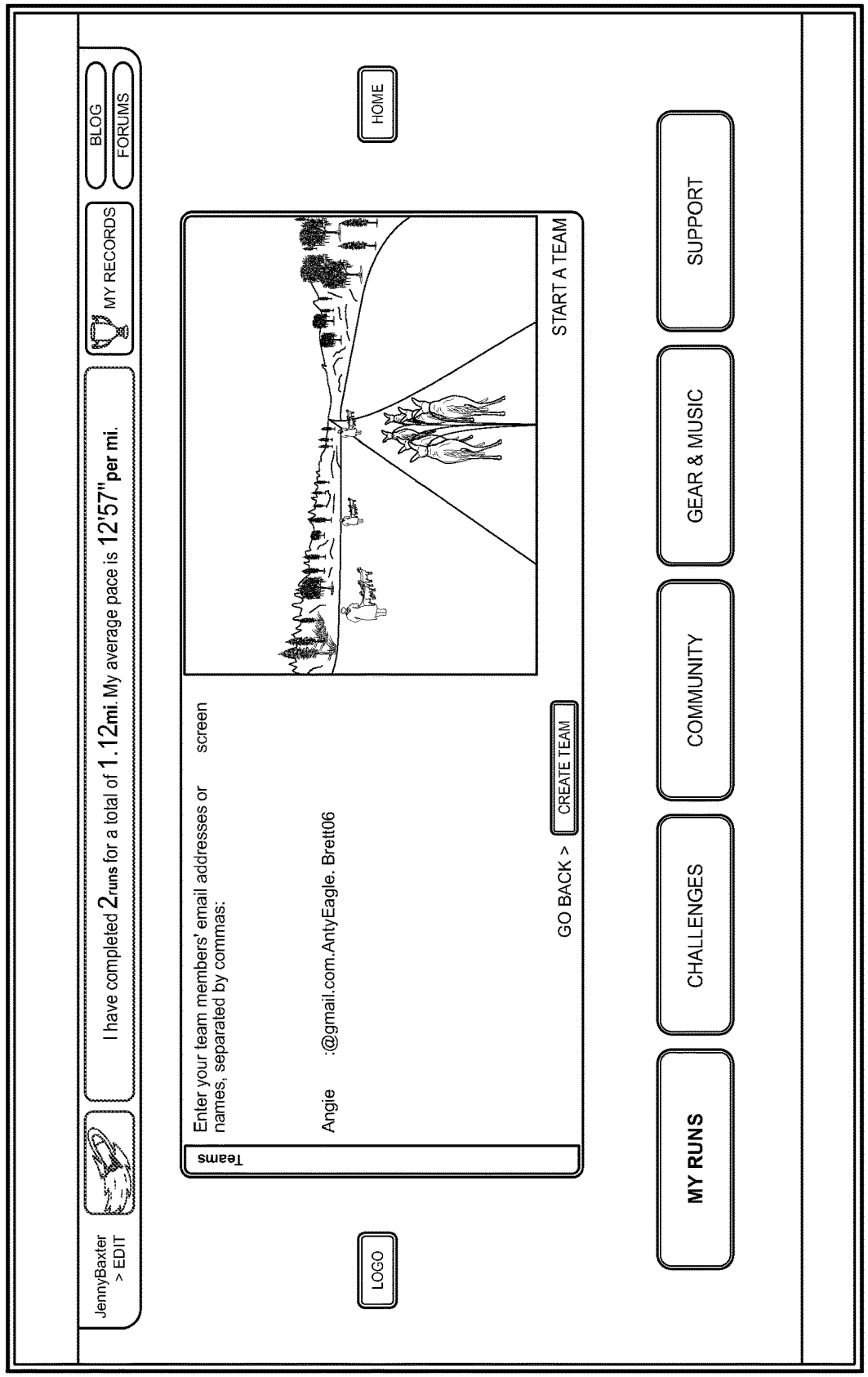
Figure 68:
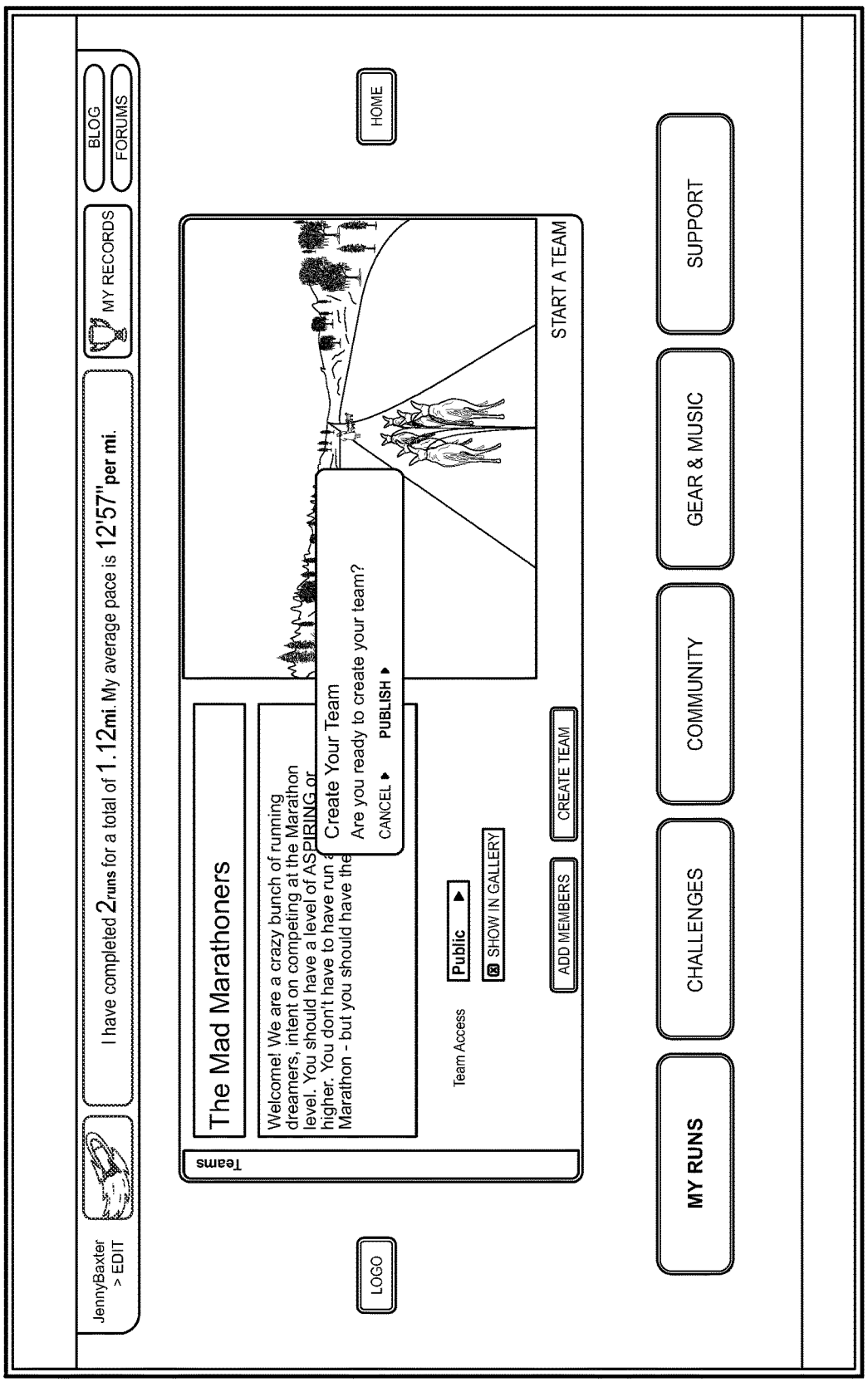

FIG. 66 illustrates the creation of a new team. A user or athlete may name the team, provide a narrative description of the team, and/or an image representative of the team. At this point, the user or athlete may determine the team access (e.g., public, team members only, or other selected groups or individuals). Further, the user or athlete may decide whether their newly created team will be shown in a gallery of teams or not. Such an option may be available only if, for example, the team access is set to public. FIG. 67 illustrates that team members may be added to the team by entering their email address, their username within the user interface 1700, or the like. In an embodiment, the email addresses, usernames, or the like may be available in an address book (e.g., as populated by email addresses, usernames, and the like from previously created teams). FIG. 68 illustrates that once the user or athlete enters the team name, description, image, access, and team and/or team members, they may publish the team.

Figure 69:
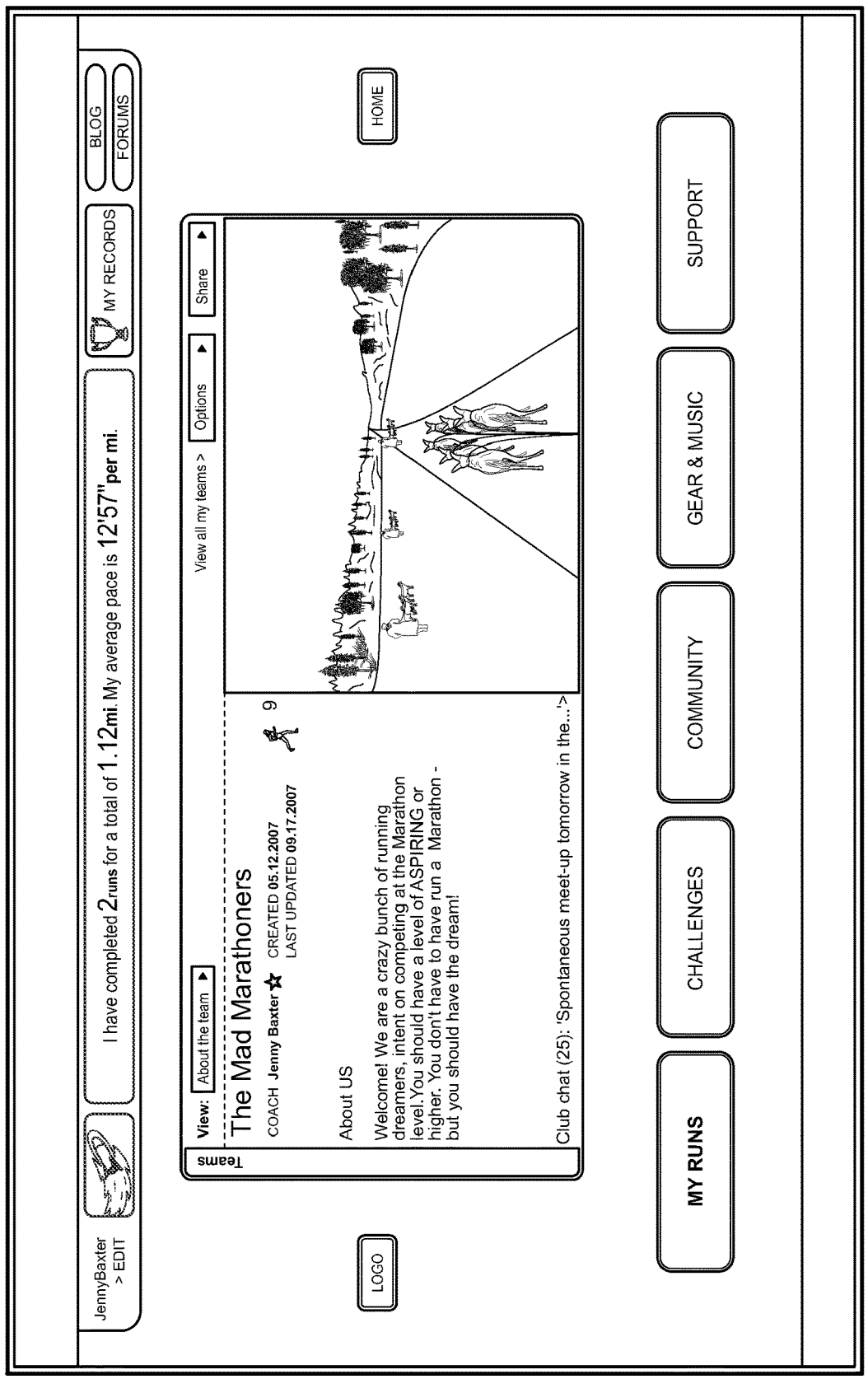

Thereafter, the team may be viewed as illustrated by FIG. 69. For example, in addition to the team name, image, and narrative description, user interface 1700 may also display the team coach, the date that the team was created, the date that the team (or description thereof) was last updated, and the number of members of the team. Further, the user interface may include at least a portion of the team chat, if one has been established. In an embodiment, user interface 1700 may display the most recently posted addition to the chat as well as an indication as to the number of additional posts within the chat.

Figure 70:
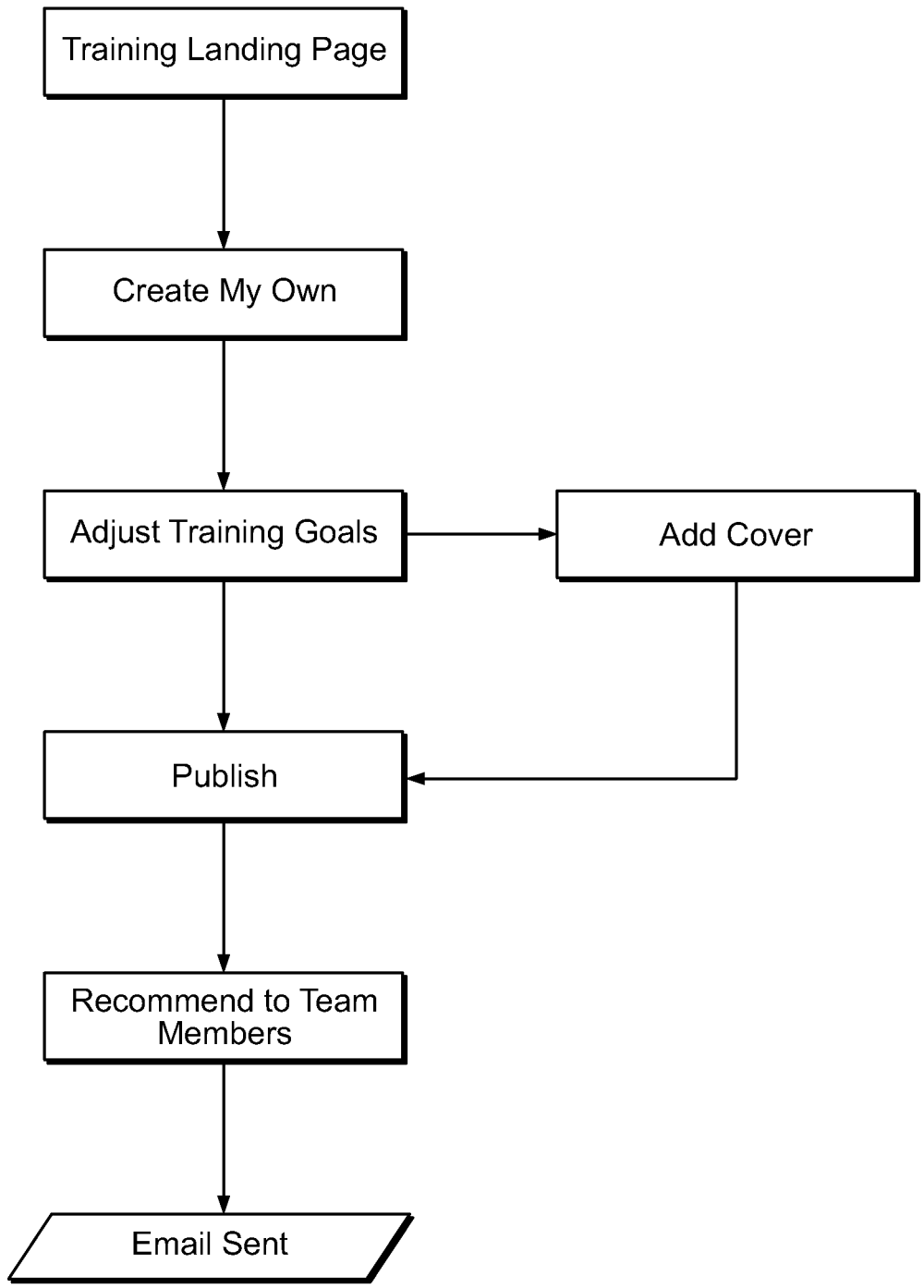

FIGS. 70-77 illustrate that a coach may create a training program for a team, organization, club, or the like. In an embodiment, in particular for a well-known or famous coach or athlete, the coach or athlete may further make their training program available to the public. For example, FIG. 70 illustrates the process flow of a coach creating a training program. From a team landing page, a coach may create and adjust training goals (e.g., daily goal distance, time, pace, etc., as introduced above). Thereafter, the coach may add a cover (e.g., training program title, narrative description, image, etc.) to their training program. When complete, the coach may publish their training program to make it available to users and athletes. In an embodiment, a coach may recommend their training program to specific individuals or team members (e.g., by sending them an email). For such an embodiment, the coach's training program may or may not be to the public or otherwise. Said differently, in an embodiment, a coach may control access to their training program so that only team members have access.

FIG. 71 illustrates an embodiment for which a coach or well-known athlete has provided their training program to the public via user interface 1700 (i.e., to all users or athletes subscribing to the user interface 1700). In an embodiment, the user interface 1700 may periodically, or incident with a particular event (e.g., the New York or Boston marathons), offer one or more featured training programs based on the event or the well-known or famous coach or athlete. As further illustrated by FIG. 71, a user or athlete may also at this point design or create their own training program or join and train with a team (e.g., those teams that are available to the public).

Figure 72:
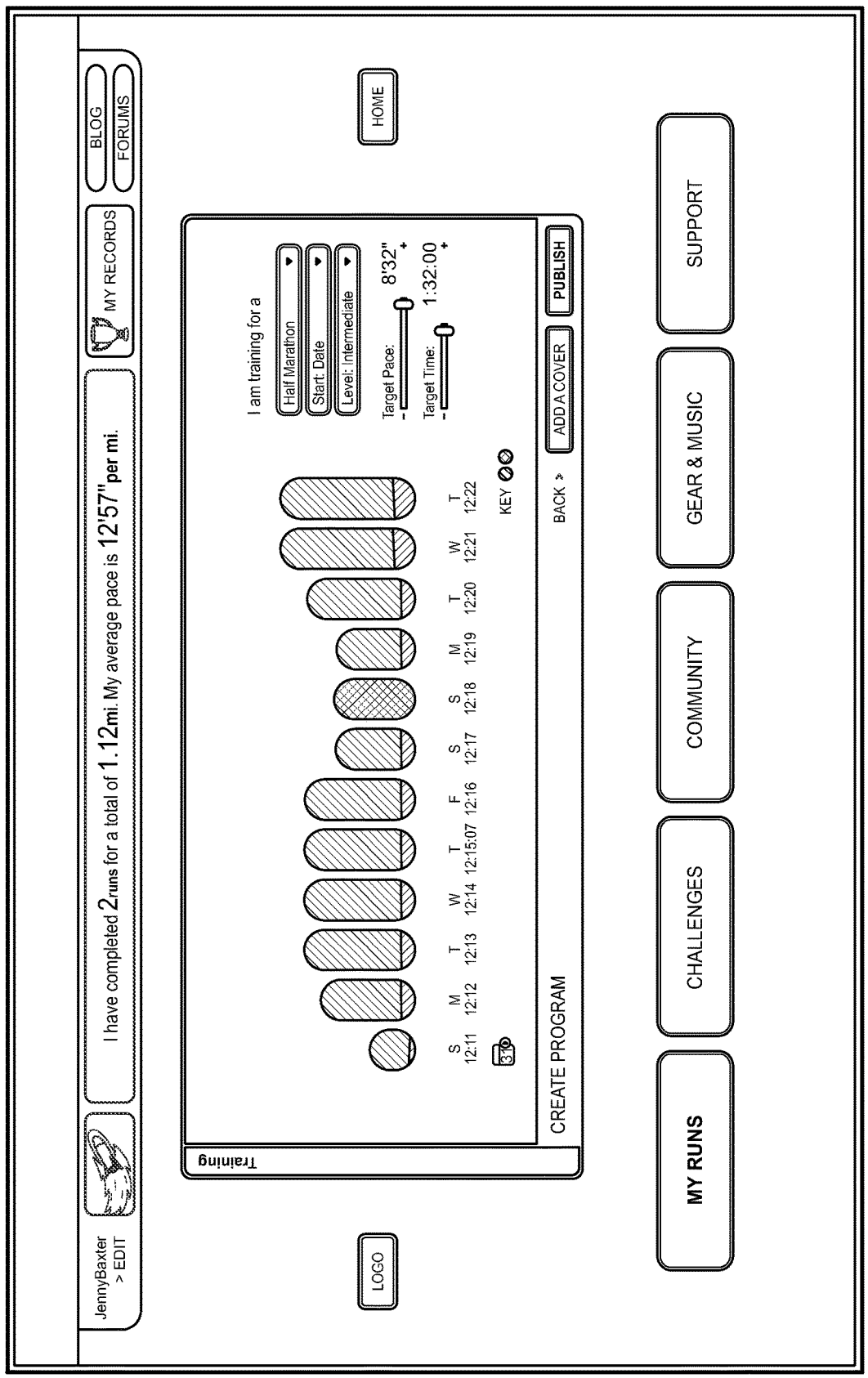
Figure 73:
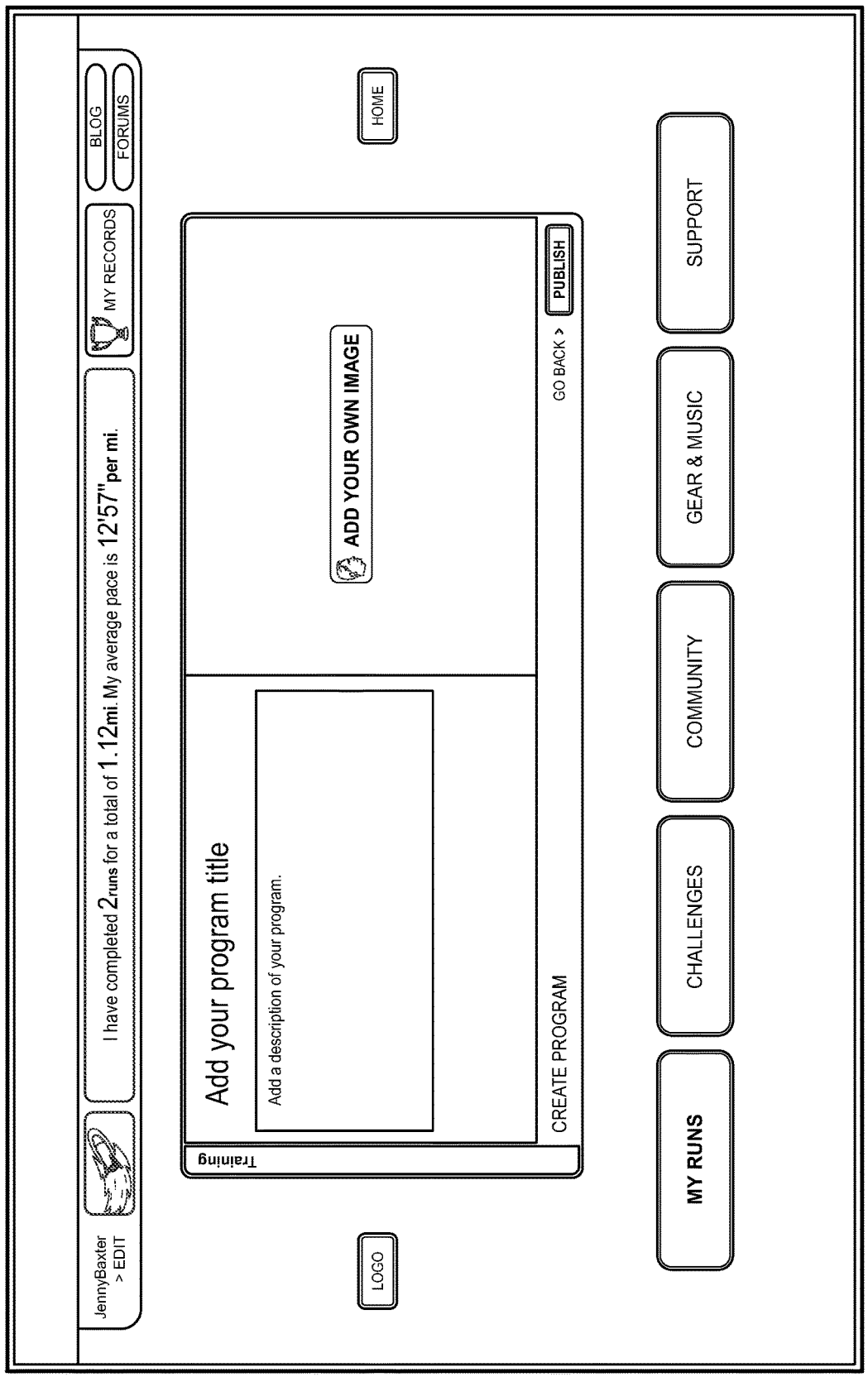
Figure 74:
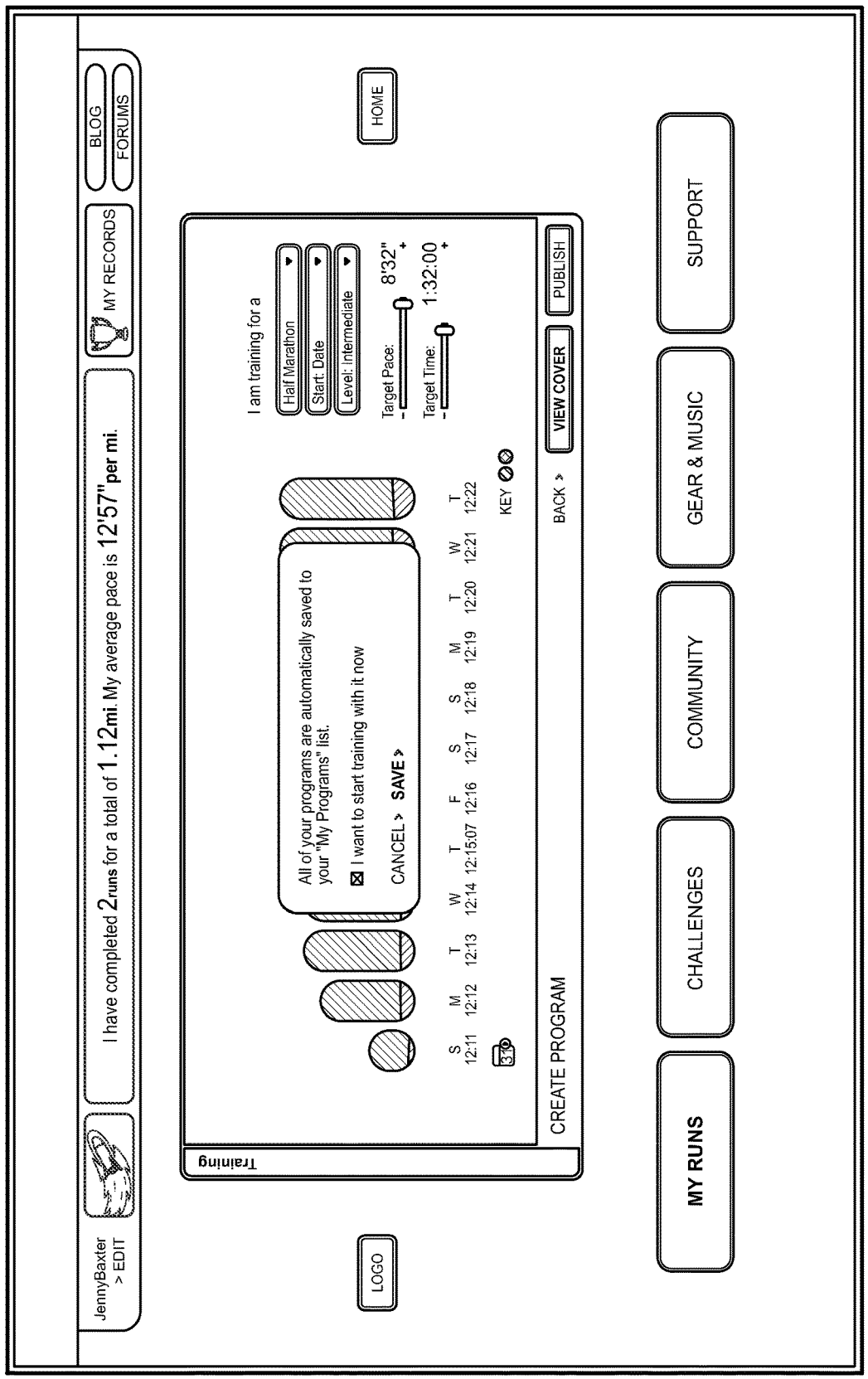
Figure 75:
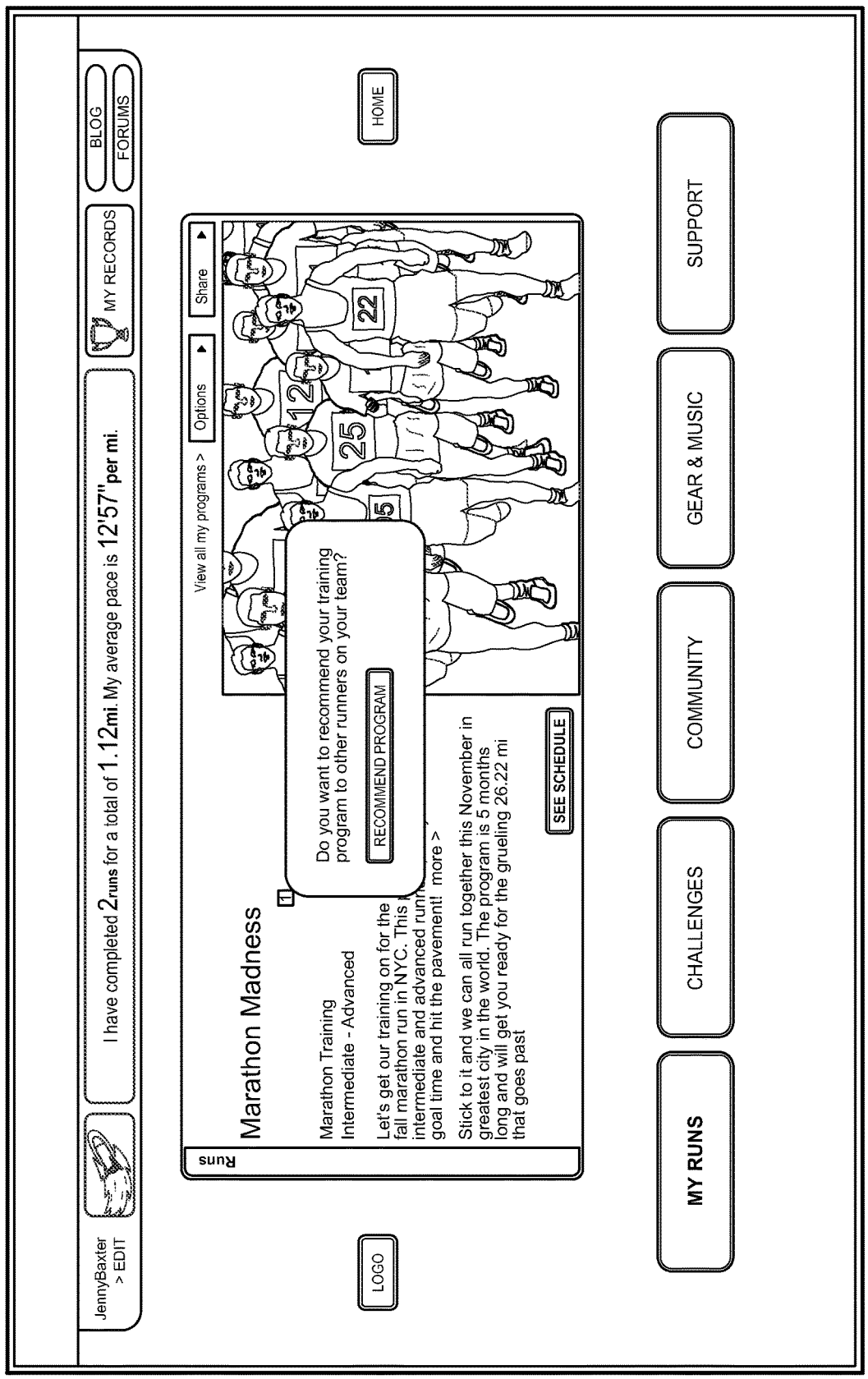
Figure 76:
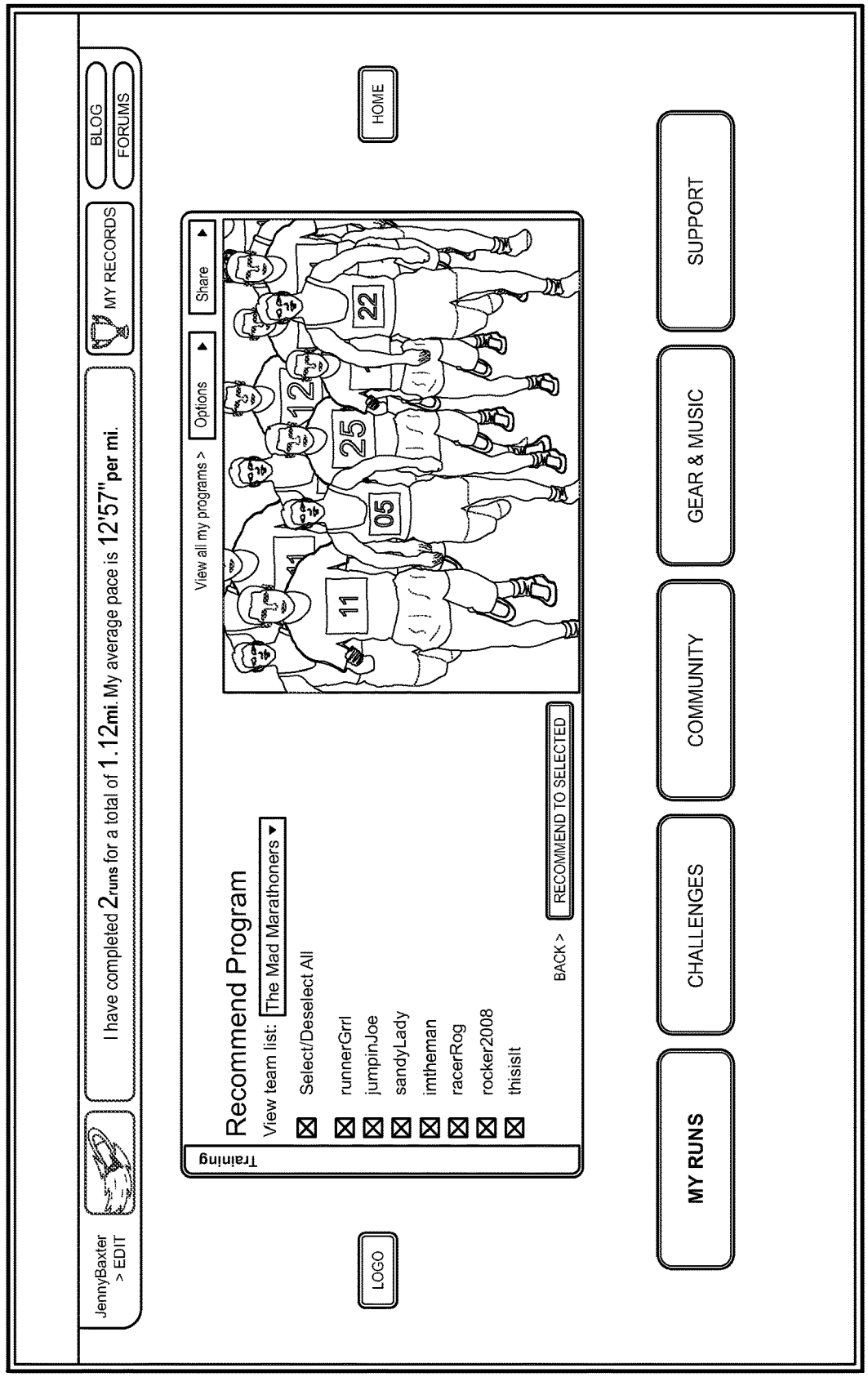
Figure 77:

FIG. 72 illustrates the creation of a training program by, for example, a coach. As described with respect to preceding figures, the coach may determine the title of the training program, start date of the training program, duration of the program, the distance of the daily runs, the target pace or target time of the daily runs, the suggested skill level, and any other details associated with the training program. For example, FIG. 73 illustrates that the coach may create a program title, narrative description, and/or image representative of the training program. FIG. 74 illustrates that the coach may edit the details of the training program and may save the completed training program. FIG. 75 illustrates that once the training program is complete, the coach may recommend the program to one or members of the team, organization, or club. For example, FIG. 76 illustrates that the coach may select one or more teams, organizations, or clubs with which they are associated. The coach may then select one or more individual team, organization, or club members from a list populated based on their selection of team, organization, or club. FIG. 77 illustrates the recommendation from the coach as received by a team, organization, or club member.

Figure 78:
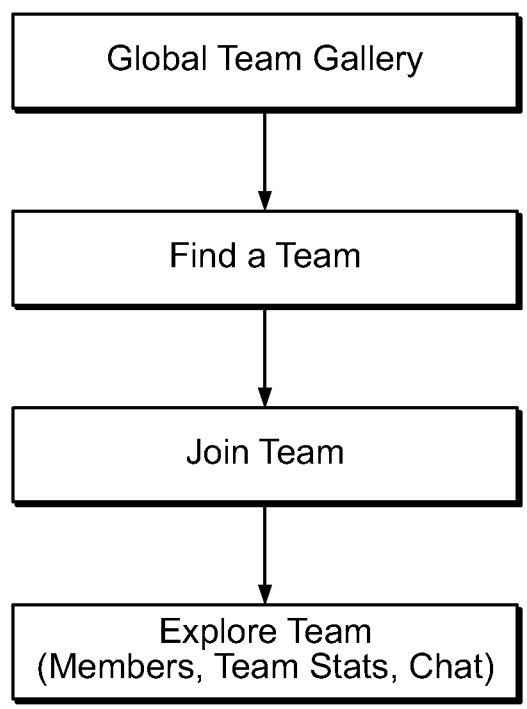
Figure 79:
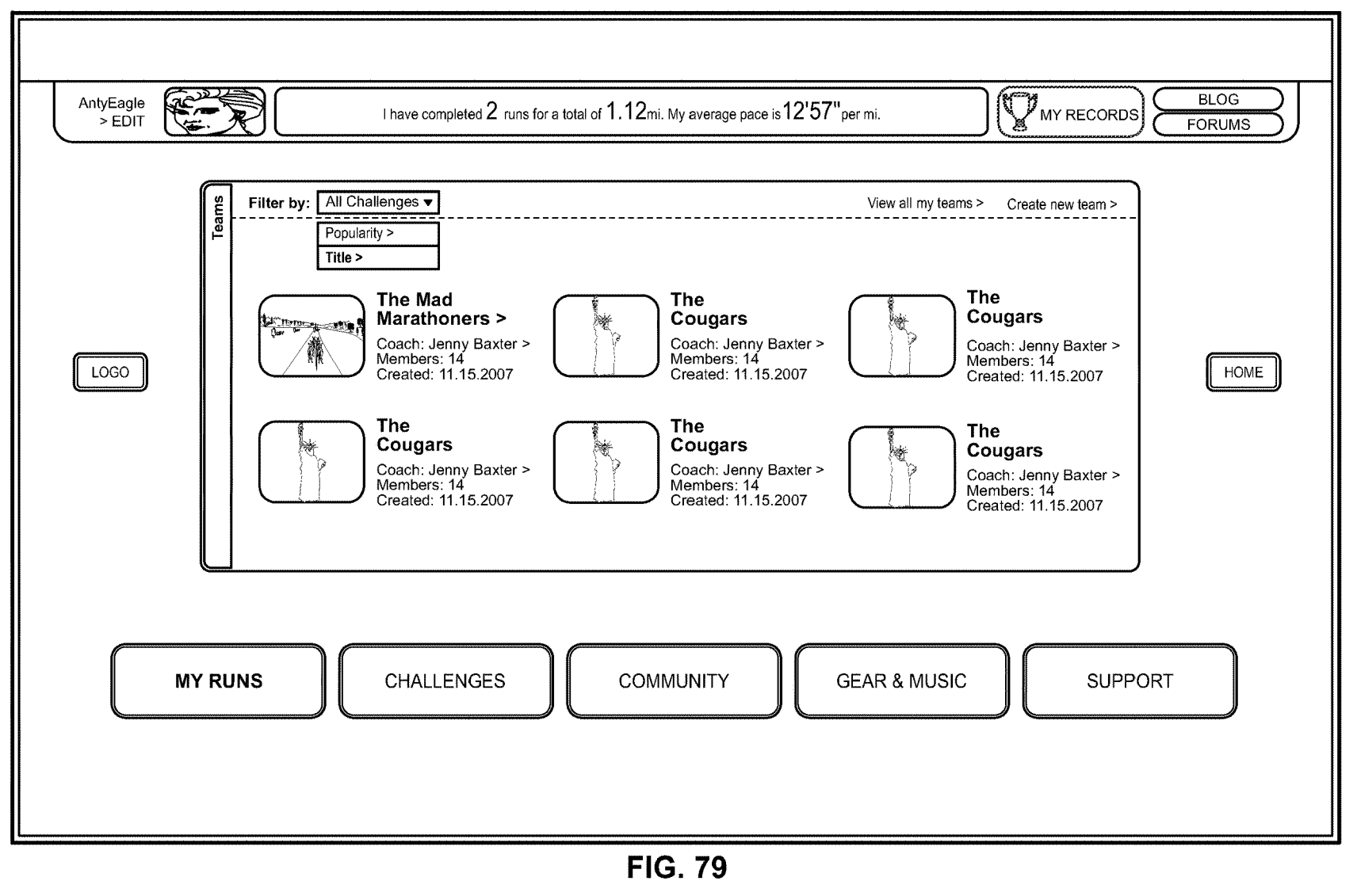
Figure 80:
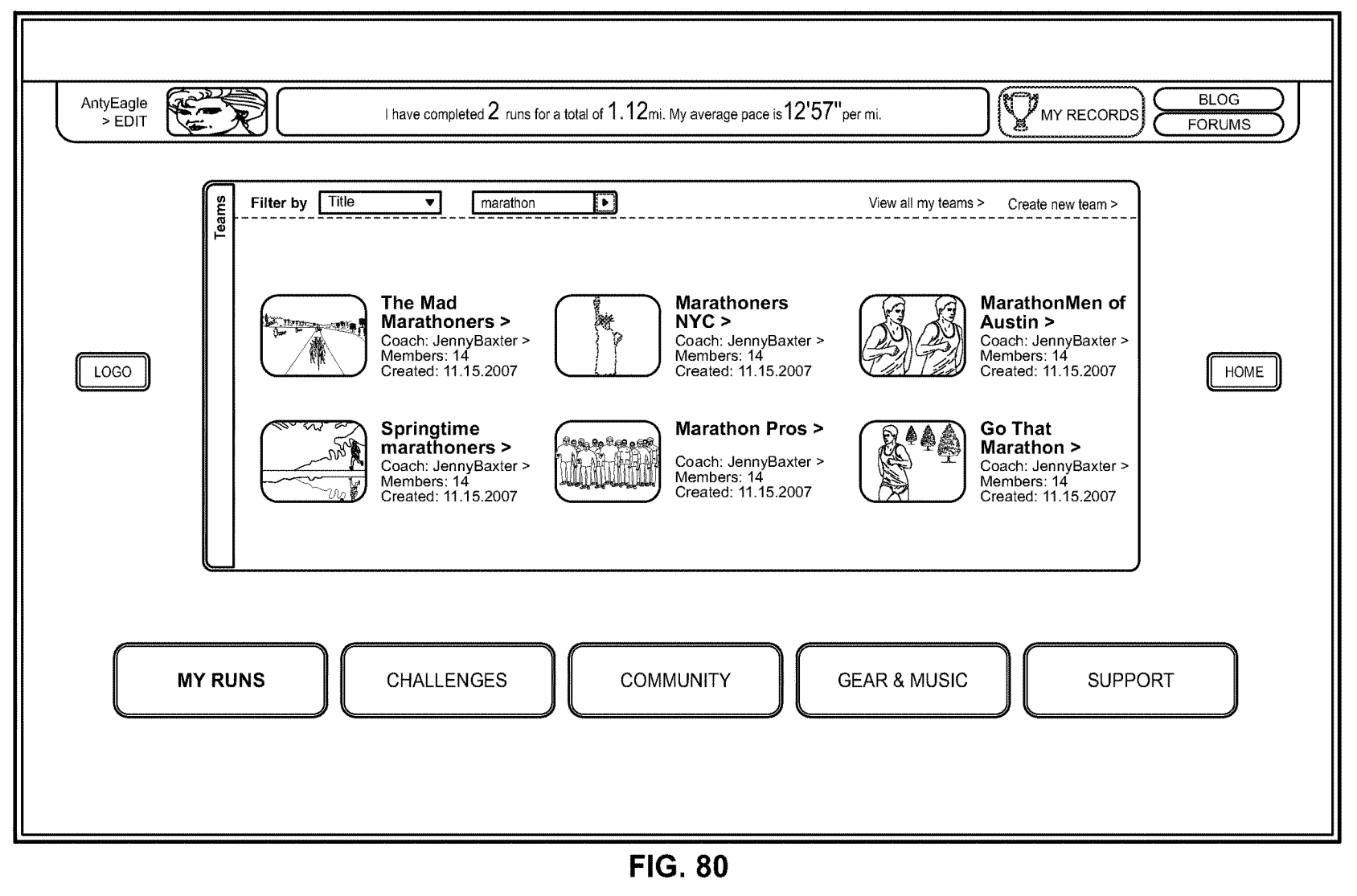
Figure 81:
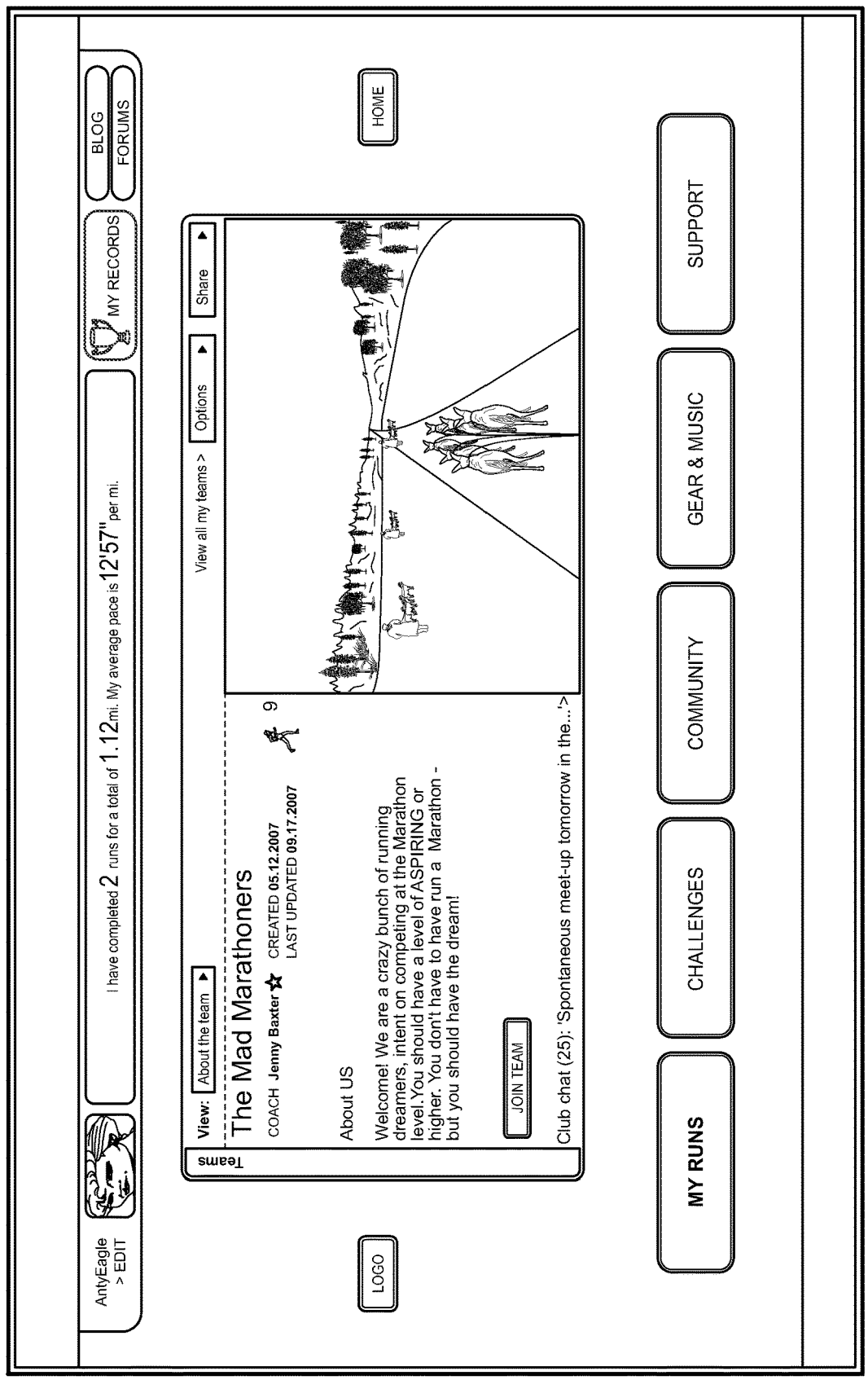
Figure 82:
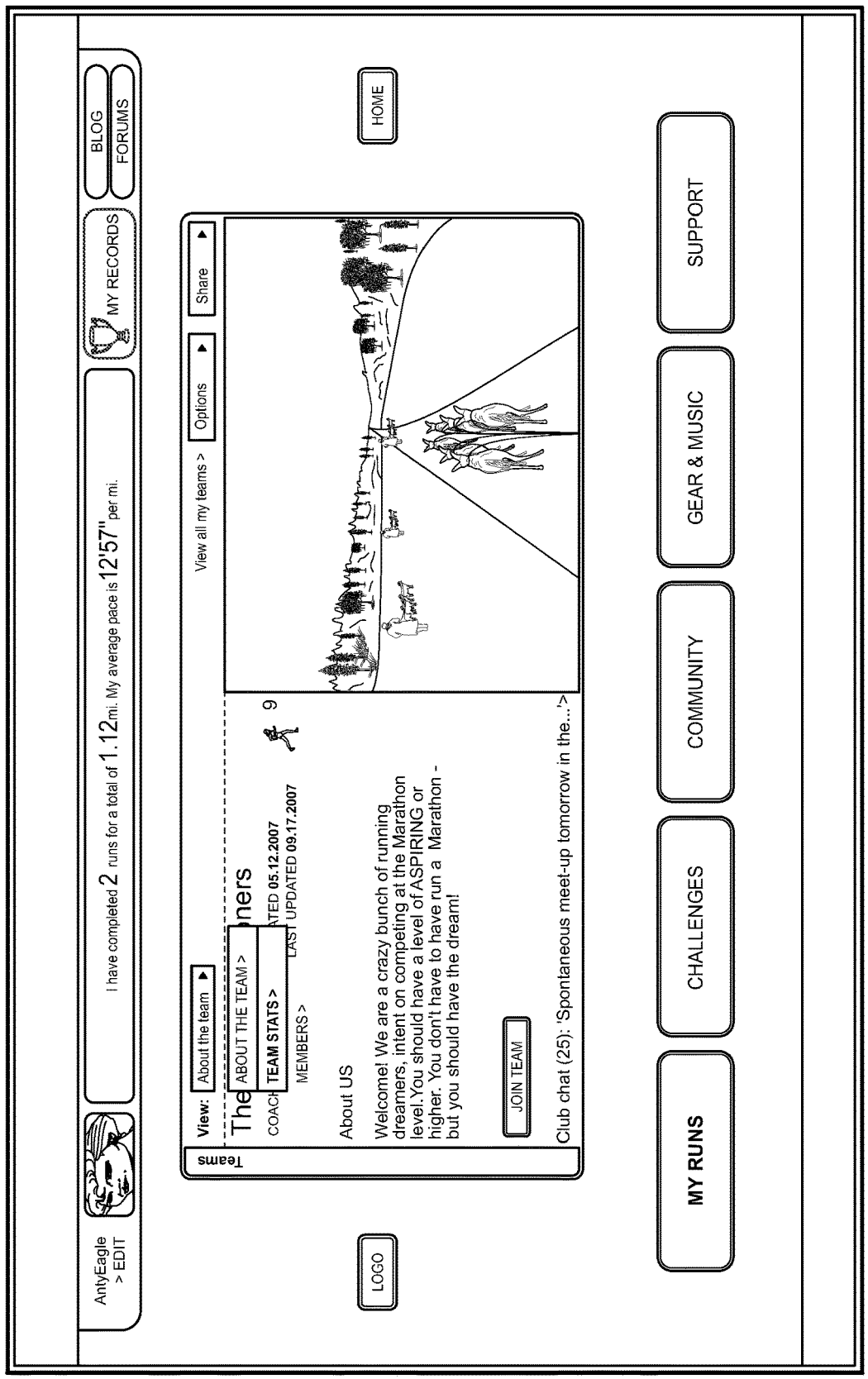

FIGS. 78-86 illustrate that a user or athlete may utilize the user interface 1700 of an embodiment to find and join a team. For example, FIG. 78 illustrates that a user or athlete may view a global team gallery, locate a team in the gallery, join the team, and then interact with the team (e.g., explore details associated with the team members, join team chats, and the like). FIG. 79 illustrates a global team gallery from which the user or athlete may select one or more teams to join. In an embodiment, the user or athlete may filter the global team gallery based on team title and/or team popularity. FIG. 80 illustrates that the user or athlete may filter the global team gallery based on the goal of the training program, for example to prepare for a marathon. FIG. 81 illustrates that the user or athlete may select a team to view its title, coach, date of creation, date last updated, number of team members, narrative description, image associated with the training program, and/or at least a portion of a chat, if any, among team members. FIG. 82 illustrates that the user or athlete may further view team statistics and details associated with individual team members. If a user finds a team he or she wishes to join, the user may request membership in that team. The user might only be added to the team upon approval by a team member, coach, a majority of team members or team leader of the desired team.

Figure 83:
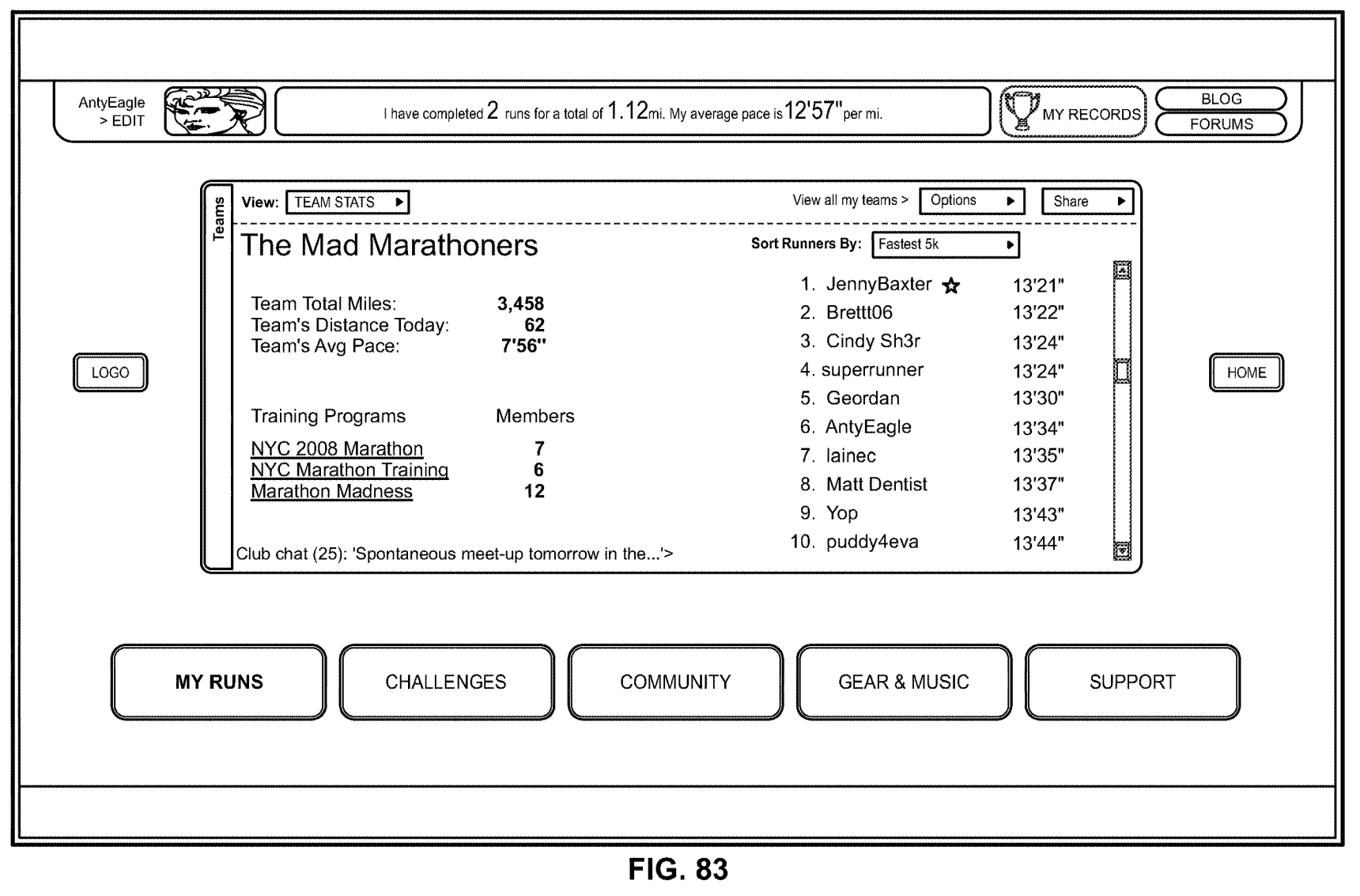
Figure 84:
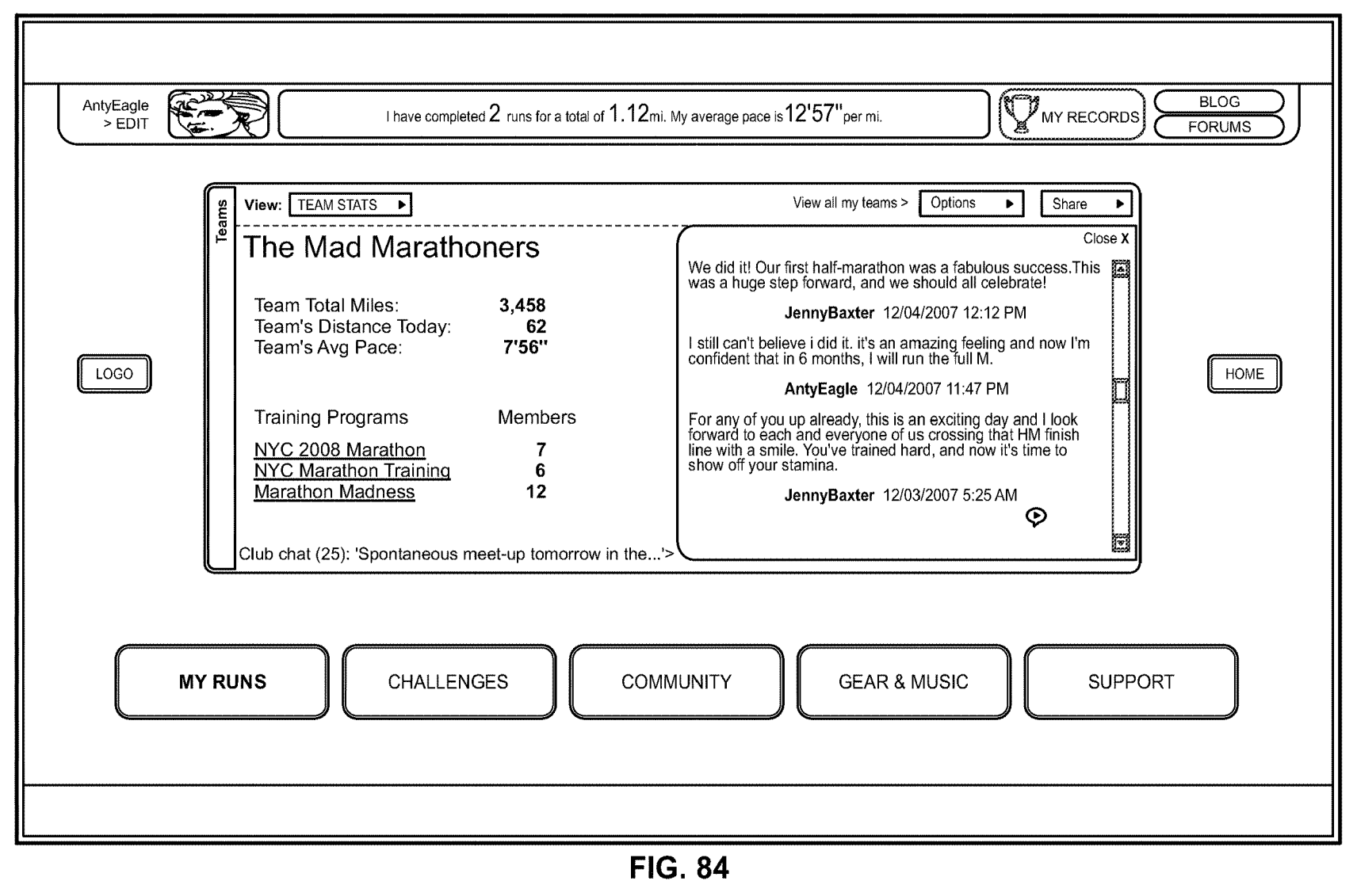

More specifically, FIG. 83 illustrates that for a particular team, organization, or club, the user or athlete may view the team, organization, or club's total miles, total distance for the current day, and average pace per mile. Additionally, the user or athlete may view the one or more training programs in which the team members are participating, and how many team members are participating in each training program. The user or athlete may further view a list of all team members, for example by username. The list of all team members may be sorted alphabetically or may be sorted by, for example, their fastest run for a particular distance (e.g., one mile, five kilometers, ten kilometers, half marathon, marathon, and the like). Accordingly, the user or athlete has a sense not only of the team performance averages, but also the performance of individuals on the team. FIG. 84 illustrates that the user interface 1700 may further display a chat among the team members.

Figure 85:
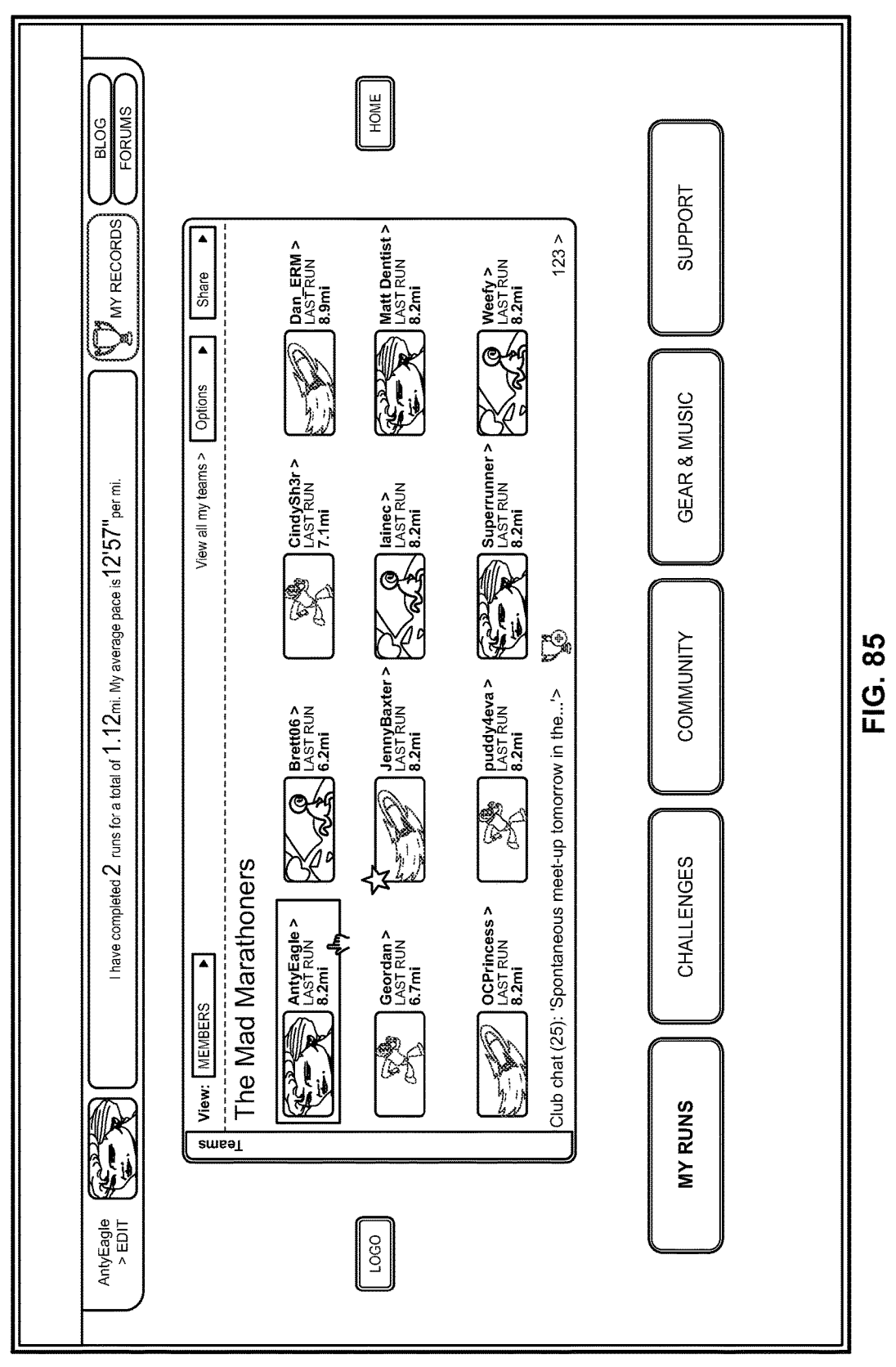
Figure 86:
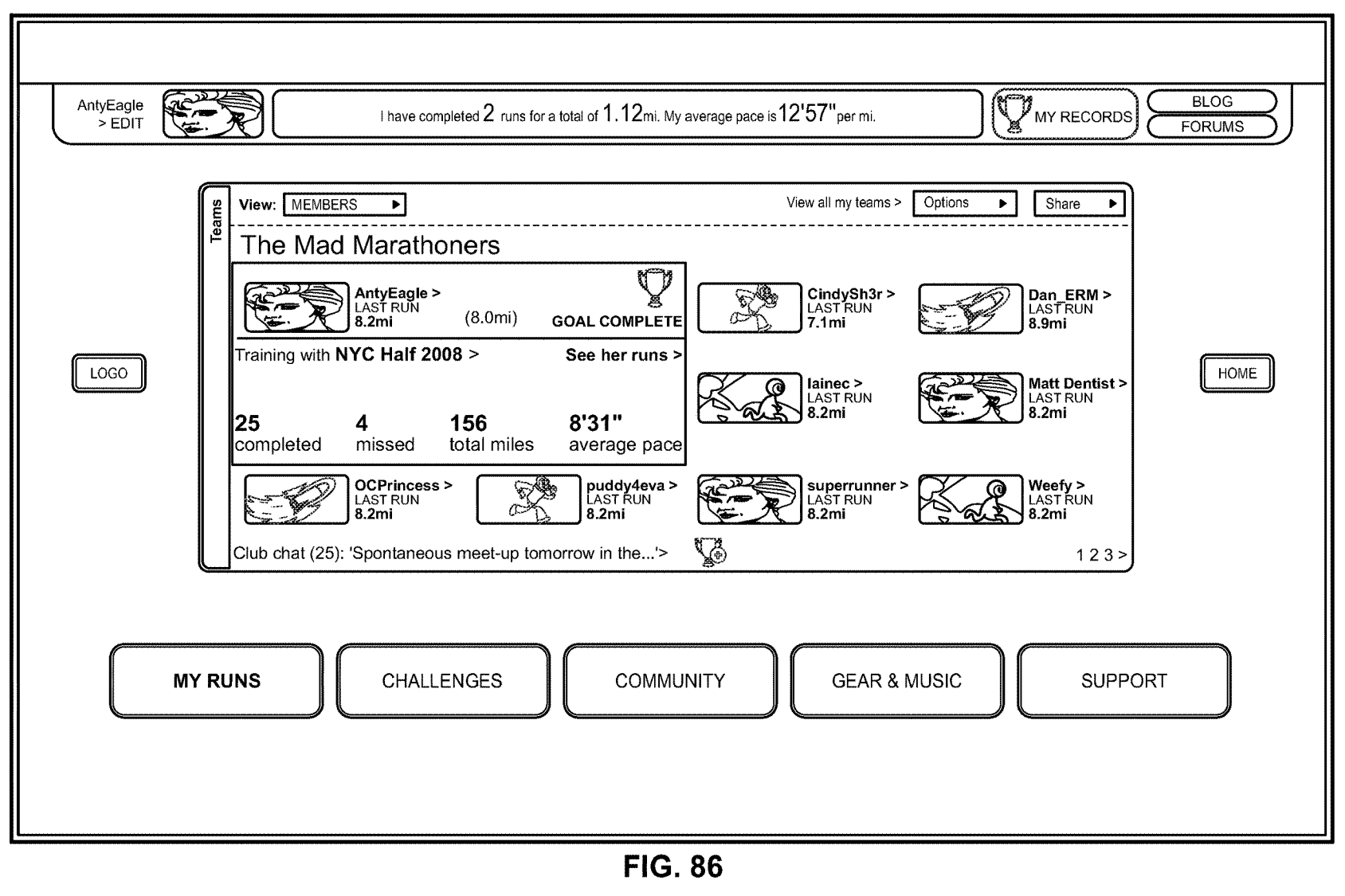

FIG. 85 illustrates an alternate view of the team members. For example, the team members may be displayed by username, avatar, and the distance of their last run. FIG. 86 illustrates that additional details associated with the team member may be displayed, such as the training program in which they are participating, the goal distance of their last run, whether or not their actual performance met the goal distance, number of training program days they have completed, number of training program days they have missed, total miles run, and average pace per mile. Further, the user interface 1700 may display one or more rewards or gifts that the team member may have received for completing a training program, reaching a goal or milestone, or the like.

In an embodiment, the user interface 1700 may display the entire team. In a further embodiment, the coach, trainer, or team leader may sort the members of the team based on one or more criteria. For example, a coach, trainer, or team leader may wish to sort for team members that have not reached a particular daily training program goal or who are behind the training program schedule or pace to offer those team members additional assistance.

Figure 87:
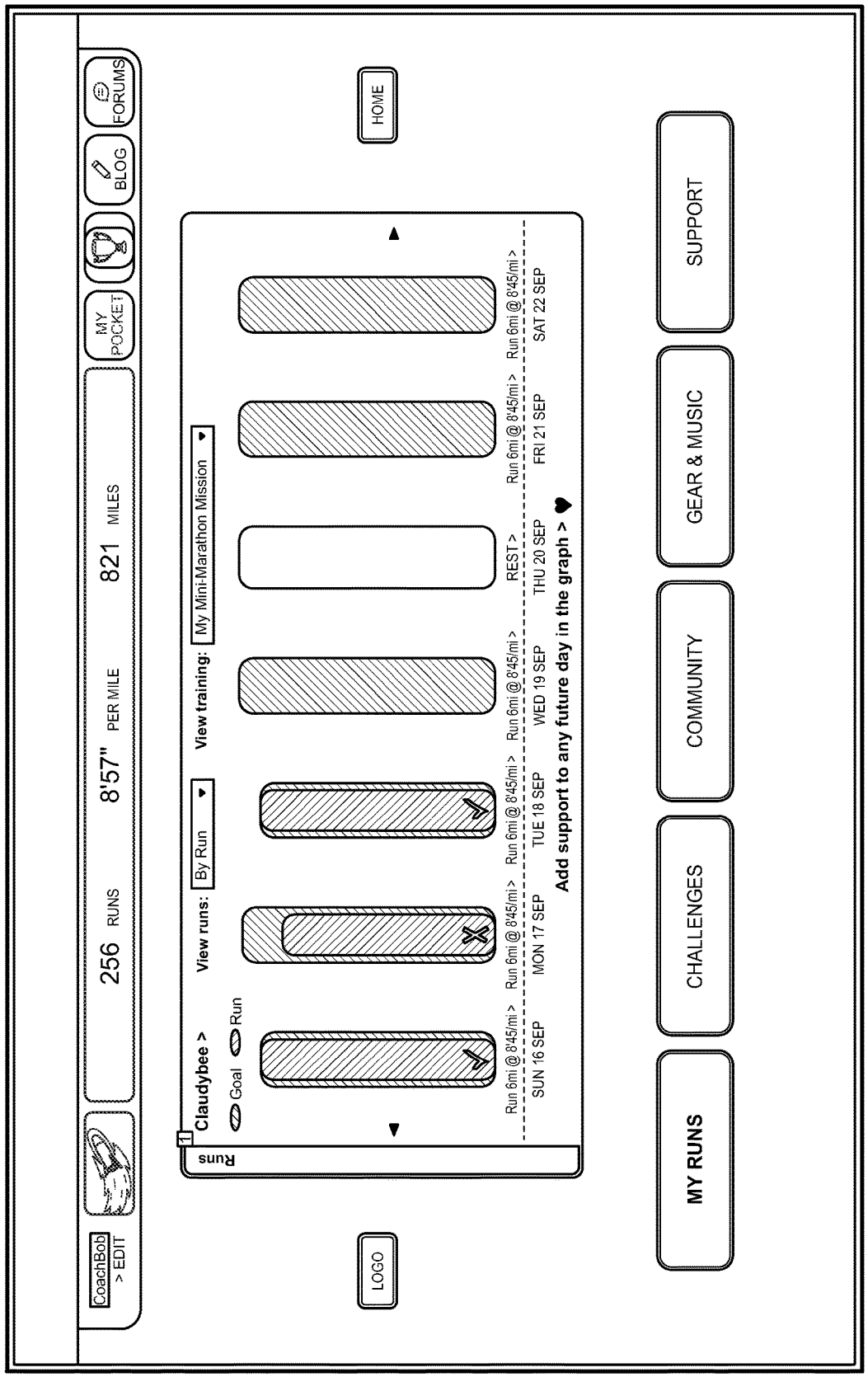
Figure 88:
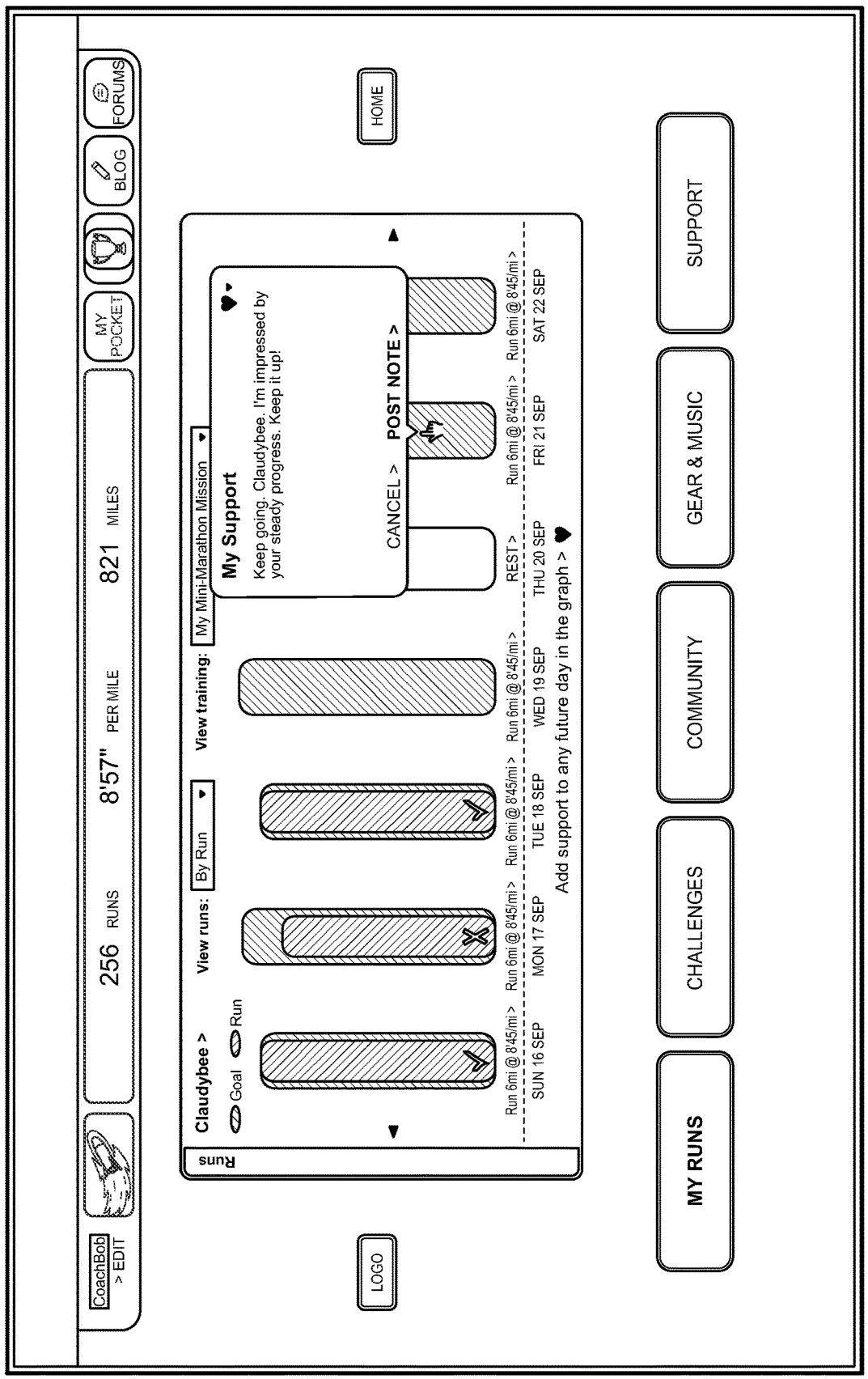

FIGS. 87 and 88 illustrate that within any of the coaching and team related user interface 1700 embodiments, a coach, trainer, team leader, or team member may offer comments or support to another team member. For example, the coach, trainer, team leader, or team member may view another team member's training program and actual performance and may add a comment or support to one or more days in the form of a link, bubble, overlay, or the like. In an embodiment, the coach, trainer, team leader, or team member may only add comments or support to future days as additional incentive to provide constructive and positive support versus comments about not reaching a particular day's goal or similar. According to one arrangement, a user receiving a comment may be notified by an e-mail or some other notification method. In one example, upon a first user adding a comment to a second user's training program or progress, the training system may send a notification message to the second user that a comment has been posted by or received from the first user.

In addition to comments or support, a coach, trainer, or team leader may further provide a "carrot" or gift that a team member may receive upon the completion of a particular goal. For example, the coach, trainer, team leader or other team member may indicate to another team member (e.g., with a comment or the like) that a gift may be available upon the completion of a specific goal, benchmark, milestone, or the like. In an embodiment, the gift may be a virtual gift that may accompany the details of the team member. For example, the virtual gift may be an icon, picture, or other graphical object that the user interface 1700 may display alongside the team member's avatar or the like so that anyone viewing the details of the team member (including the team member his/herself) may have an indication of the team member's success. Further, the carrot or gift may encourage competition if there are a limited number of gifts available. For example, a coach, trainer, or team leader may offer a gift to the first team member to achieve a goal, benchmark, milestone or the like. A team member may accumulate multiple gifts.

CONCLUSION

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

What is claimed is:

1. A computer-implemented method comprising:
   creating a virtual team of a plurality of athletes;
   formulating a team training program for reaching a team goal comprising a route having a plurality of locations having at least a first location and a second location; and
   tracking progress of at least a first athlete and a second athlete of the team comprising:
   displaying the training program in a user interface including a plurality of visual interactive elements corresponding to a plurality of tasks in the training program, wherein a first visual interactive element is configured to control at least one attribute of a first task and a second visual interactive element is configured to control at least one attribute of a second task;
   receiving user input corresponding to a modification of an attribute of the first task of the plurality of tasks, wherein the user input includes interaction with the first visual interactive element;
   automatically revising at least the second task scheduled for a time after the first task to compensate for the modification to the first task, wherein revising at least the second task is performed based on a predefined completion date for reaching the team goal and wherein automatically revising at least the second task includes modifying an appearance of the second visual interactive element;
   receiving locational data of the first athlete and second athlete traversing over the route during performance of an athletic activity; and
   receiving athletic performance data for each of the first athlete and the second athlete performing the athletic performance and storing the athletic performance data in association with the route;
   receiving from an electronic source, an indication of audio data presented to each of the first athlete and the second athlete while traversing over the route between at least the first and the second location;
   generating a route map on a user interface showing the route, generating the route map including:
   receiving a zip code associated with a location;
   displaying a map of the location associated with the zip code;
   receiving user input drawing a route on the displayed map, drawing the route including displaying a total distance of the route as the route is drawn and drawing the route including highlighting the route on the map,
   wherein the route map further includes one or more markers on the route identifying at least one metric of the athletic performance data;
   generating a playlist of audio data based upon the audio data presented to the first and second athlete during performance of the athletic activity respective to the first location and the second location; and
   responsive to receiving a user input interacting with a first marker of the user interface associated with the first location, providing information relating to the playlist generated, wherein a simultaneous provision of the generated playlist of the audio data and the at least one metric is selectively achieved along the route map of the user interface.

2. The method of claim 1, wherein there are at least two portions of the route between the first location and the second location, wherein the at least one metric comprises pace, and wherein generating the route map comprises:
   selecting different colors for different portions of the route depending on a pace of at least one of the first athlete and the second athlete during traversal of different portions.

3. The method of claim 1, wherein there are at least two portions of the route between the first location and the second location, wherein the audio data comprises a first song having a first tempo and a second song having a second tempo, and wherein generating the route map comprises:

selecting different colors for different portions of the route depending on a tempo of at least one of the first song and the second song during traversal of the different portions.

4. The method of claim 1, further comprising:
storing a plurality of goals set for the team.

5. The method of claim 4, further comprising:
generating a user interface displaying a list of the plurality of goals set for the team.

6. The method of claim 1, wherein the audio data comprises a first song having a first tempo and a second song having a second tempo.

7. The method of claim 4, wherein the plurality of goals includes a race at a predefined initiation time and wherein a display module is further configured to display a route for the race.

8. The method of claim 1, further comprising a privacy module configured to prevent non-team members from viewing team information.

9. A system comprising:
a team creation module configured to create a virtual team of a plurality of athletes;
a goal module configured to:
  determine a team training program for reaching a team goal comprising a route having a plurality of locations comprising at least a first location and a second location; and
  track progress of at least a first and a second athlete of the team in reaching the team goal comprising:
    display the training program in a user interface including a plurality of visual interactive elements corresponding to a plurality of tasks in the training program, wherein a first visual interactive element is configured to control at least one attribute of a first task and a second visual interactive element is configured to control at least one attribute of a second task;
    receive user input corresponding to a modification of an attribute of the first task of the plurality of tasks, wherein the user input includes interaction with the first visual interactive element;
    automatically revise at least the second task scheduled for a time after the first task to compensate for the modification to the first task, wherein revising at least the second task is performed based on a predefined completion date for reaching the team goal and wherein automatically revising at least the second task includes modifying an appearance of the second visual interactive element;
    receive from a first sensor, locational data of the first and second athletes traversing over the route during performance of an athletic activity; and
    receive from a second sensor, athletic performance data of at least one metric for the first and the second athletes performing the athletic performance and storing the athletic performance data of the athletic activity in association with the route;
an audio module configured to:
  receive from an electronic source, an indication of audio data presented to each of the first and the second athlete while traversing over the route between at least the first and the second location;
a processor; and
a non-transitory computer-readable medium comprising computer-executable instructions that when executed by the processor perform at least:
  generating a route map showing the route, wherein the route map further includes one or more markers on the route identifying at least one metric of the athletic performance data, wherein generating the route map includes:
    receiving a zip code associated with a location;
    displaying a map of the location associated with the zip code;
    receiving user input drawing a route on the displayed map, drawing the route including displaying a total distance of the route as the route is drawn and drawing the route including highlighting the route on the map;
  generating a playlist of audio data based upon the audio data presented to the first and second athlete during performance of the athletic activity; and
  responsive to receiving a user input from an athlete of the team interacting with a first marker associated with the first location, providing information relating to playlist generated, wherein a simultaneous provision of the generated playlist of the audio data and the at least one metric is selectively achieved.

10. The system of claim 9, wherein there are at least two portions of the route between the first location and the second location, wherein the at least one metric comprises pace and wherein generating the route map comprises:
selecting different colors for different portions of the route depending on a pace of at least one of the first athlete and the second athlete during each of the different portions.

11. The system of claim 9, wherein there are at least two portions of the route between the first location and the second location, wherein the audio data comprises a first song having a first tempo and a second song having a second tempo, and wherein generating the route map comprises:
selecting different colors for different portions of the route depending on a tempo of at least one of the first song and the second song during each of the different portions.

12. The system of claim 9, wherein the goal module is further configured to store a plurality of goals set for the team.

13. The system of claim 12, further comprising a display module configured to generate a user interface displaying a list of the plurality of goals set for the team.

14. The system of claim 9, wherein the audio data comprises a first song having a first tempo and a second song having a second tempo.

15. The system of claim 12, wherein the plurality of goals includes a race at a predefined initiation time and wherein a display module is further configured to display a route for the race.

* * * * *